United States Patent
Chen et al.

(10) Patent No.: US 12,275,800 B2
(45) Date of Patent: Apr. 15, 2025

(54) ANTI-COAGULATION FACTOR XI ANTIBODIES

(71) Applicants: Merck Sharp & Dohme LLC, Rahway, NJ (US); Adimab, LLC, Lebanon, NH (US)

(72) Inventors: Zhu Chen, Warren, NJ (US); Kenneth Ellsworth, Cranbury, NJ (US); James Milligan, Sevierville, TN (US); Elizabeth Oldham, Santa Clara, CA (US); Dietmar Seiffert, Lawrence Township, NJ (US); Bianka Prinz, Lebanon, NH (US); Vaishnavi Ganti, Foster City, CA (US); Mohammad Tabrizifard, Moranga, CA (US)

(73) Assignees: Merck Sharp & Dohme LLC, Rahway, NJ (US); Adimab, LLC, Lebanon, NH (US)

( * ) Notice: Subject to any disclaimer, the term of this patent is extended or adjusted under 35 U.S.C. 154(b) by 80 days.

(21) Appl. No.: 18/302,033

(22) Filed: Apr. 18, 2023

(65) Prior Publication Data
US 2023/0287141 A1    Sep. 14, 2023

Related U.S. Application Data

(60) Continuation of application No. 16/864,559, filed on May 1, 2020, now Pat. No. 11,661,460, which is a division of application No. 15/619,620, filed on Jun. 12, 2017, now Pat. No. 10,676,536.

(60) Provisional application No. 62/349,888, filed on Jun. 14, 2016.

(51) Int. Cl.
*C07K 16/36* (2006.01)
*A61K 39/395* (2006.01)
*A61K 39/00* (2006.01)

(52) U.S. Cl.
CPC .......... *C07K 16/36* (2013.01); *A61K 39/3955* (2013.01); *A61K 2039/505* (2013.01); *A61K 2039/58* (2013.01); *C07K 2317/75* (2013.01); *C07K 2317/76* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,391,299 B1 | 5/2002 | Blackburn et al. |
| 7,022,500 B1 | 4/2006 | Queen et al. |
| 8,236,316 B2 | 8/2012 | Gruber et al. |
| 8,388,959 B2 | 3/2013 | Gruber et al. |
| 8,399,648 B2 | 3/2013 | Gruber et al. |
| 8,568,724 B2 | 10/2013 | Hack |
| 8,940,883 B2 | 1/2015 | Gruber et al. |
| 9,096,673 B2 | 8/2015 | Tocker et al. |
| 9,102,725 B2 | 8/2015 | Korman et al. |
| 9,102,738 B2 | 8/2015 | Terrett et al. |
| 9,119,839 B2 | 9/2015 | Huang et al. |
| 9,125,895 B2 | 9/2015 | Gruber et al. |
| 9,138,475 B2 | 9/2015 | Vistica et al. |
| 9,181,330 B2 | 11/2015 | Marks et al. |
| 9,234,043 B1 | 1/2016 | Campbell et al. |
| 9,255,153 B2 | 2/2016 | Cunningham et al. |
| 9,266,964 B2 | 2/2016 | Sexton et al. |
| 9,273,135 B2 | 3/2016 | Korman et al. |
| 9,284,589 B2 | 3/2016 | Vaughan et al. |
| 9,315,573 B2 | 4/2016 | Harding et al. |
| 9,387,247 B2 | 7/2016 | Korman et al. |
| 9,394,370 B2 | 7/2016 | Tawara et al. |
| 9,428,572 B2 | 8/2016 | Throsby et al. |
| 9,428,579 B2 | 8/2016 | Giles-Komar et al. |
| 9,481,731 B2 | 11/2016 | Cunningham et al. |
| 9,486,523 B2 | 11/2016 | Simard |
| 9,492,539 B2 | 11/2016 | Korman et al. |
| 9,492,540 B2 | 11/2016 | Korman et al. |
| 9,522,957 B2 | 12/2016 | Cunningham et al. |
| 9,540,448 B2 | 1/2017 | Scheinberg et al. |
| 9,562,108 B2 | 2/2017 | Walker et al. |
| 9,631,025 B2 | 4/2017 | Vistica et al. |
| 9,631,029 B2 | 4/2017 | Chiusaroli et al. |
| 9,636,399 B2 | 5/2017 | Gruber et al. |
| 9,637,550 B2 | 5/2017 | Gruber et al. |
| 10,053,515 B2 | 8/2018 | Chen et al. |
| 10,584,179 B2 | 3/2020 | Chen et al. |
| 10,676,536 B2 | 6/2020 | Chen et al. |
| 11,479,615 B2 | 10/2022 | Chen et al. |
| 11,661,460 B2 | 5/2023 | Chen et al. |
| 2011/0250207 A1 | 10/2011 | Gruber et al. |

(Continued)

FOREIGN PATENT DOCUMENTS

| | | |
|---|---|---|
| AU | 2016203944 A1 | 7/2016 |
| AU | 2013258043 B2 | 11/2017 |

(Continued)

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*

(Continued)

*Primary Examiner* — Michael Szperka
(74) *Attorney, Agent, or Firm* — John David Reilly; John C. Todaro

(57) ABSTRACT

Antibodies that bind the apple 3 domain of human coagulation Factor XI and inhibit activation of FXI by coagulation factor XIIa as well as activation of FIX by FXIa are described.

18 Claims, 29 Drawing Sheets
Specification includes a Sequence Listing.

(56) References Cited

U.S. PATENT DOCUMENTS

| | | |
|---|---|---|
| 2014/0194600 A1 | 7/2014 | Hack |
| 2014/0322219 A1 | 10/2014 | Gruber et al. |
| 2015/0093395 A1 | 4/2015 | Gruber |
| 2015/0099298 A1 | 4/2015 | Wilmen |
| 2015/0203574 A1 | 7/2015 | Rajpal et al. |
| 2015/0259436 A1 | 9/2015 | Scheinberg et al. |
| 2015/0322163 A1 | 11/2015 | Gruber |
| 2015/0329641 A1 | 11/2015 | Braun et al. |
| 2016/0009796 A9 | 1/2016 | Mike et al. |
| 2016/0017036 A1 | 1/2016 | Merchant et al. |
| 2016/0024221 A1 | 1/2016 | Vistica et al. |
| 2016/0046707 A1 | 2/2016 | Imai et al. |
| 2016/0060343 A1 | 3/2016 | Huang et al. |
| 2016/0075782 A1 | 3/2016 | Korman et al. |
| 2016/0102150 A1 | 4/2016 | Sexton et al. |
| 2016/0115228 A1 | 4/2016 | Smith |
| 2016/0152700 A1 | 6/2016 | Comeau et al. |
| 2016/0168265 A1 | 6/2016 | Marks et al. |
| 2016/0228570 A1 | 8/2016 | Nissim et al. |
| 2016/0237147 A1 | 8/2016 | Wild, Jr. et al. |
| 2016/0251443 A1 | 9/2016 | Tocker et al. |
| 2016/0304596 A1 | 10/2016 | Wild, Jr. et al. |
| 2016/0340440 A1 | 11/2016 | Fanslow, III et al. |
| 2016/0347845 A1 | 12/2016 | Kumar et al. |
| 2017/0073408 A1 | 3/2017 | Han et al. |
| 2017/0073421 A1 | 3/2017 | Kjaergaard et al. |
| 2017/0088620 A1 | 3/2017 | Nioi et al. |
| 2017/0088630 A1 | 3/2017 | Scheinberg et al. |
| 2017/0096474 A1 | 4/2017 | Marks et al. |
| 2017/0106095 A1 | 4/2017 | Batt et al. |
| 2017/0107273 A1 | 4/2017 | Wakita et al. |
| 2017/0115307 A1 | 4/2017 | Garcia-Martinez et al. |
| 2017/0204195 A1 | 7/2017 | Gruber et al. |

FOREIGN PATENT DOCUMENTS

| | | | |
|---|---|---|---|
| CN | 104684932 A | 6/2015 | |
| EP | 2222707 B1 | 1/2016 | |
| EP | 3002298 A1 | 4/2016 | |
| JP | H0656382 A | 3/1994 | |
| JP | 2011504371 A | 2/2011 | |
| TW | 201722993 A | 7/2017 | |
| WO | 8912463 A1 | 12/1989 | |
| WO | 199726010 A1 | 7/1997 | |
| WO | 2003080672 A1 | 10/2003 | |
| WO | WO-2009067660 A2 * | 5/2009 | ......... A61K 39/3955 |
| WO | 2009154461 A1 | 12/2009 | |
| WO | 2010080623 A2 | 7/2010 | |
| WO | 2012009568 A2 | 1/2012 | |
| WO | 2013167669 A1 | 11/2013 | |
| WO | 2013173255 A2 | 11/2013 | |
| WO | 2016023019 A2 | 2/2016 | |
| WO | 2016164637 A1 | 10/2016 | |
| WO | 2016201389 A2 | 12/2016 | |
| WO | 2016207858 A1 | 12/2016 | |
| WO | 2017015619 A8 | 3/2017 | |
| WO | 2017127468 A1 | 7/2017 | |
| WO | 2018054813 A1 | 3/2018 | |

OTHER PUBLICATIONS

Edwards et al., J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Lescar, et al. Journal of Biological Chemistry 270.30 (1995): 18067-18076.*
Kanyavuz et al., Nat Rev Immunol. Jun. 2019;19(6):355-368. doi: 10.1038/S41577-019-0126-7.*
Van den Bremer et al., MAbs. Jul.-Aug 2015; 7(4): 672-680. Published online Jun. 2, 2015. doi: 10.1080/19420862.2015. 1046665 PMCID: PMC4622059 PMID: 26037225.*
Akiyama et al., Mechanism of Activation of Coagulation Factor Xi by Factor XIIa Studied with Monoclonal Antibodies, J. Clin. Invest., 1986, p. 1631, 78.
Angal et al., A Single Amino Acid Substitution Abolishes the Heterogeneity of Chimeric Mouse/Human (IgG4) Antibody, Molecular Immunology, 1993, pp. 105-108, vol. 30(1).
Baglia et al., A Binding Site for Thrombin in the Apple 1 Domain of Factor XI, JBC, 1996, p. 3652, 271.
Baglia et al., Functional Domains in the Heavy-Chain Region of Factor XI: A high Molecular Weight Kininogen-binding site and a substrate-binding site for factor IX, Blood, 1989, p. 244, 74.
C. Lloyd et al., Modelling the human immune response: performance of a 10" human antibody repertoire against a proad panel of therapeutically relevant antigens, Protein Engineering Design & Selection, 2009, 159-168, 22-3.
Dennis, Mark, CDR Repair: A Novel Approach to Antibody Humanization, Current Trends in Monoclonal Antibody Development and Manufacturing, 2010, 9-28, Chapter 2.
Edwards, B. et al., The Remarkable Flexibility of the Human Antibody Repertoire; Isolation of Over One Thousand Different Antibodies to a Single Protein, BLyS, Jounal of Molecular Biology, 2003, 103-118, 334.
Fujikawa et al., Amino Acid Sequence of Human Factor XI, a Blood Coagulation Factor for Tandem Repeats that are Highly Homologous with Plasma Prekallikrein, Biochem., 1986, p. 2417, 25.
Goel, M. et al., Plasticity within the Antigen-Combining Site May Manifest as Molecular Mimicry in the Humoral Immune Response, The Journal of Immunology, 2004, 7358-7367, 173.
Herren Wu et al., Humanization of a Murine Monoclonal Antibody by Simultaneous Optimization of Framework and CDR Residues, J. Mol. Biol., 1999, 151-162, 294.
Janeway, C et al. Immunobiology, The Immune System in Health and Disease, Structure of the Antibody Molecule and Immunoglobulin Genes, Third Edition, (1997), p. 3:1-3:11.
Kanyavuz, A. et al., Breaking the laww: unconventional strategies for antibody diversification, Nature Reviews Immunology, 2019, 355-368, 19.
Kipriyanov, Sergey M. et al., Generation and Production of Engineered Antibodies, Molecular Biotechnology, 2004, 39-60, 26(1).
Labrijn et al., Therapeutic IgG4 antibodies engage in Fab-arm exchange with endogenous human IgG4 in vivo, Nat. Biotechnol., 2009, p. 767, 27.
Leung et al., Inhibition of Factor XII Mediated Activation of Factor XI Provides Protection Against Experimental Acute Ischemic Stroke in Mice, Translational Stroke Research, 2012, No. 3, pp. 381-389, 3.
Lifei, Peng et al., Use of FXI As a New Target of Antithrombotic Therapy and Its Research Progress, Chinese Journal of Pharmacology and Toxicology, 2011, 16, 25.
McMullen et al., Location of the Disulfide Bonds in Human Coagulation Factor XI: The Presence of Tandem Apple Domains, Biochem., 1991, p. 2056, 30.
Nishkado et al., Murine Monoclonal Antibodies to Human Factor XI, Thromb Res, 1986, p. 225, 42.
Puy et al., Activated factor XI increases the procoagulant activity of the extrinsic pathway by inactivating tissue factor pathway inhibitor, Thrombosis and Hemotasis, 2015, No. 9, pp. 1488-1496, 125.
Rudikoff, S et al., Single amino acid substitution altering antigen-binding specificity, PNAS, 1982, pp. 1979-1983, 79.
Sinha et al., Functional Characterization of Human Blood Coagulation Factor XIa Using Hybridoma Antibodies, JBC, 1985, p. 10714, 260.
Stern et al., Acquired Antibody to Factor XI in a Patient with Congenital Factor XI Deficiency, J. Clin. Invest., 1982, p. 1270, 69.
Sun et al., Identification of a Factor IX Binding Site on the Third Apple Domain of Activated Factor XI, JBC, 1996, p. 29023, 271.
Tamura, Midori et al., Structural Correlates of an Anticarcinoma Antibody: Identification of Specificity-Determining Residues (SDRs) and Development of a Minimally Immunogenic Antibody Variant by Retention of SDRs Only, Journal of Immunology, 2000, 1432-1441, 164(3).

(56) References Cited

OTHER PUBLICATIONS

Van Montfoort et al., Two Novel Inhibitory anti-human factor XI antibodies prevent cessation of blood flow in a murine venous thrombosis model, Thrombosis and Haemostasis, 2013, No. 5, pp. 1065-1073, 110.

Zhu et al., FXIa and platelet polyphosphate as therapeutic targets during human blood clotting on collagen/tissue factor surfaces under flow, Blood, 2015, No. 12, pp. 1494-1502, 126.

Al-Horani, Rami A., Factor XI(a) inhibitors for thrombosis: an updated patent review (2016-present), Expert Opin. Ther. Pat., 30(1), 39-55, 2020.

Bane, Charles E. Jr., et al., Factor XI as a target for antithrombotic therapy, Drug Discov Today, 19(9), 1454-1458, 2014.

* cited by examiner

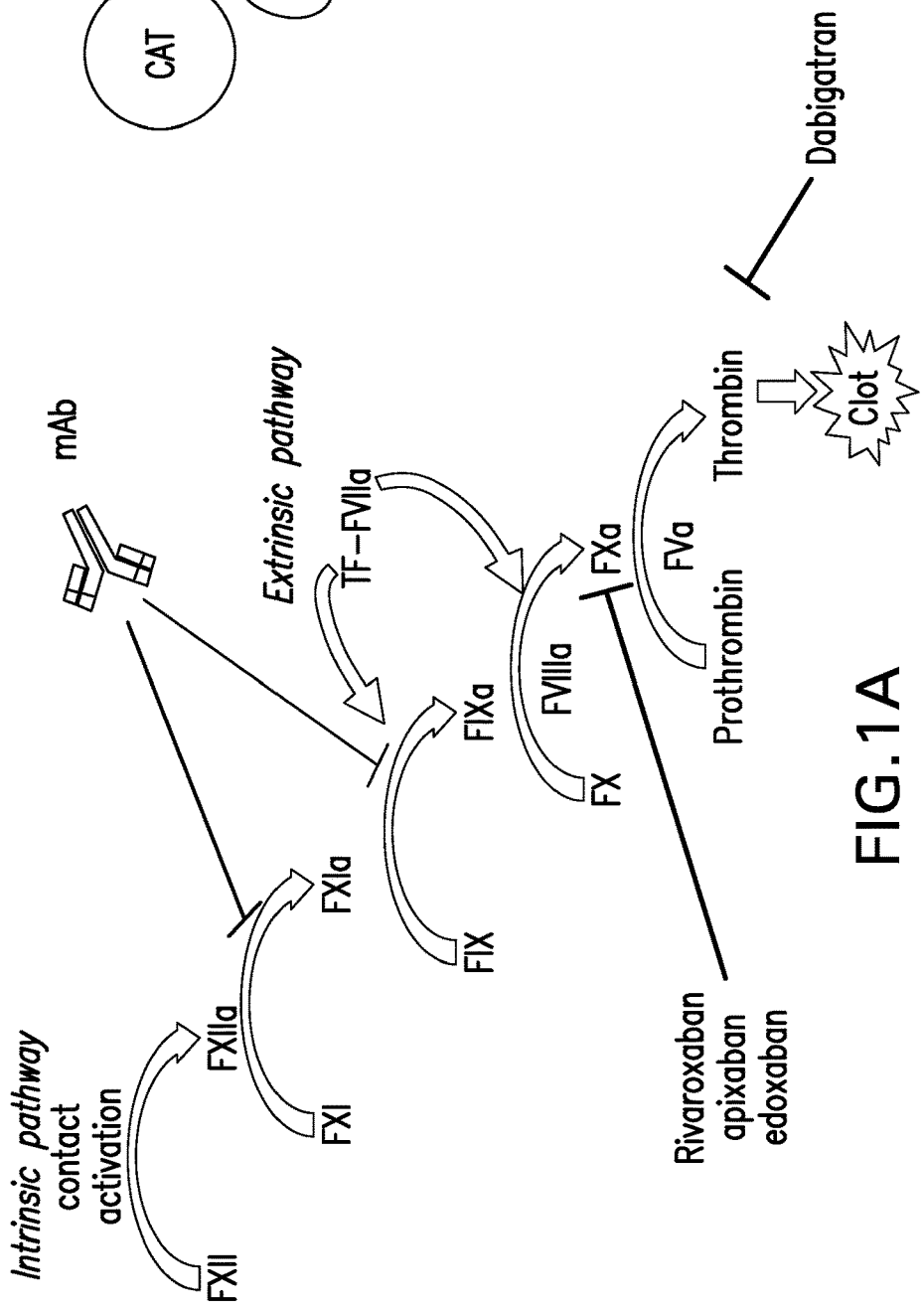
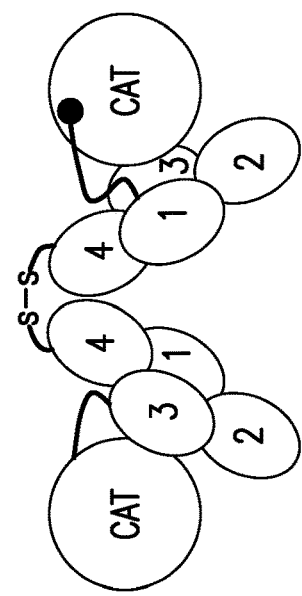
FIG. 1A
FIG. 1B

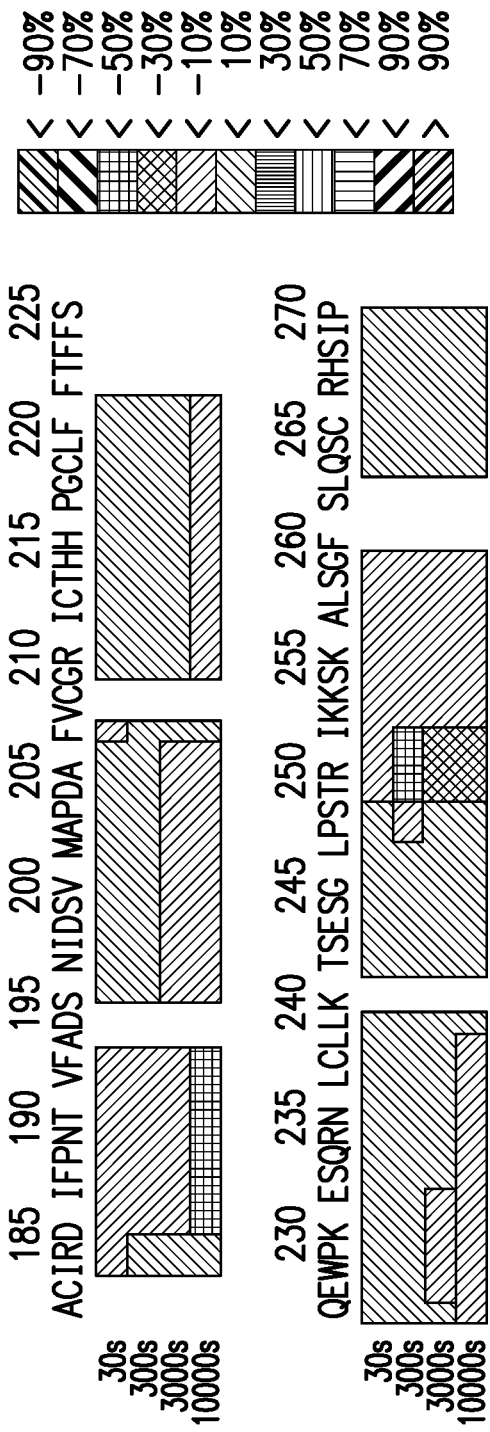
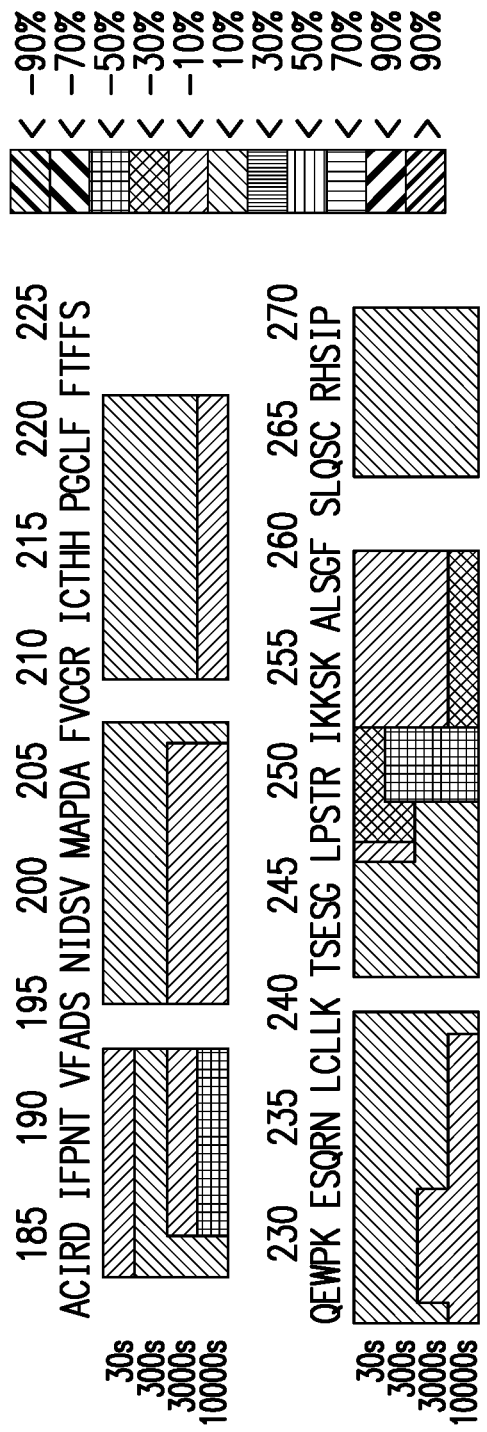
FIG.3A
FIG.3B

Heavy Chain variable domain of αFXI-18611p(E1)(M105) (SEQ ID NO:22)

```
          1         2         3         4         5         6         7         8         9
1234567890123456789012345678901234567890123456789012345678901234567890123456789012abc3456789012 34
EVQLQESGPGLVKPSETLSLTCAVSGYSISSGYFWGWIRQPPGKGLEWIGSILHSGVTYNPSLKSRVTISVDTSKNQFSLKLSSVTAADTAVYYCAR
                               HC-CDR1                HC-CDR2
  1
  0
567890abcde123456789 0123
DRTTVSMIEYFQHWGQGTLVTVSS
    HC-CDR3
```

Heavy Chain variable domain of αFXI-18611(E1)(L105) (SEQ ID NO:24)

```
          1         2         3         4         5         6         7         8         9
1234567890123456789012345678901234567890123456789012345678901234567890123456789012abc3456789012 34
EVQLQESGPGLVKPSETLSLTCAVSGYSISSGYFWGWIRQPPGKGLEWIGSILHSGVTYNPSLKSRVTISVDTSKNQFSLKLSSVTAADTAVYYCAR
                               HC-CDR1                HC-CDR2
  1
  0
567890abcde123456789 0123
DRTTVSLIEYFQHWGQGTLVTVSS
    HC-CDR3
```

FIG.4A

Heavy Chain variable domain of αFXI-18611p(Q1)(M105) (SEQ ID NO:21)

```
         1         2         3         4         5         6         7         8         9
123456789012345678901234567890123456789012345678901234567890123456789012345678901234
QVQLQESGPGLVKPSETLSLTCAVSGYSISSGYFWGWIRQPPGKGLEWIGSILHSGVTYNPSLKSRVTISVDTSKNQFSLKLSSVTAADTAVYYCAR
                          HC-CDR1                      HC-CDR2
  1
  0
567890abcde1234567890123
DRTTVSMIEYFQHWGQGTLVTVSS
      HC-CDR3
```

Heavy Chain variable domain of αFXI-18611(Q1)(L105) (SEQ ID NO:23)

```
         1         2         3         4         5         6         7         8         9
123456789012345678901234567890123456789012345678901234567890123456789012345678901234
QVQLQESGPGLVKPSETLSLTCAVSGYSISSGYFWGWIRQPPGKGLEWIGSILHSGVTYNPSLKSRVTISVDTSKNQFSLKLSSVTAADTAVYYCAR
                          HC-CDR1                      HC-CDR2
  1
  0
567890abcde1234567890123
DRTTVSLIEYFQHWGQGTLVTVSS
      HC-CDR3
```

FIG.4B

Light Chain variable domain of αFXI-18611p and αFXI-18611 families (SEQ ID NO:25)

```
         1         2         3         4         5         6         7         8         9
1234567890123456789012345678901234567890123456789012345678901234567890123456789012345678901234567 8
DIQMTQSPSSLSASVGDRVTITCQASQDISNYLNWYQQKPGKAPKLLIYDASNLETGVPSRFSGSGSGTDFTFTISSLQPEDIATYYCQQFHLLPITF
                          HC-CDR1                  HC-CDR2                                HC-CDR3

1
 0
8901234 56
GGGTKVEIK
```

FIG.4C

Heavy Chain variable domain of αFXI-18623p(Q1) (SEQ ID NO:28)

```
         1         2         3         4         5         6         7         8         9
1234567890123456789012345678901234567890123456789012345678901234567890123abc345678901234
QVQLQESGPGLVKPSQTLSLTCTVSGGSIYSGAYYWSWIRQHPGKGLEWIGSIHYSGLTYYNPSLKSRVTISVDTSKNQFSLKLSSVTAADTAVYYCAR
                           789012345ab               0123456789012abc
                           HC-CDR1                    HC-CDR2

1
 0
567890abcdefg123456789 0123
DVDDSSGDEHYGMDVWGQGTTVTVSS
HC-CDR3
```

Heavy Chain variable domain of αFXI-18623p(E1) (SEQ ID NO:29)

```
         1         2         3         4         5         6         7         8         9
1234567890123456789012345678901234567890123456789012345678901234567890123abc345678901234
EVQLQESGPGLVKPSQTLSLTCTVSGGSIYSGAYYWSWIRQHPGKGLEWIGSIHYSGLTYYNPSLKSRVTISVDTSKNQFSLKLSSVTAADTAVYYCAR
                           789012345ab               0123456789012abc
                           HC-CDR1                    HC-CDR2

1
 0
567890abcdefg123456789 0123
DVDDSSGDEHYGMDVWGQGTTVTVSS
HC-CDR3
```

FIG.5A

Light Chain variable domain of the αFXI-18623p family (SEQ ID NO:30)

```
         1         2         3         4         5         6         7         8         9
1234567890123456789012345678901234567890123456789012345678901234567890123456789012345678901234567 8
DIQMTQSPSSVSASVGDRVTITCRASQGIDSWLAWYQQKPGKAPKLLIYAASSLQSGVPSRFSGSGSGTDFTLTISSLQPEDFATYYCQQYHIVPITF
                      └──HC-CDR1──┘            └HC-CDR2┘                              └─HC-CDR3─┘
  1
  0
8901234567
GGGTKVEIK
```

FIG.5B

```
                       SEQUENCE LISTING

Sequence total quantity: 85
SEQ ID NO: 1             moltype = AA  length = 10
FEATURE                  Location/Qualifiers
REGION                   1..10
                         note = alpha-FXI-18611p and alpha-FXI -18611 HC-CDR1
source                   1..10
                         mol_type = protein
                         organism = synthetic construct
SEQUENCE: 1
YSISSGYFWG                                                            10

SEQ ID NO: 2             moltype = AA  length = 16
FEATURE                  Location/Qualifiers
REGION                   1..16
                         note = alpha-FXI-18611p and alpha-FXI -18611 HC-CDR2
source                   1..16
                         mol_type = protein
                         organism = synthetic construct
SEQUENCE: 2
SILHSGVTYY NPSLKS                                                     16

SEQ ID NO: 3             moltype = AA  length = 15
FEATURE                  Location/Qualifiers
REGION                   1..15
                         note = alpha-FXI-18611p HC-CDR3
source                   1..15
                         mol_type = protein
                         organism = synthetic construct
SEQUENCE: 3
ARDRTTVSMI EYFQH                                                      15

SEQ ID NO: 4             moltype = AA  length = 15
FEATURE                  Location/Qualifiers
REGION                   1..15
                         note = alpha-FXI -18611 HC-CDR3
source                   1..15
                         mol_type = protein
                         organism = synthetic construct
SEQUENCE: 4
ARDRTTVSLI EYFQH                                                      15

SEQ ID NO: 5             moltype = AA  length = 11
```

```
FEATURE              Location/Qualifiers
REGION               1..11
                     note = alpha-FXI-18611p and alpha-FXI -18611 LC-CDR1
source               1..11
                     mol_type = protein
                     organism = synthetic construct
SEQUENCE: 5
QASQDISNYL N                                                              11

SEQ ID NO: 6         moltype = AA  length = 7
FEATURE              Location/Qualifiers
REGION               1..7
                     note = alpha-FXI-18611p and alpha-FXI -18611 LC-CDR2
source               1..7
                     mol_type = protein
                     organism = synthetic construct
SEQUENCE: 6
DASNLET                                                                    7

SEQ ID NO: 7         moltype = AA  length = 9
FEATURE              Location/Qualifiers
REGION               1..9
                     note = alpha-FXI-18611p and alpha-FXI -18611 LC-CDR3
source               1..9
                     mol_type = protein
                     organism = synthetic construct
SEQUENCE: 7
QQFHLLPIT                                                                  9

SEQ ID NO: 8         moltype = AA  length = 11
FEATURE              Location/Qualifiers
REGION               1..11
                     note = alpha-FXI-18623p HC-CDR1
source               1..11
                     mol_type = protein
                     organism = synthetic construct
SEQUENCE: 8
GSIYSGAYYW S                                                              11

SEQ ID NO: 9         moltype = AA  length = 16
FEATURE              Location/Qualifiers
REGION               1..16
                     note = alpha-FXI-18623p HC-CDR2
source               1..16
                     mol_type = protein
                     organism = synthetic construct
SEQUENCE: 9
SIHYSGLTYY NPSLKS                                                         16

SEQ ID NO: 10        moltype = AA  length = 17
FEATURE              Location/Qualifiers
REGION               1..17
                     note = alpha-FXI-18623p HC-CDR3
source               1..17
                     mol_type = protein
                     organism = synthetic construct
SEQUENCE: 10
ARDVDDSSGD EHYGMDV                                                        17

SEQ ID NO: 11        moltype = AA  length = 11
FEATURE              Location/Qualifiers
REGION               1..11
                     note = alpha-FXI-18623p LC-CDR1
source               1..11
                     mol_type = protein
                     organism = synthetic construct
SEQUENCE: 11
RASQGIDSWL A                                                              11

SEQ ID NO: 12        moltype = AA  length = 7
FEATURE              Location/Qualifiers
REGION               1..7
                     note = alpha-FXI-18623p LC-CDR2
source               1..7
                     mol_type = protein
                     organism = synthetic construct
SEQUENCE: 12
AASSLQS                                                                    7
```

| | | |
|---|---|---|
| SEQ ID NO: 13 | moltype = AA length = 9 | |
| FEATURE | Location/Qualifiers | |
| REGION | 1..9 | |
| | note = alpha-FXI-18623 pLC-CDR3 | |
| source | 1..9 | |
| | mol_type = protein | |
| | organism = synthetic construct | |
| SEQUENCE: 13 | | |
| QQYHIVPIT | | 9 |
| | | |
| SEQ ID NO: 14 | moltype = AA length = 20 | |
| FEATURE | Location/Qualifiers | |
| REGION | 1..20 | |
| | note = LC Leader Sequence A | |
| source | 1..20 | |
| | mol_type = protein | |
| | organism = synthetic construct | |
| SEQUENCE: 14 | | |
| MSVPTQVLGL LLLWLTDARC | | 20 |
| | | |
| SEQ ID NO: 15 | moltype = AA length = 19 | |
| FEATURE | Location/Qualifiers | |
| REGION | 1..19 | |
| | note = HC Leader Sequence B | |
| source | 1..19 | |
| | mol_type = protein | |
| | organism = synthetic construct | |
| SEQUENCE: 15 | | |
| MEWSWVFLFF LSVTTGVHS | | 19 |
| | | |
| SEQ ID NO: 16 | moltype = AA length = 327 | |
| FEATURE | Location/Qualifiers | |
| REGION | 1..327 | |
| | note = Human IgG4 HC constant domain: (S228P) S at position | |
| | 108 replacedwith P | |
| source | 1..327 | |
| | mol_type = protein | |
| | organism = synthetic construct | |
| SEQUENCE: 16 | | |
| ASTKGPSVFP LAPCSRSTSE STAALGCLVK DYFPEPVTVS WNSGALTSGV HTFPAVLQSS | | 60 |
| GLYSLSSVVT VPSSSLGTKT YTCNVDHKPS NTKVDKRVES KYGPPCPPCP APEFLGGPSV | | 120 |
| FLFPPKPKDT LMISRTPEVT CVVVDVSQED PEVQFNWYVD GVEVHNAKTK PREEQFNSTY | | 180 |
| RVVSVLTVLH QDWLNGKEYK CKVSNKGLPS SIEKTISKAK GQPREPQVYT LPPSQEEMTK | | 240 |
| NQVSLTCLVK GFYPSDIAVE WESNGQPENN YKTTPPVLDS DGSFFLYSRL TVDKSRWQEG | | 300 |
| NVFSCSVMHE ALHNHYTQKS LSLSLGK | | 327 |
| | | |
| SEQ ID NO: 17 | moltype = AA length = 326 | |
| FEATURE | Location/Qualifiers | |
| REGION | 1..326 | |
| | note = Human IgG4 constant domain: (S228P) S at position | |
| | 108 replacedwith P; C-terminal K-less | |
| source | 1..326 | |
| | mol_type = protein | |
| | organism = synthetic construct | |
| SEQUENCE: 17 | | |
| ASTKGPSVFP LAPCSRSTSE STAALGCLVK DYFPEPVTVS WNSGALTSGV HTFPAVLQSS | | 60 |
| GLYSLSSVVT VPSSSLGTKT YTCNVDHKPS NTKVDKRVES KYGPPCPPCP APEFLGGPSV | | 120 |
| FLFPPKPKDT LMISRTPEVT CVVVDVSQED PEVQFNWYVD GVEVHNAKTK PREEQFNSTY | | 180 |
| RVVSVLTVLH QDWLNGKEYK CKVSNKGLPS SIEKTISKAK GQPREPQVYT LPPSQEEMTK | | 240 |
| NQVSLTCLVK GFYPSDIAVE WESNGQPENN YKTTPPVLDS DGSFFLYSRL TVDKSRWQEG | | 300 |
| NVFSCSVMHE ALHNHYTQKS LSLSLG | | 326 |
| | | |
| SEQ ID NO: 18 | moltype = AA length = 330 | |
| FEATURE | Location/Qualifiers | |
| REGION | 1..330 | |
| | note = Human IgG1 HC constant domain | |
| source | 1..330 | |
| | mol_type = protein | |
| | organism = synthetic construct | |
| SEQUENCE: 18 | | |
| ASTKGPSVFP LAPSSKSTSG GTAALGCLVK DYFPEPVTVS WNSGALTSGV HTFPAVLQSS | | 60 |
| GLYSLSSVVT VPSSSLGTQT YICNVNHKPS NTKVDKKVEP KSCDKTHTCP PCPAPELLGG | | 120 |
| PSVFLFPPKP KDTLMISRTP EVTCVVVDVS HEDPEVKFNW YVDGVEVHNA KTKPREEQYN | | 180 |
| STYRVVSVLT VLHQDWLNGK EYKCKVSNKA LPAPIEKTIS KAKGQPREPQ VYTLPPSRDE | | 240 |
| LTKNQVSLTC LVKGFYPSDI AVEWESNGQP ENNYKTTPPV LDSDGSFFLY SKLTVDKSRW | | 300 |
| QQGNVFSCSV MHEALHNHYT QKSLSLSPGK | | 330 |
| | | |
| SEQ ID NO: 19 | moltype = AA length = 329 | |
| FEATURE | Location/Qualifiers | |

```
REGION                  1..329
                        note = Human IgG1 HC constant domain C-terminal K-less
source                  1..329
                        mol_type = protein
                        organism = synthetic construct
SEQUENCE: 19
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 20           moltype = AA   length = 107
FEATURE                 Location/Qualifiers
REGION                  1..107
                        note = Human kappa LC constant domain
source                  1..107
                        mol_type = protein
                        organism = synthetic construct
SEQUENCE: 20
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 21           moltype = AA   length = 122
FEATURE                 Location/Qualifiers
REGION                  1..122
                        note = alpha-FXI-18611p HC-variable region; (Q1) (M105)
source                  1..122
                        mol_type = protein
                        organism = synthetic construct
SEQUENCE: 21
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQGTLVTV   120
SS                                                                  122

SEQ ID NO: 22           moltype = AA   length = 122
FEATURE                 Location/Qualifiers
REGION                  1..122
                        note = alpha-FXI-18611p HC-variable region; (E1) (M105)
source                  1..122
                        mol_type = protein
                        organism = synthetic construct
SEQUENCE: 22
EVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQGTLVTV   120
SS                                                                  122

SEQ ID NO: 23           moltype = AA   length = 122
FEATURE                 Location/Qualifiers
REGION                  1..122
                        note = alpha-FXI -18611 HC-variable region; (Q1) (L105)
source                  1..122
                        mol_type = protein
                        organism = synthetic construct
SEQUENCE: 23
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SS                                                                  122

SEQ ID NO: 24           moltype = AA   length = 122
FEATURE                 Location/Qualifiers
REGION                  1..122
                        note = alpha-FXI -18611 HC-variable region; (E1) (L105)
source                  1..122
                        mol_type = protein
                        organism = synthetic construct
SEQUENCE: 24
EVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SS                                                                  122

SEQ ID NO: 25           moltype = AA   length = 107
FEATURE                 Location/Qualifiers
REGION                  1..107
                        note = alpha-FXI-18611p and alpha-FXI -18611 LC-variable
                          region
source                  1..107
                        mol_type = protein
```

```
                        organism = synthetic construct
SEQUENCE: 25
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FHLLPITFGG GTKVEIK                 107

SEQ ID NO: 26          moltype = AA   length = 214
FEATURE                Location/Qualifiers
REGION                 1..214
                       note = alpha-FXI-18611p and alpha-FXI -18611 kappa LC
source                 1..214
                       mol_type = protein
                       organism = synthetic construct
SEQUENCE: 26
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ FHLLPITFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 27          moltype = AA   length = 645
FEATURE                Location/Qualifiers
REGION                 1..645
                       note = DNA encoding alpha-FXI-18611p and alpha-FXI -18611
                        kappa LC
source                 1..645
                       mol_type = protein
                       organism = synthetic construct
SEQUENCE: 27
GACATCCAGA TGACCCAGAG CCCTAGCAGC CTGAGCGCCA GCGTGGGCGA CAGAGTGACC    60
ATCACCTGTC AAGCCTCCCA GGACATCTCC AACTACCTGA ACTGGTACCA GCAGAAGCCC   120
GGCAAGGCTC CCAAGCTGCT GATCTACGAC GCCTCCAACC TGGAGACCGG CGTGCCTAGC   180
AGATTTAGCG GCAGCGGCTC CGGCACAGAC TTCACCTTCA CCATCAGCTC CCTGCAGCCC   240
GAGGACATTG CCACCTACTA CTGCCAGCAG TTTCACCTGC TGCCTATCAC CTTCGGCGGC   300
GGCACCAAGG TGGAGATCAA AAGGACCGTC GCCGCCCCTA GCGTGTTCAT CTTCCCCCCT   360
AGCGACGAGC AGCTCAAGTC CGGCACCGCC AGCGTGGTGT GTCTGCTCAA CAACTTCTAC   420
CCCAGGGAGG CCAAGGTGCA GTGGAAGGTG GACAACGCCC TGCAGAGCGG CAACAGCCAG   480
GAGAGCGTGA CAGAACAGGA CAGCAAGGAT TCCACATACA GCCTGAGCTC CACCCTGACC   540
CTGAGCAAGG CCGACTACGA GAAGCACAAG GTGTACGCCT GTGAGGTGAC ACACCAGGGC   600
CTCAGCTCCC CCGTGACCAA GAGCTTCAAC AGAGGCGAAT GCTGA                  645

SEQ ID NO: 28          moltype = AA   length = 125
FEATURE                Location/Qualifiers
REGION                 1..125
                       note = alpha-FXI-18623p HC-variable region; (Q1)
source                 1..125
                       mol_type = protein
                       organism = synthetic construct
SEQUENCE: 28
QVQLQESGPG LVKPSQTLSL TCTVSGGSIY SGAYYWSWIR QHPGKGLEWI GSIHYSGLTY    60
YNPSLKSRVT ISVDTSKNQF SLKLSSVTAA DTAVYYCARD VDDSSGDEHY GMDVWGQGTT   120
VTVSS                                                               125

SEQ ID NO: 29          moltype = AA   length = 125
FEATURE                Location/Qualifiers
REGION                 1..125
                       note = alpha-FXI-18623p HC-variable region; (E1)
source                 1..125
                       mol_type = protein
                       organism = synthetic construct
SEQUENCE: 29
EVQLQESGPG LVKPSQTLSL TCTVSGGSIY SGAYYWSWIR QHPGKGLEWI GSIHYSGLTY    60
YNPSLKSRVT ISVDTSKNQF SLKLSSVTAA DTAVYYCARD VDDSSGDEHY GMDVWGQGTT   120
VTVSS                                                               125

SEQ ID NO: 30          moltype = AA   length = 107
FEATURE                Location/Qualifiers
REGION                 1..107
                       note = alpha-FXI-18623p LC-variable region
source                 1..107
                       mol_type = protein
                       organism = synthetic construct
SEQUENCE: 30
DIQMTQSPSS VSASVGDRVT ITCRASQGID SWLAWYQQKP GKAPKLLIYA ASSLQSGVPS    60
RFSGSGSGTD FTLTISSLQP EDFATYYCQQ YHIVPITFGG GTKVEIK                 107

SEQ ID NO: 31          moltype = AA   length = 214
FEATURE                Location/Qualifiers
REGION                 1..214
                       note = alpha-FXI-18623p kappa LC
source                 1..214
```

```
                     mol_type = protein
                     organism = synthetic construct
SEQUENCE: 31
DIQMTQSPSS  VSASVGDRVT  ITCRASQGID  SWLAWYQQKP  GKAPKLLIYA  ASSLQSGVPS   60
RFSGSGSGTD  FTLTISSLQP  EDFATYYCQQ  YHIVPITFGG  GTKVEIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 32         moltype = DNA  length = 645
FEATURE               Location/Qualifiers
misc_difference       1..645
                     note = DNA encoding alpha-FXI-18623p kappa LC
source                1..645
                     mol_type = other DNA
                     organism = synthetic construct
SEQUENCE: 32
gacatccaga tgacccagag ccctagcagc gtgagcgcca gcgtgggcga tagggtgacc   60
atcacctgca gagcctccca gggcatcgac agctggctgg cctggtacca gcagaagccc  120
ggcaaggccc ctaagctgct gatctacgcc gctagcagcc tgcagagcgg cgtgcctagc  180
aggttcagcg gaagcggcag cggcaccgac ttcacactga ccatcagcag cctgcaacct  240
gaggacttcg ccacctacta ctgccagcag tatcacatcg tgcccatcac cttcggcggc  300
ggaaccaagg tggagattaa gaggaccgtg gccgccccca gcgtgtttat cttcccccc   360
agcgatgagc agctgaagag cggaaccgcc agcgtggtgt gcctgctgaa caacttctac  420
cccagagagg ccaaggtgca gtggaaggtg gacaacgccc tgcagtccgg aaacagccag  480
gagagcgtga ccgagcagga ttccaaggat agcacctaca gcctgagcag cacccctgaca  540
ctgagcaagg ccgactacga aagcacaag gtgtacgcct gtgaggtgac ccatcagggc  600
ctgagcagcc ctgtgaccaa gagcttcaac aggggcgagt gctga                 645

SEQ ID NO: 33         moltype = AA  length = 449
FEATURE               Location/Qualifiers
REGION                1..449
                     note = alpha-FXI-18611p IgG4 HC (S228P) (Q1) (M105)
source                1..449
                     mol_type = protein
                     organism = synthetic construct
SEQUENCE: 33
QVQLQESGPG  LVKPSETLSL  TCAVSGYSIS  SGYFWGWIRQ  PPGKGLEWIG  SILHSGVTYY   60
NPSLKSRVTI  SVDTSKNQFS  LKLSSVTAAD  TAVYYCARDR  TTVSMIEYFQ  HWGQGTLVTV  120
SSASTKGPSV  FPLAPCSRST  SESTAALGCL  VKDYFPEPVT  VSWNSGALTS  GVHTFPAVLQ  180
SSGLYSLSSV  VTVPSSSLGT  KTYTCNVDHK  PSNTKVDKRV  ESKYGPPCPP  CPAPEFLGGP  240
SVFLFPPKPK  DTLMISRTPE  VTCVVVDVSQ  EDPEVQFNWY  VDGVEVHNAK  TKPREEQFNS  300
TYRVVSVLTV  LHQDWLNGKE  YKCKVSNKGL  PSSIEKTISK  AKGQPREPQV  YTLPPSQEEM  360
TKNQVSLTCL  VKGFYPSDIA  VEWESNGQPE  NNYKTTPPVL  DSDGSFFLYS  RLTVDKSRWQ  420
EGNVFSCSVM  HEALHNHYTQ  KSLSLSLGK                                    449

SEQ ID NO: 34         moltype = DNA  length = 1350
FEATURE               Location/Qualifiers
misc_difference       1..1350
                     note = DNA encoding alpha-FXI-18611p IgG4 HC (S228P)(Q1)
                     (M105); xxx=CAG or CAA (Q)
misc_difference       1..3
                     note = n is a, c, g, or t
source                1..1350
                     mol_type = other DNA
                     organism = synthetic construct
CDS                   1..3
                     note = nnn= CAG or CAA
SEQUENCE: 34
nnngtccagc tgcaggagag cggccctggc ctggtgaagc ctagcgagac actgtccctg   60
acctgcgccg tgagcggcta cagcatctcc agcggctatt tctggggatg gatcagacag  120
ccccctggca agggcctgga atggatcggt tctatcctgc actccggcgt gacatactat  180
aaccctagcc tgaagagcag ggtgaccatc tccgtggata ccagcaagaa tcagttcagc  240
ctgaagctca gcagcgtgac cgccgccgat accgctgtgt actactgcgc cagagacagg  300
accaccgtct ccatgatcga gtacttccag cactgggcc aaggcacccgtg ggtcaccgtg  360
tcctccgcct ccaccaaggg ccctagcgtg tttcctctgg cccctgctc cagatccaca  420
agcgagagca ccgctgccct gggctgtctg gtcaaggact acttcccga gcccgtgaca  480
gtgtcctgga cagcggcgc cctgacaagc ggcgtccata cattcccgc cgtgctgcag  540
tccagcggac tgtatagcct gagctccgtg gtgaccgtgc cttccagcag cctgggaacc  600
aagacatata cctgcaacgt ggaccataag cccagcaaca caaagtcga caagggggtg  660
gagagcaagt acggaccccc ttgtccccct tgtcctgctc ccgagttcct cggcggacct  720
agcgtgttcc tgtttcctcc caagcccaag gataccctga tgatcagcag gacccctgag  780
gtcacctgcg tggtggtcga cgtgtcccag gaggacctg aggtccagtt taactggtac  840
gtggacgagt ggaggtgca caacgccaag accaagccca gagaggagca gttcaattcc  900
acctacaggg tggtgagcgt gctgaccgtg ctgcaccagg actggctgaa cgggaaggag  960
tacaaatgca aggtctccaa caagggcctc cctagcagca tcgagaagac catctccaag 1020
gccaagggcc agcctaggga gccccaggtg tacaccctgc ctcctagcca ggaggaaatg 1080
accaagaacc aggtgtccct gacatgcctg gtgaagggct ctatcctag cgacatcgcc 1140
gtggagtggg agagcaatgg ccagcccgag aataactaca agaccacccc ccctgtgctc 1200
gatagcgacg gcagcttctt tctgtacagc aggctgaccg tggacaagag caggtggcaa 1260
```

```
gagggcaacg tgtttagctg ctccgtcatg cacgaggccc tgcataacca ctacacccaa   1320
aaatccctgt ccctgtccct gggcaagtga                                    1350
```

| SEQ ID NO: 35 | moltype = AA  length = 449 |
|---|---|
| FEATURE | Location/Qualifiers |
| REGION | 1..449 |
|  | note = alpha-FXI-18611p IgG4 HC (S228P) (E1) (M105) |
| source | 1..449 |
|  | mol_type = protein |
|  | organism = synthetic construct |

SEQUENCE: 35
```
EVQLQESGPG LVKPSETLSL TCAVSGYSIS SGYFWGWIRQ PPGKGLEWIG SILHSGVTYY   60
NPSLKSRVTI SVDTSKNQFS LKLSSVTAAD TAVYYCARDR TTVSMIEYFQ HWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449
```

| SEQ ID NO: 36 | moltype = DNA  length = 1350 |
|---|---|
| FEATURE | Location/Qualifiers |
| misc_difference | 1..1350 |
|  | note = DNA encoding alpha-FXI-18611p IgG4 HC S228P) ;(E1) (M105)xxx=GAA or GAG (E) |
| misc_difference | 1..3 |
|  | note = n is a, c, g, or t |
| source | 1..1350 |
|  | mol_type = other DNA |
|  | organism = synthetic construct |
| CDS | 1..3 |
|  | note = nnn=GAA or GAG |

SEQUENCE: 36
```
nnngtccagc tgcaggagag cggccctggc ctggtgaagc ctagcgagac actgtccctg    60
acctgcgccg tgagcggcta cagcatctcc agcggctatt tctggggatg gatcagacag   120
cccccctggc agggcctgga atggatcggc tctatcctgc actccggcgt gacatactat   180
aaccctagcc tgaagagcag ggtgaccatc tccgtggata ccagcaagaa tcagttcagc   240
ctgaagctca gcagcgtgac cgccgccgat accgctgtgt actactgcgc cagagacagg   300
accaccgtct ccatgatcga gtacttccag cactggggcc aaggcaccct ggtcaccgtg   360
tcctccgcct ccaccaaggg ccctagcgtg tttcctctgg cccccctgct cagatccaca   420
agcgagagca ccgctgccct gggctgtctg gtcaaggact acttcccgga cccgtgaca    480
gtgtcctgga cagcggcgc cctgacaagc ggcgtccata cattcccgc cgtgctgcag     540
tccagcggac tgtatagcct gagctccgtg gtgaccgtgc cttccagcag cctgggaacc   600
aagacatata cctgcaacgt ggaccataag cccagcaaca caaagtcga caagagggtg    660
gagagcaagt acggaccccc ttgtcccctt gtcctgctc ccgagttcct cggcggacct    720
agcgtgttcc tgtttcctcc caagcccaag gatccctga tgatcagcag gaccctgag    780
gtcacctgcg tggtggtcga cgtgtccag gaggacctga ggtccagtt taactggtac     840
gtggacggag tggaggtgca aacgccaag accaagccca gagaggagca gttcaattcc    900
acctacaggg tggtgagcgt cctgaccgtg ctgcaccagg actggctgaa tggaaaggag   960
tacaaatgca aggtctccaa caagggcctc cctagcagca tcgagaagac catctccaag  1020
gccaagggcc agcctaggga gccccagtg tacaccctgc ctcctagcca ggaggaaatg   1080
accaagaacc aggtgtccct gacatgcctg gtgaagggct tctatcctag cgacatcgcc  1140
gtggagtggg agagcaatgg ccagcccgag aataactaca agaccaccc ccctgtgctc    1200
gatagcgacg gcagcttctt tctgtacagc aggctgaccg tggacaagag caggtggcaa   1260
gagggcaacg tgtttagctg ctccgtcatg cacgaggccc tgcataacca ctacacccaa   1320
aaatccctgt ccctgtccct gggcaagtga                                    1350
```

| SEQ ID NO: 37 | moltype = AA  length = 449 |
|---|---|
| FEATURE | Location/Qualifiers |
| REGION | 1..449 |
|  | note = alpha-FXI-18611 IgG4 HC S228P) (Q1) (L105) |
| source | 1..449 |
|  | mol_type = protein |
|  | organism = synthetic construct |

SEQUENCE: 37
```
QVQLQESGPG LVKPSETLSL TCAVSGYSIS SGYFWGWIRQ PPGKGLEWIG SILHSGVTYY   60
NPSLKSRVTI SVDTSKNQFS LKLSSVTAAD TAVYYCARDR TTVSLIEYFQ HWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449
```

| SEQ ID NO: 38 | moltype = DNA  length = 1350 |
|---|---|
| FEATURE | Location/Qualifiers |
| misc_difference | 1..1350 |
|  | note = DNA encoding alpha-FXI-18611 IgG4 HC S228P);(Q1) (L105) xxx=CAG or CAA (Q) |

```
                              -continued misc_difference         1..3
                        note = n is a, c, g, or t
source                  1..1350
                        mol_type = other DNA
                        organism = synthetic construct
CDS                     1..3
                        note = nnn= CAG or CAA
SEQUENCE: 38
nnngtccagc tgcaggagag cggccctgga ctcgtgaagc cctccgaaac cctgagcctc     60
acatgcgccg tctccggata cagcatcagc agcggatact ctgggggctg gatcagacag    120
cccccaggca aaggcctgga gtggatcggt tctattctcc acagcggcgt gacatactac    180
aaccctctcc tgaagagcag ggtgaccatc agcgtggaca cctccaagaa ccagttttcc    240
ctcaagctga gcagcgtgac cgccgctgac acagccgtgt attactgcgc cagggacagg    300
accaccgtgt ccctgattga gtacttccag cattggggcc agggcacact ggtgaccgtc    360
agcagcgcca gcaccaaggg cccttccgtc ttccctctgg cccccttgca gcagaagacc    420
tccgagtcca cagccgccct gggatgcctc gtgaaggatt acttcccga gcccgtcaca     480
gtctcctgga actccggcgc tctgaccagc ggagtgcaca ccttcccgc cgtgctgcaa     540
agcagcggcc tgtacagcct gtccagcgtg gtcaccgtgc cttcctccag cctgggcacc    600
aagacctaca catgcaacgt ggaccacaag ccttccaaca ccaaggtgga caagagagtg    660
gaaagcaagt acggcccccc ctgccccct tgtcctgccc ccgagtttct ggggaggacc     720
tccgtgttcc tctttcctcc caagcctaag gacaccctga tgatctccag gacccccgaa    780
gtgacctgcg tggtcgtgga cgtgtcccag gaggaccctg aggtgcagtt taactggtac    840
gtggacggcg tggaggtgca caacgccaag accaagccca gggaggagca gttcaatagc    900
acctacaggg tggtgtccgt gctgaccgtg ctgcaccagg actggctgaa cggcaaagag    960
tacaagtgca agtcagcaa caagggcctg ccctcctcca tcgagaagac cattagcaag    1020
gccaagggcc agcctaggga gcctcaggtg tacaccctgc cccccagcca ggaggagatg    1080
accaagaacc aggtgtccct gacctgcctg gtcaagggat tttacccag cgacatcgct    1140
gtggaatggg agagcaatgg ccagcccgag aacaactaca agaccacccc tcccgtgctc    1200
gattccgacg gcagcttttt cctgtacagc aggctgaccg tggataagag caggtggcag    1260
gaaggcaacg tgttctcctg ttccgtgatg catgaggccc tgcacaacca ctacacacag    1320
aagagcctgt ccctgtccct gggcaagtga                                    1350

SEQ ID NO: 39          moltype = AA  length = 449
FEATURE                Location/Qualifiers
REGION                 1..449
                       note = alpha-FXI-18611 IgG4 HC (S228P) (E1) (L105)
source                 1..449
                       mol_type = protein
                       organism = synthetic construct
SEQUENCE: 39
EVQLQESGPG LVKPSETLSL TCAVSGYSIS SGYFWGWIRQ PPGKGLEWIG SILHSGVTYY     60
NPSLKSRVTI SVDTSKNQFS LKLSSVTAAD TAVYYCARDR TTVSLIEYFQ HWGQGTLVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGK                                     449

SEQ ID NO: 40          moltype = DNA  length = 1350
FEATURE                Location/Qualifiers
misc_difference        1..1350
                       note = DNA encoding alpha-FXI-18611 IgG4 HC (S228P) (Q1)
                           (L105) xxx=GAAor GAG (E)
misc_difference        1..3
                       note = n is a, c, g, or t
source                 1..1350
                       mol_type = other DNA
                       organism = synthetic construct
CDS                    1..3
                       note = nnn=GAA or GAG
SEQUENCE: 40
nnngtccagc tgcaggagag cggccctgga ctcgtgaagc cctccgaaac cctgagcctc     60
acatgcgccg tctccggata cagcatcagc agcggatact ctgggggctg gatcagacag    120
cccccaggca aaggcctgga gtggatcggt tctattctcc acagcggcgt gacatactac    180
aaccctctcc tgaagagcag ggtgaccatc agcgtggaca cctccaagaa ccagttttcc    240
ctcaagctga gcagcgtgac cgccgctgac acagccgtgt attactgcgc cagggacagg    300
accaccgtgt ccctgattga gtacttccag cattggggcc agggcacact ggtgaccgtc    360
agcagcgcca gcaccaaggg cccttccgtc ttccctctgg cccccttgca gcagaagacc    420
tccgagtcca cagccgccct gggatgcctc gtgaaggatt acttcccga gcccgtcaca     480
gtctcctgga actccggcgc tctgaccagc ggagtgcaca ccttcccgc cgtgctgcaa     540
agcagcggcc tgtacagcct gtccagcgtg gtcaccgtgc cttcctccag cctgggcacc    600
aagacctaca catgcaacgt ggaccacaag ccttccaaca ccaaggtgga caagagagtg    660
gaaagcaagt acggcccccc ctgccccct tgtcctgccc ccgagtttct ggggaggacc     720
tccgtgttcc tctttcctcc caagcctaag gacaccctga tgatctccag gacccccgaa    780
gtgacctgcg tggtcgtgga cgtgtcccag gaggaccctg aggtgcagtt taactggtac    840
gtggacggcg tggaggtgca caacgccaag accaagccca gggaggagca gttcaatagc    900
acctacaggg tggtgtccgt gctgaccgtg ctgcaccagg actggctgaa cggcaaagag    960
tacaagtgca agtcagcaa caagggcctg ccctcctcca tcgagaagac cattagcaag   1020
```

```
gccaagggcc agcctaggga gcctcaggtg tacaccctgc ccccagccaa ggaggagatg 1080
accaagaacc aggtgtccct gacctgcctg gtcaagggat tttacccag cgacatcgct 1140
gtggaatggg agagcaatgg ccagcccgag aacaactaca agaccacccc tcccgtgctc 1200
gattccgacg gcagctttt cctgtacagc aggctgaccg tggataagag caggtggcag 1260
gaaggcaacg tgttctcctg ttccgtgatg catgaggccc tgcacaacca ctacacacag 1320
aagagcctgt ccctgtccct gggcaagtga                                   1350

SEQ ID NO: 41              moltype = AA  length = 452
FEATURE                    Location/Qualifiers
REGION                     1..452
                           note = alpha-FXI-18623p HC-IgG4 (S228P) (Q1)
source                     1..452
                           mol_type = protein
                           organism = synthetic construct
SEQUENCE: 41
QVQLQESGPG LVKPSQTLSL TCTVSGGSIY SGAYYWSWIR QHPGKGLEWI GSIHYSGLTY   60
YNPSLKSRVT ISVDTSKNQF SLKLSSVTAA DTAVYYCARD VDDSSGDEHY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GK                                452

SEQ ID NO: 42              moltype = DNA  length = 1359
FEATURE                    Location/Qualifiers
misc_difference            1..1359
                           note = DNA encoding alpha-FXI-18623 pHC-IgG4 (S228P) (Q1)
                            xxx= CAG orCAA (Q)
misc_difference            1..3
                           note = n is a, c, g, or t
source                     1..1359
                           mol_type = other DNA
                           organism = synthetic construct
CDS                        1..3
                           note = nnn= CAG or CAA
SEQUENCE: 42
nnngtccagc tgcaggaatc cggacccggc ctggtgaagc ctagccagac ccctgagcctg   60
acctgtaccg tgtccggcgg aagcatctat tccggcgcct actactggtc ctggattagg  120
cagcaccccg gcaagggcct ggaatggatc ggctccatcc actacagcgg cctgacctat  180
tacaaccccc ccctgaagtc cagggtgacc atcagcgtcg acacaagcaa gaaccagttc  240
tccctcaagc tgagcagcgt gaccgccgcc gacaccgccg tgtattattg cgccagagac  300
gtggacgact cctccggaga cgagcactac ggcatggacg tctggggcca gggcacaaca  360
gtgacagtga gcagcgccag caccaaagga ccctccgtct tccctctggc ccttgctcc  420
aggagcacaa gcgaaagcac agccgccctg gctgcctgg tgaaggacta cttccccgag  480
cccgtgaccg tgagctggaa tagcggagcc ctcacctccg gagtccacac atttccgcc  540
gtcctgcaga gcagcggcct gtactccctg agctccgtgg tgaccgtgcc ttcctccagc  600
ctgggcacca agacctacac ctgcaacgtg gaccacaagc ctagcaatac caaggtggac  660
aagagggtgg aatccaagta cggccccct tgccctcctt gtcctgcccc cgaatttctg  720
ggcggcccct ccgtgttcct gttccctccc aagcccaagg atacctgat gatcagcagg  780
accctgaccg tgacctgtgt ggtggtggac gtgagccagg aggacccgga ggtgcagttc  840
aactggtacg tggatggcgt ggaagtgcac aatgccaaga caaagccag ggaggagcag  900
ttcaatagca cctacagggt ggtcagcgtg ctcacagtgc tgcaccagga ctggctgaac  960
ggaaaggagt acaagtgcaa agtgtccaac aagggcctgc cctcctccat cgaaaagacc 1020
atctccaagg ccaaaggcca gcccagggag cccaagtgt ataccctccc ccctagccag 1080
gaggaaatga ccaaaaacca ggtctccctg acctgtctgt gaagggctt ctatcccagc 1140
gacatcgctg tggagtggga gagcaacggc caacccgaga caactataa gaccacaccc 1200
cccgtcctgg actccgatgg ctccttcttc ctgtacagca ggctgaccgt cgacaagtcc 1260
aggtggcagg aaggaaacgt gttctcctgt agcgtcatgc acgaggccct gcacaaccac 1320
tatacccaga agtccctgtc cctgagcctg ggcaagtga                         1359

SEQ ID NO: 43              moltype = AA  length = 452
FEATURE                    Location/Qualifiers
REGION                     1..452
                           note = alpha-FXI-18623p HC-IgG4 (S228P) (E1)
source                     1..452
                           mol_type = protein
                           organism = synthetic construct
SEQUENCE: 43
EVQLQESGPG LVKPSQTLSL TCTVSGGSIY SGAYYWSWIR QHPGKGLEWI GSIHYSGLTY   60
YNPSLKSRVT ISVDTSKNQF SLKLSSVTAA DTAVYYCARD VDDSSGDEHY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GK                                452

SEQ ID NO: 44              moltype = DNA  length = 1359
```

```
FEATURE                 Location/Qualifiers
misc_difference         1..1359
                        note = DNA encoding alpha-FXI-18623p HC-IgG4 (S228P) (E1)
                        xxx=GAA or GAG(E)
misc_difference         1..3
                        note = n is a, c, g, or t
source                  1..1359
                        mol_type = other DNA
                        organism = synthetic construct
CDS                     1..3
                        note = nnn=GAA or GAG
SEQUENCE: 44
nnngtccagc tgcaggaatc cggacccggc ctggtgaagc ctagccagac cctgagcctg    60
acctgtaccg tgtccggcgg aagcatctat tccggcgcct actactggtc ctggattagg   120
cagcaccccg gcaagggcct ggaatggatc ggctccatcc actacagcgg cctgacctat   180
tacaacccct ccctgaagtc cagggtgacc atcagcgtcg acacaagcaa gaaccagttc   240
tccctcaagc tgagcagcgt gaccgccgcc gacaccgccg tgtattattg cgccagagac   300
gtggacgact cctccggaga cgagcactac ggcatggacg tctggggcca gggcacaaca   360
gtgacagtga gcagcgccag caccaaagga ccctccgtct tccctctggc ccttgctcc   420
aggagcacaa gcgaaagcac agccgccctg gctgcctggt gaaggacta ctttcccgag   480
cccgtgaccg tgagctggaa tagcggagcc ctcacctccg gagtccacac atttcccgcc   540
gtcctgcaga gcagcggcct gtactccctg agctccgtga cccgtgcc ttcctccagc   600
ctgggcacca agacctacac ctgcaacgtg gaccacaagc ctagcaatac caaggtggac   660
aagagggtgg aatccaagta cggccccct tgccctcctt gtcctgcccc cgaatttctg   720
ggcggcccct ccgtgttcct gttccctccc aagcccaagg ataccctgat gatcagcagg   780
acccctgagg tgacctgtgt ggtggtggac gtgagccagg aggacccga ggtgcagttc   840
aactggtacg tggatggcgt ggaagtgcac aatgccaaga caaagccag ggaggagcag   900
ttcaatagca cctacagggt ggtcagcgtg ctcacagtgc tgcaccagga ctggctgaac   960
ggaaaggagt acaagtgcaa agtgtccaac aagggcctgc cctcctccat cgaaaagacc  1020
atctccaagg ccaaagggca gcccagggag cccaagtgt atccctccc ccctagccag  1080
gaggaaatga ccaaaaacca ggtctccctg acctgtctgt gaagggctt ctatcccagc  1140
gacatcgctg tggagtggga gagcaacggc caacccgaga caactataa gccacaccc  1200
cccgtcctgg actccgatgg ctccttcttc ctgtacagca ggctgaccgt cgacaagtcc  1260
aggtggcagg aaggaaacgt gttctcctgt agcgtcatgc acgaggccct gcacaaccac  1320
tatacccaga agtccctgtc cctgagcctg ggcaagtga                         1359

SEQ ID NO: 45           moltype = AA  length = 452
FEATURE                 Location/Qualifiers
REGION                  1..452
                        note = alpha-FXI-18611p HC IgG1 (Q1) (M105)
source                  1..452
                        mol_type = protein
                        organism = synthetic construct
SEQUENCE: 45
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 46           moltype = DNA  length = 1359
FEATURE                 Location/Qualifiers
misc_difference         1..1359
                        note = DNA encoding alpha-FXI-18611p HC IgG1 (Q1)
                        (M105)xxx= CAG orCAA (Q)
misc_difference         1..3
                        note = n is a, c, g, or t
source                  1..1359
                        mol_type = other DNA
                        organism = synthetic construct
CDS                     1..3
                        note = nnn= CAG or CAA
SEQUENCE: 46
nnngtccagc tgcaggagag cggccctggc ctggtgaagc ctagcgagac actgtccctg    60
acctgcgccg tgagcggcta cagcatctcc agcggctatt tctggggatg gatcagacag   120
cccctggca agggcctgga atggatcggt tctatcctga gccggctg gacatactat   180
aaccctagcc tgaagagcag ggtgaccatc tccgtggata ccagcaagaa tcagttcagc   240
ctgaagctca gcagcgtgac cgccgccgat accgctgtgt actactgcgc cagagacagg   300
accaccgtct ccatgatcga gtacttccag cactggggcc aaggcaccct ggtcaccgtg   360
tcctccgcta gcacaaaagg accaagcgtg tttccactgg cacctagcag caaatccacc   420
agcggcacag ccgcactggg ctgtctggtg aaggatt acttccctga gccagtcaca   480
gtgtcctgga actccggagc cctgacatcc ggcgtgcaca ccttcccgc tgtgctgcaa   540
tccagcggac tgtatagcct cagctccgtc gtgacagtcc cttccagcag cctgggcaca   600
cagacttaca tttgcaacgt gaaccacaaa ccttccaaca ctaaggtgga caaaaaggtg   660
gaacccaaat cctgtgataa gacccataca tgcccacctt gtcccgctcc tgagctgctg   720
gggggacctt ccgtctttct gtttcctcca aaaccaaaag acacactcat gatcagcgg   780
```

```
acccccgaag tcacctgtgt ggtggtggac gtcagccacg aagatccaga ggtcaagttc  840
aattggtacg tggatggagt ggaagtccac aacgcaaaaa ccaaacctag agaagaacag  900
tacaatagca catacagggt ggtgtccgtc ctgacagtgc tccaccagga ctggctcaat  960
ggcaaagagt ataagtgcaa ggtgagcaac aaggccctgc ctgcaccaat tgagaaaaca 1020
attagcaagg caaaggggca gccacgggaa ccccaggtgt atacccctgc cccaagccgg 1080
gatgaactga ccaaaaacca ggtcagcctg acatgcctgg tgaaagggtt ttacccaagc 1140
gatattgccg tcgagtggga gagcaacgga cagccagaaa acaattacaa aaccacccca 1200
cctgtgctgg actccgatgg gagctttttc ctgtacagca agctcacagt ggacaagtcc 1260
agatggcaac agggcaacgt gttttcctgc tccgtgatgc acgaggccct ccacaaccac 1320
tatacacaaa agtccctctc cctcagccca ggaaagtga                        1359

SEQ ID NO: 47            moltype = AA  length = 452
FEATURE                  Location/Qualifiers
REGION                   1..452
                         note = alpha-FXI-18611p HC IgG1 (E1) (M105)
source                   1..452
                         mol_type = protein
                         organism = synthetic construct
SEQUENCE: 47
EVQLQESGPG LVKPSETLSL TCAVSGYSIS SGYFWGWIRQ PPGKGLEWIG SILHSGVTYY  60
NPSLKSRVTI SVDTSKNQFS LKLSSVTAAD TAVYYCARDR TTVSMIEYFQ HWGQGTLVTV 120
SSASTKGPSV FPLAPSSKST SGGTAALGCL VKDYFPEPVT VSWNSGALTS GVHTFPAVLQ 180
SSGLYSLSSV VTVPSSSLGT QTYICNVNHK PSNTKVDKKV EPKSCDKTHT CPPCPAPELL 240
GGPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GK                               452

SEQ ID NO: 48            moltype = DNA  length = 1359
FEATURE                  Location/Qualifiers
misc_difference          1..1359
                         note = DNA encoding alpha-FXI-18611p HC IgG1 (Q1) (M105)
                          xxx=GAA or GAG(E)
misc_difference          1..3
                         note = n is a, c, g, or t
source                   1..1359
                         mol_type = other DNA
                         organism = synthetic construct
CDS                      1..3
                         note = nnn=GAA or GAG
SEQUENCE: 48
nnngtccagc tgcaggagag cggccctggc ctggtgaagc ctagcgagac actgtccctg   60
acctgcgccg tgagcggcta cagcatctcc agcggctatt tctggggctg gatcagacag  120
cccccctggca agggcctgga atggatcggt tctatcctgc actccggcgt gacatactat  180
aaccctagcc tgaagagcag ggtgaccatc tccgtggata ccagcaagaa tcagttcagc  240
ctgaagctca gcagcgtgac cgccgccgat accgctgtgt actactgcgc cagagacagg  300
accaccgtct ccatgatcga gtacttccag cactggggcc aaggcaccct ggtcaccgtg  360
tcctccgcta gcacaaaagg accaagcgtg tttccactgg cacctagcag caaatccacc  420
agcggcggaa cagcagccct cggggccctg tgaaggatt acttccctga gccagtcaca  480
gtgtcctgga actccggagc cctgacatcc ggcgtgcaca ccttccccgc tgtgctgcaa  540
tccagcggac tgtatagcct cagctccgtc gtgacagtgc cttccagcag cctgggcaca  600
cagactta cattgcaacgt gaaccacaaa ccttccaaca ctaaggtgga caaaaaggtg  660
gaacccaaat cctgtgataa gacccataca tgcccacctt gtcccgctcc tgagctgctg  720
ggggggacct tccgtctttct gtttcctcca aaaccaaaag acacactcat gatcagccgg  780
acccccgaag tcacctgtgt ggtggtggac gtcagccacg aagatccaga ggtcaagttc  840
aattggtacg tggatggagt ggaagtccac aacgcaaaaa ccaaacctag agaagaacag  900
tacaatagca catacagggt ggtgtccgtc ctgacagtgc tccaccagga ctggctcaat  960
ggcaaagagt ataagtgcaa ggtgagcaac aaggccctgc ctgcaccaat tgagaaaaca 1020
attagcaagg caaaggggca gccacgggaa ccccaggtgt atacccctgc cccaagccgg 1080
gatgaactga ccaaaaacca ggtcagcctg acatgcctgg tgaaagggtt ttacccaagc 1140
gatattgccg tcgagtggga gagcaacgga cagccagaaa acaattacaa aaccacccca 1200
cctgtgctgg actccgatgg gagctttttc ctgtacagca agctcacagt ggacaagtcc 1260
agatggcaac agggcaacgt gttttcctgc tccgtgatgc acgaggccct ccacaaccac 1320
tatacacaaa agtccctctc cctcagccca ggaaagtga                        1359

SEQ ID NO: 49            moltype = AA  length = 452
FEATURE                  Location/Qualifiers
REGION                   1..452
                         note = alpha-FXI-18611 HC IgG1 (Q1)(L105)
source                   1..452
                         mol_type = protein
                         organism = synthetic construct
SEQUENCE: 49
QVQLQESGPG LVKPSETLSL TCAVSGYSIS SGYFWGWIRQ PPGKGLEWIG SILHSGVTYY  60
NPSLKSRVTI SVDTSKNQFS LKLSSVTAAD TAVYYCARDR TTVSLIEYFQ HWGQGTLVTV 120
SSASTKGPSV FPLAPSSKST SGGTAALGCL VKDYFPEPVT VSWNSGALTS GVHTFPAVLQ 180
SSGLYSLSSV VTVPSSSLGT QTYICNVNHK PSNTKVDKKV EPKSCDKTHT CPPCPAPELL 240
GGPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
```

DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GK 452

SEQ ID NO: 50          moltype = DNA  length = 1359
FEATURE                Location/Qualifiers
misc_difference        1..1359
                       note = DNA encoding alpha-FXI-18611 HC IgG1 (Q1)(L105)xxx=
                       CAG or CAA(Q)
misc_difference        1..3
                       note = n is a, c, g, or t
source                 1..1359
                       mol_type = other DNA
                       organism = synthetic construct
CDS                    1..3
                       note = nnn= CAG or CAA
SEQUENCE: 50
nnngtccagc tgcaggagag cggccctgga ctcgtgaagc cctccgaaac cctgagcctc  60
acatgcgccg tctccggata cagcatcagc agcggatact ctgggggctg gatcagacag  120
ccccccggca aaggcctgga gtggatcggt tctattctcc acagcggcgt gacatactac  180
aacccctccc tgaagagcag ggtgaccatc agcgtggaca cctccaagaa ccagttttcc  240
ctcaagctga gcagcgtgac cgccgctgac acagccgtgt attactgcgc cagggacagg  300
accaccgtgt ccctgattga gtacttccag cattggggcc agggcacact ggtgaccgtc  360
agcagcgcta gcacaaaagg accaagcgtg tttccactgg cacctagcag caaatccacc  420
agcggcggaa cagcagccct cggtgcctg tgaaggatt acttccctga ccagtcaca  480
gtgtcctgga actccggagc cctgacatcc ggcgtgcaca cctccccgc tgtgctgcaa  540
tccagcggac tgtatagcct cagctccgtc gtgacagtcc cttccagcag cctgggcaca  600
cagacttaca tttgcaacgt gaaccacaaa ccttccaaca ctaaggtgga caaaaaggtg  660
gaacccaaat cctgtgataa gacccataca tgcccacctt gtcccgctcc tgagctgctg  720
gggggaccct ccgtctttct gtttcctcca aaaccaaaag acacactcat gatcagccgg  780
acccccgaag tcacctgtgt ggtggtggac gtcagccacg aagatccaga ggtcaagttc  840
aattggtacg tggatggtgt ggaagtccac aacgcaaaa ccaaacctag agaagaacag  900
tacaatagca catacagggt ggtgtccgtc ctgacagtgc tccaccagga ctggctcaat  960
ggcaaagagt ataagtgcaa ggtgagcaac aaggccctgc ctgcaccaat tgagaaaaca  1020
attagcaagg caaaggggca gccacgggaa ccccaggtgt atacccctcc cccaagcagg  1080
gatgaactga ccaaaaacca ggtcagcctg acatgcctgg tgaaagggtt ttacccaagc  1140
gatattgccg tcgagtggga gagcaacgga cagccagaaa acaattacaa accacccca  1200
cctgtgctgg actccgatgg gagcttttc ctgtacagca agctcacagt ggacaagtcc  1260
agatggcaac agggcaacgt gttttcctgc tccgtgatgc acgaggccct ccacaaccac  1320
tatacacaaa agtccctctc cctcagccca ggaaagtga                         1359

SEQ ID NO: 51          moltype = AA  length = 452
FEATURE                Location/Qualifiers
REGION                 1..452
                       note = alpha-FXI-18611 HC IgG1 (E1)(L105)
source                 1..452
                       mol_type = protein
                       organism = synthetic construct
SEQUENCE: 51
EVQLQESGPG LVKPSETLSL TCAVSGYSIS SGYFWGWIRQ PPGKGLEWIG SILHSGVTYY  60
NPSLKSRVTI SVDTSKNQFS LKLSSVTAAD TAVYYCARDR TTVSLIEYFQ HWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK 452

SEQ ID NO: 52          moltype = DNA  length = 1359
FEATURE                Location/Qualifiers
misc_difference        1..1359
                       note = DNA encoding alpha-FXI-18611 HC IgG1
                       (E1)(L105)xxx=GAA or GAG(E)
misc_difference        1..3
                       note = n is a, c, g, or t
source                 1..1359
                       mol_type = other DNA
                       organism = synthetic construct
CDS                    1..3
                       note = nnn=GAA or GAG
SEQUENCE: 52
nnngtccagc tgcaggagag cggccctgga ctcgtgaagc cctccgaaac cctgagcctc  60
acatgcgccg tctccggata cagcatcagc agcggatact ctgggggctg gatcagacag  120
ccccccggca aaggcctgga gtggatcggt tctattctcc acagcggcgt gacatactac  180
aacccctccc tgaagagcag ggtgaccatc agcgtggaca cctccaagaa ccagttttcc  240
ctcaagctga gcagcgtgac cgccgctgac acagccgtgt attactgcgc cagggacagg  300
accaccgtgt ccctgattga gtacttccag cattggggcc agggcacact ggtgaccgtc  360
agcagcgcta gcacaaaagg accaagcgtg tttccactgg cacctagcag caaatccacc  420
agcggcggaa cagcagccct cggtgcctg tgaaggatt acttccctga ccagtcaca  480
gtgtcctgga actccggagc cctgacatcc ggcgtgcaca cctccccgc tgtgctgcaa  540

-continued

```
tccagcggac tgtatagcct cagctccgtc gtgacagtcc cttccagcag cctgggcaca    600
cagacttaca tttgcaacgt gaaccacaaa ccttccaaca ctaaggtgga caaaaaggtg    660
gaacccaaat cctgtgataa gacccataca tgcccaccct gtcccgctcc tgagctgctg    720
gggggacctt ccgtctttct gtttcctcca aaaccaaaag acacactcat gatcagccgg    780
accccgaag  tcacctgtgt ggtggtggac gtcagccacg aagatccaga ggtcaagttc    840
aattggtacg tggatggagt ggaagtccca aacgcaaaaa ccaaacctag agaagaacag    900
tacaatagca catacagggt ggtgtccgtc ctgacagtgc tccaccagga ctggctcaat    960
ggcaaagagt ataagtgcaa ggtgagcaac aaggccctgc ctgcaccaat gagaaaaca   1020
attagcaagg caaaggggca gccacgggaa ccccaggtgt atccctgcc  cccaagccgg   1080
gatgaactgc ccaaaaacca ggtcagcctg acatgcctgg tgaaagggt  ttacccaagc   1140
gatattgccg tcgagtggga gagcaacgga cagccagaaa acaattacaa aaccaccca   1200
cctgtgctgg actccgatgg gagcttttc  ctgtacagca agctcacagt ggacaagtcc   1260
agatggcaac agggcaacgt gttttcctgc tccgtgatgc acgaggccct ccacaaccac   1320
tatacacaaa agtccctctc cctcagccca ggaaagtga                          1359

SEQ ID NO: 53         moltype = AA  length = 455
FEATURE               Location/Qualifiers
REGION                1..455
                      note = alpha-FXI-18623p HC IgG1 (1Q)
source                1..455
                      mol_type = protein
                      organism = synthetic construct
SEQUENCE: 53
QVQLQESGPG LVKPSQTLSL TCTVSGGSIY SGAYYWSWIR QHPGKGLEWI GSIHYSGLTY    60
YNPSLKSRVT ISVDTSKNQF SLKLSSVTAA DTAVYYCARD VDDSSGDEHY GMDVWGQGTT   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 54         moltype = DNA  length = 1368
FEATURE               Location/Qualifiers
misc_difference       1..1368
                      note = DNA encoding alpha-FXI-18623p HC IgG1 (1Q) xxx= CAG
                       or CAA (Q)
misc_difference       1..3
                      note = n is a, c, g, or t
source                1..1368
                      mol_type = other DNA
                      organism = synthetic construct
CDS                   1..3
                      note = nnn= CAG or CAA
SEQUENCE: 54
nnngtccagc tgcaggaatc cggacccggc ctggtgaagc ctagccagac cctgagcctg    60
acctgtaccg tgtccggcgg aagcatctat tccggctact actactggtc ctggattagg   120
cagcacccgg gcaagggcct ggaatggatc ggctccatcc actacagcgg cctgacctat   180
tacaacccct ccctgaagtc cagggtgacc atcagcgtcg acacaagcaa gaaccagttc   240
tccctcaagc tgagcagcgt gaccgccgcc gacaccgccg tgtattattg cgccagagac   300
gtggacgata cctccggaga cgagcactac ggcatggacg tctggggcca gggcacaaca   360
gtgacagtga gcagcgctag cacaaaagga ccaagcgtgt tccactggcc acctagcagc   420
aaatccacca gcggcggaac agcagccctc ggtgcctggt gaaggatta  cttccctgag   480
ccagtcacag tgtcctggaa ctccggagcc ctgacatccg gcgtgcacac cttccccgct   540
gtgctgcaat ccagcggact gtatagcctc agctccgtcg tgacagtccc ttccagcagc   600
ctgggcacac agacttacat ttgcaacgtg aaccacaaac cttccaacac taaggtggac   660
aaaaaggtgg aacccaaatc ctgtgataag acccatacat gcccacctt  tcccgctcct   720
gagctgctgg gggaccttc  cgtctttctg tttcctccaa aaccaaaaga cacactcatg   780
atcagccgga ccccgaagt  cacctgtgtg gtggtggacg tcagccacga agatccagag   840
gtcaagttca attggtacgt ggatggagtg gaagtccca  aacgcaaaaa ccaaacctaga    900
gaagaacagt acaatagcac atacagggtg gtgtccgtcc tgacagtgct ccaccaggac   960
tggctcaatg gcaaagagta taagtgcaag gtgagcaaca aggccctgcc tgcaccaatt  1020
gagaaaaaca ttagcaaggc aaaggggcag ccacgggaac cccaggtgta tccctgccc   1080
ccaagccggg atgaactgac caaaaaccag gtcagcctga catgcctggt gaaagggttc  1140
tacccaagcg atattgccgt cgagtgggag agcaacggac agccagaaaa caattacaaa  1200
accaccccac ctgtgctgga ctccgatggg agcttttcc  tgtacagcaa gctcacagtg  1260
gacaagtcca gatggcaaca gggcaacgtg ttttcctgct ccgtgatgca cgaggcctc  1320
cacaaccact atacacaaaa gtccctctcc ctcagcccag gaaagtga              1368

SEQ ID NO: 55         moltype = AA  length = 455
FEATURE               Location/Qualifiers
REGION                1..455
                      note = alpha-FXI-18623p HC IgG1 (1E)
source                1..455
                      mol_type = protein
                      organism = synthetic construct
SEQUENCE: 55
EVQLQESGPG LVKPSQTLSL TCTVSGGSIY SGAYYWSWIR QHPGKGLEWI GSIHYSGLTY    60
YNPSLKSRVT ISVDTSKNQF SLKLSSVTAA DTAVYYCARD VDDSSGDEHY GMDVWGQGTT   120
```

```
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                             455

SEQ ID NO: 56           moltype = DNA   length = 1368
FEATURE                 Location/Qualifiers
misc_difference         1..1368
                        note = DNA encoding alpha-FXI-18623p HC IgG1 (1E) xxx=GAA
                        or GAG (E)
misc_difference         1..3
                        note = n is a, c, g, or t
source                  1..1368
                        mol_type = other DNA
                        organism = synthetic construct
CDS                     1..3
                        note = nnn=GAA or GAG
SEQUENCE: 56
nnngtccagc tgcaggaatc cggacccggc ctggtgaagc ctagccagac cctgagcctg    60
acctgtaccg tgtccggcgg aagcatctat tccggcgtct actactggtc ctggattagg   120
cagcaccccg gcaagggcct ggaatggatc ggctccatcc actacagcgg cctgacctat   180
tacaacccct ccctgaagtc cagggtgacc atcagcgtcg acacaagcaa gaaccagttc   240
tccctcaagc tgagcagcgt gaccgccgcc gacaccgccg tgtattattg cgccagagac   300
gtggacgact cctccggaga cgagcactac ggcatgggcc tctggggcca gggcacaaca   360
gtgacagtga gcagcgctag cacaaaagga ccaagcgtgt tccactggcc acctagcagc   420
aaatccacca gcggcggaac agcagccctc gggtgcctgg tgaaggatta cttccctgag   480
ccagtcacag tgtcctggaa ctccggagcc ctgacatccg gcgtgcacac cttccccgct   540
gtgctgcaat ccagcggact gtatagcctc agctccgtcg tgacagtgcc ttccagcagc   600
ctgggcacac agacttacat ttgcaacgtg aaccacaaac cttccaacac taaggtggac   660
aaaaaggtgg aacccaaatc ctgtgataag acccatacat gcccaccttg tccggctcct   720
gagctgctgg gggaccttc cgtctttctg tttcctccaa aaccaaaaga cactctcatg   780
atcagccgga ccccccaagt cacctgtgtg gtggtggacg tcagccacga agatccagag   840
gtcaagttca attggtacgt ggatggagtg gaagtccaca acgcaaaaac caaacctaga   900
gaagaacagt acaatagcac atacagggtg gtgtccgtcc tgacagtgct ccaccaggac   960
tggctcaatg gcaaagagta taagtgcaag gtgagcaaca aggccctgcc tgcaccaatt  1020
gagaaaacaa ttagcaaggc aaaggggcag ccacgggaac cccaggtgta cacctgcccc  1080
ccaagccggg atgaactgac caaaaaccag gtcagcctga tgcctggt gaaagggttt    1140
tacccaagcg atattgccgt cgagtgggag agcaacggac agccagaaaa caattacaaa  1200
accaccccac ctgtgctgga ctccgatggg agctttttcc tgtacagcaa gctcacagtg  1260
gacaagtcca gatggcaaca gggcaacgtg ttttcctgct ccgtgatgca cgaggccctc  1320
cacaaccact atacacaaaa gtccctctcc ctcagcccag gaaagtga               1368

SEQ ID NO: 57           moltype = AA   length = 448
FEATURE                 Location/Qualifiers
REGION                  1..448
                        note = alpha-FXI-18611p IgG4 HC (S228P) (Q1) (M105)
                        (C-terminal K-less)
source                  1..448
                        mol_type = protein
                        organism = synthetic construct
SEQUENCE: 57
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQTLVTV   120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                     448

SEQ ID NO: 58           moltype = DNA   length = 1344
FEATURE                 Location/Qualifiers
misc_difference         1..1344
                        note = DNA encoding alpha-FXI-18611p IgG4 HC (S228P) (Q1)
                        (M105); xxx=CAG or CAA (Q) (C-terminal K-less)
misc_difference         1..3
                        note = n is a, c, g, or t
source                  1..1344
                        mol_type = other DNA
                        organism = synthetic construct
CDS                     1..3
                        note = nnn= CAG or CAA
SEQUENCE: 58
nnngtccagc tgcaggagag cggccctggc ctggtgaagc ctagcgagac actgtccctg    60
acctgcgccg tgagcggcta cagcatctcc agcggctatt tctggggatg gatcagacag   120
ccccctggca aagggcctga atggatcggt tctatcctgc actccggcgt gacatactat   180
aaccctagcc tgaagagcag ggtgaccatc tccgtggata ccagcaagaa tcagttcagc   240
```

```
ctgaagctca gcagcgtgac cgccgccgat accgctgtgt actactgcgc cagagacagg    300
accaccgtct ccatgatcga gtacttccag cactggggcc aaggcaccct ggtcaccgtg    360
tcctccgcct ccaccaaggg ccctagcgtg tttcctctgg cccccgctc cagatccaca    420
agcgagagca ccgctgccct gggctgtctg gtcaaggact acttccccga gcccgtgaca    480
gtgtcctgga acagcggcgc cctgacaagc ggcgtccata cattccccgc cgtgctgcag    540
tccagcggac tgtatagcct gagctccgtg gtgaccgtgc cttccagcag cctgggaacc    600
aagacatata cctgcaacgt ggaccataag cccagcaaca caaaagtcga caagagggtg    660
gagagcaagt acggaccccc ttgtcccct tgtcctgctc ccgagttcct cggcggacct    720
agcgtgttcc tgtttcctcc caagcccaag gatccctga tgatcagcag gacccctgga    780
gtcacctgcg tggtggtcga cgtgtcccag gaggaccctg aggtccagtt taactggtac    840
gtggacggag tggaggtgca caacgccaag accaagccca gagaggagca gttcaattcc    900
acctacaggg tggtgagcgt cctgaccgtg ctgcaccagg actggctgaa tggaaaggag    960
tacaaatgca aggtctccaa caagggcctc cctagcagca tcgagaagac catctccaag   1020
gccaagggcc agcctaggga gccccaggtg tacaccctgc ctcctagcca ggaggaaatg   1080
accaagaacc aggtgtccct gacatgcctg gtgaagggct ctatcctag cgacatcgcc   1140
gtggagtggg agagcaatgg ccagcccgag aataactaca agaccacccc ccctgtgctc   1200
gatagcgacg gcagcttctt tctgtacagc aggctgaccg tggacaagag caggtggcaa   1260
gagggcaacg tgtttagctg ctccgtcatg cacgaggccc tgcataacca ctacacccaa   1320
aaatccctgt ccctgtccct gggc                                          1344

SEQ ID NO: 59           moltype = AA  length = 448
FEATURE                 Location/Qualifiers
REGION                  1..448
                        note = alpha-FXI-18611p IgG4 HC (S228P) (E1) (M105)
                        (C-terminal K-less)
source                  1..448
                        mol_type = protein
                        organism = synthetic construct
SEQUENCE: 59
EVQLQESGPG LVKPSETLSL TCAVSGYSIS SGYFWGWIRQ PPGKGLEWIG SILHSGVTYY     60
NPSLKSRVTI SVDTSKNQFS LKLSSVTAAD TAVYYCARDR TTVSMIEYFQ HWGQGTLVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                      448

SEQ ID NO: 60           moltype = DNA  length = 1344
FEATURE                 Location/Qualifiers
misc_difference         1..1344
                        note = DNA encoding alpha-FXI-18611p IgG4 HC S228P) ;(E1)
                        (M105)xxx=GAA or GAG (E) (C-terminal K-less)
misc_difference         1..3
                        note = n is a, c, g, or t
source                  1..1344
                        mol_type = other DNA
                        organism = synthetic construct
CDS                     1..3
                        note = nnn=GAA or GAG
SEQUENCE: 60
nnngtccagc tgcaggagag cggccctggc ctggtgaagc ctagcgagac actgtccctg     60
acctgcgccg tgagcggcta cagcatctcc agcggctatt tctggggatg gatcagacag    120
ccccctggca agggcctgga atggatcggt tctatcctgc actccggcgt gacatactat    180
aaccctagcc tgaagagcag ggtgaccatc tccgtggaca ccagcaagaa tcagttcagc    240
ctgaagctca gcagcgtgac cgccgccgat accgctgtgt actactgcgc cagagacagg    300
accaccgtct ccatgatcga gtacttccag cactggggcc aaggcaccct ggtcaccgtg    360
tcctccgcct ccaccaaggg ccctagcgtg tttcctctgg cccccgctc cagatccaca    420
agcgagagca ccgctgccct gggctgtctg gtcaaggact acttccccga gcccgtgaca    480
gtgtcctgga acagcggcgc cctgacaagc ggcgtccata cattccccgc cgtgctgcag    540
tccagcggac tgtatagcct gagctccgtg gtgaccgtgc cttccagcag cctgggaacc    600
aagacatata cctgcaacgt ggaccataag cccagcaaca caaaagtcga caagagggtg    660
gagagcaagt acggaccccc ttgtcccct tgtcctgctc ccgagttcct cggcggacct    720
agcgtgttcc tgtttcctcc caagcccaag gatccctga tgatcagcag gacccctgga    780
gtcacctgcg tggtggtcga cgtgtcccag gaggaccctg aggtccagtt taactggtac    840
gtggacggag tggaggtgca caacgccaag accaagccca gagaggagca gttcaattcc    900
acctacaggg tggtgagcgt cctgaccgtg ctgcaccagg actggctgaa tggaaaggag    960
tacaaatgca aggtctccaa caagggcctc cctagcagca tcgagaagac catctccaag   1020
gccaagggcc agcctaggga gccccaggtg tacaccctgc ctcctagcca ggaggaaatg   1080
accaagaacc aggtgtccct gacatgcctg gtgaagggct ctatcctag cgacatcgcc   1140
gtggagtggg agagcaatgg ccagcccgag aataactaca agaccacccc ccctgtgctc   1200
gatagcgacg gcagcttctt tctgtacagc aggctgaccg tggacaagag caggtggcaa   1260
gagggcaacg tgtttagctg ctccgtcatg cacgaggccc tgcataacca ctacacccaa   1320
aaatccctgt ccctgtccct gggc                                          1344

SEQ ID NO: 61           moltype = AA  length = 448
FEATURE                 Location/Qualifiers
REGION                  1..448
                        note = alpha-FXI-18611 IgG4 HC S228P) (Q1) (L105)
```

```
                            (C-terminal K-less)
source                      1..448
                            mol_type = protein
                            organism = synthetic construct
SEQUENCE: 61
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                     448

SEQ ID NO: 62               moltype = DNA   length = 1344
FEATURE                     Location/Qualifiers
misc_difference             1..1344
                            note = DNA encoding alpha-FXI-18611 IgG4 HC S228P);(Q1)
                            (L105) xxx=CAG or CAA (Q) (C-terminal K-less)
misc_difference             1..3
                            note = n is a, c, g, or t
source                      1..1344
                            mol_type = other DNA
                            organism = synthetic construct
CDS                         1..3
                            note = nnn= CAG or CAA
SEQUENCE: 62
nnngtccagc tgcaggagag cggccctgga ctcgtgaagc cctccgaaac cctgagcctc     60
acatgcgccg tctccggata cagcatcagc agcggatact tctggggctg gatcagacag    120
cccccgggca aaggcctgga gtggatcggt tctattctcc acagcggtgc gacatactac    180
aaccccctcc tgaagagcag ggtgaccatc agcgtggaca cctccaagaa ccagtttttcc   240
ctcaagctga gcagcgtgac cgccgctgac acagccgtgt attactgcgc cagggacagg    300
accaccgtgt ccctgattga gtacttccag cattggggcc agggcacact ggtgaccgtc    360
agcagcgcca gcaccaaggg cccttccgtc ttccctctgg ccccttgcag cagaagcacc    420
tccgagtcca cagccgccct gggatgcctc gtgaaggatt acttcccga gcccgtcaca    480
gtctcctgga actccggcgc tctgaccagc ggagtgcaca cctttcccgc cgtgctgcaa    540
agcagcggcc tgtacagcct gtccagcgtg gtcaccgtgc cttcctccag cctgggcacc    600
aagacctaca tgcaacgtg gaccacaag ccttccaaca ccaaggtgga caagagagtg     660
gaaagcaagt acggcccccc ctgccccccct tgtcctgccc ccgagtttct ggggggaccc   720
tccgtgttcc tcttttcctcc caagcctaag gacaccctga tgatctccag gacccccgaa   780
gtgacctgcg tggtcgtgga cgtgtcccag gaggaccctg aggtgcagtt taactggtac    840
gtggacggcg tggaggtgca caacgccaag accaagccca gggaggagca gttcaatagc   900
acctacaggg tggtgtccgt gctgaccgtg ctgcaccagg actggctgaa cggcaaagag   960
tacaagtgca agtcagcaa caagggcctg ccctcctcca tcgagaagac cattagcaag  1020
gccaagggcc agcctaggga gcctcaggtg tacaccctgc ccccagcca ggaggagatg  1080
accaagaacc aggtgtccct gacctgcctg gtcaaggat tttaccccag cgacatcgct  1140
gtggaatggg agagcaatgg ccagcccgag aacaactaca agaccacccc tcccgtgctc  1200
gattccgacg gcagcttttt cctgtacagc aggctgaccg tggataagag caggtggcag  1260
gaaggcaacg tgttctcctg ttccgtgatg catgaggccc tgcacaacca ctacacacag  1320
aagagcctgt ccctgtccct gggc                                        1344

SEQ ID NO: 63               moltype = AA   length = 448
FEATURE                     Location/Qualifiers
REGION                      1..448
                            note = alpha-FXI-18611 IgG4 HC (S228P) (E1) (L105)
                            (C-terminal K-less)
source                      1..448
                            mol_type = protein
                            organism = synthetic construct
SEQUENCE: 63
EVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                     448

SEQ ID NO: 64               moltype = DNA   length = 1344
FEATURE                     Location/Qualifiers
misc_difference             1..1344
                            note = DNA encoding alpha-FXI-18611 IgG4 HC (S228P) (Q1)
                            (L105) xxx=GAAor GAG (E) (C-terminal K-less)
misc_difference             1..3
                            note = n is a, c, g, or t
source                      1..1344
                            mol_type = other DNA
                            organism = synthetic construct
```

| | | |
|---|---|---|
| CDS | 1..3 | |
| | note = nnn=GAA or GAG | |

SEQUENCE: 64
```
nnngtccagc tgcaggagag cggccctgga ctcgtgaagc cctccgaaac cctgagcctc   60
acatgcgccg tctccggata cagcatcagc agcggatact tctggggctg gatcagacag  120
cccccccggca aaggcctgga gtggatcggt tctattctcc acagcggcgt gacatactac  180
aacccctccc tgaagagcag ggtgaccatc agcgtggaca cctccaagaa ccagttttcc  240
ctcaagctga gcagcgtgac cgccgctgac acagccgtgt attactgcgc cagggacagg  300
accaccgtgt ccctgattga gtacttccag cattggggcc agggcacact ggtgaccgtc  360
agcagcgcca gcaccaaggg cccttccgtc ttccctctgg cccttgcag cagaagcacc  420
tccgagtcca cagccgccct gggatgcctc gtgaaggatt acttcccga gcccgtcaca  480
gtctcctgga actccggcgc tctgaccagc ggagtgcaca ccttcccgc cgtgctgcaa  540
agcagcggcc tgtacagcct gtccagcgtg gtcaccgtgc cttcctccag cctgggcacc  600
aagacctaca catgcaacgt ggaccacaag ccttccaaca ccaaggtgac caagagagtg  660
gaaagcaagt acggcccccc ctgcccccct tgtcctgccc ccgagtttct gggaggaccc  720
tccgtgttcc tctttcctcc caagcctaag gacaccctga tgatctccag gaccccccgaa  780
gtgacctgcg tggtcgtgga cgtgtcccag gaggacctg aggtgcagtt taactggtac  840
gtggaggtgca caacgccaag accaagccca gggaggagca gttcaatagc  900
acctacaggg tggtgtccgt gctgaccgtg ctgcaccagg actggctgaa cggcaaagag  960
tacaagtgca aagtcagcaa caagggcctg ccctcctcca tcgagaagac cattagcaag 1020
gccaaggcc agcctaggga gcctcaggtg tacaccctgc cccccagcca ggaggagatg 1080
accaagaacc aggtgtccct gacctgcctg gtcaagggat tttaccccag cgacatcgct 1140
gtggaatggg agagcaatgg ccagcccgag aacaactaca agaccacccc tcccgtgctc 1200
gattccgacg gcagctttt cctgtacagc aggctgaccg tggataagag caggtggcag 1260
gaaggcaacg tgttctcctg ttccgtgatg catgaggccc tgcacaacca ctacacacag 1320
aagagcctgt ccctgtccct gggc                                         1344
```

| | | |
|---|---|---|
| SEQ ID NO: 65 | moltype = AA length = 451 | |
| FEATURE | Location/Qualifiers | |
| REGION | 1..451 | |
| | note = alpha-FXI-18623p HC-IgG4 (S228P) (Q1) (C-terminal K-less) | |
| source | 1..451 | |
| | mol_type = protein | |
| | organism = synthetic construct | |

SEQUENCE: 65
```
QVQLQESGPG LVKPSQTLSL TCTVSGGSIY SGAYYWSWIR QHPGKGLEWI GSIHYSGLTY   60
YNPSLKSRVT ISVDTSKNQF SLKLSSVTAA DTAVYYCARD VDDSSGDEHY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451
```

| | | |
|---|---|---|
| SEQ ID NO: 66 | moltype = DNA length = 1353 | |
| FEATURE | Location/Qualifiers | |
| misc_difference | 1..1353 | |
| | note = DNA encoding alpha-FXI-18623p HC-IgG4 (S228P) (Q1) xxx= CAG orCAA (Q) (C-terminal K-less) | |
| misc_difference | 1..3 | |
| | note = n is a, c, g, or t | |
| source | 1..1353 | |
| | mol_type = other DNA | |
| | organism = synthetic construct | |
| CDS | 1..3 | |
| | note = nnn= CAG or CAA | |

SEQUENCE: 66
```
nnngtccagc tgcaggaatc cggaccggc ctggtgaagc ctagccagac cctgagcctg   60
acctgtaccg tgtccggcgg aagcatctat tccggcgcct actactggtc ctggattagg  120
cagcaccccg gcaagggcct ggaatggatc ggctccatcc actacagcgg cctgacctat  180
tacaaccccct ccctgaagtc cagggtgacc atcagcgtcg acacaagcaa gaaccagttc  240
tccctcaagc tgagcagcgt gaccgccgcc gacaccgccg tgtattattg cgccagagac  300
gtggacgact cctccggaga cgagcactac ggcatggacg tctgggggca gggcacaaca  360
gtgacagtga gcagcgccag caccaaagga ccctccgtct ccctctggc cccttgctcc  420
aggagcacaa gcgaaagcac agccgccctg ggctgcctgg tgaaggacta ctttcccgag  480
cccgtgaccg tgagctggaa tagcggagcc ctcacctccg gagtccacac atttcccgcc  540
gtcctgcaga gcagcggcct gtactccctg agctccgtgg tgaccgtgcc ttcctccagc  600
ctgggcacca agacctacac ctgcaacgtg gaccacaag caagtgac caaggtggac  660
aagagggtgg aatccaagta cggcccccct tgcctccctt gtcctgcccc cgaatttctg  720
ggcggccctt ccgtgttcct gttccctccc aagcccaagg ataccctgat gatcagcagg  780
acccctgagg tgacctgtgt ggtggtggac gtgagccagg aggaccccga ggtgcagttc  840
aactggtacg tggatggcgt ggaagtgcac aatgccaaga caaagcccag ggaggagcag  900
ttcaatagca cctacagggt ggtcagcgtg ctgaccgtgc tggaac  960
ggaaaggagt acaagtgcaa agtgtccaac aagggcctgc cctcctccat cgaaaagacc  1020
atctccaagg ccaaaggcca gcctagggag cctcaagtgt acaccctccc cctagccag 1080
gaggaaatga ccaaaaacca ggtctccctg acctgtctgg tgaagggctt ctatcccagc  1140
gacatcgctg tggagtggga gagcaacggc caacccgaga caactataa gaccacaccc  1200
cccgtcctgg actccgatgg ctccttcttc ctgtacagca ggctgaccgt cgacaagtcc  1260
```

```
aggtggcagg aaggaaacgt gttctcctgt agcgtcatgc acgaggccct gcacaaccac   1320
tatacccaga agtccctgtc cctgagcctg ggc                                1353

SEQ ID NO: 67           moltype = AA  length = 451
FEATURE                 Location/Qualifiers
REGION                  1..451
                        note = alpha-FXI-18623p HC-IgG4 (S228P) (E1) (C-terminal
                        K-less)
source                  1..451
                        mol_type = protein
                        organism = synthetic construct
SEQUENCE: 67
EVQLQESGPG LVKPSQTLSL TCTVSGGSIY SGAYYWSWIR QHPGKGLEWI GSIHYSGLTY    60
YNPSLKSRVT ISVDTSKNQF SLKLSSVTAA DTAVYYCARD VDDSSGDEHY GMDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 68           moltype = DNA  length = 1353
FEATURE                 Location/Qualifiers
misc_difference         1..1353
                        note = DNA encoding alpha-FXI-18623p HC-IgG4 (S228P) (E1)
                        xxx=GAA or GAG(E) (C-terminal K-less)
misc_difference         1..3
                        note = n is a, c, g, or t
source                  1..1353
                        mol_type = other DNA
                        organism = synthetic construct
CDS                     1..3
                        note = nnn=GAA or GAG
SEQUENCE: 68
nnngtccagc tgcaggaatc cggaccggc ctggtgaagc ctagccgac cctgagcctg     60
acctgtaccg tgtccggcgg aagcatctat tccggcgcct actactgtc ctggattagg   120
cagcaccccg gcaagggcct ggaatggatc ggctccatcc actacagcgg cctgacctat   180
tacaacccct ccctgaagtc cagggtgacc atcagcgtcg acaagcaa gaaccagttc    240
tccctcaagc tgagcagcgt gaccgccgcc gacaccgtc tgtattattg cgccagagac   300
gtggacgact cctccggaga cgagcactac ggcatggacg tctggggcca gggcacaaca   360
gtgacagtga gcagcgccag caccaaagga ccctccgtct tccctctggc cccttgctcc   420
aggagcacaa gcgaaagcac agccgccctg ggctgcctgg tgaaggacta ctttcccgag   480
cccgtgaccg tgagctggaa tagcggagcc ctcacctccg gagtccacac atttcccgcc   540
gtcctgcaga gcagcggcct gtactccctg agctccgtgg tgaccgtgcc ttcctccagc   600
ctgggcacca gacctacac ctgcaacgtg gaccacaagc ctagcaatac caaggtggac   660
aagagggtgg aatccaagta cggcccccct tgccctcctt gtcctgcccc cgaatttctg   720
ggcggccctt ccgtgttcct gttccctccc aagcccaagg ataccctgat gatcagcagg   780
accccctgagg tgacctgtgt ggtggtggac gtgagccagg aggacccga ggtgcagttc    840
aactggtacg tggatggcgt ggaagtgcac aatgccaaga caaagccag ggaggagcag    900
ttcaatagca cctacagggt ggtcagcgtg ctcacagtgc tgcaccagga ctggctgaac   960
ggaaaggagt acaagtgcaa agtgtccaac aagggcctgc cctcctccat cgaaaagact   1020
atctccaagg ccaaggcca gccaggagg ccccaagtgt ataccctccc cctagccag    1080
gagaaatga ccaaaaacca ggtctccctg acctgtctgg tgaagggctt ctatcccagc   1140
gacatcgctg tggagtggga gagcaacggc caacccgaga caactataa gaccacaccc    1200
cccgtcctgg actccgatgg ctccttcttc ctgtacagca ggctgaccgt cgacaagtcc   1260
aggtggcagg aaggaaacgt gttctcctgt agcgtcatgc acgaggccct gcacaaccac   1320
tatacccaga agtccctgtc cctgagcctg ggc                                1353

SEQ ID NO: 69           moltype = AA  length = 451
FEATURE                 Location/Qualifiers
REGION                  1..451
                        note = alpha-FXI-18611p HC IgG1 (Q1) (M105) (C-terminal
                        K-less)
source                  1..451
                        mol_type = protein
                        organism = synthetic construct
SEQUENCE: 69
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                  451

SEQ ID NO: 70           moltype = DNA  length = 1353
FEATURE                 Location/Qualifiers
misc_difference         1..1353
```

|  | note = DNA encoding alpha-FXI-18611p HC IgG1 (Q1) (M105)xxx= CAG orCAA (Q) (C-terminal K-less) |
| --- | --- |
| misc_difference | 1..3 |
|  | note = n is a, c, g, or t |
| source | 1..1353 |
|  | mol_type = other DNA |
|  | organism = synthetic construct |
| CDS | 1..3 |
|  | note = nnn= CAG or CAA |

SEQUENCE: 70

```
nnngtccagc tgcaggagag cggcctggc ctggtgaagc ctagcgagac actgtccctg    60
acctgcgccg tgagcggcta cagcatctcc agcggctatt tctggggatg gatcagacag   120
ccccctggca agggcctgga atggatcggt tctatcctgc actccggcgt gacatactat   180
aaccctagcc tgaagagcag ggtgaccatc tccgtggaca ccagcaagaa tcagttcagc   240
ctgaagctca gcagcgtgac cgccgccgat accgctgtgt actactgcgc cagagacagg   300
accaccgtct ccatgatcga gtacttccag cactggggcc aaggcaccct ggtcaccgtg   360
tcctccgcta gcacaaaagg accaagcgtg tttccactgg cacctagcag caaatccacc   420
agcggcggaa cagcagccct cggtgcctg gtgaaggatt acttccctga gccagtcaca   480
gtgtcctgga actccggagc cctgacatcc ggcgtgcaca ccttcccgc tgtgctgcaa   540
tccagcggac tgtatagcct cagctccgtc gtgacagtcc cttccagcag cctgggcaca   600
cagacttaca tttgcaacgt gaaccacaaa ccttccaaca ctaaggtgga caaaaaggtg   660
gaacccaaat cctgtgataa gacccataca tgcccaccttt gtcccgctcc tgagctgctg   720
gggggacctt ccgtctttct gtttcctcca aaaccaaaag acacactcat gatcagccgg   780
acccccgaag tcacctgtgt ggtggtggac gtcagccacg aagatccaga ggtcaagttc   840
aattggtacg tggatggagt ggaagtccac aacgcaaaaa ccaaacctag agaagaacag   900
tacaatagca catacagggt ggtgtccgtc tccaccagga ctggctcaat   960
ggcaaagagt ataagtgcaa ggtgagcaac aaggccctgc ctgcaccaat tgagaaaaca  1020
attagcaagg caaaggggca gccacgggaa cccaggtgt ataccctgcc ccaagccgg  1080
gatgaactga ccaaaaacca ggtcagcctg acatgcctgg tgaaagggtt tacccaagc  1140
gatattgccg tcgagtggga gagcaacgga cagccagcaa acattacaa aaccacccca  1200
cctgtgctgg actccgatgg gagctttttc ctgtacagca agctcacagt ggacaagtcc  1260
agatggcaac agggcaacgt gttttcctgc tccgtgatgc acgaggccct ccacaaccac  1320
tatacacaaa agtccctctc cctcagccca gga                              1353
```

| SEQ ID NO: 71 | moltype = AA   length = 451 |
| --- | --- |
| FEATURE | Location/Qualifiers |
| REGION | 1..451 |
|  | note = alpha-FXI-18611p HC IgG1 (E1) (M105) (C-terminal K-less) |
| source | 1..451 |
|  | mol_type = protein |
|  | organism = synthetic construct |

SEQUENCE: 71

```
EVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSMIEYFQ HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                 451
```

| SEQ ID NO: 72 | moltype = DNA   length = 1353 |
| --- | --- |
| FEATURE | Location/Qualifiers |
| misc_difference | 1..1353 |
|  | note = DNA encoding alpha-FXI-18611p HC IgG1 (Q1) (M105) xxx=GAA or GAG(E) (C-terminal K-less) |
| misc_difference | 1..3 |
|  | note = n is a, c, g, or t |
| source | 1..1353 |
|  | mol_type = other DNA |
|  | organism = synthetic construct |
| CDS | 1..3 |
|  | note = nnn=GAA or GAG |

SEQUENCE: 72

```
nnngtccagc tgcaggagag cggcctggc ctggtgaagc ctagcgagac actgtccctg    60
acctgcgccg tgagcggcta cagcatctcc agcggctatt tctggggatg gatcagacag   120
ccccctggca agggcctgga atggatcggt tctatcctgc actccggcgt gacatactat   180
aaccctagcc tgaagagcag ggtgaccatc tccgtggaca ccagcaagaa tcagttcagc   240
ctgaagctca gcagcgtgac cgccgccgat accgctgtgt actactgcgc cagagacagg   300
accaccgtct ccatgatcga gtacttccag cactggggcc aaggcaccct ggtcaccgtg   360
tcctccgcta gcacaaaagg accaagcgtg tttccactgg cacctagcag caaatccacc   420
agcggcggaa cagcagccct cggtgcctg gtgaaggatt acttccctga gccagtcaca   480
gtgtcctgga actccggagc cctgacatcc ggcgtgcaca ccttcccgc tgtgctgcaa   540
tccagcggac tgtatagcct cagctccgtc gtgacagtcc cttccagcag cctgggcaca   600
cagacttaca tttgcaacgt gaaccacaaa ccttccaaca ctaaggtgga caaaaaggtg   660
gaacccaaat cctgtgataa gacccataca tgcccaccttt gtcccgctcc tgagctgctg   720
gggggacctt ccgtctttct gtttcctcca aaaccaaaag acacactcat gatcagccgg   780
acccccgaag tcacctgtgt ggtggtggac gtcagccacg aagatccaga ggtcaagttc   840
```

```
                       -continued
aattggtacg tggatggagt ggaagtccac aacgcaaaaa ccaaacctag agaagaacag    900
tacaatagca catacagggt ggtgtccgtc ctgacagtgc tccaccagga ctggctcaat    960
ggcaaagagt ataagtgcaa ggtgagcaac aaggccctgc ctgcaccaat tgagaaaaca   1020
attagcaagg caaaggggca gccacgggaa ccccaggtgt ataccctgcc cccaagccgg   1080
gatgaactga ccaaaaacca ggtcagcctg acatgcctgg tgaaagggtt ttacccaagc   1140
gatattgccg tcgagtggga gagcaacgga cagccagaaa acaattacaa aaccacccca   1200
cctgtgctgg actccgatgg gagcttttc ctgtacagca agctcacagt ggacaagtcc    1260
agatggcaac agggcaacgt gttttcctgc tccgtgatgc acgaggccct ccacaaccac   1320
tatacacaaa agtccctctc cctcagccca gga                                1353

SEQ ID NO: 73            moltype = AA  length = 451
FEATURE                  Location/Qualifiers
REGION                   1..451
                         note = alpha-FXI-18611 HC IgG1 (Q1)(L105) (C-terminal
                         K-less)
source                   1..451
                         mol_type = protein
                         organism = synthetic construct
SEQUENCE: 73
QVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                  451

SEQ ID NO: 74            moltype = DNA  length = 1353
FEATURE                  Location/Qualifiers
misc_difference          1..1353
                         note = DNA encoding alpha-FXI-18611 HC IgG1 (Q1)(L105)xxx=
                         CAG or CAA(Q) (C-terminal K-less)
misc_difference          1..3
                         note = n is a, c, g, or t
source                   1..1353
                         mol_type = other DNA
                         organism = synthetic construct
CDS                      1..3
                         note = nnn= CAG or CAA
SEQUENCE: 74
nnngtccagc tgcaggagag cggccctgga ctcgtgaagc cctccgaaac cctgagcctc     60
acatgcgccg tctccggata cagcatcagc agcggatact ctggggctg gatcagacag    120
cccccggca aaggcctgga gtggatcggt tctattctcc acagcggcgt gacatactac    180
aacccctccc tgaagagcag ggtgaccatc agcgtggaca cctccaagaa ccagtttttcc   240
ctcaagctga gcagcgtgac cgccgctgac acagccgtgt attactgcgc cagggacagg    300
accaccgtgt ccctgattga gtacttccag cattggggcc agggcacact ggtgaccgtc    360
agcagcgcta gcacaaaagg accaagcgtg tttccactgg cacctagcag caaatccacc    420
agcggcggaa cagcagccct cggggcctgt gtgaaggatt acttccctga gccagtcaca    480
gtgtcctgga actccggagc cctgacatcc ggcgtgcaca ccttccccgc tgtgctgcaa    540
tccagcggac tgtatagcct cagctccgtc gtgacagtgc cttccagcag cctgggcaca    600
cagacttaca tttgcaacgt gaaccacaaa ccttccaaca ctaaggtgga caaaaaggtt    660
gaacccaaat cctgtgataa acccatacat gcccaccctt gtcccgctcc tgagctgctg    720
gggggaccttt ccgtctttct gtttcctcca aaaccaaaag acacactcat gatcagccgg   780
accccgaag tcacctgtgt ggtggtggac gtcagccacg aagatccaga ggtcaagttc    840
aattggtacg tggatggagt ggaagtccac aacgcaaaaa ccaaacctag agaagaacag    900
tacaatagca catacagggt ggtgtccgtc ctgacagtgc tccaccagga ctggctcaat    960
ggcaaagagt ataagtgcaa ggtgagcaac aaggccctgc ctgcaccaat tgagaaaaca   1020
attagcaagg caaaggggca gccacgggaa ccccaggtgt ataccctgcc cccaagccgg   1080
gatgaactga ccaaaaacca ggtcagcctg acatgcctgg tgaaagggtt ttacccaagc   1140
gatattgccg tcgagtggga gagcaacgga cagccagaaa acaattacaa aaccacccca   1200
cctgtgctgg actccgatgg gagcttttc ctgtacagca agctcacagt ggacaagtcc    1260
agatggcaac agggcaacgt gttttcctgc tccgtgatgc acgaggccct ccacaaccac   1320
tatacacaaa agtccctctc cctcagccca gga                                1353

SEQ ID NO: 75            moltype = AA  length = 451
FEATURE                  Location/Qualifiers
REGION                   1..451
                         note = alpha-FXI-18611 HC IgG1 (E1)(L105) (C-terminal
                         K-less)
source                   1..451
                         mol_type = protein
                         organism = synthetic construct
SEQUENCE: 75
EVQLQESGPG LVKPSETLSL TCAVSGYSIS SGYFWGWIRQ PPGKGLEWIG SILHSGVTYY    60
NPSLKSRVTI SVDTSKNQFS LKLSSVTAAD TAVYYCARDR TTVSLIEYFQ HWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
```

```
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 76          moltype = DNA   length = 1353
FEATURE                Location/Qualifiers
misc_difference        1..1353
                       note = DNA encoding alpha-FXI-18611 HC IgG1
                       (E1)(L105)xxx=GAA or GAG(E) (C-terminal K-less)
misc_difference        1..3
                       note = n is a, c, g, or t
source                 1..1353
                       mol_type = other DNA
                       organism = synthetic construct
CDS                    1..3
                       note = nnn=GAA or GAG
SEQUENCE: 76
nnngtccagc tgcaggagag cggccctgga ctcgtgaagc cctccgaaac cctgagcctc     60
acatgcgccg tctccggata cagcatcagc agcggatact tctggggctg gatcagacag    120
ccccccggca aggcctggag gtggatcggt tctattctcc acagcggcgt gacatactac    180
aacccctccc tgaagagcag ggtgaccatc agcgtggaca cctccaagaa ccagttttcc    240
ctcaagctga gcagcgtgac cgccgctgac acagccgtgt attactgcgc cagggacagg    300
accaccgtgt ccctgattga gtacttccag cattggggcc agggcacact ggtgaccgtc    360
agcagcgcta gcacaaaagg accaagcgtg tttccactgg cacctagcag caaatccacc    420
agcggcggaa cagcagccct cggggtgcctg gtgaaggatt acttccctga gccagtcaca    480
gtgtcctgga actccggagc cctgacatcc ggcgtgcaca cccttcccgc tgtgctgcaa    540
tccagcggac tgtatagcct cagctccgtc gtgacagtcc cttccagcag cctgggcaca    600
cagacttaca tttgcaacgt gaaccacaaa ccttccaaca ctaaggtgga caaaaaggtg    660
gaacccaaat cctgtgataa gacccataca tgcccacctt gtcccgctcc tgagctgctg    720
ggggaccttt ccgtcttct gttctcctcca aaaccaaaag acacactcat gatcagccgg    780
acccccgaag tcacctgtgt ggtggtggac gtcagccacg aagatccaga ggtcaagttc    840
aattggtacg tggatggagt ggaagtccac aacgcaaaaa ccaaacctag agaagaacag    900
tacaatagca catacagggt ggtgtccgtc ctgacagtgc tccaccagga ctggctcaat    960
ggcaaagagt ataagtgcaa ggtgagcgga aaggcccctgc ctgccaccat tgagaaaaca   1020
attagcaagg caaaggggca gccacggcga ccccaggtgt ataccctgcc cccaagccgg   1080
gatgaactga ccaaaaacca ggtcagcctg acatgcctgg tgaaagggtt ttacccaagc   1140
gatattgccg tcgagtggga gagcaacgga cagccagaaa acaattacaa accaccccca   1200
cctgtgctgg actccgatgg gagcttttc ctgtacagca gctcacagt ggacaagtcc   1260
agatggcaac agggcaacgt gttttcctgc tccgtgatgc acgaggccct ccacaaccac   1320
tatacacaaa agtccctctc cctcagccca gga                                1353

SEQ ID NO: 77          moltype = AA   length = 454
FEATURE                Location/Qualifiers
REGION                 1..454
                       note = alpha-FXI-18623p HC IgG1 (1Q) (C-terminal K-less)
source                 1..454
                       mol_type = protein
                       organism = synthetic construct
SEQUENCE: 77
QVQLQESGPG LVKPSQTLSL TCTVSGGSIY SGAYYWSWIR QHPGKGLEWI GSIHYSGLTY     60
YNPSLKSRVT ISVDTSKNQF SLKLSSVTAA DTAVYYCARD VDDSSGDEHY GMDVWGQGTT    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
ELLGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALPAPI EKTISKAKGQ PREPQVYTLP    360
PSRDELTKNQ VSLTCLVKGF YPSDIAVEWE SNGQPENNYK TTPPVLDSDG SFFLYSKLTV    420
DKSRWQQGNV FSCSVMHEAL HNHYTQKSLS LSPG                               454

SEQ ID NO: 78          moltype = DNA   length = 1362
FEATURE                Location/Qualifiers
misc_difference        1..1362
                       note = DNA encoding alpha-FXI-18623p HC IgG1 (1Q) xxx= CAG
                       or CAA (Q)(C-terminal K-less)
misc_difference        1..3
                       note = n is a, c, g, or t
source                 1..1362
                       mol_type = other DNA
                       organism = synthetic construct
CDS                    1..3
                       note = nnn= CAG or CAA
SEQUENCE: 78
nnngtccagc tgcaggaatc cggacccggc ctgtgaagc ctagccagac cctgagcctg     60
acctgtaccg tgtccggcgg aagcatctat tccggcgcct actactggtc ctggattagg    120
cagcaccccg gcaagggcct ggaatggatc ggctccatac actacagcgg cctgacctat    180
tacaaccccct ccctgaagtc cagggtgacc atcagcgtcg acacaagcaa gaaccagttc    240
tccctcaagc tgagcagcgt gaccgccgcc gacaccgccg tgtattattg cgccagagac    300
gtggacgact cctccggaga cgagcactac ggcatggacg tctggggcca gggcacaaca    360
gtgacagtga gcagcgctag cacaaaagga ccaagcgtgt ttccactggc acctagcagc    420
aaatccacca gcggcggaac agcagccctc ggggtgcctgg tgaaggatta cttccctgag    480
```

```
ccagtcacag tgtcctggaa ctccggagcc ctgacatccg gcgtgcacac cttccccgct   540
gtgctgcaat ccagcggact gtatagcctc agctccgtcg tgacagtccc ttccagcagc   600
ctgggcacac agacttacat ttgcaacgtg aaccacaaac cttccaacac taaggtggac   660
aaaaaggtgg aacccaaatc ctgtgataag acccatacat gcccaccttg tcccgctcct   720
gagctgctgg ggggaccttc cgtctttctg tttcctccaa aaccaaaaga cacactcatg   780
atcagccgga cccccgaagt cacctgtgtg gtggtggacg tcagccacga agatccagag   840
gtcaagttca attggtacgt ggatggagtg gaagtccaca acgcaaaaac caaacctaga   900
gaagaacagt acaatagcac atacagggtg gtgtccgtcc tgacagtgct ccaccaggac   960
tggctcaatg gcaaagagta taagtgcaag gtgagcaaca aggccctgcc tgcaccaatt  1020
gagaaaacaa ttagcaaggc aaaggggcag ccacgggaac cccaggtgta taccctgccc  1080
ccaagccggg atgaactgac caaaaaccag gtcagcctga catgcctggt gaagggtttt  1140
tacccaagcg atattgccgt cgagtgggag agcaacggac agccagaaaa caattacaaa  1200
accacccccac ctgtgctgga ctccgatggg agcttttttcc tgtacagcaa gctcacagtg  1260
gacaagtcca gatggcaaca gggcaacgtg ttttcctgct ccgtgatgca cgaggccctc  1320
cacaaccact atacacaaaa gtccctctcc ctcagcccag ga                     1362

SEQ ID NO: 79           moltype = AA  length = 454
FEATURE                 Location/Qualifiers
REGION                  1..454
                        note = alpha-FXI-18623p HC IgG1 (1E) (C-terminal K-less)
source                  1..454
                        mol_type = protein
                        organism = synthetic construct
SEQUENCE: 79
EVQLQESGPG LVKPSQTLSL TCTVSGGSIY SGAYYWSWIR QHPGKGLEWI GSIHYSGLTY   60
YNPSLKSRVT ISVDTSKNQF SLKLSSVTAA DTAVYYCARD VDDSSGDEHY GMDVWGQGTT  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 80           moltype = DNA  length = 1362
FEATURE                 Location/Qualifiers
misc_difference         1..1362
                        note = DNA encoding alpha-FXI-18623p HC IgG1 (1E) xxx=GAA
                         or GAG (E)(C-terminal K-less)
misc_difference         1..3
                        note = n is a, c, g, or t
source                  1..1362
                        mol_type = other DNA
                        organism = synthetic construct
CDS                     1..3
                        note = nnn=GAA or GAG
SEQUENCE: 80
nnngtccagc tgcaggaatc cggacccggc ctggtgaagc ctagccagac cctgagcctg    60
acctgtaccg tgtccggcgg aagcatctat tccggcgcct actactggtc ctggattagg   120
cagcaccccg gcaagggcct ggaatggatc ggctccatcc actacagcgg cctgacctat   180
tacaaccctc cctgaagtc cagggtgacc atcagcgtcg acacaagcaa gaaccagttc   240
tccctcaagc tgagcagcgt gaccgccgcc gacaccgtgt gtattattg cgccagagac   300
gtggacgact cctccggaga cgagcactac ggcatggacg tctggggcca gggcacaaca   360
gtgacagtga gcagcgctag cacaaaagga ccaagcgtgt tccactggc acctagcagc   420
aaatccacca gcggcggaac agcagccctc gggtgcctgg tgaaggatta cttccctgag   480
ccagtcacag tgtcctggaa ctccggagcc ctgacatccg gcgtgcacac cttccccgct   540
gtgctgcaat ccagcggact gtatagcctc agctccgtcg tgacagtccc ttccagcagc   600
ctgggcacac agacttacat ttgcaacgtg aaccacaaac cttccaacac taaggtggac   660
aaaaaggtgg aacccaaatc ctgtgataag acccatacat gcccaccttg tcccgctcct   720
gagctgctgg ggggaccttc cgtctttctg tttcctccaa aaccaaaaga cacactcatg   780
atcagccgga cccccgaagt cacctgtgtg gtggtggacg tcagccacga agatccagag   840
gtcaagttca attggtacgt ggatggagtg gaagtccaca acgcaaaaac caaacctaga   900
gaagaacagt acaatagcac atacagggtg gtgtccgtcc tgacagtgct ccaccaggac   960
tggctcaatg gcaaagagta taagtgcaag gtgagcaaca aggccctgcc tgcaccaatt  1020
gagaaaacaa ttagcaaggc aaaggggcag ccacgggaac cccaggtgta taccctgccc  1080
ccaagccggg atgaactgac caaaaaccag gtcagcctga catgcctggt gaagggtttt  1140
tacccaagcg atattgccgt cgagtgggag agcaacggac agccagaaaa caattacaaa  1200
accacccccac ctgtgctgga ctccgatggg agcttttttcc tgtacagcaa gctcacagtg  1260
gacaagtcca gatggcaaca gggcaacgtg ttttcctgct ccgtgatgca cgaggccctc  1320
cacaaccact atacacaaaa gtccctctcc ctcagccag ga                      1362

SEQ ID NO: 81           moltype = AA  length = 607
FEATURE                 Location/Qualifiers
source                  1..607
                        mol_type = protein
                        organism = Homo sapiens
SEQUENCE: 81
ECVTQLLKDT CFEGGDITTV FTPSAKYCQV VCTYHPRCLL FTFTAESPSE DPTRWFTCVL   60
KDSVTETLPR VNRTAAISGY SFKQCSHQIS ACNKDIYVDL DMKGINYNSS VAKSAQECQE  120
RCTDDVHCHF FTYATRQFPS LEHRNICLLK HTQTGTPTRI TKLDKVVSGF SLKSCALSNL  180
```

```
ACIRDIFPNT VFADSNIDSV MAPDAFVCGR ICTHHPGCLF FTFFSQEWPK ESQRNLCLLK    240
TSESGLPSTR IKKSKALSGF SLQSCRHSIP VFCHSSFYHD TDFLGEELDI VAAKSHEACQ    300
KLCTNAVRCQ FFTYTPAQAS CNEGKGKCYL KLSSNGSPTK ILHGRGGISG YTLRLCKMDN    360
ECTTKIKPRI VGGTASVRGE WPWQVTLHTT SPTQRHLCGG SIIGNQWILT AAHCFYGVES    420
PKILRVYSGI LNQSEIKEDT SFFGVQEIII HDQYKMAESG YDIALLKLET TVNYTDSQRP    480
ICLPSKGDRN VIYTDCWVTG WGYRKLRDKI QNTLQKAKIP LVTNEECQKR YRGHKITHKM    540
ICAGYREGGK DACKGDSGGP LSCKHNEVWH LVGITSWGEG CAQRERPGVY TNVVEYVDWI    600
LEKTQAV                                                              607

SEQ ID NO: 82           moltype = AA  length = 8
FEATURE                 Location/Qualifiers
REGION                  1..8
                        note = Epitope A
source                  1..8
                        mol_type = protein
                        organism = synthetic construct
SEQUENCE: 82
DIFPNTVF                                                              8

SEQ ID NO: 83           moltype = AA  length = 13
FEATURE                 Location/Qualifiers
REGION                  1..13
                        note = Epitope B
source                  1..13
                        mol_type = protein
                        organism = synthetic construct
SEQUENCE: 83
PSTRIKKSKA LSG                                                       13

SEQ ID NO: 84           moltype = AA  length = 232
FEATURE                 Location/Qualifiers
REGION                  1..232
                        note = anti-RSV Kappa Light Chain
source                  1..232
                        mol_type = protein
                        organism = synthetic construct
SEQUENCE: 84
MAPVQLLGLL VLFLPAMRCD IQMTQSPSTL SASVGDRVTI TCKCQLSVGY MHWYQQKPGK    60
APKLLIYDTS KLASGVPSRF SGSGSGTEFT LTISSLQPDD FATYYCFQGS GYPFTFGGGT    120
KLEIKRTVAA PSVFIFPPSD EQLKSGTASV VCLLNNFYPR EAKVQWKVDN ALQSGNSQES    180
VTEQDSKDST YSLSSTLTLS KADYEKHKVY ACEVTHQGLS SPVTKSFNRG EC            232

SEQ ID NO: 85           moltype = AA  length = 466
FEATURE                 Location/Qualifiers
REGION                  1..466
                        note = anti-RSV IgG4 HC S228P
source                  1..466
                        mol_type = protein
                        organism = synthetic construct
SEQUENCE: 85
MAVVQLLGLL VLFLPAMRCQ VTLRESGPAL VKPTQTLTLT CTFSGFSLST SGMSVGWIRQ    60
PPGKALEWLA DIWWDDKKDY NPSLKSRLTI SKDTSKNQVV LKVTNMDPAD TATYYCARSM    120
ITNWYFDVWG AGTTVTVSSA STKGPSVFPL APCSRSTSES TAALGCLVKD YFPEPVTVSW    180
NSGALTSGVH TFPAVLQSSG LYSLSSVVTV PSSSLGTKTY TCNVDHKPSN TKVDKRVESK    240
YGPPCPPCPA PEFLGGPSVF LFPPKPKDTL MISRTPEVTC VVVDVSQEDP EVQFNWYVDG    300
VEVHNAKTKP REEQFNSTYR VVSVLTVLHQ DWLNGKEYKC KVSNKGLPSS IEKTISKAKG    360
QPREPQVYTL PPSQEEMTKN QVSLTCLVKG FYPSDIAVEW ESNGQPENNY KTTPPVLDSD    420
GSFFLYSRLT VDKSRWQEGN VFSCSVMHEA LHNHYTQKSL SLSLGK                   466
```

ANTI-COAGULATION FACTOR XI ANTIBODIES

CROSS REFERENCE TO RELATED APPLICATIONS

This application is a continuation application of U.S. patent application Ser. No. 16/864,559, filed May 1, 2020, which issued to U.S. patent Ser. No. 11/661,460 on May 30, 2023, and is a divisional application of U.S. patent application Ser. No. 15/619,620, filed Jun. 12, 2017, which issued to U.S. patent Ser. No. 10/676,536 on Jun. 9, 2020, and which claims benefit of U.S. Provisional Application No. 62/349,888, filed Jun. 14, 2016, each of which is herein incorporated by reference in its entirety.

REFERENCE TO SEQUENCE LISTING SUBMITTED ELECTRONICALLY

The instant application contains a Sequence Listing which has been submitted electronically in XML format and is hereby incorporated by reference in its entirety. The XML file, created on May 5, 2023, is named 24339-US-CNT-2.XML and is 172 bytes in size.

BACKGROUND OF THE INVENTION

(1) Field of the Invention

The present invention relates to antibodies that bind the apple 3 domain of human coagulation factor XI (FXI) and inhibit activation of FXI by coagulation factor XIIa as well as FXIa's activity on Factor IX (FIX).

(2) Description of Related Art

Thromboembolic disorders, including both venous and arterial thrombosis, remain the leading cause of morbidity and mortality in the Western world despite the availability of numerous class of anticoagulants, such as vitamin K antagonists (VKAs), heparins, and direct thrombin inhibitors (Weitz et al., Chest 2008, 133: 234S-256S; Hawkins, Pharmacotherapy 2004, 24:62S-65S). These drugs are effective in reducing risks of thrombosis but they are associated with multiple limitations. For example, the VKAs (eg. warfarin) have been the mainstay for oral anticoagulation yet the management of VKA therapy is complicated due to its significant bleeding risk, slow onset and offset of action, and multiple dietary and drug interactions (Hawkins, op. cit.; Ansell J et al., Chest 2008, 133:160S-198S). The non-vitamin K antagonist oral anticoagulants (NOACs, including rivaroxaban, apixaban, edoxaban, and dabigatran) have demonstrated at least non-inferior efficacy compared to warfarin, with less food and drug interactions and no need for monitoring. However, the NOACs still increase the risk of bleeding as demonstrated by the close to 15% annual incidence of major or nonmajor clinically relevant bleeding in their registrational trials for stroke prevention in atrial fibrillation (Connolly et al., N Engl J Med 2009, 361:1139-1151; Patel et al., N Engl J Med 2011, 365:883-891; Granger et al., N Engl J Med 2011, 365:981-992; Giugliano et al., N Engl J Med 2013, 369:2093-2104). This is largely ascribed to the fact that the NOACs target proteins (coagulation Factor Xa (FXa) and thrombin) that are essential for normal coagulation (hemostasis). Novel therapy with better safety profiles in prevention and treatment of thrombotic diseases or disorders is thus an unmet need.

In the classic waterfall model of the blood clotting cascade (FIG. 1A), coagulation is triggered by either the extrinsic (tissue factor (TF)-activated) pathway or the intrinsic (contact-activated) pathway, both feeding into the common pathway that culminates in thrombin generation and fibrin formation (Furie & Furie, Cell 1988, 53:505-518; Gailani & Renne, J Thromb Haemost 2007, 5:1106-1112). The extrinsic cascade is initiated when TF that is present in the subendothelium and atherosclerotic lesions becomes exposed to flowing blood and forms a complex with coagulation Factor VIIa (FVIIa). The TF-FVIIa complex (extrinsic tenase complex) then triggers the common pathway, i.e. activation of FX to form FXa which in turn converts prothrombin to thrombin. The TF-FVIIa complex can also activate coagulation Factor IX (FIX) to form FIXa. FIXa in complex with coagulation Factor VIII (FVIIIa) (intrinsic tenase complex) can cleave the FX substrate as well. The intrinsic cascade is initiated when FXIIa is formed via contact activation from negatively charged surfaces (eg. collagen and glycosaminoglycans) and propagates thrombin generation by sequential activation of FXI, FIX, FX, and prothrombin. Thrombin, as the terminal protease in the clotting cascade, may further contribute to FXIa generation by direct activation of FXI in a feedback mechanism. Platelets, another important hemostatic component in whole blood, can be activated by thrombin and may subsequently support FXIa formation as well. FXI-dependent amplification of thrombin generation may indirectly regulate fibrinolysis via activation of the thrombin-activatable fibrinolysis inhibitor (TAFI). FXI thus interacts with several components in the hemostatic system and plays a pivotal role in blood coagulation and thrombosis (Gailani & Renne op. cit.; Emsley et al., Blood 2010, 115:2569-2577).

Coagulation Factor XI (FXI) is a dimer composed of identical 80 KDa subunits, and each subunit starting from the N-terminus consists of four apple domains (A1, A2, A3, and A4) and a catalytic domain (See FIG. 1B). FXI is a zymogen that circulates in complex with High Molecular Weight Kininogen (HK). HK binds to the A2 domain in FXI and is a physiological cofactor for FXIIa activation of FXI to FXIa. The remaining apple domains in FXI also mediate important physiological functions. For example, FIX-binding exosite is localized in A3, whereas FXIIa-binding site is in A4. Residues that are critical for FXI dimerization are also localized in A4 (Emsley et al., op. cit.).

In recent years multiple lines of effort have demonstrated that FXI plays a pivotal role in the pathological process of thrombus formation with relatively small contribution to hemostasis and is thus a promising target for thrombosis. Key data supporting this notion are summarized in the following: (1) in Ionis Pharmaceuticals Inc. FXI antisense oligonucleotide (ASO) Phase II trial (Buller et al., N Engl J Med 2015, 372:232-240), FXI ASO produced significant reduction in venous thromboembolism (VTE), with a trend toward less bleeding, compared to enoxaparin, in patients undergoing total knee arthroplasty; (2) Human genetics and epidemiological studies (Duga et al., Semin Thromb Hemost 2013; Chen et al., Drug Discov Today 2014; Key, Hematology Am Soc Hematol Educ Program 2014, 2014:66-70) indicated that severe FXI deficiency (hemophilia C) confers reduced risk of ischemic stroke and deep vein thrombosis; conversely, increased levels of FXI are associated with a higher risk for VTE and ischemic stroke; and (3) Numerous lines of preclinical studies demonstrated that FXI(a) inhibition or loss-of-function mediate profound thromboprotection without compromising hemostasis (Chen et al. op. cit.). Of note, monoclonal antibodies 14E11 and 1A6 produced significant thrombus reduction in the baboon AV shunt thrombosis model (U.S. Pat. Nos. 8,388,959; 8,236,316; Tucker et al., Blood 2009, 113:936-944; Cheng et al., Blood 2010, 116:3981-3989). Moreover, 14E11 (as it cross-reacts with mouse FXI) provided protection in an experimental model of acute ischemic stroke in mice (Leung et al., Transl Stroke Res 2012, 3:381-389). Additional FXI-targeting mAbs have also been reported in preclinical models in validating FXI as an antithrombotic target with minimal bleeding risk (van Montfoort et al., Thromb Haemost 2013, 110; Takahashi et al., Thromb Res 2010, 125:464-470; van Montfoort, Ph.D. Thesis, University of Amsterdam, Amsterdam, Netherlands, 14 Nov. 2014). Inhibition of FXI is thus a promising strategy for novel antithrombotic therapy with an improved benefit-risk profile compared to current standard-of-care anticoagulants.

There is currently a large unmet medical need for antthrombotic therapies for patients that have severe or end-stage renal disease (ESRD). Roughly 650,000 patients in the US have severe or ESRD and these patients suffer an extremely high incidence of thrombotic and thromboembolic complications (MI, stroke/TIA, peripheral artery disease (PAD), vascular access failure). ESRD patients also are more likely to have bleeding events than the general population. Since anticoagulation of any kind is not commonly prescribed in ESRD patients (due to bleeding risk and lack of data for non-vitamin K antagonist oral anti-coagulants (NOACs) in ESRD), there is a need for an anti-thrombotic therapy that has an acceptable benefit-risk profile in these patients.

BRIEF SUMMARY OF THE INVENTION

The present invention provides human antibodies capable of selectively binding to coagulation Factor XI (anti-FXI antibodies) and inhibiting blood coagulation and associated thrombosis, preferably without compromising hemostasis. Compositions include anti-coagulation Factor XI antibodies capable of binding to a defined epitope of the apple 3 (A3) domain of coagulation Factor XI. These antibodies exhibit neutralizing activity by inhibiting the conversion of the zymogen form FXI to its activated form, FXIa, under the action of FXIIa, and inhibiting FXIa-mediated activation of FIX. The antibodies are useful for FXI inhibition, which may confer a clinically relevant anti-thrombotic effect with a reduced risk of bleeding complications and hence an expanded therapeutic index compared to inhibition of more downstream clotting factors such as FXa and thrombin. Therefore, these antibodies provide a therapeutic approach for the prevention of thromboembolic complications, e.g., stroke prevention in atrial fibrillation (SPAF).

One unserved cohort at risk of vascular thrombosis that may benefit from FXI inhibition is the severe and end-stage renal disease (ESRD) population, in which non-vitamin K antagonist oral anti-coagulants (NOACs) are not typically used due to concerns regarding bleeding, which have led to a lack of clinical trial experience. The antibodies herein provide a novel anti-coagulant therapy for the prevention of thrombotic complications in ESRD patients. The antibodies herein may provide clinically relevant antithrombotic efficacy accompanied by an acceptable bleeding risk in ESRD patients.

Apart from ESRD and SPAF, FXI inhibition may also be indicated in additional patient segments that are at high risk for thrombosis. These include: 1) venous thromboembolism (VTE) prophylaxis in orthopedic surgery and/or secondary prevention of VTE; 2) reduction of revascularization and/or reduction of Major Adverse Limb Events (MALE) in PAD; 3) adjuvant therapy in ACS.

The present invention provides an antibody or antigen binding fragment comprising at least the six complimentary determining regions (CDRs) of an anti-FXI antibody of the αFXI-18623p family, αFXI-18611p family, or αFXI-18611 family or at least the six complimentary determining regions (CDRs) of an anti-FXI antibody of the αFXI-18623p family, αFXI-18611p family, or αFXI-18611 family wherein one or more of the six CDRs has one, two, or three amino acid substitutions, additions, deletions, or combinations thereof, wherein an antibody of the αFXI-18623 family comprises a heavy chain (HC) variable region having the amino acid sequence shown in SEQ ID NO:28 or 29 and an LC variable region having the amino acid sequence shown in SEQ ID NO:30; an antibody of the αFXI-18611p family comprises an HC variable region having the amino acid sequence shown in SEQ ID NO:21 or 22 and a light chain (LC) variable region having the amino acid sequence shown in SEQ ID NO:25; and antibody of the αFXI-18611 family comprises an HC variable region having the amino acid sequence shown in SEQ ID NO:23 or 24 and an LC variable region having the amino acid sequence shown in SEQ ID NO:25. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the six CDRs comprise or consist of CDR1, CDR2, and CDR3 of the HC of an anti-FXI antibody of the αFXI-18623p family, αFXI-18611p family, or αFXI-18611 family and CDR1, CDR2, and CDR3 of the LC of the αFXI-18623p family, αFXI-18611p family, or αFXI-18611 family, wherein an antibody of the αFXI-118623 family comprises an HC variable region having the amino acid sequence shown in SEQ ID NO:28 or 29 and an LC variable region having the amino acid sequence shown in SEQ ID NO:30; an antibody of the αFXI-18611p family comprises a heavy chain (HC) variable region having the amino acid sequence shown in SEQ ID NO:21 or 22 and a light chain (LC) variable region having the amino acid sequence shown in SEQ ID NO:25; and, an antibody of the αFXI-18611 family comprises an HC variable region having the amino acid sequence shown in SEQ ID NO:23 or 24 and an LC variable region having the amino acid sequence shown in SEQ ID NO:25. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody or antigen binding fragment comprises an HC variable region having an amino acid sequence selected from the group of amino acid sequences consisting of SEQ ID NO:21, 22, 23, and 24; and an LC variable region having the amino acid sequence shown in SEQ ID NO:25; wherein the HC variable region framework may comprise 1, 2, 3, 4, 5, 6, 7, 8, 9, or 10 amino acid substitutions, additions, deletions, or combinations thereof and the LC variable region framework may comprise 1, 2, 3, 4, 5, 6, 7, 8, 9, or 10 amino acid substitutions, additions, deletions, or combinations thereof.

In further aspects or embodiments of the invention, the antibody or antigen binding fragment comprises an HC variable region having an amino acid sequence selected from the group of amino acid sequences consisting of SEQ ID NO:21, 22, 23, and 24; and an LC variable region having the amino acid sequence shown in SEQ ID NO:25.

In further aspects or embodiments of the invention, the antibody or antigen binding fragment comprises an HC variable region having an amino acid sequence selected from the group of amino acid sequences consisting of SEQ ID NO:28 and 29; and an LC variable region having the amino acid sequence shown in SEQ ID NO:30; wherein the HC variable region framework may comprise 1, 2, 3, 4, 5, 6, 7, 8, 9, or 10 amino acid substitutions, additions, deletions, or combinations thereof and the LC variable region framework may comprise 1, 2, 3, 4, 5, 6, 7, 8, 9, or 10 amino acid substitutions, additions, deletions, or combinations thereof.

In further aspects or embodiments of the invention, the antibody or antigen binding fragment comprises an HC variable region having an amino acid sequence selected from the group of amino acid sequences consisting of SEQ ID NO:28 and 29; and an LC variable region having the amino acid sequence shown in SEQ ID NO:30.

In further aspects or embodiments of the invention, the antibody comprises a heavy chain constant domain of the human IgG1, IgG2, IgG3, or IgG4 isotype. In further aspects, the constant domain may comprise 1, 2, 3, 4, 5, 6, 7, 8, 9, or 10 amino acid substitutions, additions, deletions, or combinations thereof. In particular aspects, the constant domain may comprise a C-terminal lysine or may lack a C-terminal lysine.

In further aspects or embodiments of the invention, the antibody comprises a heavy chain constant domain of the human IgG1 or IgG4 isotype. In a further aspect, the heavy chain constant domain is of the IgG4 isotype and further includes a substitution of the serine residue at position 228 (EU numbering) with proline, which corresponds to position 108 of SEQ ID NO:16 or 17 (Serine at position 108).

In further aspects or embodiments of the invention, the antibody comprises a HC constant domain comprising the amino acid sequence shown in SEQ ID NO:16, 17, 18, or 19.

In further aspects or embodiments of the invention, the antibody comprises a light chain constant domain of the human kappa or lambda type.

In further aspects or embodiments of the invention, the antibody comprises a LC constant domain comprising the amino acid sequence shown in SEQ ID NO:20.

In further aspects or embodiments of the invention, the antibody or antigen binding fragment comprises an HC having an amino acid sequence selected from the group of amino acid sequences consisting of SEQ ID NO:33, 35, 37, 39, 45, 47, 49, 51, 57, 59, 61, 63, 69, 71, 73, and 75; and an LC having amino acid sequence shown in SEQ ID NO:26.

In further aspects or embodiments of the invention, the antibody or antigen binding fragment comprises an HC having an amino acid sequence selected from the group of amino acid sequences consisting of SEQ ID NO:41, 43, 53, 55, 65, 67, 77, and 79; and an LC having amino acid sequence shown in SEQ ID NO:31.

The present invention further provides an antibody or antigen binding fragment comprising (a) a heavy chain (HC) variable domain having the amino acid sequence shown in SEQ ID NO: 28 and a light chain (LC) variable domain having the amino acid sequence shown in SEQ ID NO:30; (b) a heavy chain (HC) variable domain having the amino acid sequence shown in SEQ ID NO: 29 and a light chain (LC) variable domain having the amino acid sequence shown in SEQ ID NO:30; (b) a heavy chain (HC) variable domain having the amino acid sequence shown in SEQ ID NO: 21 and a light chain (LC) variable domain having the amino acid sequence shown in SEQ ID NO:25; (c) a heavy chain (HC) variable domain having the amino acid sequence shown in SEQ ID NO:22 and a light chain (LC) variable domain having the amino acid sequence shown in SEQ ID NO:25; (d) a heavy chain (HC) variable domain having the amino acid sequence shown in SEQ ID NO: 23 and a light chain (LC) variable domain having the amino acid sequence shown in SEQ ID NO:25, or (e) a heavy chain (HC) variable domain having the amino acid sequence shown in SEQ ID NO: 24 and a light chain (LC) variable domain having the amino acid sequence shown in SEQ ID NO:25.

In further embodiments, the antibody or antigen binding fragment binds the apple 3 domain of coagulation factor XI (FXI) and inhibits activation of FXI and/or Factor XIa-mediated activation of Factor IX.

In particular embodiments, the HC and LC variable regions may comprise 1, 2, 3, 4, 5, 6, 7, 8, 9, or 10 amino acid substitutions, additions, deletions, or combinations thereof.

In particular embodiments, the HC and LC constant domains may comprise 1, 2, 3, 4, 5, 6, 7, 8, 9, or 10 amino acid substitutions, additions, deletions, or combinations thereof.

In particular aspects, the constant domain may comprise a C-terminal lysine or may lack a C-terminal lysine.

In particular embodiments, the HC and LC variable regions may comprise 1, 2, 3, 4, 5, 6, 7, 8, 9, or 10 amino acid substitutions, additions, deletions, or combinations thereof and the HC and LC constant domains may comprise 1, 2, 3, 4, 5, 6, 7, 8, 9, or 10 amino acid substitutions, additions, deletions, or combinations thereof. In particular aspects, the constant domain may comprise a C-terminal lysine or may lack a C-terminal lysine.

In further aspects or embodiments of the invention, the antibody further comprises a HC constant domain comprising the amino acid sequence shown in SEQ ID NO: 16, 17, 18, or 19 or a variant thereof comprising 1, 2, 3, 4, 5, 6, 7, 8, 9, or 10 amino acid substitutions, additions, deletions, or combinations thereof.

In further aspects or embodiments of the invention, the antibody further comprises a LC constant domain comprising the amino acid sequence shown in SEQ ID NO:20 or a variant thereof comprising 1, 2, 3, 4, 5, 6, 7, 8, 9, or 10 amino acid substitutions, additions, deletions, or combinations thereof.

In a further aspect or embodiment of the invention, the antibody or antigen binding fragment comprises (a) a heavy chain (HC) variable domain having the amino acid sequence shown in SEQ ID NO: 28 and a light chain (LC) variable domain having the amino acid sequence shown in SEQ ID NO:30; (b) a heavy chain (HC) variable domain having the amino acid sequence shown in SEQ ID NO: 29 and a light chain (LC) variable domain having the amino acid sequence shown in SEQ ID NO:30; (c) a heavy chain (HC) variable domain having the amino acid sequence shown in SEQ ID NO: 21 and a light chain (LC) variable domain having the amino acid sequence shown in SEQ ID NO:25; (d) a heavy chain (HC) variable domain having the amino acid sequence shown in SEQ ID NO:22 and a light chain (LC) variable domain having the amino acid sequence shown in SEQ ID NO:25; (e) a heavy chain (HC) variable domain having the amino acid sequence shown in SEQ ID NO:23 and a light chain (LC) variable domain having the amino acid sequence shown in SEQ ID NO:25; (f) a heavy chain (HC) variable domain having the amino acid sequence shown in SEQ ID NO: 24 and a light chain (LC) variable domain having the amino acid sequence shown in SEQ ID NO:25; (g) variant of (a), (b), (c), (d), (e), or (f) wherein the HC variable region framework comprises 1, 2, 3, 4, 5, 6, 7, 8, 9, or 10 amino acid substitutions, additions, deletions, or combinations thereof; or, (h) variant of (a), (b), (c), (d), (e), (f), or (g) wherein the LC variable region framework comprises 1, 2, 3, 4, 5, 6, 7, 8, 9, or 10 amino acid substitutions, additions, deletions, or combinations thereof.

The present invention further provides an antibody comprising (a) a heavy chain (HC) having a constant domain and a variable domain wherein the variable domain comprises a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3; (b) a heavy chain (HC) having a constant domain and a variable domain wherein the variable domain comprises a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:4; or (c) a heavy chain (HC) having a constant domain and a variable domain wherein the variable domain comprises a heavy chain-complementary determining region (HC-CDR) 1 having the amino acid sequence shown in SEQ ID NO:8, a HC-CDR 2 having the amino acid sequence shown in SEQ ID NO:9, and a HC-CDR 3 having the amino acid sequence shown in SEQ ID NO:10. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody comprises a heavy chain constant domain of the human IgG1, IgG2, IgG3, or IgG4 isotype. In further aspects, the constant domain may comprise 1, 2, 3, 4, 5, 6, 7, 8, 9, or 10 amino acid substitutions, additions, deletions, or combinations thereof as compared to the amino acid sequence of the native heavy chain constant domain for the human IgG1, IgG2, IgG3, or IgG4 isotype. In particular aspects, the constant domain may comprise a C-terminal lysine or may lack a C-terminal lysine.

In further aspects or embodiments of the invention, the antibody comprises a heavy chain constant domain of the human IgG1 or IgG4 isotype. In a further aspect, the heavy chain constant domain is of the IgG4 isotype and further includes a substitution of the serine residue at position 228 (EU numbering) with proline, which corresponds to position 108 of SEQ ID NO:16 or 17 (Serine at position 108).

In further aspects or embodiments of the invention, the antibody comprises a IgG4 heavy chain constant domain comprising the amino acid sequence shown in SEQ ID NO:16 or 17. In further aspects, the constant domain may comprise 1, 2, 3, 4, 5, 6, 7, 8, 9, or 10 amino acid substitutions, additions, deletions, or combinations thereof.

In further aspects or embodiments of the invention, the antibody comprises a IgG1 heavy chain constant domain comprising the amino acid sequence shown in SEQ ID NO:18 or 19. In further aspects, the constant domain may comprise 1, 2, 3, 4, 5, 6, 7, 8, 9, or 10 amino acid substitutions, additions, deletions, or combinations thereof.

The present invention further provides an antibody or antigen binding fragment comprising:
(a) a light chain (LC) having a constant domain and a variable domain wherein the variable domain comprises a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7; or
(b) a light chain (LC) having a constant domain and a variable domain wherein the variable domain comprises a light chain comprising a light chain-complementary determining region (LC-CDR) 1 having the amino acid sequence shown in SEQ ID NO:11, a LC-CDR 2 having the amino acid sequence shown in SEQ ID NO:12, and a LC-CDR 3 having the amino acid sequence shown in SEQ ID NO:13. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the light chain (LC) comprises a human kappa light chain or human lambda light chain or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In further aspects or embodiments of the invention, the antibody comprises a light chain constant domain comprising the amino acid sequence shown in SEQ ID NO:20.

In further aspects or embodiments of the invention, the antibody comprises a IgG4 heavy chain constant domain comprising the amino acid sequence shown in SEQ ID NO:16 or 17 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody comprises a IgG1 heavy chain constant domain comprising the amino acid sequence shown in SEQ ID NO:18 or 19 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

The present invention further provides an antibody or antigen binding fragment comprising:
(a) a heavy chain (HC) having a constant domain and a variable domain wherein the variable domain comprises a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3; and
(b) a light chain (LC) having a constant domain and a variable domain wherein the variable domain comprises a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the light chain comprises a human kappa light chain or human lambda light chain, or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In further aspects or embodiments of the invention, the antibody comprises a light chain constant domain comprising the amino acid sequence shown in SEQ ID NO:20.

In further aspects or embodiments of the invention, the antibody comprises an heavy chain constant domain of the IgG1, IgG2, IgG3, or IgG4 isotype or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype, wherein the antibody or antigen binding fragment binds the apple 3 domain of coagulation factor XI (FXI) and inhibits activation of FXI and/or Factor XIa-mediated activation of Factor IX. In further aspects, the constant domain may comprise a C-terminal lysine or may lack a C-terminal lysine.

In further aspects or embodiments of the invention, the antibody comprises a heavy chain constant domain of the human IgG1 or IgG4 isotype or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In a further aspect, the heavy chain constant domain is of the IgG4 isotype and further includes a substitution of the serine residue at position 228 (EU numbering) with proline, which corresponds to position 108 of SEQ ID NO:16 or 17 (Serine at position 108).

In further aspects or embodiments of the invention, the antibody comprises a IgG4 heavy chain constant domain comprising the amino acid sequence shown in SEQ ID NO:16 or 17 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody comprises a IgG1 heavy chain constant domain comprising the amino acid sequence shown in SEQ ID NO:18 or 19 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

The present invention further provides an antibody or antigen binding fragment comprising:
  (a) a heavy chain (HC) having a constant domain and a variable domain wherein the variable domain comprises a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:4; and
  (b) a light chain (LC) having a constant domain and a variable domain wherein the variable domain comprises a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the light chain comprises a human kappa light chain or human lambda light chain, or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In further aspects or embodiments of the invention, the antibody comprises a light chain constant domain comprising the amino acid sequence shown in SEQ ID NO:20.

In further aspects or embodiments of the invention, the antibody comprises an heavy chain constant domain of the IgG1, IgG2, IgG3, or IgG4 isotype or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype, wherein the antibody or antigen binding fragment binds the apple 3 domain of coagulation factor XI (FXI) and inhibits activation of FXI and/or Factor XIa-mediated activation of Factor IX. In further aspects, the constant domain may comprise a C-terminal lysine or may lack a C-terminal lysine.

In further aspects or embodiments of the invention, the antibody comprises a heavy chain constant domain of the human IgG1 or IgG4 isotype or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In a further aspect, the heavy chain constant domain is of the IgG4 isotype and further includes a substitution of the serine residue at position 228 (EU numbering) with proline, which corresponds to position 108 of SEQ ID NO:16 or 17 (Serine at position 108).

In further aspects or embodiments of the invention, the antibody comprises a IgG4 heavy chain constant domain comprising the amino acid sequence shown in SEQ ID NO:16 or 17 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody comprises a IgG1 heavy chain constant domain comprising the amino acid sequence shown in SEQ ID NO:18 or 19 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

The present invention further provides an antibody or antigen binding fragment comprising:
  (a) a heavy chain (HC) having a constant domain and a variable domain wherein the variable domain comprises a heavy chain-complementary determining region (HC-CDR) 1 having the amino acid sequence shown in SEQ ID NO:8, a HC-CDR 2 having the amino acid sequence shown in SEQ ID NO:9, and a HC-CDR 3 having the amino acid sequence shown in SEQ ID NO:10; and (b) a light chain (LC) having a constant domain and a variable domain wherein the variable domain comprises a light chain-complementary determining region (LC-CDR) 1 having the amino acid sequence shown in SEQ ID NO:11, a LC-CDR 2 having the amino acid sequence shown in SEQ ID NO:12, and a LC-CDR 3 having the amino acid sequence shown in SEQ ID NO:13. In further embodiments, the antibody or antigen binding fragment binds the apple 3 domain of coagulation factor XI (FXI) and inhibits activation of FXI and/or Factor XIa-mediated activation of Factor IX.

In further aspects or embodiments of the invention, the light chain comprises a human kappa light chain or human lambda light chain or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In further aspects or embodiments of the invention, the antibody comprises a light chain constant domain comprising the amino acid sequence shown in SEQ ID NO:20.

In further aspects or embodiments of the invention, the antibody comprises an heavy chain constant domain of the IgG1, IgG2, IgG3, or IgG4 isotype or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype, wherein the antibody or antigen binding fragment binds the apple 3 domain of coagulation factor XI (FXI) and inhibits activation of FXI and/or Factor XIa-mediated activation of Factor IX. In further aspects, the constant domain may comprise a C-terminal lysine or may lack a C-terminal lysine.

In further aspects or embodiments of the invention, the antibody comprises a heavy chain constant domain of the human IgG1 or IgG4 isotype or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX. In a further aspect, the heavy chain constant domain is of the IgG4 isotype and further includes a substitution of the serine residue at position 228 (EU numbering) with proline, which corresponds to position 108 of SEQ ID NO:16 or 17 (Serine at position 108).

In further aspects or embodiments of the invention, the antibody comprises a IgG4 heavy chain constant domain comprising the amino acid sequence shown in SEQ ID NO:16 or 17 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

In further aspects or embodiments of the invention, the antibody comprises a IgG1 heavy chain constant domain comprising the amino acid sequence shown in SEQ ID NO:18 or 19 or variant thereof comprising 1, 2, 3, 4, 5, 6, 7, 8, 9, or 10 amino acid substitutions, additions, deletions, or combinations thereof, wherein the antibody or antigen binding fragment binds the apple 3 domain of coagulation factor XI (FXI) and inhibits activation of FXI and/or Factor XIa-mediated activation of Factor IX.

In further aspects or embodiments of the invention, the present invention provides an antibody comprising: (a) a heavy chain (HC) having a constant domain and a variable domain wherein the variable domain comprises (i) an HC framework and heavy chain-complementary determining region (HC-CDR) 1 having the amino acid sequence shown in SEQ ID NO:8, an HC-CDR 2 having the amino acid sequence shown in SEQ ID NO:9, and an HC-CDR 3 having the amino acid sequence shown in SEQ ID NO:10; (ii) an HC framework and heavy chain-complementary determining region (HC-CDR) 1 having the amino acid sequence shown in SEQ ID NO:1, an HC-CDR 2 having the amino acid sequence shown in SEQ ID NO:2, and an HC-CDR 3 having the amino acid sequence shown in SEQ ID NO:3; (iii) an HC framework and heavy chain-complementary determining region (HC-CDR) 1 having the amino acid sequence shown in SEQ ID NO:1, an HC-CDR 2 having the amino acid sequence shown in SEQ ID NO:2, and an HC-CDR 3 having the amino acid sequence shown in SEQ ID NO:4; (iv) variant of (i), (ii), or (iii) wherein at least one of HC CDR 1, HC-CDR 2, or CDR 3 comprises 1, 2, or 3 amino acid substitutions, additions, deletions, or combinations thereof; or (v) variant of (i), (ii), (iii), or (iv) wherein the HC framework comprises 1, 2, 3, 4, 5, 6, 7, 8, 9, or 10 amino acid substitutions, additions, deletions, or combinations thereof; (b) a light chain (LC) having a constant domain and a variable domain wherein the variable domain comprises (i) an LC framework and light chain comprising a light chain-complementary determining region (LC-CDR) 1 having the amino acid sequence shown in SEQ ID NO:11, an LC-CDR 2 having the amino acid sequence shown in SEQ ID NO:12, and an LC-CDR 3 having the amino acid sequence shown in SEQ ID NO:13; (ii) an LC framework and light chain-complementary determining region (LC-CDR) 1 having the amino acid sequence shown in SEQ ID NO:5, an LC-CDR 2 having the amino acid sequence shown in SEQ ID NO:6, and an LC-CDR 3 having the amino acid sequence shown in SEQ ID NO:7; (iii) variant of (i) or (ii) wherein at least one of LC CDR 1, LC-CDR 2, or LC-CDR 3 comprises 1, 2, or 3 amino acid substitutions, additions, deletions, or combinations thereof; or (iv) variant of (i), (ii), or (iii) wherein the LC framework comprises 1, 2, 3, 4, 5, 6, 7, 8, 9, or 10 amino acid substitutions, additions, deletions, or combinations thereof; or (c) an HC from (a) and an LC from (b); wherein the antibody binds the apple 3 domain of coagulation factor XI (FXI) and inhibits activation of FXI and/or Factor XIa-mediated activation of Factor IX.

In further aspects or embodiments of the invention, the antibody of claim 18, wherein the HC constant domain comprises the amino acid sequence shown in SEQ ID NO:16, 17, 18, or 19.

In further aspects or embodiments of the invention, the antibody of claim 18 or 19, wherein the LC constant domain comprises the amino acid sequence shown in SEQ ID NO:20.

The present invention further provides an antibody comprising a heavy chain having the amino acid sequence shown in SEQ ID NO: 33 and a light chain having the amino acid sequence shown in SEQ ID NO: 26.

The present invention further provides an antibody comprising a heavy chain having the amino acid sequence shown in SEQ ID NO: 35 and a light chain having the amino acid sequence shown in SEQ ID NO: 26.

The present invention further provides an antibody comprising a heavy chain having the amino acid sequence shown in SEQ ID NO: 45 and a light chain having the amino acid sequence shown in SEQ ID NO: 26.

The present invention further provides an antibody comprising a heavy chain having the amino acid sequence shown in SEQ ID NO: 47 and a light chain having the amino acid sequence shown in SEQ ID NO: 26.

The present invention further provides an antibody comprising a heavy chain having the amino acid sequence shown in SEQ ID NO: 49 and a light chain having the amino acid sequence shown in SEQ ID NO: 26.

The present invention further provides an antibody comprising a heavy chain having the amino acid sequence shown in SEQ ID NO: 51 and a light chain having the amino acid sequence shown in SEQ ID NO: 26.

The present invention further provides an antibody comprising a heavy chain having the amino acid sequence shown in SEQ ID NO: 59 and a light chain having the amino acid sequence shown in SEQ ID NO: 26.

The present invention further provides an antibody comprising a heavy chain having the amino acid sequence shown in SEQ ID NO: 61 and a light chain having the amino acid sequence shown in SEQ ID NO: 26.

The present invention further provides an antibody comprising a heavy chain having the amino acid sequence shown in SEQ ID NO: 63 and a light chain having the amino acid sequence shown in SEQ ID NO: 26.

The present invention further provides an antibody comprising a heavy chain having the amino acid sequence shown in SEQ ID NO: 69 and a light chain having the amino acid sequence shown in SEQ ID NO: 26.

The present invention further provides an antibody comprising a heavy chain having the amino acid sequence shown in SEQ ID NO: 33 and a light chain having the amino acid sequence shown in SEQ ID NO: 26.

The present invention further provides an antibody comprising a heavy chain having the amino acid sequence shown in SEQ ID NO: 71 and a light chain having the amino acid sequence shown in SEQ ID NO: 26.

The present invention further provides an antibody comprising a heavy chain having the amino acid sequence shown in SEQ ID NO: 73 and a light chain having the amino acid sequence shown in SEQ ID NO: 26.

The present invention further provides an antibody comprising a heavy chain having the amino acid sequence shown in SEQ ID NO: 75 and a light chain having the amino acid sequence shown in SEQ ID NO: 26.

The present invention further provides an antibody comprising a heavy chain having the amino acid sequence shown in SEQ ID NO: 39 and a light chain having the amino acid sequence shown in SEQ ID NO: 31.

The present invention further provides an antibody comprising a heavy chain having the amino acid sequence shown in SEQ ID NO: 41 and a light chain having the amino acid sequence shown in SEQ ID NO: 31.

The present invention further provides an antibody comprising a heavy chain having the amino acid sequence shown in SEQ ID NO: 43 and a light chain having the amino acid sequence shown in SEQ ID NO: 31.

The present invention further provides an antibody comprising a heavy chain having the amino acid sequence shown in SEQ ID NO: 53 and a light chain having the amino acid sequence shown in SEQ ID NO: 31.

The present invention further provides an antibody comprising a heavy chain having the amino acid sequence shown in SEQ ID NO: 55 and a light chain having the amino acid sequence shown in SEQ ID NO: 31.

The present invention further provides an antibody comprising a heavy chain having the amino acid sequence shown in SEQ ID NO: 57 and a light chain having the amino acid sequence shown in SEQ ID NO: 31.

The present invention further provides an antibody comprising a heavy chain having the amino acid sequence shown in SEQ ID NO: 65 and a light chain having the amino acid sequence shown in SEQ ID NO: 31.

The present invention further provides an antibody comprising a heavy chain having the amino acid sequence shown in SEQ ID NO: 67 and a light chain having the amino acid sequence shown in SEQ ID NO: 31.

The present invention further provides an antibody comprising a heavy chain having the amino acid sequence shown in SEQ ID NO: 69 and a light chain having the amino acid sequence shown in SEQ ID NO: 31.

The present invention further provides an antibody comprising a heavy chain having the amino acid sequence shown in SEQ ID NO: 77 and a light chain having the amino acid sequence shown in SEQ ID NO: 31.

The present invention further provides an antibody comprising a heavy chain having the amino acid sequence shown in SEQ ID NO: 79 and a light chain having the amino acid sequence shown in SEQ ID NO: 31.

The present invention further provides an antibody or antigen binding fragment that cross-blocks or competes with the binding of an antibody comprising a heavy chain having the amino acid sequence shown in SEQ ID NO: 33, 35, 37, 45, 47, 49, 51, 59, 61, 63, 69, 71, 73, or 75 and a light chain having the amino acid sequence shown in SEQ ID NO: 26; or an antibody comprising a heavy chain having the amino acid sequence shown in SEQ ID NO:39, 41, 43, 53, 55, 57, 65, 67, 69, 77, or 79 and a light chain having the amino acid sequence shown in SEQ ID NO:31 with the proviso that the antibody or antigen binding fragment does not comprise murine or rat amino acid sequences.

In a further embodiment, the antibody or antigen binding fragment does not comprise non-human amino acid sequences.

In a further embodiment, the antibody comprises (i) a human IgG1 constant domain or variant or modified derivative thereof or (ii) a human IgG4 constant domain or variant or modified derivative thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG4 constant domain is a variant that comprises at least a substitution of the serine at position 228 (EU numbering) or position 108 as shown herein with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides a human antibody or antigen binding fragment that cross-blocks or competes with the binding of an antibody comprising a heavy chain having the amino acid sequence shown in SEQ ID NO: 33, 35, 37, 45, 47, 49, 51, 59, 61, 63, 69, 71, 73, or 75 and a light chain having the amino acid sequence shown in SEQ ID NO: 26; or an antibody comprising a heavy chain having the amino acid sequence shown in SEQ ID NO:39, 41, 43, 53, 55, 57, 65, 67, 69, 77, or 79 and a light chain having the amino acid sequence shown in SEQ ID NO:31.

In a further embodiment, the antibody or antigen binding fragment does not comprise non-human amino acid sequences.

In a further embodiment, the antibody comprises (i) a human IgG1 constant domain or variant or modified derivative thereof or (ii) a human IgG4 constant domain or variant or modified derivative thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG4 constant domain is a variant that comprises at least a substitution of the serine at position 228 (EU numbering) or position 108 as shown herein with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides an antibody or antigen binding fragment that binds to an epitope on coagulation factor XI (FXI) comprising the amino acid sequence DIFPNTVF (SEQ ID NO:82) and amino acid sequence PSTRIKKSKALSG (SEQ ID NO:83) with the proviso that the antibody or antigen binding fragment does not comprise murine or rat amino acid sequences. In particular embodiments, the binding to the epitope is determined by hydrogen deuterium exchange mass spectrometry.

In a further embodiment, the antibody or antigen binding fragment does not comprise non-human amino acid sequences.

In a further embodiment, the antibody comprises (i) a human IgG1 constant domain or variant or modified derivative thereof or (ii) a human IgG4 constant domain or variant or modified derivative thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, or 4 amino acid substitutions, additions, deletions, or combinations thereof.

In a further embodiment, the IgG4 constant domain is a variant that comprises at least a substitution of the serine at position 228 (EU numbering) or position 108 as shown herein with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides a human antibody or antigen binding fragment that binds to an epitope on coagulation factor XI (FXI) comprising the amino acid sequence DIFPNTVF (SEQ ID NO:82) and amino acid sequence PSTRIKKSKALSG (SEQ ID NO:83) with the proviso that the antibody comprises (i) a human IgG1 constant domain or variant or modified derivative thereof or (ii) a human IgG4 constant domain or variant or modified derivative thereof. In particular embodiments, the binding to the epitope is determined by hydrogen deuterium exchange mass spectrometry.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG4 constant domain is a variant that comprises at least a substitution of the serine at position 228 (EU numbering) or position 108 as shown herein with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides an isolated nucleic acid molecule encoding the light chain variable domain or the heavy chain variable domain of any one of the aforementioned antibodies or antigen binding fragments.

The present invention further provides a humanized antibody or antigen binding fragment that binds to an epitope on coagulation factor XI (FXI) comprising the amino acid sequence DIFPNTVF (SEQ ID NO:82) and amino acid sequence PSTRIKKSKALSG (SEQ ID NO:83) with the proviso that the antibody comprises (i) a human IgG1 constant domain or variant or modified derivative thereof or (ii) a human IgG4 constant domain or variant or modified derivative thereof. In particular embodiments, the binding to the epitope is determined by hydrogen deuterium exchange mass spectrometry.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG4 constant domain is a variant that comprises at least a substitution of the serine at position 228 (EU numbering) or position 108 as shown herein with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides an isolated nucleic acid molecule encoding the light chain variable domain or the heavy chain variable domain of any one of the aforementioned antibodies or antigen binding fragments.

The present invention further provides a composition comprising the antibody or antigen binding fragment of any one of the aforementioned antibodies or antigen binding fragments and a pharmaceutically acceptable carrier or diluent.

The present invention further provides a method of treating a thromboembolic disorder or disease in a subject comprising administering to the subject an effective amount of the antibody or antigen binding fragment of any one of the aforementioned antibodies or antigen binding fragments.

The present invention further provides a method of treating a thromboembolic disorder or disease in a subject comprising administering to a subject in need thereof an effective amount of the antibody or antigen binding fragments of any one of the aforementioned antibodies or antigen binding fragments.

The present invention further provides for the use of an antibody of any one of the aforementioned antibodies or antigen binding fragments for the manufacture of a medicament for treating a thromboembolic disorder or disease.

The present invention further provides an antibody of any one of the aforementioned antibodies or antigen binding fragments for the treatment of a thromboembolic disorder or disease.

The present invention further provides a method for producing an antibody or antigen binding fragment comprising (i) a heavy chain having a constant domain and a variable domain wherein the variable domain comprises a heavy chain comprising a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3 or 4; and (ii) a light chain having a constant domain and a variable domain wherein the variable domain comprises a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7, the method comprising providing a host cell comprising a nucleic acid molecule encoding the heavy chain and a nucleic acid molecule encoding the light chain; and cultivating the host cell under conditions and a time sufficient to produce the antibody or antigen binding fragment.

In further aspects or embodiments of the invention the antibody comprises a heavy chain constant domain of the IgG1, IgG2, IgG3, or IgG4 isotype.

In further aspects or embodiments of the invention the antibody comprises a heavy chain constant domain of the IgG4 isotype.

In further aspects or embodiments of the invention the antibody comprises a heavy chain constant domain comprising the amino acid sequence shown in SEQ ID NO: 16, 17, 18, or 19.

In further aspects or embodiments of the invention, the light chain comprises a human kappa light chain or human lambda light chain.

In further aspects or embodiments of the invention, the antibody comprises a light chain constant domain comprising the amino acid sequence shown in SEQ ID NO:20.

In further aspects or embodiments of the invention, the host cell is a Chinese hamster ovary cell or a human embryo kidney 293 cell.

In further aspects or embodiments of the invention, the host cell is a yeast or filamentous fungus cell.

The present invention further provides a method for producing an antibody or antigen binding fragment comprising (i) a heavy chain having a constant domain and a variable domain wherein the variable domain comprises a heavy chain comprising a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3 or 4; and (ii) a light chain having a constant domain and a variable domain wherein the variable domain comprises a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7, the method comprising providing a host cell comprising a nucleic acid molecule encoding the heavy chain and a nucleic acid molecule encoding the light chain; and cultivating the host cell under conditions and a time sufficient to produce the antibody or antigen binding fragment.

In further aspects or embodiments of the invention the antibody comprises a heavy chain constant domain of the IgG1, IgG2, IgG3, or IgG4 isotype.

In further aspects or embodiments of the invention the antibody comprises a heavy chain constant domain of the IgG4 isotype.

In further aspects or embodiments of the invention the antibody comprises a heavy chain constant domain comprising the amino acid sequence shown in SEQ ID NO:16, 17, 18, or 19.

In further aspects or embodiments of the invention, the light chain comprises a human kappa light chain or human lambda light chain.

In further aspects or embodiments of the invention, the antibody comprises a light chain constant domain comprising the amino acid sequence shown in SEQ ID NO:20.

In further aspects or embodiments of the invention, the host cell is a Chinese hamster ovary cell or a human embryo kidney 293 cell.

In further aspects or embodiments of the invention, the host cell is a yeast or filamentous fungus cell.

A method for producing an antibody or antigen binding fragment comprising (i) a heavy chain variable domain comprising a heavy chain-complementary determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3 or 4 or an HC-CDR 1 having the amino acid sequence shown in SEQ ID NO:8, an HC-CDR 2 having the amino acid sequence shown in SEQ ID NO:9, and an HC-CDR 3 having the amino acid sequence shown in SEQ ID NO:10; and (ii) a light chain variable domain comprising a light chain-complementary determining region (LC-CDR) 1 having the amino acid sequence shown in SEQ ID NO:5, a LC-CDR 2 having the amino acid sequence shown in SEQ ID NO:6, and a LC-CDR 3 having the amino acid sequence shown in SEQ ID NO:7 or an LC-CDR 1 having the amino acid sequence shown in SEQ ID NO:11, an LC-CDR 2 having the amino acid sequence shown in SEQ ID NO:12, and an LC-CDR 3 having the amino acid sequence shown in SEQ ID NO:13, the method comprising: providing a host cell comprising a nucleic acid molecule encoding the heavy chain and a nucleic acid molecule encoding the light chain; and cultivating the host cell under conditions and a time sufficient to produce the antibody or antigen binding fragment.

In further aspects or embodiments of the invention the antibody comprises a heavy chain constant domain of the IgG1, IgG2, IgG3, or IgG4 isotype.

In further aspects or embodiments of the invention the antibody comprises a heavy chain constant domain of the IgG4 isotype.

In further aspects or embodiments of the invention the antibody comprises a heavy chain constant domain comprising the amino acid sequence shown in SEQ ID NO:16, 17, 18, or 19.

In further aspects or embodiments of the invention, the light chain comprises a human kappa light chain or human lambda light chain.

In further aspects or embodiments of the invention, the antibody comprises a light chain constant domain comprising the amino acid sequence shown in SEQ ID NO:20.

In further aspects or embodiments of the invention, the host cell is a Chinese hamster ovary cell or a human embryo kidney 293 cell.

In further aspects or embodiments of the invention, the host cell is a yeast or filamentous fungus cell.

The present invention further provides a composition comprising any one of the aforementioned antibodies and a pharmaceutically acceptable carrier. In particular embodiments, the composition comprises a mixture of antibodies comprising a heavy chain having a C-terminal lysine and antibodies comprising a heavy chain lacking a C-terminal lysine. In particular embodiments, the composition comprises an antibody disclosed herein wherein the predominant antibody form comprises a heavy chain having a C-terminal lysine. In particular embodiments, the composition comprises an antibody disclosed herein wherein the predominant antibody form comprises a heavy chain lacking a C-terminal lysine. In particular embodiments, the composition comprises an antibody disclosed herein wherein about 100% of the antibodies in the composition comprise a heavy chain lacking a C-terminal lysine.

Definitions

As used herein, "antibody" refers both to an entire immunoglobulin, including recombinantly produced forms and includes any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, biparatopic antibodies, and chimeric antibodies. "Parental antibodies" are antibodies obtained by exposure of an immune system to an antigen prior to modification of the antibodies for an intended use, such as humanization of an antibody for use as a human therapeutic antibody.

An "antibody" refers, in one embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The heavy chain of an antibody may or may not contain a terminal lysine (K), or a terminal glycine and lysine (GK). Thus, in particular embodiments of the antibodies herein comprising a heavy chain constant region amino acid sequence shown herein lacking a terminal lysine but terminating with a glycine residue further include embodiments in which the terminal glycine residue is also lacking. This is because the terminal lysine and sometimes glycine and lysine together are cleaved during expression of the antibody.

As used herein, "antigen binding fragment" refers to fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; single-chain antibody molecules, e.g., sc-Fv; nanobodies and multispecific antibodies formed from antibody fragments.

As used herein, a "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

As used herein, a "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule. As used herein, a "F(ab')$_2$ fragment" contains two light chains and two heavy chains containing the $V_H$ domain and a portion of the constant region between the $C_H1$ and $C_H2$ domains, such that an interchain disulfide bond is formed between the two heavy chains. An F(ab')$_2$ fragment thus is composed of two Fab' fragments that are held together by a disulfide bond between the two heavy chains. An "F(ab')$_2$ fragment" can be the product of pepsin cleavage of an antibody.

As used herein, an "Fv region" comprises the variable regions from both the heavy and light chains, but lacks the constant regions.

These and other potential constructs are described at Chan & Carter (2010) Nat. Rev. Immunol. 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, an "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

As used herein, a "diabody" refers to a small antibody fragment with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementarity domains of another chain and create two antigen-binding sites. Diabodies are described more fully in, e.g., EP 404, 097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, a "bispecific antibody" is an artificial hybrid antibody having two different heavy/light chain pairs and thus two different binding sites. For example, a bispecific antibody may comprise a first heavy/light chain pair comprising one heavy and one light chain of a first antibody comprising at least the six CDRs of antibody αFXI-13654p, αFXI-13716p, or αFXI-13716 or embodiments wherein one or more of the six CDRs has one, two, or three amino acid substitutions, additions, deletions, or combinations thereof along with a second heavy/light chain pair comprising one heavy and one light chain of a second antibody having specificity for an antigen of interest other than FXI. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

As used herein, "isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

As used herein, a "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

As used herein, a "chimeric antibody" is an antibody having the variable domain from a first antibody and the constant domain from a second antibody wherein (i) the first and second antibodies are from different species (U.S. Pat. No. 4,816,567; and Morrison et al., (1984) Proc. Natl. Acad. Sci. USA 81: 6851-6855) or (ii) the first and second antibodies are from different isotypes, e.g., variable domain from an IgG1 antibody and the constant domains from an IgG4 antibody, for example αFXI-13465p-IgG4 (S228P). In one aspect, the variable domains are obtained from a human antibody (the "parental antibody"), and the constant domain sequences are obtained from a non-human antibody (e.g., mouse, rat, dog, monkey, gorilla, horse). In another aspect, the variable domains are obtained from a non-human antibody (the "parental antibody")(e.g., mouse, rat, dog, monkey, gorilla, horse), and the constant domain sequences are obtained from a human antibody. In a further aspect, the variable domains are obtained from a human IgG1 antibody (the "parental antibody"), and the constant domain sequences are obtained from human IgG4 antibody.

As used herein, a "humanized antibody" refers to forms of antibodies that contain sequences from both human and non-human (e.g., murine, rat) antibodies. In general, the humanized antibody will comprise all of at least one, and typically two, variable domains, in which the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

As used herein, a "fully human antibody" refers to an antibody that comprises human immunoglobulin amino acid sequences or variant sequences thereof comprising mutations introduced recombinantly to provide a fully human antibody with modified function or efficacy compared to the antibody lacking said mutations. A fully human antibody does not comprise non-human immunoglobulin amino acid sequences, e.g., constant domains and variable domains, including CDRs comprise human sequences apart from that generated from the mutations discussed above. A fully human antibody may include amino acid sequences of antibodies or immunoglobulins obtained from a fully human antibody library where diversity in the library is generated in silico (See for example, U.S. Pat. No. 8,877,688 or 8,691, 730). A fully human antibody includes such antibodies produced in a non-human organism, for example, a fully human antibody may contain murine carbohydrate chains if produced in a mouse, in a mouse cell, or in a hybridoma derived from a mouse cell. Similarly, "mouse or murine antibody" refers to an antibody that comprises mouse or murine immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

As used herein, "non-human amino acid sequences" with respect to antibodies or immunoglobulins refers to an amino acid sequence that is characteristic of the amino acid sequence of a non-human mammal. The term does not include amino acid sequences of antibodies or immunoglobulins obtained from a fully human antibody library where diversity in the library is generated in silico (See for example, U.S. Pat. No. 8,877,688 or 8,691,730).

As used herein, "effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) *Nature* 342:878-883.

As used herein, "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure).

As used herein, "framework" or "FR" residues refers to those variable domain residues other than the hypervariable region residues defined herein as CDR residues.

As used herein, "conservatively modified variants" or "conservative substitution" refers to substitutions of amino acids with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in the table below.

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the term "epitope" or "antigenic determinant" refers to a site on an antigen (e.g., FXI) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides (e.g., from FXI) are tested for reactivity with a given antibody (e.g., anti-FXI antibody). Methods of determining spatial conformation of epitopes include techniques in the art and those described herein, for example, x-ray crystallography, 2-dimensional nuclear magnetic resonance, and HDX-MS (see, e.g., Epitope Mapping Protocols in Methods in Molecular Biology, Vol. 66, G. E. Morris, Ed. (1996)).

The term "epitope mapping" refers to the process of identification of the molecular determinants on the antigen involved in antibody-antigen recognition.

The term "binds to the same epitope" with reference to two or more antibodies means that the antibodies bind to the same segment of amino acid residues, as determined by a given method. Techniques for determining whether antibodies bind to the "same epitope on FXI" with the antibodies described herein include, for example, epitope mapping methods, such as, x-ray analyses of crystals of antigen: antibody complexes, which provides atomic resolution of the epitope, and hydrogen/deuterium exchange mass spectrometry (HDX-MS). Other methods that monitor the binding of the antibody to antigen fragments (e.g. proteolytic fragments) or to mutated variations of the antigen where loss of binding due to a modification of an amino acid residue within the antigen sequence is often considered an indication of an epitope component (e.g. alanine scanning mutagenesis—Cunningham & Wells (1985) Science 244:1081). In addition, computational combinatorial methods for epitope mapping can also be used. These methods rely on the ability of the antibody of interest to affinity isolate specific short peptides from combinatorial phage display peptide libraries.

Antibodies that "compete with another antibody for binding to a target such as FXI" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, "specifically binds" refers, with respect to an antigen or molecule such as FXI, to the preferential association of an antibody or other ligand, in whole or part, with FXI and not to other molecules, particularly molecules found in human blood or serum. Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, in particular embodiments a $K_D$ of $10^{-8}$ M or less, or $5 \times 10^{-9}$ M or less, or between $10^{-8}$ M and $10^{-11}$ M or less, but does not bind with high affinity to unrelated antigens. The kinetics of binding may be determined by Surface Plasmon Resonance as described in Example 1 herein.

An antigen is "substantially identical" to a given antigen if it exhibits a high degree of amino acid sequence identity to the given antigen, for example, if it exhibits at least 80%, at least 90%, at least 95%, at least 97%, or at least 99% or greater amino acid sequence identity to the amino acid sequence of the given antigen. By way of example, an antibody that binds specifically to human FXI may also cross-react with FXI from certain non-human primate species (e.g., cynomolgus monkey), but may not cross-react with FXI from other species, or with an antigen other than FXI.

As used herein, "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

As used herein, "treat" or "treating" means to administer a therapeutic agent, such as a composition containing any of the antibodies or antigen binding fragments thereof of the present invention, internally or externally to a subject or patient having one or more disease symptoms, or being suspected of having a disease, for which the agent has therapeutic activity or prophylactic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a human or animal subject with a disorder, disease or symptom, or with the potential to develop such a disorder, disease or symptom.

As used herein, "treatment," as it applies to a human or veterinary subject, refers to therapeutic treatment, as well as diagnostic applications. "Treatment" as it applies to a human or veterinary subject, encompasses contact of the antibodies or antigen binding fragments of the present invention to a human or animal subject.

As used herein, "therapeutically effective amount" refers to a quantity of a specific substance sufficient to achieve a desired effect in a subject being treated. For instance, this may be the amount necessary to inhibit activation of FXI or the amount necessary to inhibit coagulation for at least 192 to 288 hours as determined in an aPTT assay. When administered to a subject, a dosage will generally be used that will achieve target tissue concentrations that have been shown to achieve a desired in vitro effect.

As used herein, "thrombosis" refers to the formation or presence of a clot (also called a "thrombus") inside a blood vessel, obstructing the flow of blood through the circulatory system. Thrombosis is usually caused by abnormalities in the composition of the blood, quality of the vessel wall and/or nature of the blood flow. The formation of a clot is often caused by an injury to the vessel wall (such as from trauma or infection) and by the slowing or stagnation of blood flow past the point of injury. In some cases, abnormalities in coagulation cause thrombosis.

As used herein, "without compromising hemostasis" means little or no detectable bleeding is observed in a subject or patient following administration of an antibody or antibody fragment disclosed herein to the subject or patient. In case of targeting Factor XI, inhibiting Factor XI conversion to Factor XIa or activation of Factor IX by Factor XIa inhibits coagulation and associated thrombosis without bleeding. In contrast, inhibiting Factor XI conversion or activity inhibits coagulation but also induces bleeding or increases the risk of bleeding.

BRIEF DESCRIPTION OF THE DRAWINGS

FIG. 1A and FIG. 1B show the coagulation cascade, FXI, FXI mAb, and four new oral anticoagulants (NOACs). FIG. 1A is a cartoon depicting FXI in the coagulation cascade (that is composed of the intrinsic and extrinsic pathways). A FXI-targeting mAb can exert functional neutralization via blocking FXI activation by XIIa and/or thrombin, or FXIa activity on FIX. The antibodies herein may exert dual blockade on FXIa-mediated activation of FIX, and FXI conversion to FXIa mediated by at least FXIIa. The four NOACs (rivaroxaban, apixaban, edoxaban, dabigatran) targeting either FXa or thrombin are shown. FIG. 1B shows the domain structure of FXI. FXI is a dimer composed of identical 80 kDa subunits, and each subunit starting from the N-terminus consists of the four apple domains (1, 2, 3, and 4) and a catalytic domain (CAT). The antibodies disclosed herein bind the apple 3 domain.

FIGS. 3A and 3B show a deuterium labeling difference heatmap of the FXI amino acid residues bound by anti-FXI antibodies αFXI-18611 IgG4 HC (S228P)(E1) (L105)/LC Kappa and αFXI-18623p IgG4 HC (S228P)(Q1)/LC Kappa, respectively.

FIGS. 4A, 4B, and 4C shows the amino acid sequence of the HC and LC domains of the αFXI 18611p and αFXI 18611 family antibodies. The Heavy Chain and Light Chain CDRs are identified as HC-CDR1, HC-CDR-2, HC-CDR3, LC-CDR1, LC-CDR2, and LC-CDR3, respectively.

FIGS. 5A and 5B show the amino acid sequence of the HC and LC domains of the αFXI 18623p family antibodies. The Heavy Chain and Light Chain CDRs are identified as HC-CDR1, HC-CDR-2, HC-CDR3, LC-CDR1, LC-CDR2, and LC-CDR3, respectively.

FIG. 14A, Clot weight measured after 2 consecutive AV shunts in the same animal. The animals were administered vehicle during the first shunt (Shunt #1), followed by the administration of the antibody (0.01-1.0 mg/kg IV) as shown during the second shunt (Shunt #2). Increasing doses of the antibody resulted in the formation of smaller clots. The percent inhibition of clot weight (FIG. 14B) and the percent change in aPTT (FIG. 14C) increased with increasing plasma concentration of the antibody. In contrast, PT (FIG. 14D) remained relatively unchanged at all concentrations of the antibody.

DETAILED DESCRIPTION OF THE INVENTION

Figure 2:
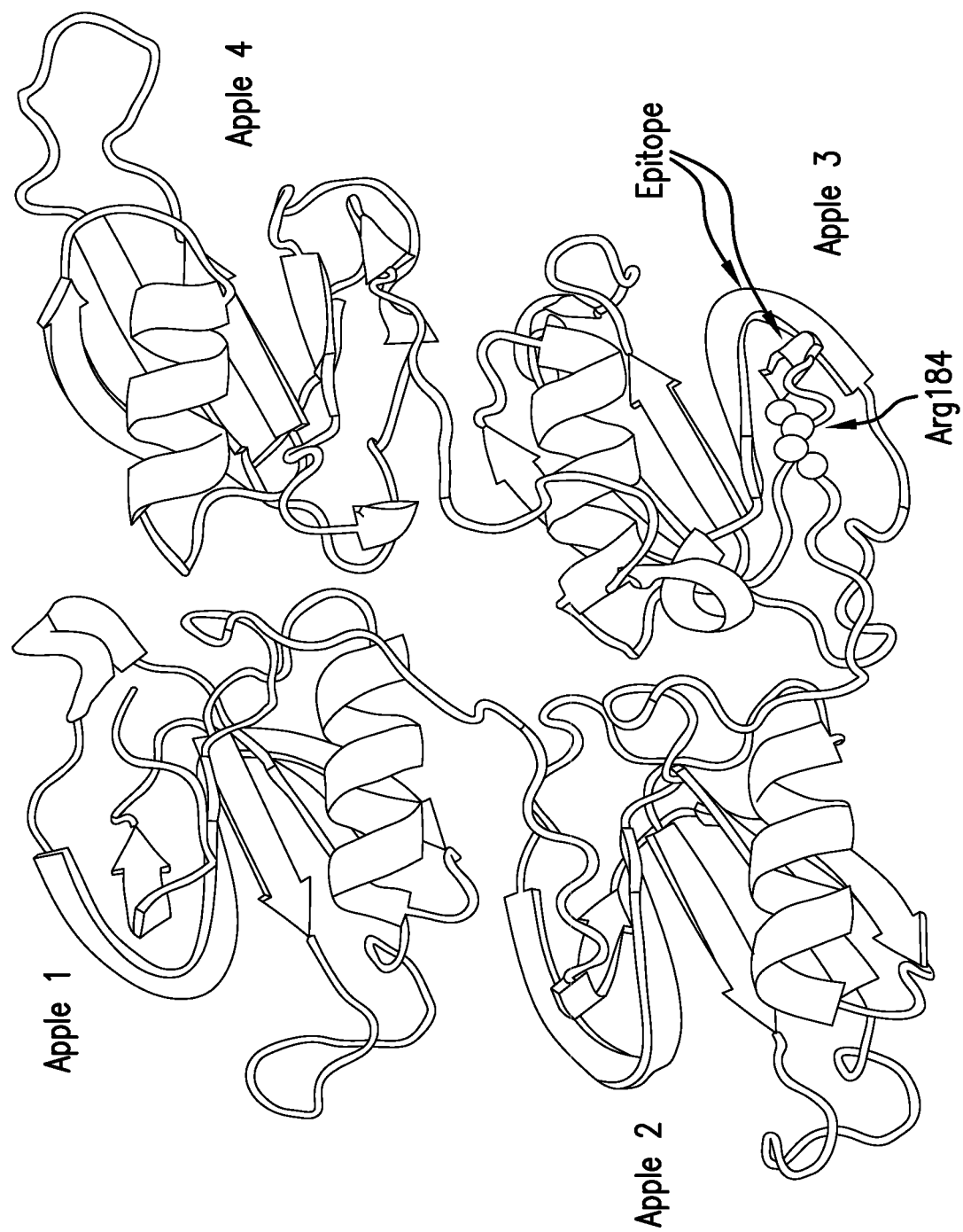
FIG. 2 shows the structure of Factor XI and the apple 3 domain with the epitope peptides protected from deuteration by αFXI-18611 and αFXI-18623p family anti-FXI antibodies identified. Arginine 184 residue, a critical residue in the FIX binding exocite is shown. The catalytic domain is not shown.
Figure 6:
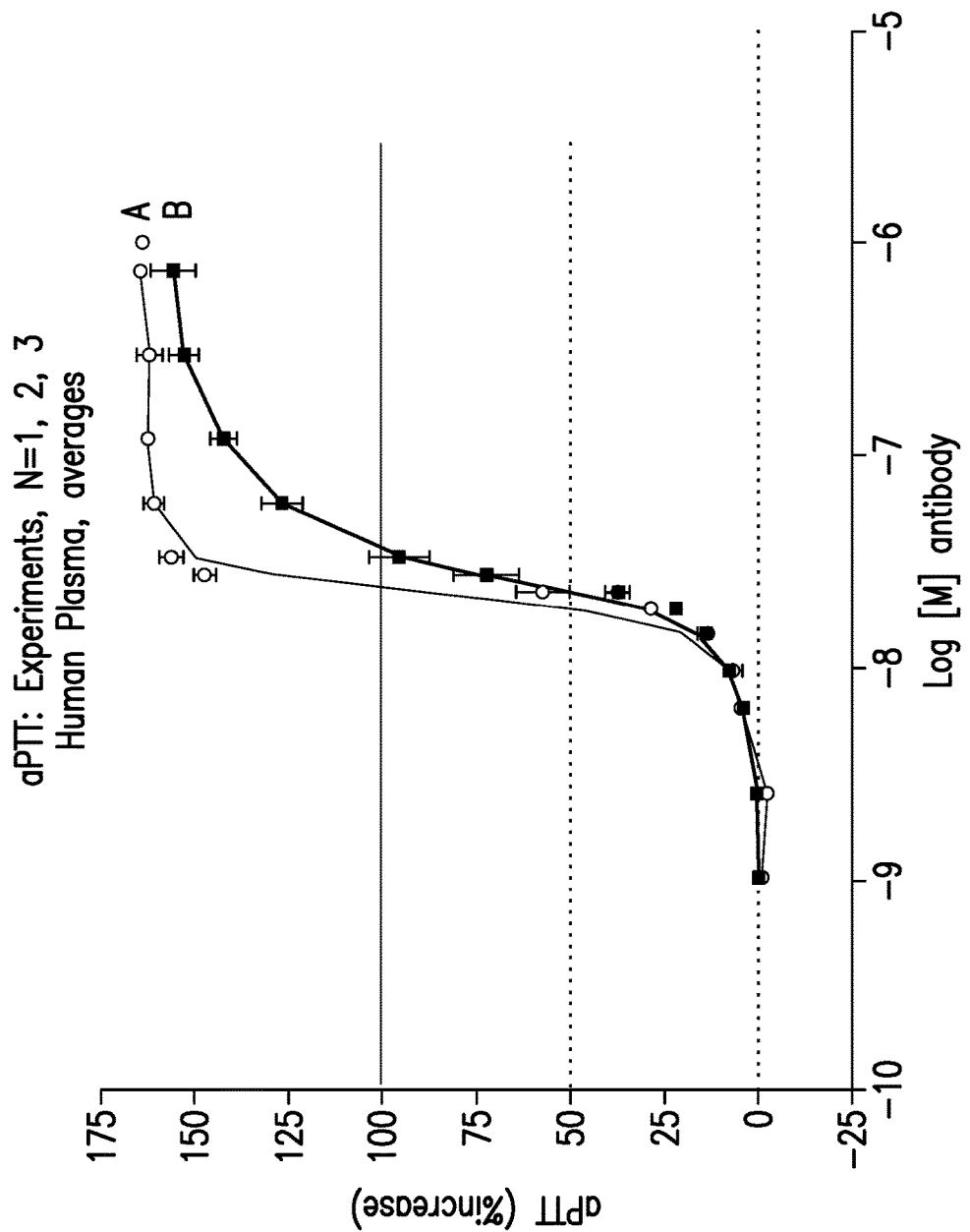
FIG. 6 shows the results of an activated Partial Thromboplastin Time (aPTT) assay of αFXI-18611 IgG4 HC (S228P)(E1)(L105)/LC kappa (A) and αFXI-18623p IgG4 HC (S228P)(Q1)/LC kappa (B) in human plasma, expressed as % increase over baseline.
Figure 7:
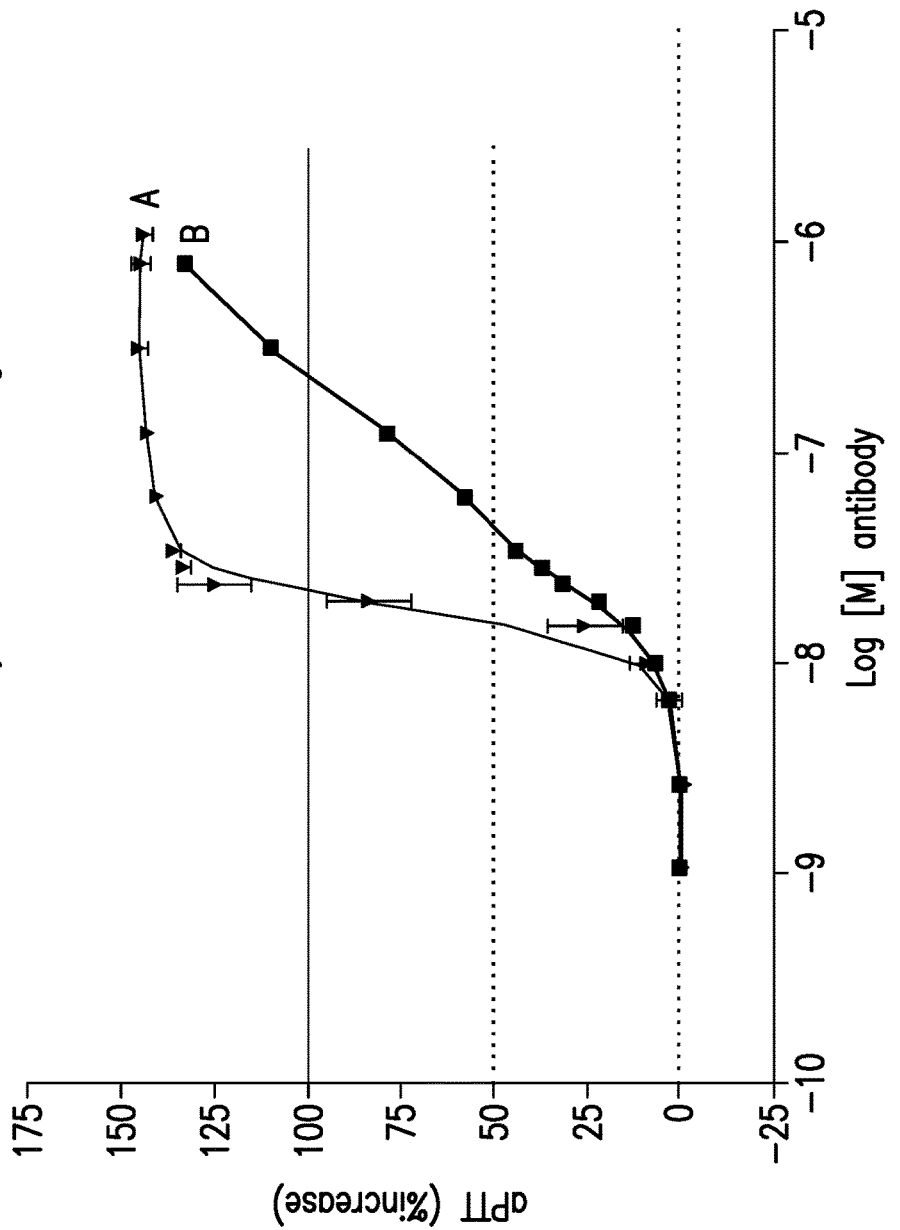
FIG. 7 shows the results of an activated Partial Thromboplastin Time (aPTT) assay of αFXI-18611 IgG4 HC (S228P)(E1)(L105)/LC kappa (A) and αFXI-18623p IgG4 HC (S228P)(Q1)/LC kappa (B) in cynomolgus monkey plasma, expressed as % increase over baseline.
Figure 8:
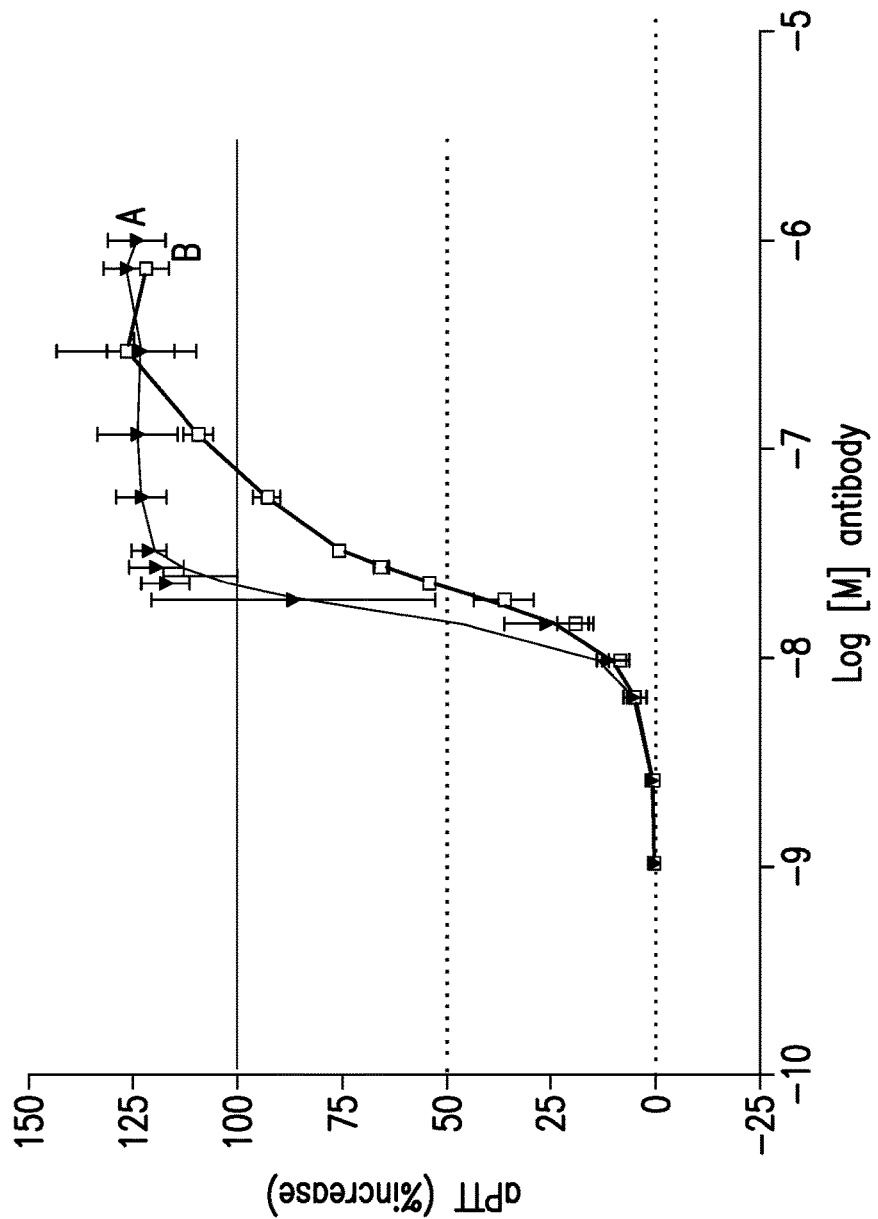
FIG. 8 shows the results of an activated Partial Thromboplastin Time (aPTT) assay of αFXI-18611 IgG4 HC (S228P)(E1)(L105)/LC kappa (A) and αFXI-18623p IgG4 HC (S228P)(Q1)/LC kappa (B) in rhesus monkey plasma, expressed as % increase over baseline.
Figure 9:
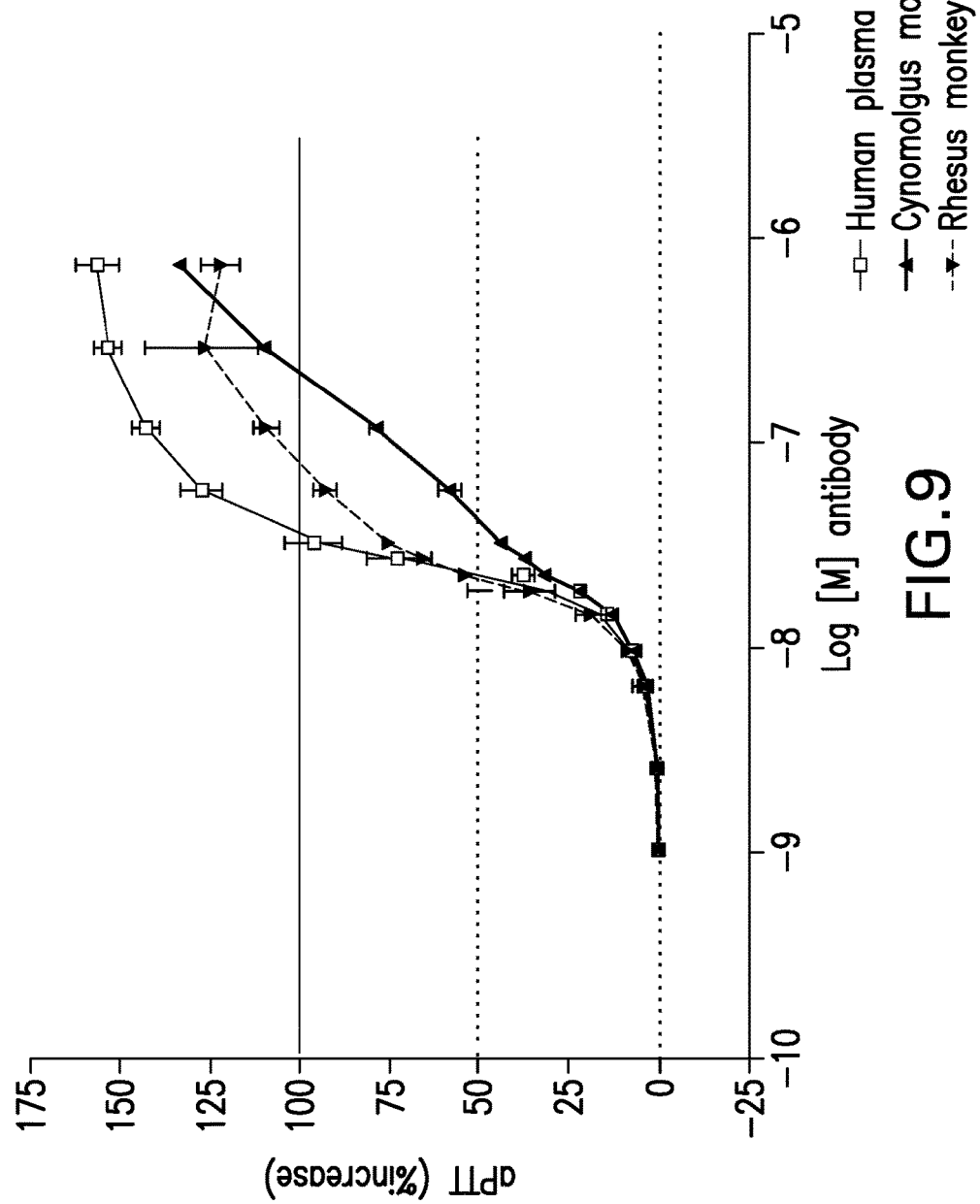
FIG. 9 shows a comparison of aPTT results for αFXI-18611 IgG4 HC (S228P)(E1)(L105)/LC kappa in human plasma, cynomolgus monkey, and rhesus monkey plasma expressed as % increase over baseline.
Figure 10:
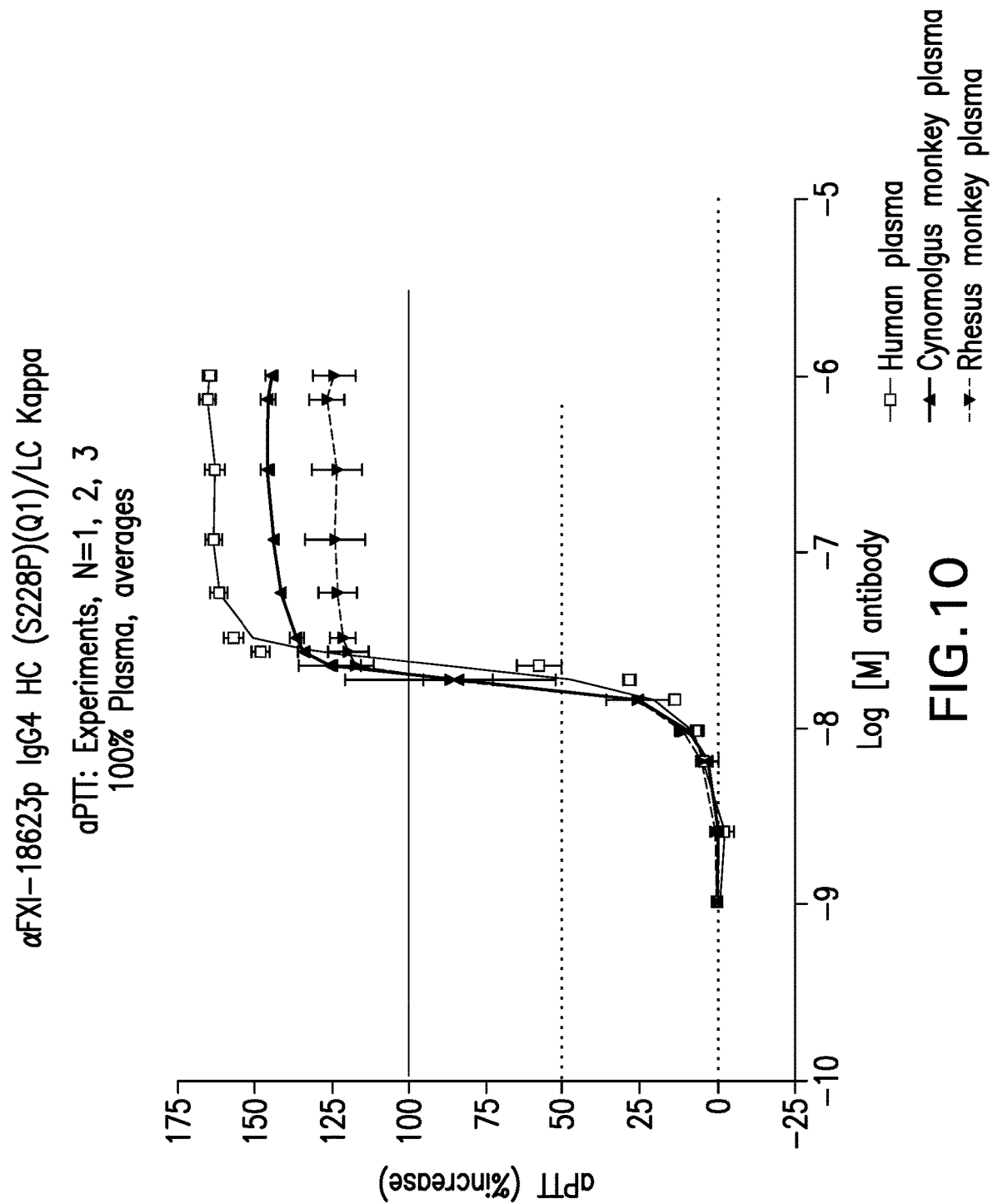
FIG. 10 shows a comparison of aPTT results for αFXI-18623p IgG4 HC (S228P)(Q1)/LC kappa in human plasma, cynomolgus monkey, and rhesus monkey plasma expressed as % increase over baseline.

The present invention provides anti-coagulation Factor XI antibodies that bind the apple 3 domain of coagulation Factor XI (FXI). These anti-FXI antibodies are inhibitors of FXI activation by Factor XIIa and are useful for inhibiting blood coagulation and associated thrombosis without compromising hemostasis (anti-thrombotic indications). For example, the anti-FXI antibodies may be used for treatment and prevention of venous thromboembolism (VTE), Stroke Prevention in Atrial Fibrillation (SPAF), or treatment and prevention of certain medical device-related thromboembolic disorders (e.g., stents, endovascular stent grafts, catheters (cardiac or venous), continuous flow ventricular assist devices (CF-LVADS), hemodialysis, cardiopulmonary bypass and Extracorporeal Membrane Oxygenation (ECMO), ventricular assist devices (VADS)). Therefore, the anti-FXI antibodies disclosed herein are useful in therapies for treating a thromboembolic disorder or disease in a patient or subject in need of such therapies.

FXI is a homodimeric serine protease having the domain structure shown in FIG. 1B and an integral component of the intrinsic pathway of the coagulation cascade. FXI zymogen can be cleaved by Factor XIIa to its activated form FXIa. FXIa then activates Factor IX and ultimately triggers thrombin generation and clot formation. The anti-FXI antibodies disclosed herein inhibit the conversion of FXI to FXIa (See FIG. 1A).

Anti-FXI antibody molecules were obtained from a fully human synthetic IgG1/kappa library displayed at the surface of engineered yeast strains. The library was screened with FXI or FXIa to identify antibodies capable of binding to human FXI at subnanomolar affinity to human and non-human primate (NHP) FXI and having no binding to human and NHP plasma kallikrein (a protein displaying 56% amino acid identity to FXI), or to other human coagulation cascade proteins (FII//IIa, FVII/VIIa, FIX/IXa, FX/Xa, and FXII/XIIa). Two antibodies were identified that had these properties: αFXI-18611p and αFXI-18623p. These antibodies are fully human antibodies comprising a human kappa (κ) light chain and a human IgG1 (γ1) isotype heavy chain. The antibodies selectively bind to an epitope of the FXI zymogen comprising SEQ ID NOs:82 and 83 located in the apple 3 domain of FXI. These antibodies also bind FXIa with comparable affinity to FXI zymogen.

Antibodies of the αFXI-18611p family comprise heavy chain (HC) complimentary determining regions (CDRs) 1, 2, and 3 having the amino acid sequences shown in SEQ ID NO:1, SEQ ID NO:2, and SEQ ID NO:3, respectively, and light chain (LC) CDRs 1, 2, and 3 having the amino acid sequences shown in SEQ ID NO:5, SEQ ID NO:6, and SEQ ID NO:7, respectively. αFXI-18611p family includes antibodies comprising a heavy chain (HC) variable domain comprising the amino acid sequence shown in SEQ ID NO:21 or 22 and a light chain (LC) variable domain comprising the amino acid sequence in SEQ ID NO:25.

Antibodies of the αFXI-18611 family comprise heavy chain (HC) complimentary determining regions (CDRs) 1, 2, and 3 having the amino acid sequences shown in SEQ ID NO:1, SEQ ID NO:2, and SEQ ID NO:4, respectively, and light chain (LC) CDRs 1, 2, and 3 having the amino acid sequences shown in SEQ ID NO:5, SEQ ID NO:6, and SEQ ID NO:7, respectively. αFXI-18611 family includes antibodies comprising a heavy chain (HC) variable domain comprising the amino acid sequence shown in SEQ ID NO:23 or 24 and a light chain (LC) variable domain comprising the amino acid sequence in SEQ ID NO:25.

Antibodies of the αFXI-18623p family comprise HC CDRs 1, 2, and 3 having the amino acid sequences shown in SEQ ID NO:8, SEQ ID NO:9, and SEQ ID NO:10, respectively, and LC CDRs 1, 2, and 3 having the amino acid sequences shown in SEQ ID NO:11, SEQ ID NO:12, and SEQ ID NO:13, respectively. αFXI-13716p family includes antibodies comprising a heavy chain (HC) variable domain comprising the amino acid sequence shown in SEQ ID NO:28 or 29 and a light chain (LC) variable domain comprising the amino acid sequence in SEQ ID NO:30. The antibodies of this family were obtained from a different germline than the former families.

The present invention further provides anti-FXI antibodies comprising at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and methods of using the antibodies for treating anti-thrombotic indications, for example SPAF.

In particular aspects, the anti-FXI antibodies comprise at least the HC variable domain of an anti-FXI antibody of the αFXI-18611p family, αFXI-18611 family, or αFXI-18623p family or a variant thereof wherein the HC variable domain comprises 1, 2, 3, 4, 5, 6, 7, 8, 9, or 10 amino acid substitutions, additions, deletions, or combinations thereof.

In particular aspects, the anti-FXI antibodies comprise at least the LC variable domain of an anti-FXI antibody of the αFXI-18611p family, αFXI-18611 family, or αFXI-18623p family or a variant thereof wherein the LC variable domain comprising 1, 2, 3, 4, 5, 6, 7, 8, 9, or 10 amino acid substitutions, additions, deletions, or combinations thereof.

In particular aspects, the anti-FXI antibodies comprise at least the HC variable domain of an anti-FXI antibody of the αFXI-18611p family, αFXI-18611 family, or αFXI-18623p family or a variant thereof wherein the HC variable domain comprising 1, 2, 3, 4, 5, 6, 7, 8, 9, or 10 amino acid substitutions, additions, deletions, or combinations thereof and the LC variable domain of an anti-FXI antibody of the αFXI-18611p family, αFXI-18611 family, or αFXI-18623 family or a variant thereof wherein the LC variable domain comprising 1, 2, 3, 4, 5, 6, 7, 8, 9, or 10 amino acid substitutions, additions, deletions, or combinations thereof.

In particular embodiments, the antibodies herein comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and further comprise a heavy chain (HC) that is of the human IgG1, IgG2, IgG3, or IgG4 isotype and the light chain (LC) may be of the kappa type or lambda type. In other embodiments, the antibodies comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and further may be of the IgM, IgD, IgA, or IgE class. In particular embodiments, the human IgG1, IgG2, IgG3, or IgG4 isotype may include 1, 2, 3, 4, 5, 6, 7, 8, 9, or 10 amino acid substitutions, additions, deletions, or combinations thereof.

In particular embodiments, the antibodies may comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and further comprise an HC constant domain that is of the IgG4 isotype. An IgG4 framework provides an antibody with little or no effector function. In a further aspect of the invention, the antibodies may comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and further comprise HC constant domain that is of the IgG4 isotype fused to an HC variable domain that is of the IgG1 isotype. In a further aspect of the invention, the antibodies may comprise at least the HC variable domain and LC variable domain of an anti-FXI antibody of the αFXI-18611p family, αFXI-18611 family, or αFXI-18623p family or variants thereof in which the HC and LC variable domains independently comprise 1, 2, 3, 4, 5, 6, 7, 8, 9, or 10 amino acid substitutions, additions, deletions, or combinations thereof and further comprise an HC constant domain that is of the IgG4 isotype. In a further aspect of the invention, the antibodies may comprise at least the HC variable domain and LC of an anti-FXI antibody of the αFXI-18611p family, αFXI-18611 family, or αFXI-18623p family or variants thereof in which the HC and LC independently comprise 1, 2, 3, 4, 5, 6, 7, 8, 9, or 10 amino acid substitutions, additions, deletions, or combinations thereof and further comprises an HC constant domain that is of the IgG4 isotype.

The antibodies of the present invention further includes, but are not limited to, monoclonal antibodies (including full length monoclonal antibodies), polyclonal antibodies, multispecific antibodies (e.g., bispecific antibodies), biparatopic antibodies, fully human antibodies, and chimeric antibodies.

In general, the amino acid sequence of the heavy chain of an antibody such as IgG1 or IgG4 has a lysine at the C-terminus of the heavy chain constant domain. In some instances, to improve the homogeneity of an antibody product, the antibody may be produced lacking a C-terminal lysine. The anti-FXI antibodies of the present invention include embodiments in which the C-terminal lysine is present and embodiments in which the C-terminal lysine is absent. For example, an IgG1 HC constant domain may have amino acid sequence shown in SEQ ID NO:18 or 19 and an IgG4 HC constant domain may have the amino acid sequence shown in SEQ ID NO:16 or 17.

In particular embodiments, the N-terminal amino acid of the HC may be a glutamine residue. In particular embodiments, the N-terminal amino acid of the HC may be a glutamic acid residue. In particular aspects, the N-terminal amino acid is modified to be a glutamic acid residue.

The present invention further provides anti-FXI antigen-binding fragments that comprise at least the six CDRs of an anti-FXI antibody of the αFXI-1861 ip family, αFXI-18611 family, or αFXI-18623p family or embodiments thereof wherein one or more of the six CDRs has one, two, or three amino acid substitutions, additions, deletions, or combinations thereof.

The present invention further provides anti-FXI Fab fragments that comprise at least the six CDRs of an anti-FXI antibody of the αFXI-1861 ip family, αFXI-18611 family, or αFXI-18623p family or embodiments thereof wherein one or more of the six CDRs has one, two, or three amino acid substitutions, additions, deletions, or combinations thereof.

The present invention further provides anti-FXI antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and antigen-binding fragments thereof which comprise an Fc region and methods of use thereof.

The present invention further provides anti-FXI Fab' fragments that comprise at least the six CDRs of an anti-FXI antibody of the αFXI-1861 ip family, αFXI-18611 family, or αFXI-18623p family or embodiments thereof wherein one or more of the six CDRs has one, two, or three amino acid substitutions, additions, deletions, or combinations thereof.

The present invention further provides anti-FXI F(ab')$_2$ that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

The present invention further provides anti-FXI Fv fragments that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

The present invention further provides anti-FXI scFv fragments that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

The present invention further provides anti-FXI domain antibodies that comprise at least the three HC CDRs or three LC CDRs of an anti-FXI antibody of the αFXI-18611p family, αFXI-18611 family, or αFXI-18623p family or embodiments thereof wherein one or more of the HC or LC CDRs has one, two, or three amino acid substitutions, additions, deletions, or combinations thereof. In an embodiment of the invention, the domain antibody is a single domain antibody or nanobody. In an embodiment of the invention, a domain antibody is a nanobody comprising at least the αFXI-18611p family, αFXI-18611 family, or αFXI-18623p family CDRs or embodiments wherein one or more of the CDRs has one, two, or three amino acid substitutions, additions, deletions, or combinations thereof.

The present invention further provides anti-FXI bivalent antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

The present invention further provides bispecific antibodies and antigen-binding fragments having a binding specificity for FXI and another antigen of interest and methods of use thereof.

Biparatopic antibodies are antibodies having binding specificity for different epitopes on the same antigen. The present invention further provides biparatopic antibodies having first heavy/light chain pair of a first antibody that comprises at least the six CDRs of an anti-FXI antibody of the αFXI-18611p family, αFXI-18611 family, or αFXI-18623p family or embodiments thereof wherein one or more of the CDRs has one, two, or three amino acid substitutions, additions, deletions, or combinations thereof and a second heavy/light chain pair of a second antibody having specificity for an FXI epitope which is different from the epitope recognized by the first heavy/light chain pair.

The present invention further provides anti-FXI antibodies and antigen-binding fragments thereof comprising a first heavy/light chain pair of an antibody that comprises at least the six CDRs of an antibody of the αFXI-18611p or αFXs-18611 family or embodiments thereof wherein one or more of the CDRs has one, two, or three amino acid substitutions, additions, deletions, or combinations thereof and a second heavy/light chain pair of an antibody that comprises at least the six CDRs of an antibody αFXI-18623p family or embodiments thereof wherein one or more of the CDRs has one, two, or three amino substitutions, additions, deletions, or combinations thereof.

The present invention further provides anti-FXI diabodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

An antibody that comprises at least the six CDRs of an anti-FXI antibody of the αFXI-18611p family, αFXI-18611 family, or αFXI-18623p family or embodiments thereof wherein one or more of the CDRs has one, two, or three amino acid substitutions, additions, deletions, or combinations thereof may be modified in some way such that it retains at least 10% of its FXI binding activity (when compared to the parental antibody, i.e., an antibody of the respective αFXI-18611p family, αFXI-18611 family, or αFXI-18623p family) when that activity is expressed on a molar basis. Preferably, an antibody or antigen-binding fragment of the invention retains at least 20%, 50%, 70%, 80%, 90%, 95% or 100% or more of the FXI binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention further provides isolated anti-FXI antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and antigen-binding fragments thereof and methods of use thereof as well as isolated polypeptide immunoglobulin chains thereof and isolated polynucleotides encoding such polypeptides and isolated vectors including such polynucleotides.

The present invention further provides monoclonal anti-FXI antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and antigen-binding fragments thereof as well as monoclonal compositions comprising a plurality of isolated monoclonal antibodies.

The present invention further provides anti-FXI chimeric antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof.

The present invention includes anti-FXI fully human antibodies that comprise at least the six CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and antigen-binding fragments thereof and methods of use thereof. In an embodiment of the invention, a fully human anti-FXI antibody or antigen-binding fragment thereof is the product of isolation from a transgenic animal, e.g., a mouse (e.g., a HUMAB mouse, see e.g., U.S. Pat. Nos. 5,545,806; 5,569,825; 5,625,126; 5,633,425; 5,661,016; 5,770,429; 5,789,650; 5,814,318; 5,874,299 and 5,877,397; and Harding, et al., (1995) Ann. NY Acad. Sci. 764:536 546; or a XENOMOUSE, see e.g., Green et al., 1999, J. Immunol. Methods 231:11-23), which has been genetically modified to have fully human immunoglobulin genes; or the product of isolation from a phage or virus which expresses the immunoglobulin chains of the anti-FXI fully human antibody or antigen-binding fragment thereof.

In some embodiments, different constant domains may be appended to $V_L$ and $V_H$ regions derived from the CDRs provided herein. For example, if a particular intended use of an antibody (or fragment) of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. The present invention includes anti-FXI antibodies and antigen-binding fragments thereof which comprise an IgG4 constant domain, e.g., antagonist human anti-FXI antibodies and fragments, and methods of use thereof. In one embodiment, the IgG4 constant domain can differ from the native human IgG4 constant domain (Swiss-Prot Accession No. P01861.1) at a position corresponding to position 228 in the EU system and position 241 in the KABAT system, wherein the native serine at position 108 (Ser108) of the HC constant domain is replaced with proline (Pro), in order to prevent a potential inter-chain disulfide bond between the cysteine at position 106 (Cys106) and the cysteine at position 109 (Cys109), which correspond to to positions Cys226 and Cys229 in the EU system and positions Cys239 and Cys242 in the KABAT system) that could interfere with proper intra-chain disulfide bond formation. See Angal et al. Mol. Imunol. 30:105 (1993); see also (Schuurman et. al., Mol. Immunol. 38: 1-8, (2001); SEQ ID NOs:14 and 41). In other instances, a modified IgG1 constant domain which has been modified to reduce effector function can be used, for example, the IgG1 isotype may include substitutions of IgG2 residues at positions 233-236 and IgG4 residues at positions 327, 330 and 331 to greatly reduce ADCC and CDC (Armour et al., Eur J Immunol. 29(8):2613-24 (1999); Shields et al., J Biol Chem. 276(9):6591-604(2001)). In another embodiment, the IgG HC is modified genetically to lack N-glycosylation of the asparagine (Asn) residue at around position 297. The consensus sequence for N-glycosylation is Asn-Xaa-Ser/Thr (wherein Xaa is any amino acid except Pro); in IgG1 the N-glycosylation consensus sequence is Asn-Ser-Thr. The modification may be achieved by replacing the codon for the Asn at position 297 in the nucleic acid molecule encoding the HC with a codon for another amino acid, for example Gln. Alternatively, the codon for Ser may be replaced with the codon for Pro or the codon for Thr may be replaced with any codon except the codon for Ser. Such modified IgG1 molecules have little or no detectable effector function. Alternatively, all three codons are modified.

In an embodiment of the invention, the anti-FXI antibodies comprising at least the six CDRs of an ani-FXb antibody of the αFXI-18611p family, αFXI-18611 family, or αFXI-18623p family or embodiments thereof wherein one or more of the six CDRs has one, two, or three amino acid substitutions, additions, deletions, or combinations thereof comprise a full tetrameric structure having two light chains and two heavy chains, including constant regions. The variable regions of each light/heavy chain pair form the antibody binding site. Thus, in general, an intact antibody has two binding sites. Except in bispecific antibodies, the two binding sites are, in general, the same.

In specific embodiments, the present invention provides the anti-FXI antibodies shown in the Table 1.

TABLE 1

| Family | Antibody | Heavy Chain (HC) SEQ ID NO: | Light Chain (LC) SEQ ID NO: |
|---|---|---|---|
| αFXI-18611p | αFXI-18611p IgG4 HC (S228P)(Q1)(M105)/LC kappa | 33 | 26 |
|  | αFXI-18611p IgG4 HC (S228P)(E1)(M105)/LC kappa | 35 | 26 |
|  | αFXI-18611p IgG1 HC (Q1)(M105)/LC kappa | 45 | 26 |
|  | αFXI-18611p IgG1 HC (E1)(M105)/LC kappa | 47 | 26 |
|  | αFXI-18611p IgG4 HC (S228P)(Q1)(M105)(K-)/LC kappa | 57 | 26 |
|  | αFXI-18611p IgG4 HC (S228P)(E1)(M105)(K-)/LC kappa | 59 | 26 |
|  | αFXI-18611p IgG1 HC (Q1)(M105)(K-)/LC kappa | 69 | 26 |
|  | αFXI-18611p IgG1 HC (E1)(M105)(K-)/LC kappa | 71 | 26 |
| αFXI-18611 | αFXI-18611 IgG4 HC (S228P)(Q1)(L105)/LC kappa | 37 | 26 |
|  | αFXI-18611 IgG4 HC (S228P)(E1)(L105)/LC kappa | 39 | 26 |
|  | αFXI-18611 IgG1 HC (Q1)(L105)/LC kappa | 49 | 26 |
|  | αFXI-18611 IgG1 HC (E1)(L105)/LC kappa | 51 | 26 |
|  | αFXI-18611 IgG4 HC (S228P)(Q1)(L105)(K-)/LC kappa | 61 | 26 |
|  | αFXI-18611 IgG4 HC (S228P)(E1)(L105)(K-)/LC kappa | 63 | 26 |
|  | αFXI-18611 IgG1 HC (Q1)(L105)(K-)/LC kappa | 73 | 26 |
|  | αFXI-18611 IgG1 HC (E1)(L105)(K-)/LC kappa | 75 | 26 |
| αFXI-18623p | αFXI-18623p IgG4 HC (S228P)(Q1)/LC kappa | 41 | 31 |
|  | αFXI-18623p IgG4 HC (S228P)(E1)/LC kappa | 43 | 31 |
|  | αFXI-18623p IgG1 HC (Q1)/LC kappa | 53 | 31 |
|  | αFXI-18623p IgG1 HC (E1)/LC kappa | 55 | 31 |
|  | αFXI-18623p IgG1 HC (S228P)(Q1)(K-)/LC kappa | 65 | 31 |
|  | αFXI-18623p IgG4 HC (S228P)(E1)(K-)/LC kappa | 67 | 31 |
|  | αFXI-18623p IgG1 HC (Q1)(K-)/LC kappa | 77 | 31 |
|  | αFXI-18623p IgG1 HC (E1)(K-)/LC kappa | 79 | 31 |

Epitope mapping by hydrogen-deuterium exchange mass spectrometry (HDX-MS) as described in Example 3 showed that the anti-FXI antibodies comprising the aforementioned HC and LC CDRs bind to a particular epitope on the apple 3 domain comprising SEQ ID NO:82 and SEQ ID NO:83.

Thus, the antibodies disclosed herein bind to the apple 3 domain of FXI and inhibit FXI activation by FXIIa and also behave as allosteric, competitive inhibitors of FIX activation by FXIa. Epitope mapping results suggesting the "footprint" of the αFXI-18623p family on Apple 3 overlaps with the FIX-binding exosite in FXIa.

Pharmaceutical Compositions and Administration

To prepare pharmaceutical or sterile compositions of the anti-FXI antibodies or binding fragment thereof, the antibody or antigen binding fragments thereof is admixed with a pharmaceutically acceptable carrier or excipient. See, e.g., Remington's Pharmaceutical Sciences and U.S. Pharmacopeia: National Formulary, Mack Publishing Company, Easton, PA (1984) and continuously updated on the Internet by the U.S. Pharmacopeial Convention (USP) 12601 Twinbrook Parkway, Rockville, MD 20852-1790, USA.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, NY; Gennaro (2000) Remington: The Science and Practice of Pharmacy, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY).

In a further embodiment, a composition comprising an antibody or antibody fragment disclosed herein is administered to a subject in accordance with the Physicians' Desk Reference 2017 (Thomson Healthcare; 75st edition (Nov. 1, 2002)).

The mode of administration can vary. Suitable routes of administration is preferably parenteral or subcutaneous, Other routes of administration may include oral, transmucosal, intradermal, direct intraventricular, intravenous, intranasal, inhalation, insufflation, or intra-arterial.

In particular embodiments, the anti-FXI antibody or antigen binding fragment thereof can be administered by an invasive route such as by injection. In further embodiments of the invention, an anti-FXI antibody or antigen binding fragment thereof, or pharmaceutical composition thereof, may be administered intravenously, subcutaneously, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the antibody or antibody binding fragment and the particular therapeutic effect to be achieved, and (b) the limitations inherent in the art of compounding such an active molecules for the treatment of sensitivity in individuals. (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144).

Kits

Further provided are kits comprising one or more components that include, but are not limited to, an anti-FXI antibody or antigen-binding fragment, as discussed herein in association with one or more additional components including, but not limited to, a further therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-FXI antibody or antigen-binding fragment thereof or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-FXI antibody or antigen-binding fragment thereof or pharmaceutical composition thereof in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and the anti-FXI antibody or antigen-binding fragment thereof, e.g., wherein the injection device includes the antibody or fragment or wherein the antibody or fragment is in a separate vessel.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Methods of Making Antibodies and Antigen Binding Fragments Thereof

The anti-FXI antibodies and fragments thereof disclosed herein may also be produced recombinantly. In this embodiment, nucleic acids encoding the antibody molecules may be inserted into a vector (plasmid or viral) and transfected or transformed into a host cell where it may be expressed and secreted from the host cell. There are several methods by which to produce recombinant antibodies which are known in the art.

Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, human embryo kidney 293 (HEK-293) cells and a number of other cell lines. Cell lines of particular preference are selected through determining which cell lines have high expression levels. Other cell lines that may be used are insect cell lines, such as Sf9 cells, amphibian cells, bacterial cells, plant cells, filamentous fungus cells (e.g. *Trichoderma reesei*), and yeast cells (e.g., *Saccharomyces cerevisiae* or *Pichia pastoris*). In particular aspects, the host cell may be a prokaryote host cell such as *E. coli*.

When recombinant expression vectors comprising a nucleic acid molecule encoding the heavy chain or antigen-binding portion or fragment thereof, the light chain and/or antigen-binding fragment thereof are introduced into host cells, the antibodies are produced by culturing the host cells under conditions and for a period of time sufficient to allow for expression of the antibody in the host cells or, more preferably, secretion of the antibody into the culture medium in which the host cells are grown. The antibodies may be recovered from the culture medium and further purified or processed to produce the antibodies of the invention.

In particular aspects, the host cells are transfected with an expression vector comprising a nucleic acid molecule encoding an HC and an LC comprising at least the HC and LC CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof.

In particular aspects, the host cells are transfected with a first expression vector comprising a nucleic acid molecule encoding an HC comprising at least the HC CDRs of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof and a second expression vector comprising a nucleic acid molecule encoding an LC comprising at least the LC CDRs of an anti-FXI antibody of the αFXI-18611p family, αFXI-18611 family, or αFXI-18623p family or embodiments thereof wherein one or more of the six CDRs has one, two, or three amino acid s substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof.

In particular embodiments, the HC and LC are expressed as a fusion protein in which the N-terminus of the HC and the LC are fused to a leader sequence to facilitate the transport of the antibody through the secretory pathway. Examples of leader sequences that may be used include MSVPTQVLGLLLLWLTDARC (SEQ ID NO:14) or MEWSWVFLFFLSVTTGVHS (SEQ ID NO:15).

The HC of exemplary antibodies herein may be encoded by a nucleic acid molecule having the nucleotide sequence shown in SEQ ID NOs:34, 36, 38, 40, 42, 44, 46, 48, 50, 52, 54, 56, 58, 60, 62, 64, 66, 68, 70, 72, 74, 76, 78, or 80.

The LC of exemplary antibodies herein may be encoded by a nucleic acid molecule having the nucleotide sequence shown in SEQ ID NO:27 or 32.

The present invention further provides a plasmid or viral vector comprising a nucleic acid molecule having the amino acid sequence of SEQ ID NOs: 34, 36, 38, 40, 42, 44, 46, 48, 50, 52, 54, 56, 58, 60, 62, 64, 66, 68, 70, 72, 74, 76, 78, or 80. The present invention further provides a plasmid or viral vector comprising a nucleic acid molecule encoding the HC of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof and a nucleic acid molecule encoding the LC of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof.

The present invention further provides a plasmid or viral vector comprising a nucleic acid molecule encoding the HC of an anti-FXI antibody of the αFXI-18611p family, αFXI-18611 family, or αFXI-18623p family and a plasmid or viral vector comprising a nucleic acid molecule encoding the LC of an anti-FXI antibody of the αFXI-18611p family, αFXI-18611 family, or αFXI-18623p family.

The present invention further provides a host cell comprising one or more plasmids or viral vectors comprising a nucleic acid molecule encoding the HC of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof and a nucleic acid molecule encoding the LC of an anti-FXI antibody of the αFXI-18611p family, αFXI-18611 family, or αFXI-18623p family or embodiments thereof wherein one or more of the six CDRs has one, two, or three amino acid substitutions, additions, deletions, or combinations thereof and/or wherein the HC and/or LC variable region framework comprises 0, 1, 2, 3, 4, 5, 6, 7, 8, 9, or 10 amino acid substitutions, additions, deletions, or combinations thereof. In particular embodiments, the host cell is a CHO or HEK-293 host cell.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions.

In general, glycoproteins produced in a particular cell line or transgenic animal will have a glycosylation pattern that is characteristic for glycoproteins produced in the cell line or transgenic animal (See for example, Croset et al., J. Biotechnol. 161: 336-348 (2012). Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have.

The following examples are intended to promote a further understanding of the present invention.

GENERAL METHODS

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, NY; Sambrook and Russell (2001) Molecular Cloning, 3rd ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, NY; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, NY; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, NY, pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272: 10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, New York; Kay et al. (1996) Phage Display of Peptides and Proteins: A Laboratory Manual, Academic Press, San Diego, CA; de Bruin et al. (1999) Nature Biotechnol. 17:397-399).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, NJ; Givan (2001) Flow Cytometry, 2nd ed.; Wiley-Liss, Hoboken, NJ; Shapiro (2003) Practical Flow Cytometry, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, OR; Sigma-Aldrich (2003) Catalogue, St. Louis, MO).

Standard methods of histology of the immune system are described (see, e.g., Muller-Harmelink (ed.) (1986) Human Thymus: Histopathology and Pathology, Springer Verlag, New York, NY; Hiatt, et al. (2000) Color Atlas of Histology, Lippincott, Williams, and Wilkins, Phila, PA; Louis, et al. (2002) Basic Histology: Text and Atlas, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

Human FXI and FIX zymogen may be obtained from Haematologic Technologies, Inc. Essex Junction, VT; High Molecular Weight (HMW) Kininogen may be obtained from Enzyme Research Laboratories, South Bend, IN; and, Ellagic acid may be obtained from Pacific Hemostasis, ThermoFisher, Waltham, MA.

Example 1

In this example, the binding kinetics of the anti-FXI antibodies αFXI-18611 IgG4 HC (S228P)(E1) (L105)/LC Kappa and αFXI-18623p IgG4 HC (S228P)(Q1)/LC Kappa and either the human FXI zymogen or non-human primate (NHP) FXI zymogen was measured using the following assays.

Human FXI/FXIa Binding Kinetics Assay Protocol

Binding kinetics and affinity of the protein-protein interaction between anti-FXI antibodies and human FXI zymogen or FXIa were determined using the ProteOn XPR36 (Bio-Rad), an SPR-based (surface plasmon resonance) optical biosensor essentially as follows.

A GLC low-density sensor chip was washed across all vertical and horizontal flow channels with 0.5% sodium dodecyl-sulfate, 50 mM sodium hydroxide, and 100 mM hydrochloric acid for 60 seconds at 30 μL/sec flow rate. The alginate chip surface for all six vertical flow channels (L1-L6) was subsequently activated with 1×EDC/sNHS at 30 μL/sec flow rate for 150 sec. A murine Fc-directed anti-human IgG polyclonal antibody (capture antibody), diluted to 1.25 μg/mL in 10 mM sodium acetate, pH 5.0, was then injected across all six vertical flow channels for 300 sec at a flow rate of 25 uL/sec to bind approximately 300 response units (RU) of capture antibody to the activated chip surface per flow channel by amine-coupling to endogenous lysine. Then, 1M ethanolamine HCl was injected across all six vertical flow channels to neutralize remaining reactive surface amines. Anti-FXI antibodies were then injected at 25 μL/min for 60 seconds, each into a distinct vertical flow channel coated with capture antibody (L2, L3, L4, L5, or L6), at a concentration of 5 μg/mL in 10 mM sodium acetate, pH 5.0, to achieve saturating capture levels of approximately 80 RU; vertical flow channel L1 was injected with 10 mM sodium acetate, pH 5.0 (buffer alone), as a reference control.

After capture of anti-FXI antibodies, running buffer (1×HBS-N, 5 mM CaCl$_2$, 0.005% P20, pH 7.4) was injected across all horizontal flow channels (A1-A6) for 5 minutes and allowed to dissociate for 20 minutes at 25 μL/min to remove any non-specifically bound anti-FXI antibodies from the chip surface. To measure on-rate ($k_a$) of human FXI or FXa to captured anti-FXI antibodies, a 6-point titration of human FXI or FXIa (0, 0.25, 0.5, 1.0, 2.0, 4.0 nM diluted in running buffer) was subsequently injected horizontally across all six vertical flow channels for 8 minutes; the bound zymogen was then allowed to dissociate for 60 minutes in running buffer at 25 μL/min to measure off-rate ($k_d$). Binding kinetics and affinity ($K_D$) were determined using instrument-specific software (Bio-Rad) and are shown in Table 2.

Non-Human Primate FXI Zymogen/FXIa Binding Kinetics Assay Protocol

Binding kinetics and affinity of the protein-protein interaction between anti-FXI antibodies and non-human primate (NHP: cynomolgus and rhesus) FXI zymogen or FXIa were determined using the ProteOn XPR36 (Bio-Rad), an SPR-based (surface plasmon resonance) optical biosensor.

A GLC low-density sensor chip was washed across all vertical and horizontal flow channels with 0.5% sodium dodecyl-sulfate, 50 mM sodium hydroxide, and 100 mM hydrochloric acid for 60 seconds at 30 μL/sec flow rate. The alginate chip surface for all six vertical flow channels (L1-L6) was subsequently activated with 1×EDC/sNHS at 30 μL/second flow rate for 150 seconds. A murine Fc-directed anti-human IgG polyclonal antibody (capture antibody), diluted to 30 μg/mL in 10 mM sodium acetate, pH 5.0, was then injected across all six vertical flow channels for 150 seconds at a flow rate of 25 μL/sec to achieve saturation-binding of approximately 4500 response units (RU) of capture antibody to the activated chip surface per flow channel by amine-coupling to endogenous lysine. Then 1M ethanolamine HCl was injected across all six vertical flow channels to neutralize any remaining reactive surface amines. Anti-FXI antibodies were then injected at 25 μL/min for 60 sec, each into a distinct vertical flow channel coated with capture antibody (L2, L3, L4, L5, or L6), at a concentration of 0.415 μg/mL in running buffer (1×HBS-N, 5 mM CaCl$_2$, 0.005% P20, pH 7.4), to achieve capture levels of approximately 40 RU; vertical flow channel L1 was injected with running buffer alone as a reference control. After capture of anti-FXI antibodies, running buffer was injected across all horizontal flow channels (A1-A6) for 5 minutes and allowed to dissociate for 20 minutes at 25 μL/minutes to remove non-specifically bound anti-FXI antibodies from the chip surface. To measure on-rate ($k_a$) of NHP FXI to captured anti-FXI antibodies, a 6-point titration of NHP FXI or FXIa (0, 0.25, 0.5, 1.0, 2.0, 4.0 nM diluted in running buffer) was subsequently injected horizontally across all six vertical flow channels for 8 minutes; the bound FXI zymogen or FXIa was then allowed to dissociate for 60 minutes in running buffer at 25 μL/min to measure off-rate ($k_d$). Binding kinetics and affinity ($K_D$) were determined using instrument-specific software (Bio-Rad). The results are shown in Table 2.

TABLE 2

Binding of αFXI-18623P and αFXI-18611 mAb to FXI/XIa

| Target | N | FXI Affinity Mean $K_D$ ± SD pM | | FXIa Affinity Mean $K_D$ ± SD pM | |
|---|---|---|---|---|---|
| | | αFXI-18611 | αFXI-18623p | αFXI-18611 | aFXI-18623P |
| Human | 3 | 100 ± 38 | 22.6 ± 2.2 | 55.4 ± 12.2 | 37.4 ± 10.4 |
| Cynomolgus monkey | 3 | 180 ± 70 | 13.0 ± 5.7 | 89.2 ± 10.4 | 19.5 ± 0.6 |
| Rhesus monkey | 3 | 52.9 ± 9.6 | 72.2 ± 31.7 | 175 ± 62.6 | 149 ± 3.8 |

αFXI-18611 = αFXI-18611 IgG4 HC (S228P)(E1) (L105)/LC Kappa
αFXI-18623p = αFXI-18623p IgG4 HC (S228P)(Q1)/LC Kappa Example 2

Effect of the anti-FXI Antibodies on Activation of FXI to FXIa by FXIIa in the Presence of high molecular weight (HMW) Kininogen and Ellagic Acid To measure the effects of anti-FXI antibodies αFXI-18611 IgG4 HC (S228P)(E1) (L105)/LC Kappa and αFXI-18623p IgG4 HC (S228P)(Q1)/LC Kappa on FXI zymogen activation, coupled enzymatic assays that measure FXIa-mediated proteolysis of a tri-peptide fluorophore (GPR-AFC) may be used to determine if the antibodies inhibit FXI activation per se. For these experiments, anti-FXI antibodies are pre-incubated with FXI zymogen for 1 hour. FXI activation to FXIa is induced by the addition of FXIIa in the presence of HMW Kininogen and ellagic acid. FXIa catalytic activity on the tripeptide fluorophore substrate is subsequently measured as a read for zymogen activation. The coupled assay is also run in the absence of HMW Kininogen as a control. 11-point dose titrations of the anti-FXI antibodies starting at 1 µM concentration with a 3-fold dilution series were pre-incubated with human FXI (Haematologic Technologies, Inc., Cat #HCXI-0150, final concentration 30 nM) and HMW kininogen (Enzyme Research Laboratories, Cat #HK, final concentration 280 nM) in 50 mM HEPES, 150 mM NaCl, 5 mM $CaCl_2$, 0.1% PEG-8000, pH 7.4 for two hours at 25° C. in Corning 3575 non-binding surface microplate. The activation reaction was then initiated by addition of ellagic-acid-containing Pacific Hemostasis APTT-XL reagent (ThermoFisher Scientific, Cat #100403, 100 µM stock concentration, final concentration 2 µM) and freshly diluted coagulation factor XIIa (Enzyme Research Laboratories, Cat #HFXIIa, final concentration 50 µM). The reaction proceeded at 25° C. for 1 hour when it was quenched by addition of 1 µM corn trypsin inhibior (Haematologic Technologies, Inc., Cat #CTI-01). The newly activated FXIa enzymatic activity was detected by the rate of cleavage of Z-GPR-AFC substrate (Sigma, Cat #C0980-10MG, final concentration 150 µM) by continuously monitoring the fluorescence at 400/505 nm for 10 minutes using a Tecan Infinite M200 platereader. The % Inhibition for each data point was recalculated from the RFU/min data and analyzed using the log(inhibitor) vs. response four parameters equation with the GraphPad Prism software. The results are shown in Table 3.

Activation of FXI to FXIa by FXIIa in the Absence of HMW Kininogen and Ellagic Acid 11-point dose titrations of the anti-FXI antibodies of this invention, starting at 1 µM concentration with a 3-fold dilution series were pre-incubated with human FXI (Haematologic Technologies, Inc., Cat #HCXI-0150, final concentration 30 nM) in 50 mM HEPES, 150 mM NaCl, 5 mM $CaCl_2$, 0.1% PEG-8000, pH 7.4 for two hours at 25° C. in Corning 3575 non-binding surface microplate. The activation reaction was then initiated by addition of freshly diluted coagulation factor XIIa (Enzyme Research Laboratories, Cat #HFXIIa, final concentration 15 nM). The reaction proceeded at 25° C. for 1 hour when it was quenched by addition of 1 µM corn trypsin inhibitor (Haematologic Technologies, Inc., Cat #CTI-01). The newly activated FXIa enzymatic activity was detected by the rate of cleavage of Z-GPR-AFC substrate (Sigma, Cat #C0980-10MG, final concentration 150 PM) by continuously monitoring the fluorescence at 400/505 nm for 10 minutes using a Tecan Infinite M200 platereader. The % Inhibition for each data point was recalculated from the RFU/min data and analyzed using the log(inhibitor) vs. response four parameters equation with the GraphPad Prism software. The results are shown in Table 3.

TABLE 3

Effect of αFXI-18623p and αFXI-18611 and on FXI Activation by FXIIa

| Antibody | N | FXIIa Activation + HK Inhibition ($IC_{50}$, nM) | FXIIa Activation no HK Inhibition ($IC_{50}$, nM) |
|---|---|---|---|
| αFXI-18611 | 3 | 7.6 ± 3.5 | 34 ± 20 |
| αFXI-18623p | 3 | 6.0 ± 1.1 | 14 ± 9.5 |

αFXI-18611 = αFXI-18611 IgG4 HC (S228P)(E1) (L105)/LC Kappa
αFXI-18623p = αFXI-18623p IgG4 HC (S228P)(Q1)/LC Kappa
$IC_{50}$s are given as mean ± SD, n = 3

Together, these mechanistic studies demonstrate that these anti-FXI antibodies functionally neutralize FXI by preventing FXI activation by FXIIa and by inhibiting FXIa catalytic activity on the native substrate.

Example 3

Epitope Mapping of Anti-FXI antibodies by Hydrogen Deuterium Exchange Mass Spectrometry Contact areas of αFXI-18611 IgG4 HC (S228P)(E1) (L105)/LC Kappa and αFXI-18623p-IgG4 (S228P) (Q1)/LC Kappa to human FXI were determined by use of hydrogen deuterium exchange mass spectrometry (HDX-MS) analysis. HDX-MS measures the incorporation of deuterium into the amide backbone of the protein and changes in this incorporation are influenced by the hydrogen's solvent exposure. A comparison of the deuterium exchange levels in antigen-alone samples and antibody-bound samples was done to identify antigen regions that may be in contact with the antibody. Human Factor XI has the amino acid sequence shown in SEQ ID NO:81. Dimeric Factor XI was pre-incubated with the antibodies before incubation in a deuterium buffer. Deuterium incorporation into Factor XI was measured by mass spectrometry.

The human Factor XI regions protected from deuteration by the antibodies are Epitope-A DIFPNTVF (Residues 185-192 of Factor XI; SEQ ID NO:82) and Epitope-B PSTRIK-KSKALSG (Residues 247-259 of Factor XI; SEQ ID NO:83). FIGS. 3A and 3B show deuterium labeling difference heatmap of the Factor XI amino acid residues bound by the antibodies αFXI-18611 IgG4 HC (S228P)(E1) (L105)/LC Kappa and αFXI-18623p IgG4 HC (S228P)(Q1)/LC Kappa, respectively. These amino acid sequences are located on the Apple 3 domain of Factor XI (FIG. 2). No significant deuteration changes were observed in the Apple 1, 2, 4 or catalytic domains, indicating they are not involved in αFXI-18623 binding. Thus, the epitope recognized by αFXI-18623p-IgG4 (S228P)/kappa comprises Epitope A and Epitope B.

Example 4

FIX is the endogenous protein substrate of FXIa, the active protease of FXI zymogen. FXIa activates FIX to FIXa, perpetuating the coagulation cascade. Inhibition of FXIa-mediated activation of FIX is one potential mechanism of action (MOA) for FXI mAbs. To interrogate this MOA, FXIa enzymatic assays using full-length FIX zymogen was developed.

FXIa Protease Activity on a Small Tripeptide Substrate

Anti-FXI antibodies were pre-incubated with human FXIa (Sekisui Diagnostics, Exton, PA, Cat #4011A, final concentration 100 µM) in 50 mM HEPES, 150 mM NaCl, 5 mM $CaCl_2$, 0.1% PEG-8000, pH 7.4 for 2 hours at 25° C. in Corning 3575 non-binding surface microplate. FXIa enzymatic activity was determined by measuring the rate of cleavage of Z-GPR-AFC substrate (Sigma, Cat #C0980-10MG, final concentration 100 PM) by continuously monitoring the fluorescence at 400/505 nm for 10 minutes using a Tecan Infinite M200 platereader. The final concentrations of the 11-point dose titration of the antibodies started at 1 µM with a 3-fold dilution series. The % Inhibition for each data point was recalculated from the RFU/minute data and analyzed using the log(inhibitor) vs. response four parameters equation with the GraphPad Prism software. The results are shown in Table 4.

Activation of FIX to FIXa by FXIa

FIX is the endogenous protein substrate of FXIa, the active protease of FXI zymogen. FXIa activates FIX to FIXa, perpetuating the coagulation cascade. Inhibition of FXIa-mediated activation of FIX is one potential MOA for FXI mAbs. To interrogate this MOA, FXIa enzymatic assays using FIX full-length was developed.

11-point dose titrations of the anti-FXI antibodies, starting at 1 μM concentration with a 3-fold dilution series were pre-incubated with human FXIa (Sekisui Diagnostics, Cat #4011A, final concentration 100 μM) in 50 mM HEPES, 150 mM NaCl, 5 mM $CaCl_2$, 0.1% PEG-8000, pH 7.4 for 2 hours at 25° C. in Corning 3575 non-binding surface microplate. The activation reaction was then initiated by addition of FIX (Haematologic Technologies, Inc., Cat #HCIX-0040-C, final concentration 300 nM) and preceded at 25° C. for 1 hour when the reaction was quenched by addition of 100 nM of an anti-FXI antibody directed to the catalytic site on the light chain of FXI (anti-FXI antibody 076D-M007-H04 disclosed in WO2013167669). The newly activated FIXa enzymatic activity was detected by the rate of cleavage of cyclohexyl-GGR-AFC substrate (CPC Scientific, Cat #839493, final concentration 300 PM) by continuously monitoring the fluorescence at 400/505 nm for 10 minutes using a Tecan Infinite M200 platereader. The % Inhibition for each data point was recalculated from the RFU/minute data and analyzed using the log(inhibitor) vs. response four parameters equation with the GraphPad Prism software. The results are shown in Table 4.

TABLE 4

Effect of αFXI-18623p and αFXI-18611 on FXIa Catalytic Activity

| Antibody | N | FXIa $IC_{50}$ nM (tri-peptide substrate) | FXIa $IC_{50}$ nM (native, full-length substrate) |
|---|---|---|---|
| αFXI-18611 | 3 | >1000 | 1.0 ± 0.3 |
| αFXI-18623p | 3 | >1000 | 0.4 ± 0.2 |

αFXI-18611 = αFXI-18611 IgG4 HC (S228P)(E1) (L105)/LC Kappa
αFXI-18623p = αFXI-18623p IgG4 HC (S228P)(Q1)/LC Kappa
$IC_{50}$s are given as mean ± SD, n = 3

As shown in Table 4, the antibodies did not inhibit FXIa catalytic activity in the enzymatic assay utilizing synthetic, tri-peptide fluorophore substrate, but both antibodies were potent inhibitors of the assay utilizing the native, full length substrate. This data is consistent with the antibodies behaving as allosteric, competitive inhibitors of FIX activation by FXIa, as well as the epitope mapping results of Example 3 suggesting the "footprint" of the antibodies on Apple 3 overlaps with the FIX-binding exosite in FXIa.

Example 5

Autoactivation of FXI to FXIa on Dextran Sulfate 11-point dose titrations of the anti-FXI antibodies of this invention starting at 1 μM concentration with a 3-fold dilution series were pre-incubated with human FXI (Haematologic Technologies, Inc., Cat #HCXI-0150, final concentration 30 nM) in 50 mM HEPES, 150 mM NaCl, 5 mM $CaCl_2$, 0.1% PEG-8000, pH 7.4 for 2 hours at 25° C. in Corning 3575 non-binding surface microplate. The autoactivation reaction was then initiated by addition of dextran sulfate (ACROS, Cat #433240250, approximate MW 800 kDa, final concentration 1 nM). The reaction preceded at 25° C. for 1 hour when newly activated FXIa enzymatic activity was detected by the rate of cleavage of Z-GPR-AFC substrate (Sigma, Cat #C0980-10MG, final concentration 150 uM) by continuously monitoring the fluorescence at 400/505 nm for 10 minutes using a Tecan Infinite M200 platereader. The % Inhibition for each data point was recalculated from the RFU/minutes data and analyzed using the log(inhibitor) vs. response four parameters equation with the GraphPad Prism software. The results are shown in Table 5.

TABLE 5

Effect of αFXI-18623p and αFXI-18611 on FXI Autoactivation

| Antibody | N | FXIAutoactivation $IC_{50}$ nM |
|---|---|---|
| αFXI-18611 | 2 | 3.3 ± 0.4 |
| αFXI-18623p | 2 | 5.5 ± 4.0 |

αFXI-18611 = αFXI-18611 IgG4 HC (S228P)(E1) (L105)/LC Kappa
αFXI-18623p = αFXI-18623p IgG4 HC (S228P)(Q1)/LC Kappa
$IC_{50}$s are given as mean ± SD, n = 3

Example 6

The ability of the anti-FXI antibodies to block in vitro coagulation was assessed using the activated Partial Thromboplastin Time (aPTT) assay. Activated partial thromboplastin time (aPTT) is a clotting test that measures the activity of the intrinsic and common pathways of coagulation.

Activated Partial Thromboplastin Time (aPTT) Assay

The test is performed in sodium citrated plasmas. Human plasma is obtained by collecting blood from healthy donors of both genders into Na citrate tubes (Sarstedt coagulation 9NC/10 mL). Blood is centrifuged at 1500×g and the plasma is collected. aPTT is checked on each individual donor and those within the normal range (28-40 seconds) are pooled, aliquoted and stored at −80 C. Plasma from other species is obtained commercially (Innovative Research, Novi, MI). Test samples are prepared by spiking inhibitors or vehicle into plasma. These spiked samples are incubated (60 minutes, RT) then run on a coagulation analyzer (STA-R Evolution, Stago Diagnostica, Parsippany, NJ). In general, the analyzer performs the following steps: FXII is activated by addition of ellagic acid (Pacific Hemostasis, ThermoFisher Scientific, Waltham, MA), and then time to clot is measured after re-calcification of the sample. Inhibition of FXI will cause aPTT clot time to be prolonged. The results are shown in Table 6. The data is expressed as percent increase over vehicle control clot time and the concentration that causes a 100% (2×) or 50% (1.5×) percent increase of clot time are reported. The aPTT results are shown in FIGS. 6, 7, 8, 9, and 10.

TABLE 6

| | Human | | Cynomolgus monkey | | Rhesus monkey | |
|---|---|---|---|---|---|---|
| Antibody | 2x (nM) | 1.5 (nM) | 2x (nM) | 1.5 (nM) | 2x (nM) | 1.5 (nM) |
| αFXI-18623p | 24 | 19 | 21 | 15 | 22 | 15 |
| αFXI-18611 | 37 | 23 | 218 | 42 | 79 | 22 |

αFXI-18611 = αFXI-18611 IgG4 HC (S228P)(E1) (L105)/LC Kappa
αFXI-18623p = αFXI-18623p IgG4 HC (S228P)(Q1)/LC Kappa Example 7

Surface Plasmon Resonance Assay for Assessment of Off-Target Binding of Anti-FXI Monoclonal Antibodies to Human and NHP Coagulation Cascade Proteins A surface plasmon resonance (SPR)-based assay (Biacore T200) was used to determine the potential non-specific interaction of the anti-Factor FXI mAbs, αFXI-18611 IgG4 HC (S228P) (E1) (L105)/LC Kappa and αFXI-18623p IgG4 HC (S228P) (Q1)/LC Kappa to other human and NHP coagulation cascade proteins (Table 7). Anti-FXI mAbs were captured on a CM5 sensor chip immobilized with anti-human IgG (Fc) capture kit (GE Healthcare) at approximately 500RU to minimize potential background from co-purifying Igs in plasma derived proteins. Negative control antibody, anti-respiratory syncytial virus (RSV) monoclonal antibody (mAb), was used as a reference and to help reduce background binding of plasma-derived proteins. Binding kinetics was measured using an analyte concentration of FXI at 5 nM; all other coagulation cascade proteins were used at an analyte concentration of 500 nM. Single concentration injections (n=2) were run at 30 µL/min, 25° C., HBS-EP+, pH 7.4.

TABLE 7

Recombinant and Plasma Derived Human and NHP Coagulation Cascade Proteins.

| Lot No./ Catalogue No. | Vendor | Common Name | Source |
| --- | --- | --- | --- |
| 00AJF | Merck, Sharp & Dohme Corp., Kenilworth, NJ USA | Rhesus monkey plasma Kallikrein | Recombinant protein C-terminal His tagged. NCBI Reference Sequence: EHH26351 |
| 65AJE | Merck, Sharp & Dohme Corp., Kenilworth, NJ USA | Cynomolgus monkey plasma Kallikrein | Recombinant protein C-terminal His tagged NCBI Reference Sequence: XP_005556538.1 |
| 97AJY/ HPK 1302 | Enzyme Research Laboratories | Human plasma preKallikrein | Isolated from human plasma |
| 98AJY/ HPKa 1303 | Enzyme Research Laboratories | Human plasma Kallikrein | Isolated from human plasma |
| 42AHG/ HCP-0010 | Haematologic Technologies Inc. | Human Factor II (α-thrombin) | Isolated from human plasma |
| 50AHK/ HCVII-0030 | Haematologic Technologies Inc. | Human Factor VII | Isolated from human plasma |
| 51AHK HCVIIA-0031 | Haematologic Technologies Inc. | Human Factor VIIa Protease | Isolated from human plasma |
| 38AHG/ HCIX-0040 | Haematologic Technologies Inc. | Human Factor IX | Isolated from human plasma |
| 14AJZ/ HFIXa 1080 | Enzyme Research Laboratories | Human Factor IXa Protease | Isolated from human plasma |
| 15AJZ/ HFX1010 | Enzyme Research Laboratories | Human Factor X | Isolated from human plasma |
| 18AJZ/ HFXa 1011 | Enzyme Research Laboratories | Human Factor Xa Protease | Isolated from human plasma |
| 19AJZ/ HFXII 1212 | Enzyme Research Laboratories | Human Factor XII | Isolated from human plasma |
| 20AJZ/ HFXII 1212a | Enzyme Research Laboratories | Human Factor XIIa Protease | Isolated from human plasma |
| 23 AIR/ HCXI-0150-C | Haematologic Technologies Inc. | Human FXI | Isolated from human plasma |
| 41AHG HCP-0010 | Haematologic Technologies Inc. | Human Factor II (Prothrombin) | Isolated from human plasma |
| 82AJK/ 2460-SE | R&D | Human FXI-His tagged | Recombinant protein C-terminal His tagged. Mouse myeloma cell line, NSO derived. NCBI Reference PO3951. |
| 23AFE | Merck, Sharp & Dohme Corp., Kenilworth, NJ USA | Anti-RSV mAb IgG4 | SEQ ID NO: 84 (LC) and SEQ ID NO: 85 (HC) |

Figure 11:
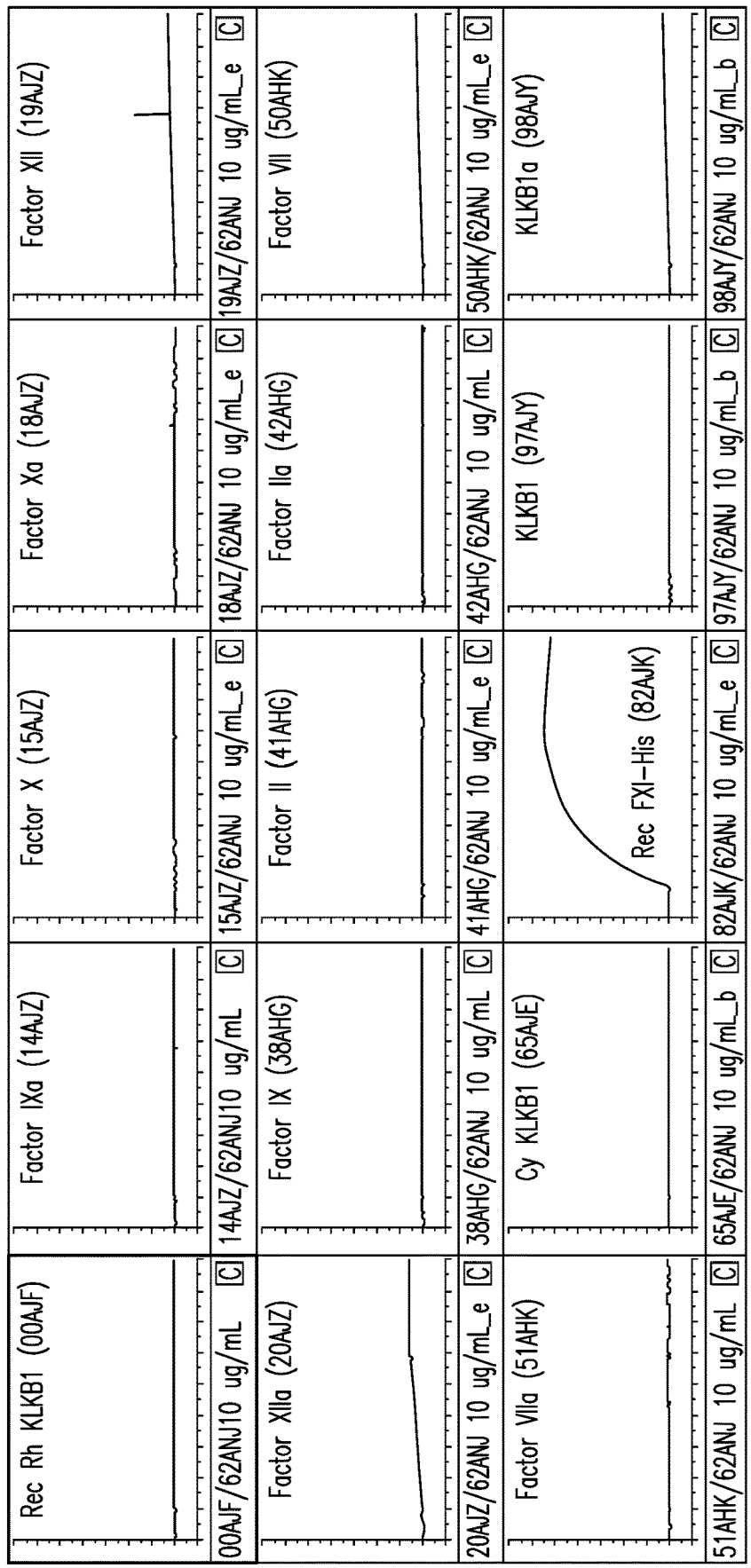
FIG. 11 shows BIAcore Sensorgrams that show the kinetics of binding of αFXI-18623p IgG4 HC (S228P)(E1)/LC Kappa to human, cynomolgus and rhesus monkey FXI and other human and NHP coagulation cascade proteins.
Figure 12:
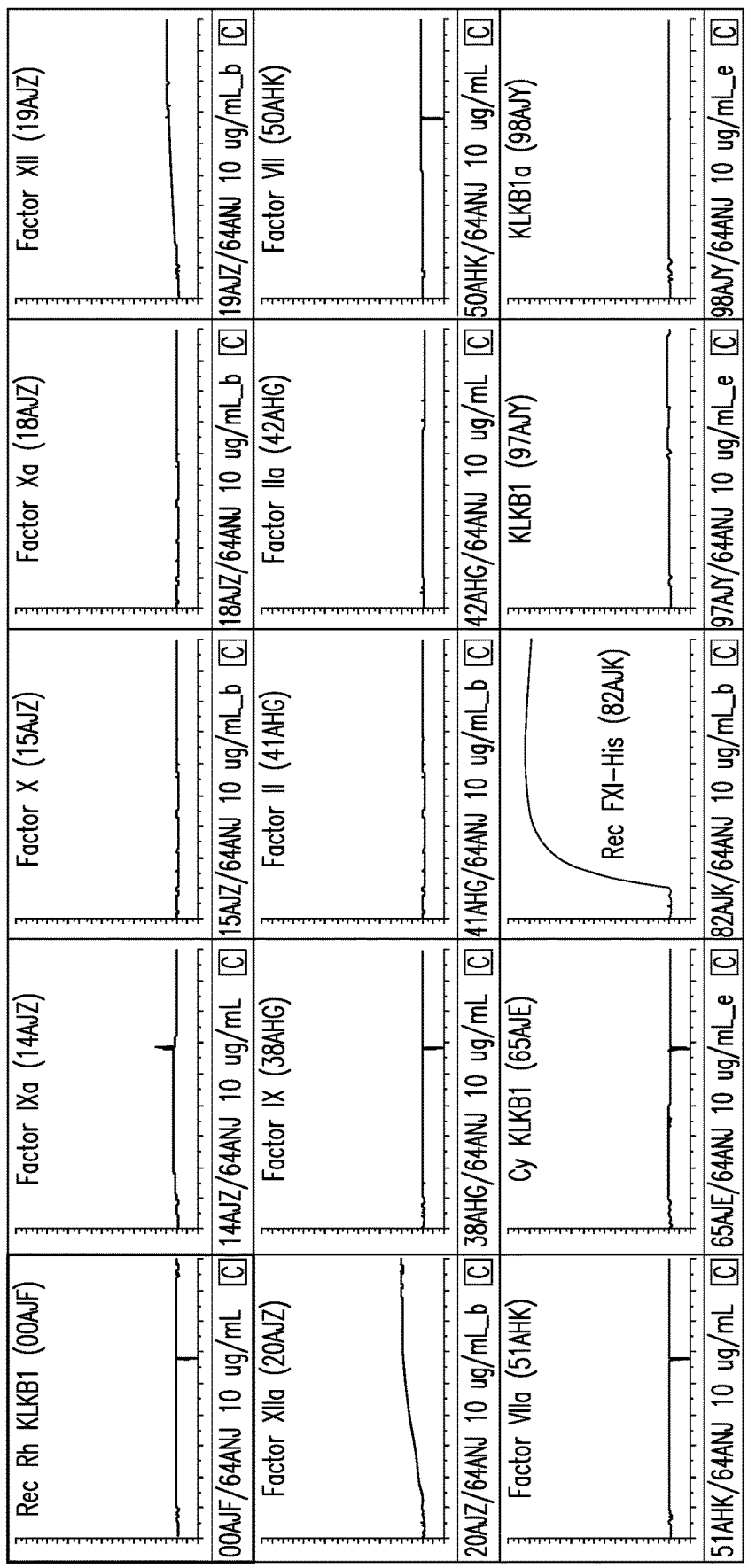
FIG. 12 shows BIAcore Sensorgrams that show the kinetics of binding of αFXI-18623p IgG4 HC (S228P)(Q1)/LC Kappa to human, cynomolgus and rhesus monkey FXI and other human and NHP coagulation cascade proteins.

The kinetics of binding of the anti-Factor FXI mAbs, αFXI-18611 IgG4 HC (S228P)(E1) (L105)/LC Kappa and αFXI-18623p IgG4 HC (S228P)(Q1)/LC Kappa to human, cynomolgus and rhesus monkey FXI, and, other human and NHP coagulation cascade proteins was measured as described above and are shown in FIG. 11 and FIG. 12). Biacore T200 evaluation software was used to fit data to a 1:1 binding model to determine the association rate constant, $k_a$ ($M^{-1}s^{-1}$, where "M" equals molar and "s" equals seconds) and the dissociation rate constant, $k_d$ ($s^{-1}$). These rate constants were used to calculate the equilibrium dissociation constant, $K_D$ (M).

αFXI-18611 IgG4 HC (S228P)(E1) (L105)/LC Kappa and αFXI-18623p IgG4 HC (S228P)(Q1)/LC Kappa captured on chip showed no cross-reactivity against non-FXI coagulation cascade proteins (FIG. 11 and FIG. 12). These monoclonal antibodies showed expected levels of strong binding to human and cyno (and Rhesus) FXI proteins.

Example 8

Cynomolgus Monkey Femoral Arteriovenous (AV) Shunt Thrombosis Model

The antithrombotic efficacy of the αFXI-18623p IgG4 HC (S228P)(E1)/LC Kappa antibody, was characterized in vivo in a cynomolgus monkey femoral arteriovenous (AV) shunt model developed at the Merck, Sharp & Dohme Corp. Research Laboratories, Kenilworh, NJ USA and Palo Alto, CA USA.

Study Design: These studies used a repeated design where each animal received 2 shunts over 2 consecutive test periods (see FIG. 13 Study Schematic). The monkeys were administered non-antibody containing vehicle (20 mM sodium acetate, 9% sucrose, pH 5.5) or the αFXI-18623p IgG4 HC (S228P)(E1)/LC Kappa antibody (dose range 0.01 to 1.0 mg/kg), during the first and second test periods, respectively. The difference between the clot weight measured during the first (vehicle) and second (antibody) test sessions determined the antithrombotic efficacy. That is, a greater decrease in clot weight during αFXI-18623p IgG4 HC (S228P)(E1)/LC Kappa antibody versus vehicle exposure would indicate greater antithrombotic effect. The use of the repeated paired design described above allows for a within animal pre- vs post-treatment assessment of antithrombotic efficacy.

Figure 13:
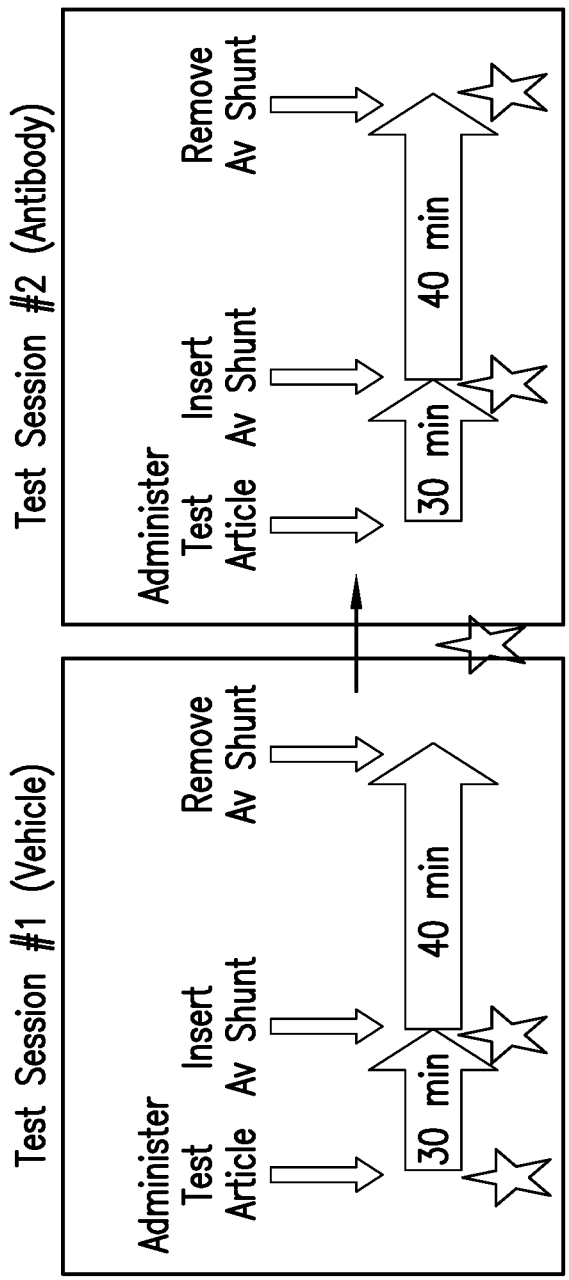
FIG. 13 shows a schematic of the cynomolgus monkey AV shunt test paradigm. Anesthetized monkeys previously instrumented with femoral arterial and venous catheters were administered vehicle or αFXI-18623p IgG4 HC (S228P)(E1)/LC Kappa (antibody) at 0.01-1.0 mg/kg by intravenous bolus (Test Article Administration). An AV shunt was inserted as described in the text (Insert AV shunt). Blood flowed through the AV shunt for 40 minutes. Contact between blood and the silk thread suspended inside of the tubing caused a clot to form. The clots were weighed as described in the text. Blood samples were obtained to measure circulating levels of the antibody, aPTT and PT (stars).

AV Shunt Placement Procedure Details: To execute this model, anesthetized cynomolgus monkeys were instrumented with femoral arterial and venous catheters. These catheters enabled the insertion and removal of an AV shunt. The AV shunts were composed of TYGON tubing with a piece of silk suture threaded through and suspended across the opening in the tube. To place the AV shunt, both arterial and venous catheters were closed to stop the blood flow. An AV shunt was then placed between the two catheters. The timing of catheter placement and removal is indicated in FIG. 13. Once the shunt was in place, the catheters were opened and blood flowed through the shunt circuit contacting the silk suture. The action of blood contacting the suture promoted clot formation. The AV shunt remained in place for 40 minutes. To remove the AV shunt, both arterial and venous catheters were closed to stop the blood flow through the AV shunt. Then, the shunt was removed and cut open to access the silk suture and blood clot. The blood clot was weighed. The data is reported as the net clot weight which is defined as the total clot weight minus silk suture weight.

The coagulation biomarkers activated partial thromboplastin time (aPTT) and prothrombin time (PT) as well as circulating plasma levels of αFXI-18623p IgG4 HC (S228P)(E1)/LC Kappa antibody were measured from blood samples collected throughout the experiment as depicted in FIG. 13. aPTT and PT were measured from thawed frozen (−80° C.) citrated plasma collected from cynomolgus monkeys using the Sta Compact Max coagulation analyzer (Stago Diagnostic, Inc). The Stago analyzer measures the time of clot formation using an electro-magnetic mechanical clot detection system. For the aPTT assay fifty microliters of plasma was mixed with 50 µL of ellagic acid mixture (APTT-XL, Pacific Hemostasis; Fisher Diagnostics cat #10-0402) at 37° C. for 3 minutes. Fifty microliters of 0.025M Calcium Chloride (Sta-CaCl$_2$ 0.025M, Stago Diagnostic, Inc., cat #00367) was added to the mixture, and the time to clot formation was measured. For the PT assay fifty microliters of plasma was incubated at 37° C. for 4 minutes. The timing for clot formation was initiated by adding 100 µL of thromboplastin reagent (Neoplastine C1 Plus 10, Stago Diagnostic, Inc., cat #00667). Plasma was measured as follows. An electrochemiluminescence-based generic hIgG4 immunoassay was used to quantify the antibody in cynomolgus monkey plasma. The assay was established with biotinylated goat anti-human IgG(H+L) from Bethyl (cat #A80-319B) as capture reagent, and sulfoTAG labeled mouse anti-human IgG (Fc specific) from Southern Biotech (cat #9190-01) for detection reagent. This assay was qualified and the lower limit of quantification of the assay was determined to be 40 ng/mL with a minimum required dilution of 100.

Figure 14A:
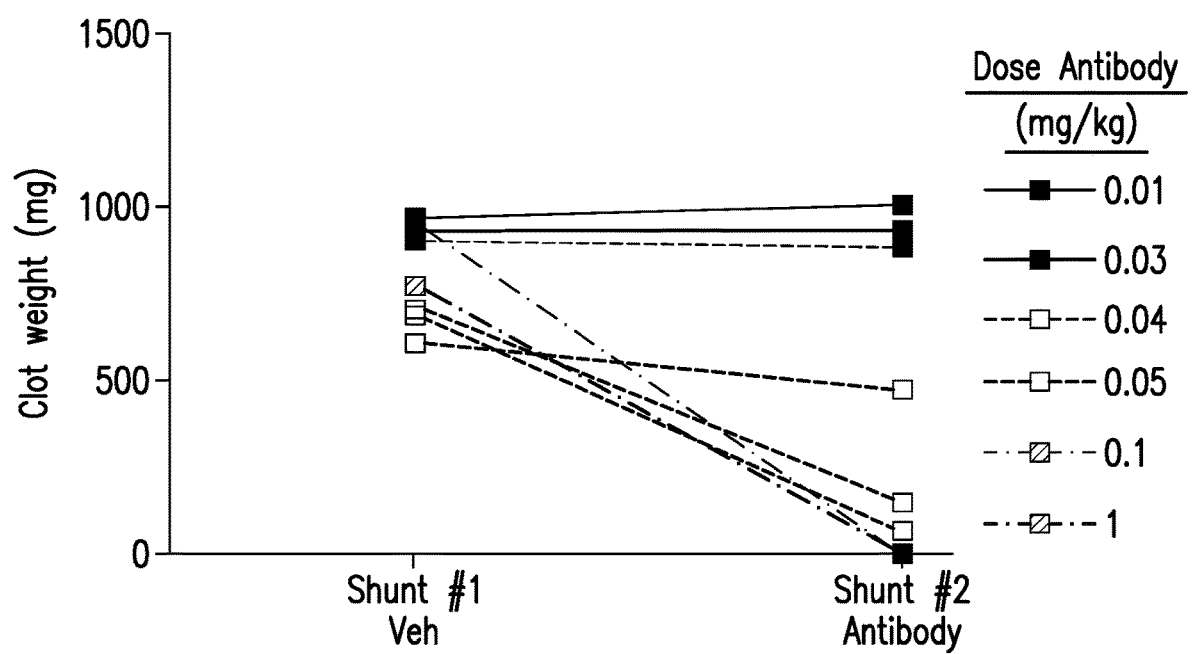
FIGS. 14A-14D show the effects of αFXI-18623p IgG4 HC (S228P)(E1)/LC Kappa (antibody) on AV shunt clot formation, aPTT and PT in the cynomolgus monkey AV shunt model.
Figure 14B:
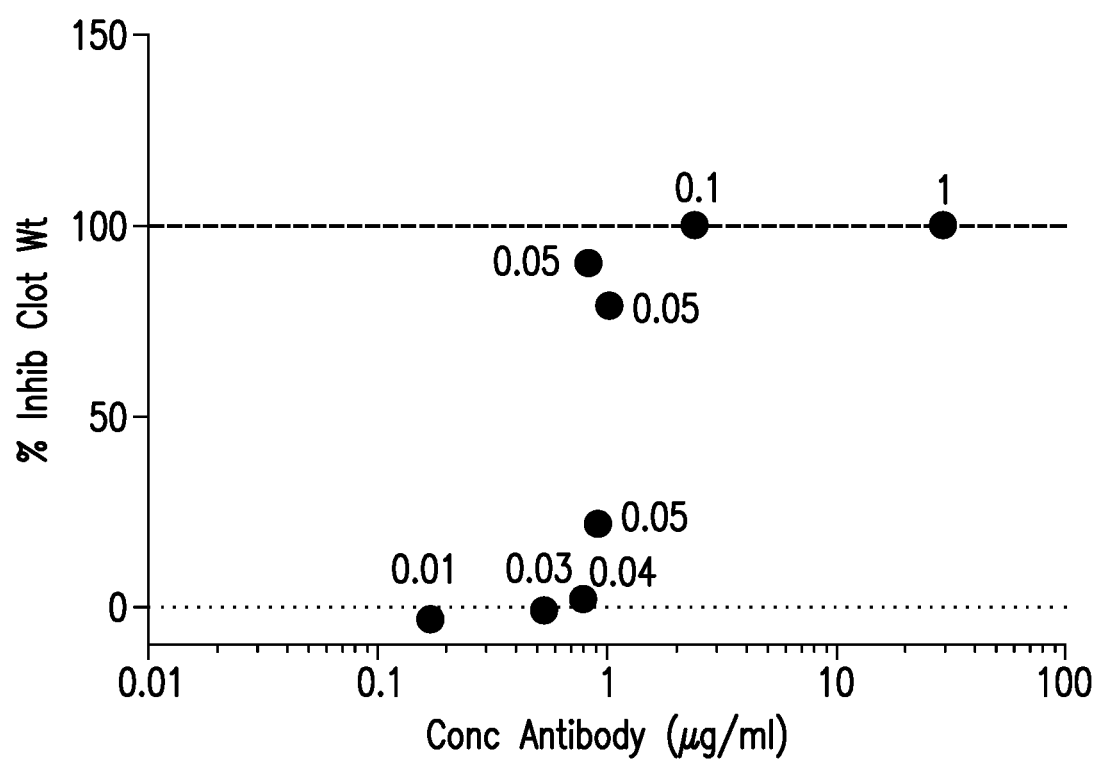
Figure 14C:
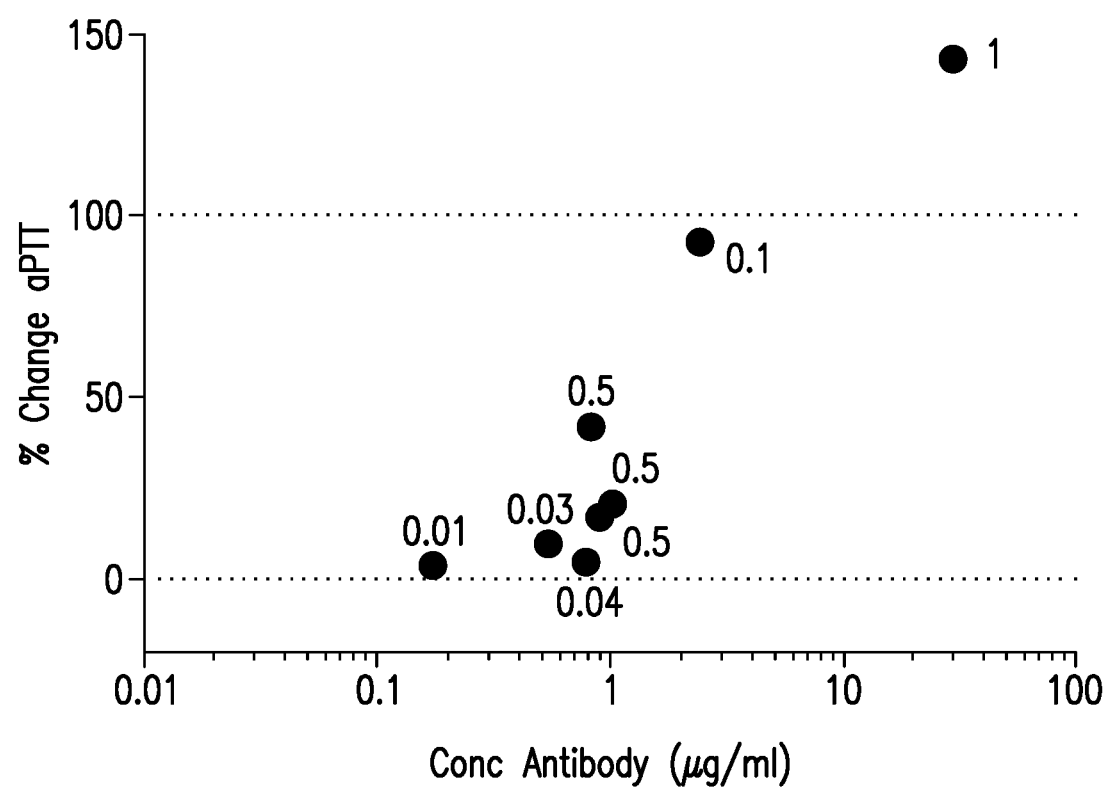
Figure 14D:
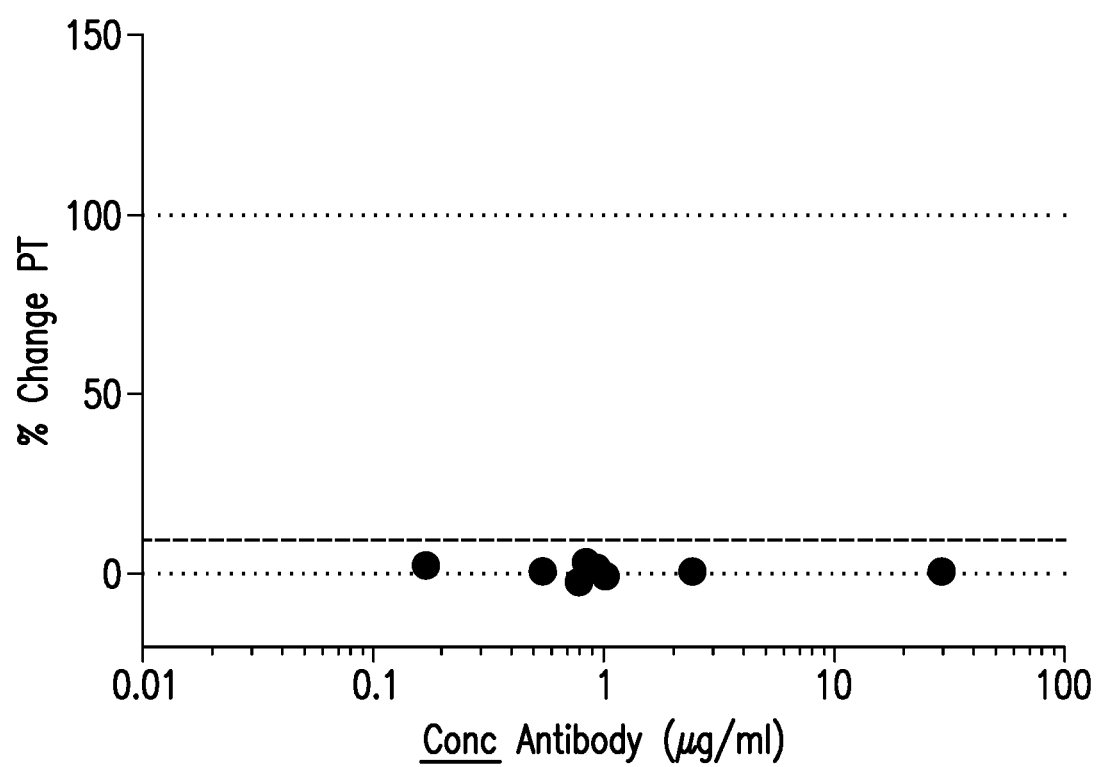

FIGS. 14A-14D summarizes the effects of administration of the αFXI-18623p IgG4 HC (S228P)(E1)/LC Kappa antibody on thrombus formation (FIG. 14A, FIG. 14B), aPTT (FIG. 14C) and PT (FIG. 14D). Table 8 summarizes Effect of αFXI-18623p IgG4 HC (S228P)(E1)/LC Kappa antibody on Clot Weight in the Cyno AV Shunt Model. Table 9 summarizes the effect of αFXI-18623p IgG4 HC (S228P)(E1)/LC Kappa antibody on aPTT and PT in the Cyno AV shunt Model.

TABLE 8

Effect of αFXI-18623p IgG4 HC (S228P)(E1)/LC Kappa antibody on Clot Weight in the Cyno AV Shunt Model

| Dose Antibody (mg/kg) | Shunt #1 (Vehicle) | Shunt #2 (Antibody) | % Inhib. Clot Weight | Conc. Antibody (µg/mL) |
|---|---|---|---|---|
| 1 | 772.0 | 1.0 | 100% | 29.13 |
| 0.1 | 957.0 | 1.0 | 100% | 2.42 |

TABLE 8-continued

Effect of αFXI-18623p IgG4 HC (S228P)(E1)/LC Kappa antibody on Clot Weight in the Cyno AV Shunt Model

| Dose Antibody (mg/kg) | Shunt #1 (Vehicle) | Shunt #2 (Antibody) | % Inhib. Clot Weight | Conc. Antibody (µg/mL) |
|---|---|---|---|---|
| 0.01 | 974.0 | 1007.0 | −3% | 0.17 |
| 0.03 | 927.0 | 935.0 | −1% | 0.54 |
| 0.04 | 909.0 | 887.0 | 2% | 0.79 |
| 0.05 | 607.0 | 472.0 | 22% | 0.91 |
| 0.05 | 710.0 | 147.0 | 79% | 1.03 |
| 0.05 | 688 | 66 | 90% | 0.83 |

TABLE 9

Effect of αFXI-18623p IgG4 HC (S228P)(E1)/LC Kappa antibody on aPTT and PT in the Cyno AV shunt Model

| Dose Antibody (mg/kg) | % Change aPTT | % Change PT | Conc. Antibody (µg/mL) |
|---|---|---|---|
| 1 | 143% | 1% | 29.13 |
| 0.1 | 93% | 1% | 2.42 |
| 0.01 | 4% | 3% | 0.17 |
| 0.03 | 10% | 1% | 0.54 |
| 0.04 | 5% | −2% | 0.79 |
| 0.05 | 17% | 2% | 0.91 |
| 0.05 | 21% | 0% | 1.03 |
| 0.05 | 42% | 3% | 0.83 |

As shown in FIG. 14A, 14B and in Table 8, the αFXI-18623p IgG4 HC (S228P)(E1)/LC Kappa antibody displayed a dose- and plasma concentration-dependent decrease in clot weight with complete efficacy (90-100% clot reduction) observed at plasma [antibody] of greater than 1 µg/mL (about 10 nM). As shown in FIG. 14C and Table 9, the antibody displayed a dose- and plasma concentration-dependent increase in aPTT. A plasma concentration of 2.4 µg/mL (~17 nM) of the αFXI-18623p IgG4 HC (S228P)(E1)/LC Kappa antibody yielded a 93% increase in aPTT, while 29 µg/mL (~200 nM) of the αFXI-18623p IgG4 HC (S228P)(E1)/LC Kappa antibody (at the highest dose tested) resulted in a 143% increase in aPTT. Unlike aPTT, as shown in FIG. 14D and Table 9, PT changed less than 10% across the concentrations of the antibody evaluated, consistent with a selective effect of FXI inhibition on the intrinsic coagulation pathway.

Example 9

Cynomolgus Monkey Template Bleeding Time Model.

The bleeding propensity of the anti-FXI mAb αFXI-18623p IgG4 HC (S228P)(E1)/LC Kappa, was characterized in vivo in a cynomolgus monkey template bleeding time model developed at the Merck, Sharp & Dohme Corp. Research Laboratories, Kenilworh, NJ USA and Palo Alto, CA USA. This model has been used previously to demonstrate significant increases in template bleeding times at multiple anatomic sites with triple antiplatelet therapy (Cai et al., Eur. J. Pharmacol. 758:107-114 (2015)).

To execute this model, template bleeding times were determined using spring-loaded lancets on the buccal mucosa (inner lip), finger pad and distal tail at varying time points to induce bleeding.

Bleeding Time Test: The bleeding time test was performed in anesthetized cynomolgus monkeys as follows.

Each test region (buccal mucosa, finger pad or distal tail) was examined to identify a suitable incision site for bleeding inducement.

To induce bleeding, a spring-loaded lancet was placed firmly against the selected test site and activated to cause a uniform linear incision. The lancet specifications determined the incision dimensions.

Blood from the incision site was allowed to flow freely and was monitored until the bleeding stopped for 30 continuous seconds. This defined the bleeding time (BT). The BT was recorded for each BT site. During the BT determinations, the distal tail incision site was superfused with warm sterile lactated Ringers solution, and the finger pad site was immersed in warm sterile lactated Ringers. Applying lactated ringers improved the ability to see blood flow for these sites.

Study Design: Each study was comprised of three 30 minute template bleeding time tests (BT) at the three test regions (see FIG. 15 Study Schematic). The first BT determined Baseline bleeding. The second BT occurred 70 minutes after a 3 minute IV infusion (4.17 ml/kg) of non-compound containing vehicle (20 mM sodium acetate, 9% sucrose, pH 5.5)(Treatment #1). The third BT occurred 70 minutes after a 3 minute IV infusion (4.17 ml/kg) of non-compound containing vehicle or αFXI-18623p IgG4 HC (S228P)(E1)/LC Kappa (10 mg/kg)(Treatment #2). Bleeding was monitored and bleeding time recorded as described above. The time when bleeding stopped was recorded for each site. Periodic blood samples were collected to determine circulating plasma levels of αFXI-18623p IgG4 HC (S228P)(E1)/LC Kappa antibody, aPTT and PT.

Each test animal had two study sessions. In study session #1, vehicle followed by vehicle constituted Treatment #1 and Treatment #2 respectively. In study session #2, vehicle followed by 10 mg/kg IV αFXI-18623p IgG4 HC (S228P)(E1)/LC Kappa constituted Treatment #1 and Treatment #2 respectively.

The 70 minute time period between the end of the test article infusion and initiation of bleeding time assessments mirrored the timing in the AV shunt model for thrombus mass determination (shunt placement 30 min post treatment+40 min blood flow through the shunt). The 10 mg/kg IV test dose of αFXI-18623p IgG4 HC (S228P)(E1)/LC Kappa was estimated to achieve 10× the projected human Cmax for αFXI-18623p IgG4 HC (S228P)(E1)/LC Kappa based on the PK/PD primate modeling studies described previously.

Figure 15:
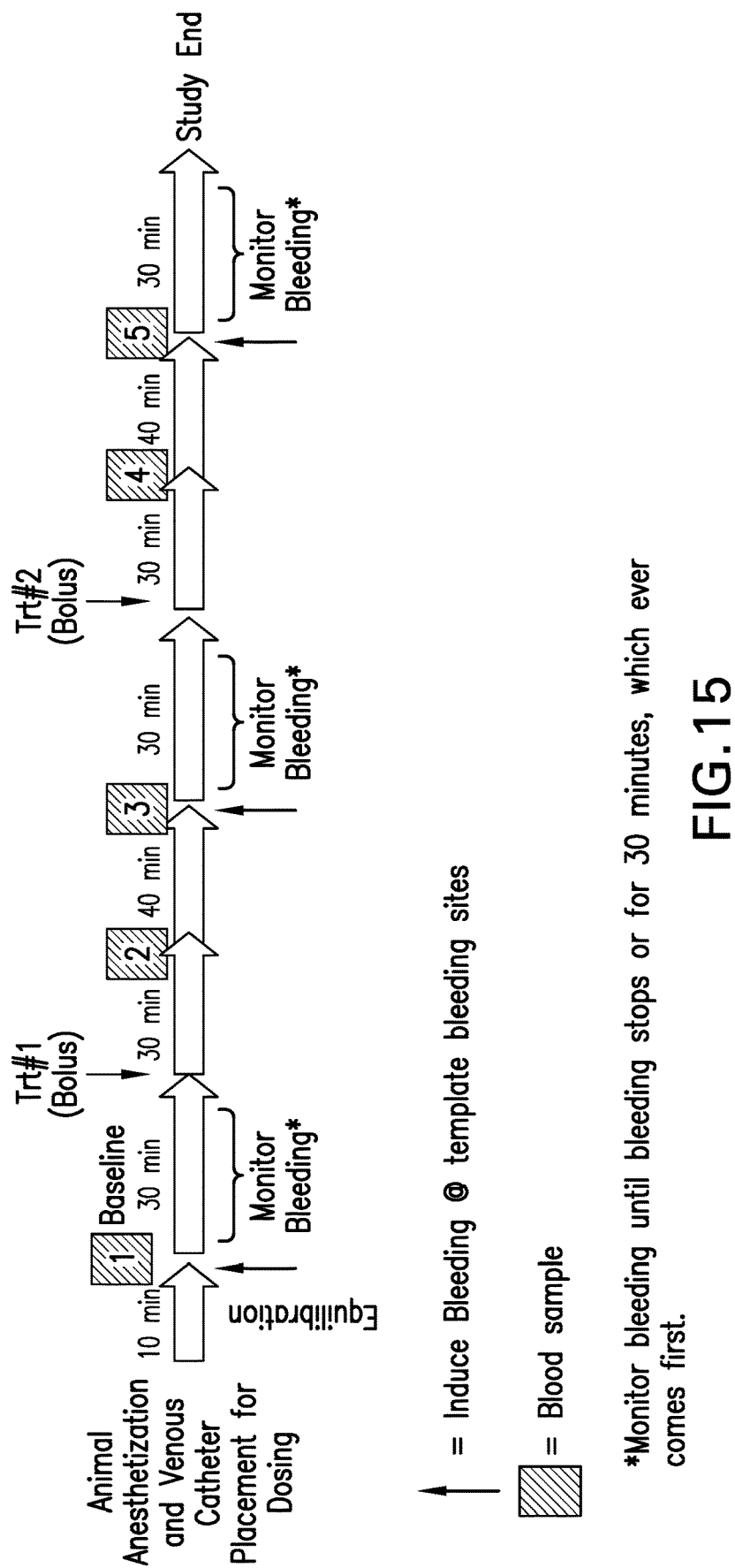
FIG. 15 shows a schematic of the cynomolgus monkey template bleeding time paradigm. Template bleeding times on the buccal mucosa (inner lip), finger pad and distal tail were determined in anesthetized cynomolgus monkeys at Baseline (prior to treatment) and after the administrations of Treatment #1 (vehicle) and Treatment #2 (vehicle or αFXI-18623p IgG4 HC (S228P)(E1)/LC Kappa, 10 mg/kg IV). Blood samples to measure circulating levels of αFXI-18623p IgG4 HC (S228P)(E1)/LC Kappa, aPTT and PT were collected as shown.
Figure 16A:
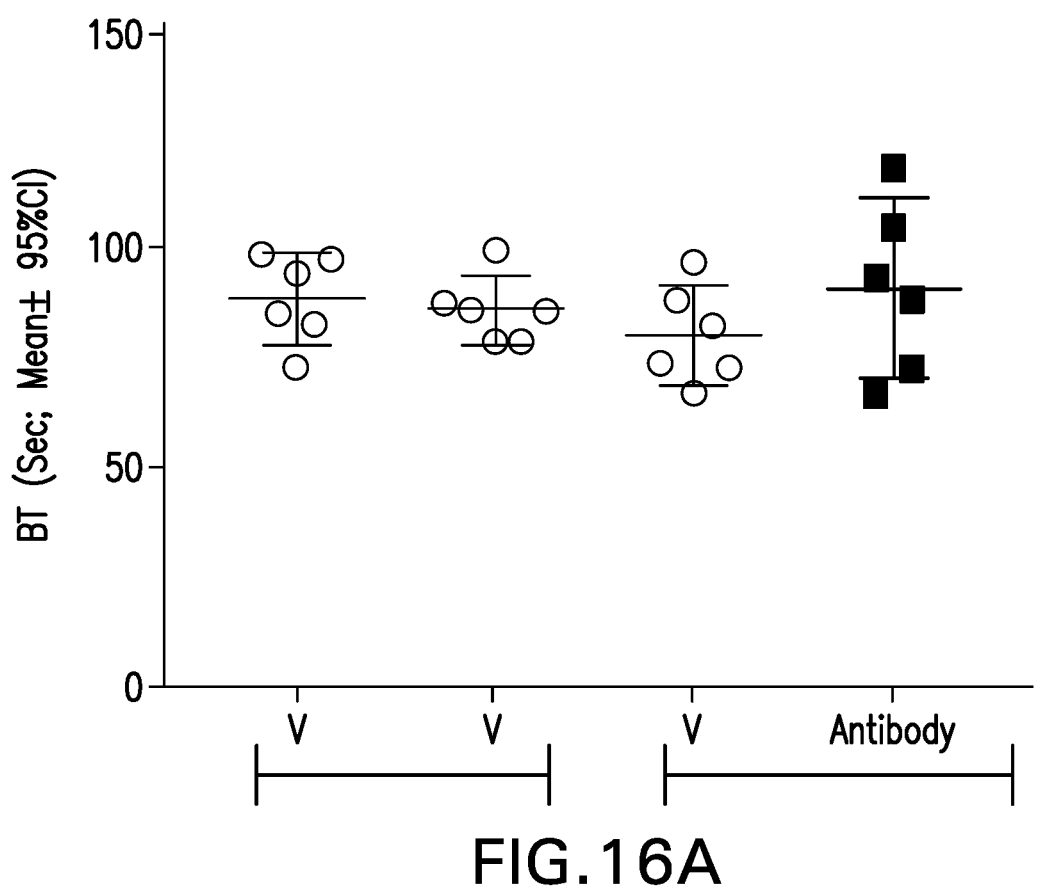
FIG. 16A-16F show the effects of αFXI-18623p IgG4 HC (S228P)(E1)/LC Kappa on template bleeding times measured in cynomolgus monkeys. Template bleeding times were measured in the buccal mucosal (FIG. 16A, 16D), finger pad (FIG. 16B, 16E) and distal tail (FIG. 16C, 16F). Treatment effects (αFXI-18623p IgG4 HC (S228P)(E1)/LC Kappa_vs vehicle) on bleeding times were assessed by comparing absolute bleeding times (left panels) and percentage changes in bleeding times (right panels), with vehicle-vehicle as Treatments #1 and 2 in study session #1, and vehicle-αFXI-18623p IgG4 HC (S228P)(E1)/LC Kappa as Treatments #1 and #2 in study session #2, using a one-tailed paired Students t-test.
Figure 16B:
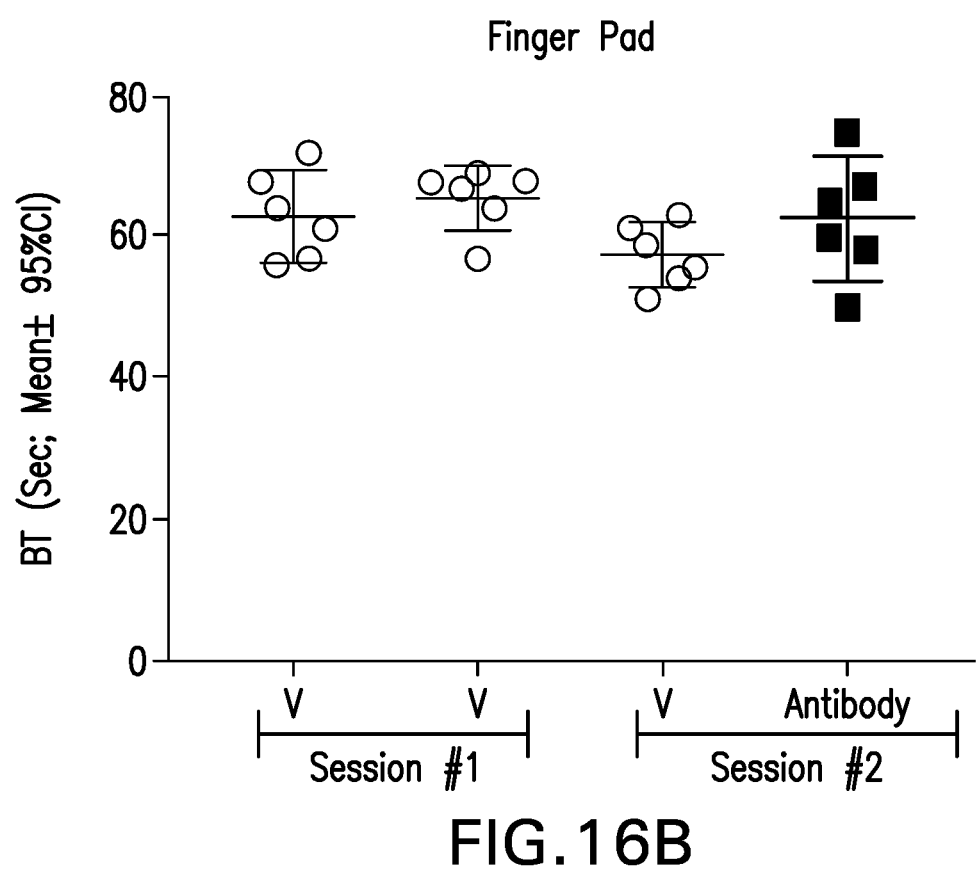
Figure 16C:
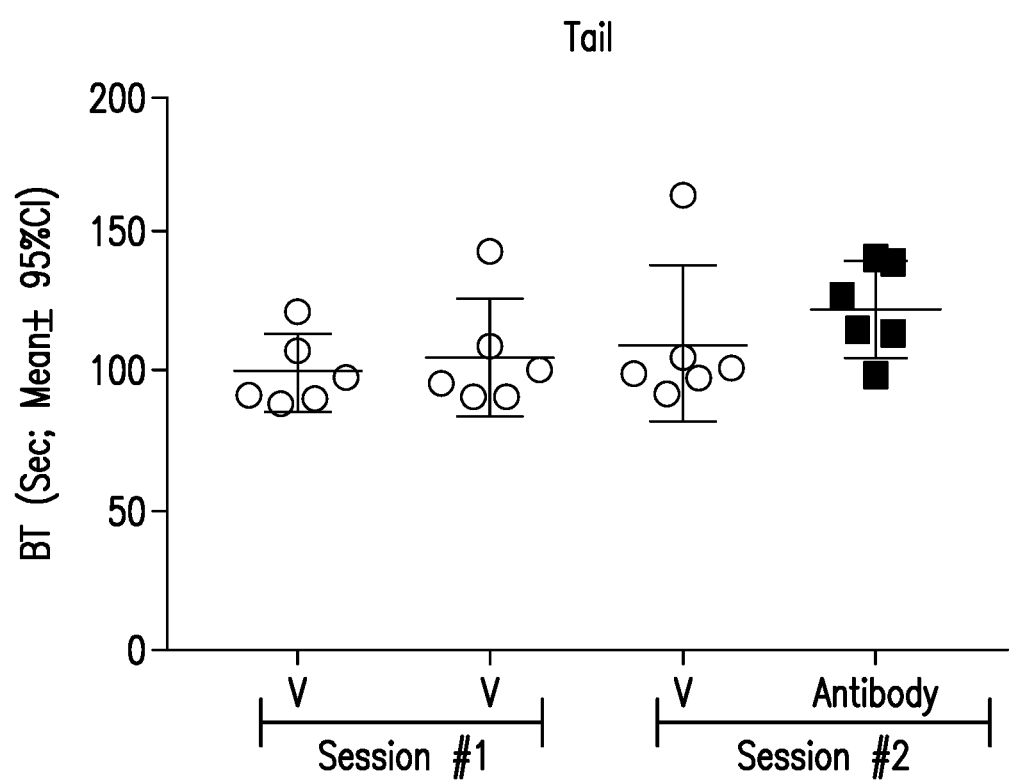
Figure 16D:
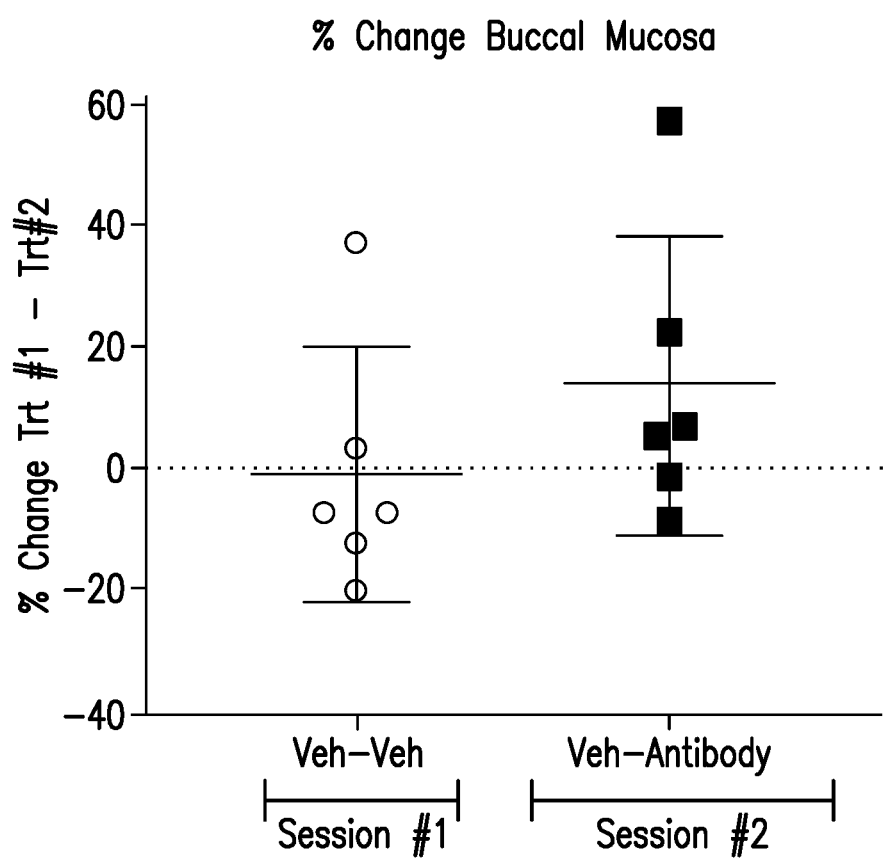
Figure 16E:
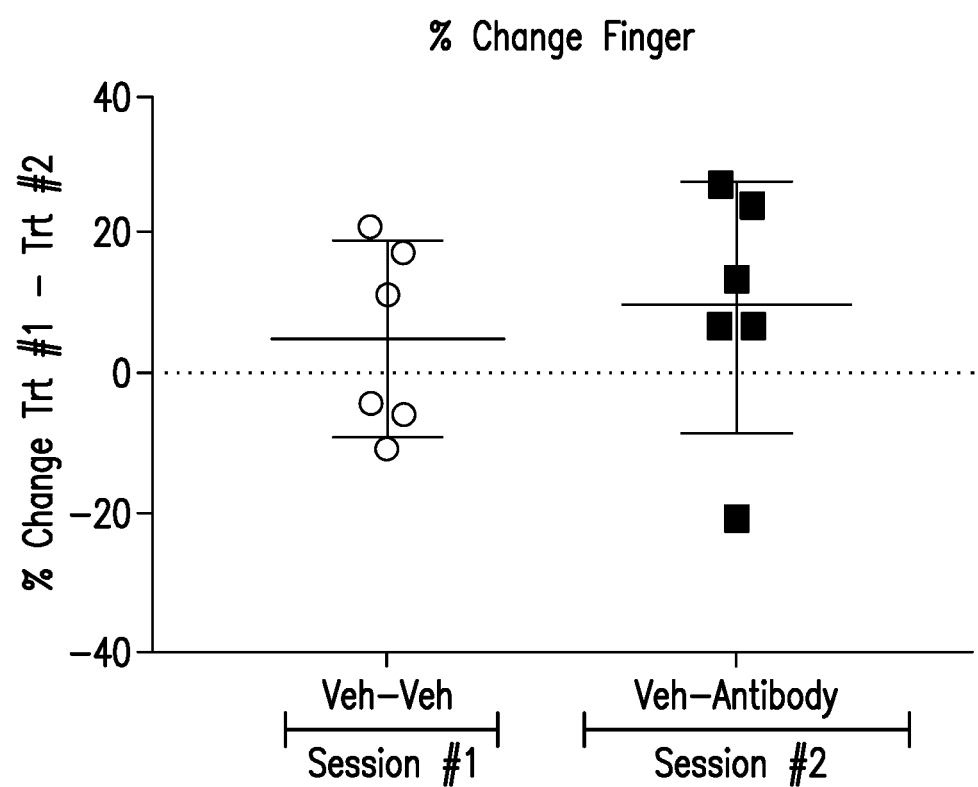
Figure 16F:
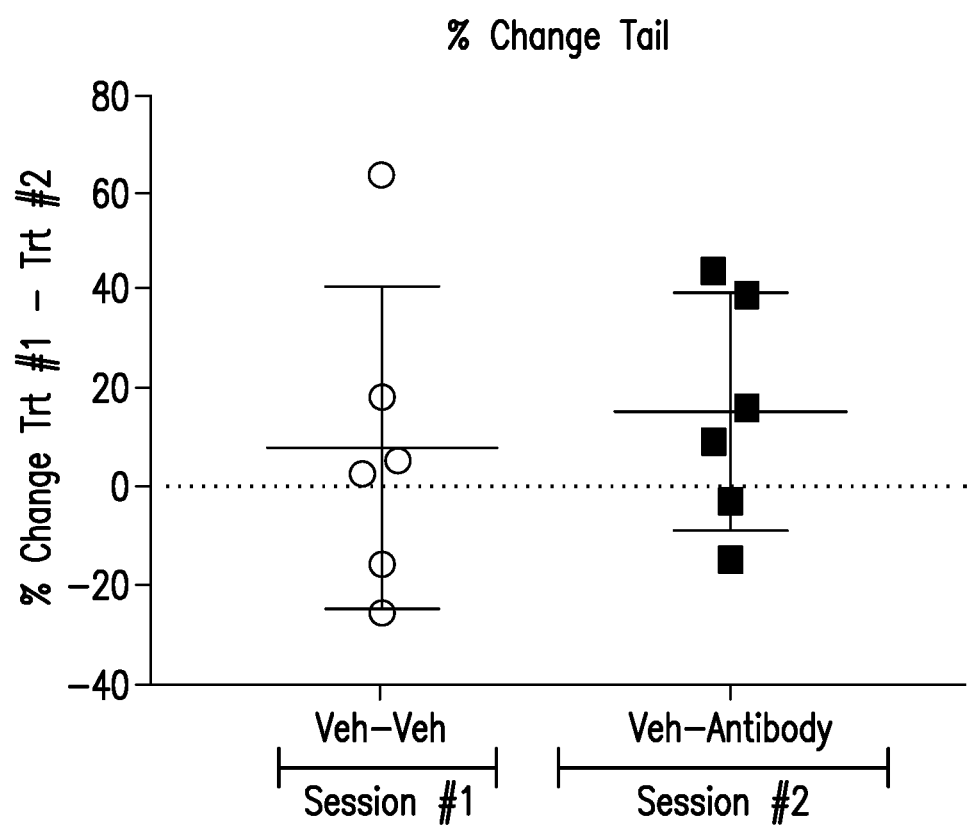

The coagulation biomarkers activated partial thromboplastin time (aPTT) and prothrombin time (PT) as well as circulating plasma levels of αFXI-18623p IgG4 HC (S228P)(E1)/LC Kappa were measured from blood samples collected throughout the experiment as depicted in FIG. 15. aPTT and PT were measured from thawed frozen (−80° C.) citrated plasma collected from the animals using the Sta-R Evolution coagulation analyzer (Stago Diagnostic, Inc). The coagulation analyzer measures the time to clot-formation using an electro-magnetic mechanical clot detection system. For the aPTT assay, the analyzer mixes 50 µL of plasma with 50 µL of ellagic acid (APTT-XL, Pacific Hemostasis; Fisher Diagnostics cat #10-0402) in a cuvette which is then incubated at 37° C. for 3 minutes. 50 µL of 0.025M Calcium Chloride (Sta-CaCl$_2$) 0.025M, Stago Diagnostic, Inc., cat #00367) is then added to the mixture to initiate clotting, and the time to clot-formation measured. For the PT assay, 50 µL of plasma was incubated in a cuvette at 37° C. for 4 minutes; clotting was initiated by adding 100 µL of solubilized thromboplastin reagent (Triniclot PT Excel, TCoag, Inc., cat #T1106).

An electrochemiluminescence-based generic hIgG4 immunoassay was used to quantify αFXI-18623p IgG4 HC (S228P)(E1)/LC kappa in rhesus monkey plasma. The assay was established with biotinylated goat anti-huIgG(H+L) from Bethyl (cat #A80-319B) as capture reagent, and sulfo-TAG labeled mouse anti-huIgG (Fc specific) from Southern Biotech (cat #9190-01) for detection reagent. This assay was qualified and the lower limit of quantification of the assay was determined to be 41 ng/mL with minimum required dilution of 100.

FIG. 16A-16F summarizes the effects of vehicle and 10 mg/kg IV αFXI-18623p IgG4 HC (S228P)(E1)/LC Kappa administration in six cynomolgus monkeys on buccal mucosal (FIG. 16A, 16D), finger pad (FIG. 16B, 16E) and distal tail (FIG. 16C, 16F) template bleeding times. Effects on bleeding times were assessed by comparing absolute bleeding times (left panels) and percentage changes in bleeding times (right panels) with vehicle-vehicle as Treatments #1 and 2 in study session #1, and vehicle-αFXI-18623p IgG4 HC (S228P)(E1)/LC Kappa as Treatments #1 and #2 in study session #2. Comparisons of both vehicle vs αFXI-18623p IgG4 HC (S228P)(E1)/LC Kappa absolute bleeding times as well as vehicle-vehicle vs vehicle-αFXI-18623p IgG4 HC (S228P)(E1)/LC Kappa percentage changes in bleeding times detected no statistically significant changes in bleeding times at any of the test sites with αFXI-18623p IgG4 HC (S228P)(E1)/LC Kappa administration at this test dose.

The plasma concentration of αFXI-18623p IgG4 HC (S228P)(E1)/LC Kappa achieved with the 10 mg/kg IV test dose in the cynomolgus bleeding time study was 290.7±17.2 (mean±SEM) g/ml (~1938.2 nM). Plasma aPTT values were 31.0±0.5 sec at baseline vs 71.3±1.6 sec following 10 mg/kg IV αFXI-18623p IgG4 HC (S228P)(E1)/LC Kappa (2.3-fold increase). Plasma PT values were 12.7±0.1 sec at baseline vs 12.6±0.1 sec following 10 mg/kg IV αFXI-18623p IgG4 HC (S228P)(E1)/LC Kappa (no appreciable increase).

Example 10

Pharmacokinetic (PK) and Pharmacodynamic (PD) Evaluation of αFXI-18623p IgG4 HC (S228P)(E1)/LC kappa Following Multiple Intravenous Administrations in Rhesus monkeys.

The PKPD properties of αFXI-18623p IgG4 HC (S228P)(E1)/LC kappa were characterized in vivo in rhesus monkey. The objective was to evaluate the PK properties and to establish a PK/PD relationship after a total of two weekly doses.

Study Design. Rhesus monkeys (four animals per dose group) were administered (IV) non-compound vehicle (10 mM Sodium Acetate, pH 5.5, 7% Sucrose, 0.02% PS-80) or αFXI-18623p IgG4 HC (S228P)(E1)/LC kappa at five dose levels of 0.1, 0.3, 1, 3 and 6 mg/kg. The duration of the study was 22 days and 1.5 mL of blood was collected for determination of drug levels and activated partial thromboplastin time (aPTT).

The coagulation biomarker (aPTT) and circulating plasma levels of αFXI-18623p IgG4 HC (S228P)(E1)/LC were measured from blood samples collected throughout the experiment as depicted in Table 10.

TABLE 10

Sample Collection Schedule

| Collection Type | Time |
|---|---|
| PK | Day −3; Day 0: predose (−1 h) and 30 min, 3 h, 6 h, 24 (Day 1), 48 (Day 2), 96 (Day 4) Day 7: predose and 1 h, 6 h, 24 h (Day 8), 48 h (Day 9), 96 h (Day 11), 168 h (Day 14), 264 h (Day 18) and 528 h (Day 22) post second dose |
| PD (evaluation of aPTT) | Day −3; Day 0: predose (−1 h) and 30 min, 3 h, 6 h, 24 (Day 1), 48 (Day 2), 96 (Day 4) Day 7: predose and 1 h, 6 h, 24 h (Day 8), 48 h (Day 9), 96 h (Day 11), 168 h (Day 14), 264 h (Day 18) and 528 h (Day 22) post second dose | aPTT was measured from thawed frozen (−80° C.) citrated plasma collected from the animals using the Sta-R Evolution coagulation analyzer (Stago Diagnostic, Inc). The coagulation analyzer measures the time to clot-formation using an electro-magnetic mechanical clot detection system. For the aPTT assay, the analyzer mixes 50 μL of plasma with 50 μL of ellagic acid (APTT-XL, Pacific Hemostasis; Fisher Diagnostics cat #10-0402) in a cuvette which is then incubated at 37° C. for 3 minutes. 50 μL of 0.025M Calcium Chloride (Sta-CaCl$_2$) 0.025M, Stago Diagnostic, Inc., cat #00367) is then added to the mixture to initiate clotting, and the time to clot-formation measured.

An electrochemiluminescence-based generic hIgG4 immunoassay was used to quantify αFXI-18623p IgG4 HC (S228P)(E1)/LC kappa in rhesus monkey plasma. The assay was established with biotinylated goat anti-huIgG(H+L) from Bethyl (cat #A80-319B) as capture reagent, and sulfo-TAG labeled mouse anti-huIgG (Fc specific) from Southern Biotech (cat #9190-01) for detection reagent. This assay was qualified and the lower limit of quantification of the assay was determined to be 41 ng/mL with minimum required dilution of 100.

Individual animal plasma concentration-time data for αFXI-18623p IgG4 HC (S228P)(E1)/LC kappa were analyzed using non-compartmental (NCA) methods (Gabrielsson and Weiner, 2000). All PK parameters were estimated or calculated using Phoenix 32 WinNonlin 6.3 (version 6.3.0.395, Certara L. P. St. Louis, MO, 2012). Noncompartmental analyses utilized Model 201 (IV). All concentration data and PK parameters were rounded to 3 significant figures. Samples with concentration values below the lower limit of quantitation (<LLOQ) were excluded from PK analysis and mean data calculations. For graphical purposes, values<LLOQ were set to be ½ of the minimal reportable concentration for individual animal concentration-time plots.

A sigmoidal $E_{max}$ response (PK/PD) model was used to characterize the relationship between exposure and aPTT using GraphPad Prism version 7.00 (GraphPad Software Inc). In the model, the $E_{max}$ value corresponds to the maximum increase in aPTT achieved from baseline and the $EC_{50}$ value corresponds to the half-maximal effective concentration. Variability was reported as 95% confidence interval (CI) for the $EC_{50}$ value provided by the software.

Figure 17A:
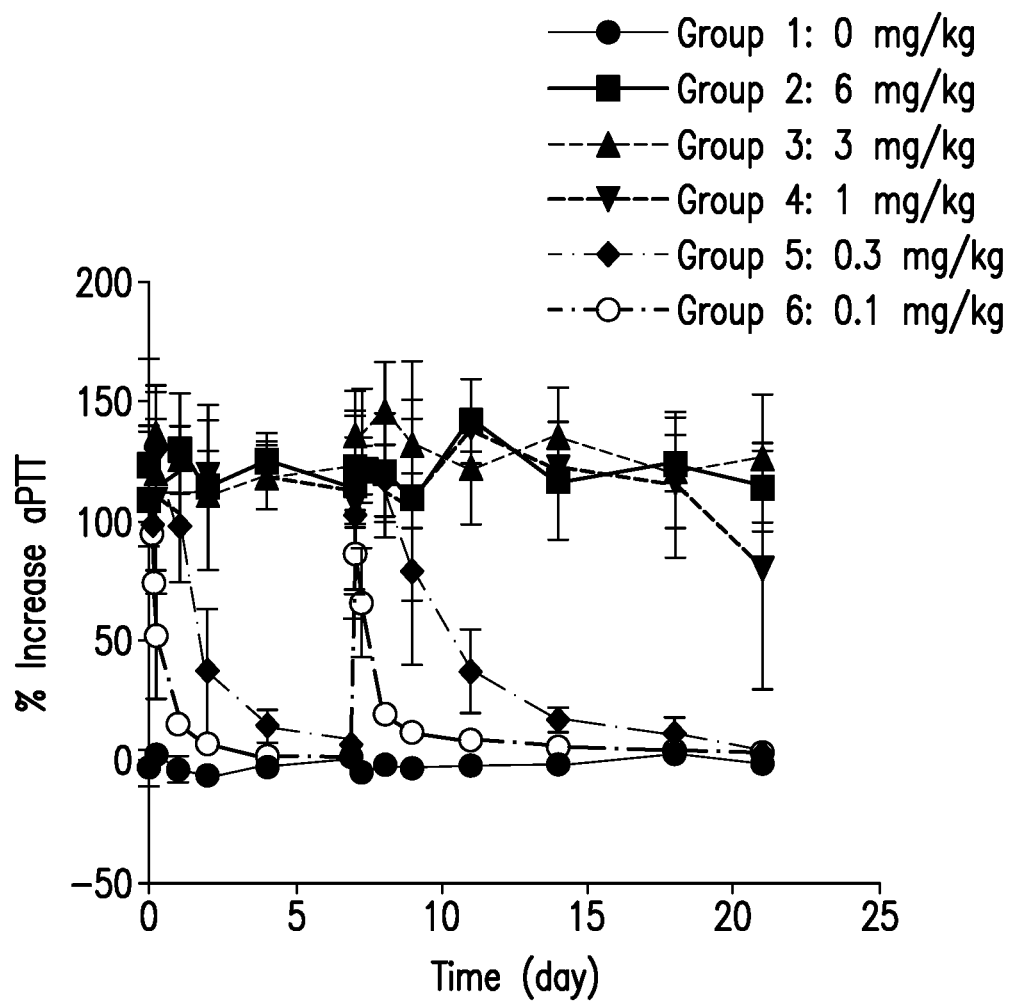
FIG. 17A shows the Concentration-time Profiles following αFXI-18623p IgG4 HC (S228P)(E1)/LC kappa IV Administration in Rhesus Monkeys. Plasma concentration-time profiles for αFXI-18623p IgG4 HC (S228P)(E1)/LC kappa in Rhesus monkeys are presented. There were 4 animals in each dose group. Each line represents a mean for a particular group.
Figure 17B:
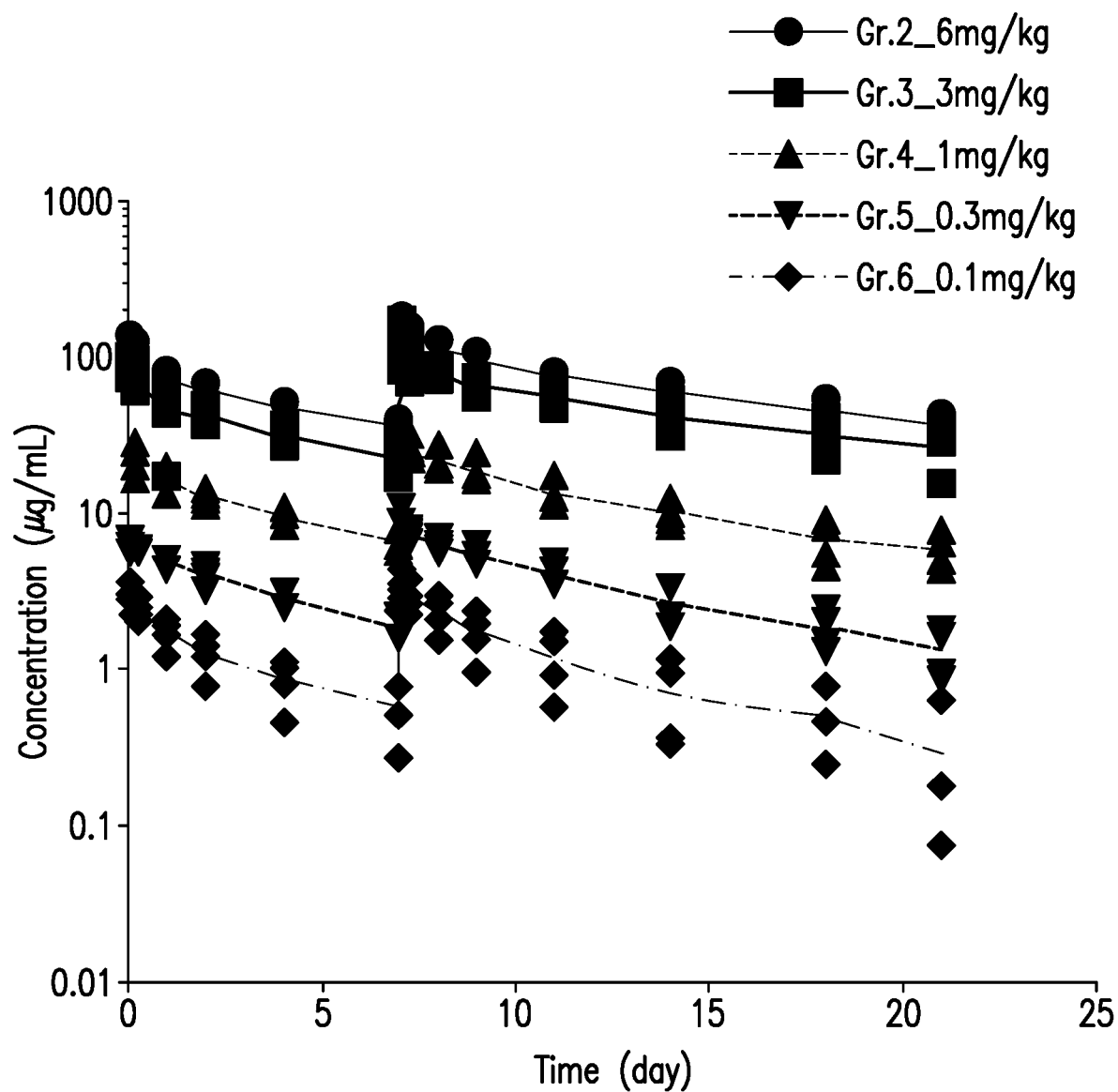
FIG. 17B shows the aPTT-time Profiles in Rhesus Monkey. The aPTT-time profiles for αFXI-18623p IgG4 HC (S228P)(E1)/LC kappa are presented for each dose group. There were 4 animals in each dose group. Each symbol represents an individual animal's aPTT time profile at each time point. Each line represents a mean for a particular group.

Results. The individual concentration-time profiles for αFXI-18623p IgG4 HC (S228P)(E1)/LC kappa are depicted in FIG. 17A. Non-linearity was observed for all PK parameters. The mean clearance values decreased from about 8 mL/kg-day for the lowest dose tested (0.1 mg/kg) to about 4 mL/kg-day for the highest dose tested (6 mg/kg). The aPTT concentration-time profiles are depicted in FIG. 17B. A dose dependent increase in aPTT was observed. The relationship between plasma concentrations of αFXI-18623p IgG4 HC (S228P)(E1)/LC kappa and aPTT best described by the sigmoidal $E_{max}$ model adequately described this relationship. The estimated $EC_{50}$ value for αFXI-18623p IgG4 HC (S228P)(E1)/LC kappa was about 3.6 μg/mL.

Table of Sequences

| SEQ ID NO: | Description | Sequence |
|---|---|---|
| 1 | αFXI-18611p and αFXI-18611 HC-CDR1 | YSISSGYFWG |
| 2 | αFXI-18611p and αFXI-18611 HC-CDR2 | SILHSGVTYYNPSLKS |
| 3 | αFXI-18611p HC-CDR3 | ARDRTTVSMIEYFQH |
| 4 | αFXI-18611 HC-CDR3 | ARDRTTVSLIEYFQH |
| 5 | αFXI-18611p and αFXI-18611 LC-CDR1 | QASQDISNYLN |

-continued

| Table of Sequences | | |
|---|---|---|
| SEQ ID NO: | Description | Sequence |
| 6 | αFXI-18611p and αFXI-18611 LC-CDR2 | DASNLET |
| 7 | αFXI-18611p and αFXI-18611 LC-CDR3 | QQFHLLPIT |
| 8 | αFXI-18623p HC-CDR1 | GSIYSGAYYWS |
| 9 | αFXI-18623p HC-CDR2 | SIHYSGLTYYNPSLKS |
| 10 | αFXI-18623p HC-CDR3 | ARDVDDSSGDEHYGMDV |
| 11 | αFXI-18623p LC-CDR1 | RASQGIDSWLA |
| 12 | αFXI-18623p LC-CDR2 | AASSLQS |
| 13 | αFXI-18623 PLC-CDR3 | QQYHIVPIT |
| 14 | LC Leader Sequence A | MSVPTQVLGLLLLWLTDARC |
| 15 | HC Leader Sequence B | MEWSWVFLFFLSVTTGVHS |
| 16 | Human IgG4 HC constant domain: (S228P) S at position 108 replaced with P | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTP PVLDSDGSFFLYSRLTVDKSRWQEGNVFSCSVMHEALHNHYTQKS LSLSLGK |
| 17 | Human IgG4 HC constant domain: (S228P) S at position 108 replaced with P; C-terminal K-less | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTP PVLDSDGSFFLYSRLTVDKSRWQEGNVFSCSVMHEALHNHYTQKS LSLSLG |
| 18 | Human IgG1 HC constant domain | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYT QKSLSLSPGK |

| SEQ ID NO: | Description | Sequence |
|---|---|---|
| 19 | Human IgG1 HC constant domain C-terminal K-less | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFELYSKLTVDKSRWQQGNVFSCSVMHEALHNHYT QKSLSLSPG |
| 20 | Human kappa LC constant domain | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |
| 21 | αFXI-18611p HC-variable region; (Q1) (M105) | QVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSMIEYFQHWGQGTLVTVSS |
| 22 | αFXI-18611p HC-variable region; (E1) (M105) | EVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSMIEYFQHWGQGTLVTVSS |
| 23 | αFXI-18611 HC-variable region; (Q1) (L105) | QVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSS |
| 24 | αFXI-18611 HC-variable region; (E1) (L105) | EVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSS |
| 25 | αFXI-18611p and αFXI-18611 LC-variable region | DIQMTQSPSSLSASVGDRVTITCQASQDISNYLNWYQQKPGKA PKLLIYDASNLETGVPSRFSGSGSGTDFTFTISSLQPEDIATYYC QQFHLLPITFGGGTKVEIK |
| 26 | αFXI-18611p and αFXI-18611 kappa LC | DIQMTQSPSSLSASVGDRVTITCQASQDISNYLNWYQQKPGKA PKLLIYDASNLETGVPSRFSGSGSGTDFTFTISSLQPEDIATYYC QQFHLLPITFGGGTKVEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSFNRGEC |
| 27 | DNA encoding αFXI-18611p and αFXI-18611 kappa LC | GACATCCAGATGACCCAGAGCCCTAGCAGCCTGAGCGCCAG CGTGGGCGACAGAGTGACCATCACCTGTCAAGCCTCCCAGG ACATCTCCAACTACCTGAACTGGTACCAGCAGAAGCCCGGC AAGGCTCCCAAGCTGCTGATCTACGACGCCTCCAACCTGGA GACCGGCGTGCCTAGCAGATTTAGCGGCAGCGGCTCCGGCA CAGACTTCACCTTCACCATCAGCTCCCTGCAGCCCGAGGAC ATTGCCACCTACTACTGCCAGCAGTTTCACCTGCTGCCTATC ACCTTCGGCGGCGGCACCAAGGTGGAGATCAAAAGGACCG TCGCCGCCCCTAGCGTGTTCATCTTCCCCCCTAGCGACGAGC AGCTCAAGTCCGGCACCGCCAGCGTGGTGTGTCTGCTCAAC AACTTCTACCCCAGGGAGGCCAAGGTGCAGTGGAAGGTGG ACAACGCCCTGCAGAGCGGCAACAGCCAGGAGAGCGTGAC AGAACAGGACAGCAAGGATTCCACATACAGCCTGAGCTCC ACCCTGACCCTGAGCAAGGCCGACTACGAGAAGCACAAGG TGTACGCCTGTGAGGTGACACACCAGGGCCTCAGCTCCCCC GTGACCAAGAGCTTCAACAGAGGCGAATGCTGA |
| 28 | αFXI-18623p HC-variable region; (Q1) | QVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSS |

Table of Sequences

| SEQ ID NO: | Description | Sequence |
|---|---|---|
| 29 | αFXI-18623p HC-variable region; (E1) | EVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSS |
| 30 | αFXI-18623p LC-variable region | DIQMTQSPSSVSASVGDRVTITCRASQGIDSWLAWYQQKPGK APKLLIYAASSLQSGVPSRFSGSGSGTDFTLTISSLQPEDFATYY CQQYHIVPITFGGGTKVEIK |
| 31 | αFXI-18623p kappa LC | DIQMTQSPSSVSASVGDRVTITCRASQGIDSWLAWYQQKPGK APKLLIYAASSLQSGVPSRFSGSGSGTDFTLTISSLQPEDFATYY CQQYHIVPITFGGGTKVEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |
| 32 | DNA encoding αFXI-18623p kappa LC | GACATCCAGATGACCCAGAGCCCTAGCAGCGTGAGCGCCA GCGTGGGCGATAGGGTGACCATCACCTGCAGAGCCTCCCAG GGCATCGACAGCTGGCTGGCCTGGTACCAGCAGAAGCCCGG CAAGGCCCCTAAGCTGCTGATCTACGCCGCTAGCAGCCTGC AGAGCGGCGTGCCTAGCAGGTTCAGCGGAAGCGGCAGCGG CACCGACTTCACACTGACCATCAGCAGCCTGCAACCTGAGG ACTTCGCCACCTACTACTGCCAGCAGTATCACATCGTGCCC ATCACCTTCGGCGGCGGAACCAAGGTGGAGATTAAGAGGA CCGTGGCCGCCCCCAGCGTGTTTATCTTTCCCCCCAGCGATG AGCAGCTGAAGAGCGGAACCGCCAGCGTGGTGTGCCTGCTG AACAACTTCTACCCCAGAGAGGCCAAGGTGCAGTGGAAGG TGGACAACGCCCTGCAGTCCGGAAACAGCCAGGAGAGCGT GACCGAGCAGGATTCCAAGGATAGCACCTACAGCCTGAGC AGCACCCTGACACTGAGCAAGGCCGACTACGAGAAGCACA AGGTGTACGCCTGTGAGGTGACCCATCAGGGCCTGAGCAGC CCTGTGACCAAGAGCTTCAACAGGGGCGAGTGCTGA |
| 33 | αFXI-18611p IgG4 HC (S228P) (Q1) (M105) | QVQLQESGPGLVKPSETLSLTCAVSGYSISSSGYFWGWIRQPPG KGLEWIGSILHSGVTYYNPSLKSRVTISVDTSKNQFSLKLSSVT AADTAVYYCARDRTTVSMIEYFQHWGQGTLVTVSSASTKGPS VFPLAPCSRSTSESTAALGCLVKDYFPEPVTVSWNSGALTSGVHTF PAVLQSSGLYSLSSVVTVPSSSLGTKTYTCNVDHKPSNTKVDKRVES KYGPPCPPCPAPEFLGGPSVFLFPPKPKDTLMISRTPEVTCVVVDV SQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDG SFFLYSRLTVDKSRWQEGNVFSCSVMHEALHNHYTQKSLSLSLGK |
| 34 | DNA encoding αFXI-18611p IgG4 HC (S228P)(Q1) (M105); xxx = CAG or CAA (Q) | xxxGTCCAGCTGCAGGAGAGCGGCCCTGGCCTGGTAAGCCT AGCGAGACACTGTCCCTGACCTGCGCCGTGAGCGGCTACAG CATCTCCAGCGGCTATTTCTGGGGATGGATCAGACAGCCCC CTGGCAAGGGCCTGGAATGGATCGGTTCTATCCTGCACTCC GGCGTGACATACTATAACCCTAGCCTGAAGAGCAGGGTGAC CATCTCCGTGGATACCAGCAAGAATCAGTTCAGCCTGAAGC TCAGCAGCGTGACCGCCGCCGATACCGCTGTGTACTACTGC GCCAGAGACAGGACCACCGTCTCCATGATCGAGTACTTCCA GCACTGGGGCCAAGGCACCCTGGTCACCGTGTCCTCCGCCT CCACCAAGGGCCCTAGCGTGTTTCCTCTGGCCCCCTGCTCCA GATCCACAAGCGAGAGCACCGCTGCCCTGGGCTGTCTGGTC AAGGACTACTTCCCCGAGCCCGTGACAGTGTCCTGGAACAG CGGCGCCCTGACAAGCGGCGTCCATACATTCCCCGCCGTGC TGCAGTCCAGCGGACTGTATAGCCTGAGCTCCGTGGTGACC GTGCCTTCCAGCAGCCTGGGAACCAAGACATATACCTGCAA CGTGGACCATAAGCCCAGCAACACAAAAGTCGACAAGAGG GTGGAGAGCAAGTACGGACCCCCTTGTCCCCCTTGTCCTGC TCCCGAGTTCCTCGGCGGACCTAGCGTGTTCCTGTTTCCTCC CAAGCCCAAGGATACCCTGATGATCAGCAGGACCCCTGAGG TCACCTGCGTGGTGGTCGACGTGTCCCAGGAGGACCCTGAG GTCCAGTTTAACTGGTACGTGGACGGAGTGGAGGTGCACAA CGCCAAGACCAAGCCCAGAGAGGAGCAGTTCAATTCCACCT ACAGGGTGGTGAGCGTCCTGACCGTGCTGCACCAGGACTGG CTGAATGGAAAGGAGTACAAATGCAAGGTCTCCAACAAGG GCCTCCCTAGCAGCATCGAGAAGACCATCTCCAAGGCCAAG GGCCAGCCTAGGGAGCCCCAGGTGTACACCCTGCCTCCTAG CCAGGAGGAAATGACCAAGAACCAGGTGTCCCTGACATGC CTGGTGAAGGGCTTCTATCCTAGCGACATCGCCGTGGAGTG GGAGAGCAATGGCCAGCCCGAGAATAACTACAAGACCACC CCCCCTGTGCTCGATAGCGACGGCAGCTTCTTTCTGTACAGC |

| SEQ ID NO: | Description | Sequence |
|---|---|---|
| | | AGGCTGACCGTGGACAAGAGCAGGTGGCAAGAGGGCAACG<br>TGTTTAGCTGCTCCGTCATGCACGAGGCCCTGCATAACCACT<br>ACACCCAAAAATCCCTGTCCCTGTCCCTGGGCAAGTGA |
| 35 | αFXI-18611p IgG4 HC (A228P) (E1)(M105) | EVQLQESGPGLVKPSETLSLTCAVSGYSISSGYFWGWIRQPPG<br>KGLEWIGSILHSGVTYYNPSLKSRVTISVDTSKNQFSLKLSSVT<br>AADTAVYYCARDRTTVSMIEYFQHWGQGTLVTVSS*ASTKGPS<br>VFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVES<br>KYGPPCPPCPAPEFLGGPSVFLFPPKPKDTLMISRTPEVTCVVVDV<br>SQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEE<br>MTKNQVSLTCLVKGFYPSDIAVEWESNGQPENNYKTTPPVLDSDG<br>SFFLYSRLTVDKSRWQEGNVFSCSVMHEALHNHYTQKSLSLSLGK* |
| 36 | DNA encoding αFXI-18611p IgG4 HC S228P); (E1)(M105) xxx = GAA or GAG (E) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCCT<br>CCACCAAGGGCCCTAGCGTGTTTCCTCTGGCCCCCTGCTCCA<br>GATCCACAAGCGAGAGCACCGCTGCCCTGGGCTGTCTGGTC<br>AAGGACTACTTCCCCGAGCCCGTGACAGTGTCCTGGAACAG<br>CGGCGCCCTGACAAGCGGCGTCCATACATTCCCCGCCGTGC<br>TGCAGTCCAGCGGACTGTATAGCCTGAGCTCCGTGGTGACC<br>GTGCCTTCCAGCAGCCTGGGAACCAAGACATATACCTGCAA<br>CGTGGACCATAAGCCCAGCAACACAAAAGTCGACAAGAGG<br>GTGGAGAGCAAGTACGGACCCCCTTGTCCCCCTTGTCCTGC<br>TCCCGAGTTCCTCGGCGGACCTAGCGTGTTCCTGTTTCCTCC<br>CAAGCCCAAGGATACCCTGATGATCAGCAGGACCCCTGAGG<br>TCACCTGCGTGGTGGTCGACGTGTCCCAGGAGGACCCTGAG<br>GTCCAGTTTAACTGGTACGTGGACGGAGTGGAGGTGCACAA<br>CGCCAAGACCAAGCCCAGAGAGGAGCAGTTCAATTCCACCT<br>ACAGGGTGGTGAGCGTCCTGACCGTGCTGCACCAGGACTGG<br>CTGAATGGAAAGGAGTACAAATGCAAGGTCTCCAACAAGG<br>GCCTCCCTAGCAGCATCGAGAAGACCATCTCCAAGGCCAAG<br>GGCCAGCCTAGGGAGCCCCAGGTGTACACCCTGCCTCCTAG<br>CCAGGAGGAAATGACCAAGAACCAGGTGTCCCTGACATGC<br>CTGGTGAAGGGCTTCTATCCTAGCGACATCGCCGTGGAGTG<br>GGAGAGCAATGGCCAGCCCGAGAATAACTACAAGACCACC<br>CCCCCTGTGCTCGATAGCGACGGCAGCTTCTTTCTGTACAGC<br>AGGCTGACCGTGGACAAGAGCAGGTGGCAAGAGGGCAACG<br>TGTTTAGCTGCTCCGTCATGCACGAGGCCCTGCATAACCACT<br>ACACCCAAAAATCCCTGTCCCTGTCCCTGGGCAAGTGA |
| 37 | αFXI-18611 IgG4 HC S228P)(Q1) (L105) | QVQLQESGPGLVKPSETLSLTCAVSGYSISSGYFWGWIRQPPG<br>KGLEWIGSILHSGVTYYNPSLKSRVTISVDTSKNQFSLKLSSVT<br>AADTAVYYCARDRTTVSLIEYFQHWGQGTLVTVSS*ASTKGPSV<br>FPLAPCSRSTSESTAALGCLVKDYFPEPVTVSWNSGALTSGVHTFP<br>AVLQSSGLYSLSSVVTVPSSSLGTKTYTCNVDHKPSNTKVDKRVESK<br>YGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQ<br>DWLNGKEYKCKVSNKGLPSSIEKTISKAKGQPREPQVYTLPPSQEE<br>MTKNQVSLTCLVKGFYPSDIAVEWESNGQPENNYKTTPPVLDSDG<br>SFFLYSRLTVDKSRWQEGNVFSCSVMHEALHNHYTQKSLSLSLGK* |
| 38 | DNA encoding αFXI-18611 IgG4 HC S228P); (Q1)(L105) xxx = CAG or CAA (Q) | xxxGTCCAGCTGCAGGAGAGCGGCCCTGGACTCGTGAAGCC<br>CTCCGAAACCCTGAGCCTCACATGCGCCGTCTCCGGATACA<br>GCATCAGCAGCGGATACTTCTGGGGCTGGATCAGACAGCCC<br>CCCGGCAAAGGCCTGGAGTGGATCGGTTCTATTCTCCACAG<br>CGGCGTGACATACTACAACCCTCCCTGAAGAGCAGGGTGA<br>CCATCAGCGTGGACACCTCCAAGAACCAGTTTTCCCTCAAG<br>CTGAGCAGCGTGACCGCCGCTGACACAGCCGTGTATTACTG<br>CGCCAGGGACAGGACCACCGTGTCCCTGATTGAGTACTTCC<br>AGCATTGGGGCCAGGGCACACTGGTGACCGTCAGCAGCGCC<br>AGCACCAAGGGCCCTTCCGTCTTCCCTCTGGCCCCTTGCAGC<br>AGAAGCACCTCCGAGTCCACAGCCGCCCTGGGATGCCTCGT<br>GAAGGATTACTTCCCCGAGCCCGTCACAGTGTCCTGGAACT<br>CCGGCGCTCTGACCAGCGGAGTGCACACCTTCCCCGCCGTG<br>CTGCAAAGCAGCGGCCTGTACAGCCTGTCCAGCGTGGTCAC |

-continued

Table of Sequences

| SEQ ID NO: | Description | Sequence |
|---|---|---|
| | | CGTGCCTTCCTCCAGCCTGGGCACCAAGACCTACACATGCA ACGTGGACCACAAGCCTTCCAACACCAAGGTGGACAAGAG AGTGGAAAGCAAGTACGGCCCCCCCTGCCCCCCTTGTCCTG CCCCCGAGTTTCTGGGAGGACCCTCCGTGTTCCTCTTTCCTC CCAAGCCTAAGGACACCCTGATGATCTCCAGGACCCCCGAA GTGACCTGCGTGGTCGTGGACGTGTCCCAGGAGGACCCTGA GGTGCAGTTTAACTGGTACGTGGACGGCGTGGAGGTGCACA ACGCCAAGACCAAGCCCAGGGAGGAGCAGTTCAATAGCAC CTACAGGGTGGTGTCCGTGCTGACCGTGCTGCACCAGGACT GGCTGAACGGCAAAGAGTACAAGTGCAAAGTCAGCAACAA GGGCCTGCCCTCCTCCATCGAGAAGACCATTAGCAAGGCCA AGGGCCAGCCTAGGGAGCCTCAGGTGTACACCCTGCCCCCC AGCCAGGAGGAGATGACCAAGAACCAGGTGTCCCTGACCT GCCTGGTCAAGGGATTTTACCCCAGCGACATCGCTGTGGAA TGGGAGAGCAATGGCCAGCCCGAGAACAACTACAAGACCA CCCCTCCCGTGCTCGATTCCGACGGCAGCTTTTTCCTGTACA GCAGGCTGACCGTGGATAAGAGCAGGTGGCAGGAAGGCAA CGTGTTCTCCTGTTCCGTGATGCATGAGGCCCTGCACAACCA CTACACACAGAAGAGCCTGTCCCTGTCCCTGGGCAAGTGA |
| 39 | αFXI-18611 IgG4 HC (S228P) (E1)(L105) | EVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSSASTKGPSV FPLAPCSRSTSESTAALGCLVKDYFPEPVTVSWNSGALTSGVHTFP AVLQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDG SFFLYSRLTVDKSRWQEGNVFSCSVMHEALHNHYTQKSLSLSLGK |
| 40 | DNA encoding αFXI-18611 IgG4 HC (S228P) (Q1)(L105) xxx = GAA or GAG (E) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACCGCTGTATTACTG CGCCAGGGACAGGACCACCGTGTCCCTGATTGAGTACTTCC AGCATTGGGGCCAGGGCACACTGGTGACCGTCAGCAGCGCC AGCACCAAGGGCCCTTCCGTCTTCCCTCTGGCCCCTTGCAGC AGAAGCACCTCCGAGTCCACAGCCGCCCTGGGATGCCTCGT GAAGGATTACTTCCCCGAGCCCGTCACAGTCTCCTGGAACT CCGGCGCTCTGACCAGCGGAGTGCACACCTTCCCCGCCGTG CTGCAAAGCAGCGGCCTGTACAGCCTGTCCAGCGTGGTCAC CGTGCCTTCCTCCAGCCTGGGCACCAAGACCTACACATGCA ACGTGGACCACAAGCCTTCCAACACCAAGGTGGACAAGAG AGTGGAAAGCAAGTACGGCCCCCCCTGCCCCCCTTGTCCTG CCCCCGAGTTTCTGGGAGGACCCTCCGTGTTCCTCTTTCCTC CCAAGCCTAAGGACACCCTGATGATCTCCAGGACCCCCGAA GTGACCTGCGTGGTCGTGGACGTGTCCCAGGAGGACCCTGA GGTGCAGTTTAACTGGTACGTGGACGGCGTGGAGGTGCACA ACGCCAAGACCAAGCCCAGGGAGGAGCAGTTCAATAGCAC CTACAGGGTGGTGTCCGTGCTGACCGTGCTGCACCAGGACT GGCTGAACGGCAAAGAGTACAAGTGCAAAGTCAGCAACAA GGGCCTGCCCTCCTCCATCGAGAAGACCATTAGCAAGGCCA AGGGCCAGCCTAGGGAGCCTCAGGTGTACACCCTGCCCCCC AGCCAGGAGGAGATGACCAAGAACCAGGTGTCCCTGACCT GCCTGGTCAAGGGATTTTACCCCAGCGACATCGCTGTGGAA TGGGAGAGCAATGGCCAGCCCGAGAACAACTACAAGACCA CCCCTCCCGTGCTCGATTCCGACGGCAGCTTTTTCCTGTACA GCAGGCTGACCGTGGATAAGAGCAGGTGGCAGGAAGGCAA CGTGTTCTCCTGTTCCGTGATGCATGAGGCCCTGCACAACCA CTACACACAGAAGAGCCTGTCCCTGTCCCTGGGCAAGTGA |
| 41 | αFXI-18623p HC-IgG4 (S228P(Q1) | QVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSSAST KGPSVFPLAPCSRSTSESTAALGCLVKDYFPEPVTVSWNSGALTSG VHTFPAVLQSSGLYSLSSVVTVPSSSLGTKTYTCNVDHKPSNTKVDK RVESKYGPPCPPCPAPEFLGGPSVFLFPPKPKDTLMISRTPEVTCV VVDVSQEDPEVQFNWYVDGVEVHNAKTKPREEQFNSTYRVVSVLT VLHQDWLNGKEYKCKVSNKGLPSSIEKTISKAKGQPREPQVYTLPP SQEEMTKNQVSLTCLVKGFYPSDIAVEWESNGQPENNYKTTPPVL |

Table of Sequences

| SEQ ID NO: | Description | Sequence |
|---|---|---|
| | | DSDGSFFLYSRLTVDKSRWQEGNVFSCSVMHEALHNHYTQKSLSL SLGK |
| 42 | DNA encoding αFXI-18623 pHC-IgG4 (S228P( (Q1) xxx = CAG or CAA (Q) | xxxGTCCAGCTGCAGGAATCCGGACCCGGCCTGGTGAAGCCT AGCCAGACCCTGAGCCTGACCTGTACCGTGTCCGGCGGAAG CATCTATTCCGGCGCCTACTACTGGTCCTGGATTAGGCAGC ACCCCGGCAAGGGCCTGGAATGGATCGGCTCCATCCACTAC AGCGGCCTGACCTATTACAACCCCTCCCTGAAGTCCAGGGT GACCATCAGCGTCGACACAAGCAAGAACCAGTTCTCCCTCA AGCTGAGCAGCGTGACCGCCGCCGACACCGCCGTGTATTAT TGCGCCAGAGACGTGGACGACTCCTCCGGAGACGAGCACTA CGGCATGGACGTCTGGGGCCAGGGCACAACAGTGACAGTG AGCAGCGCCAGCACCAAAGGACCCTCCGTCTTCCCTCTGGC CCCTTGCTCCAGGAGCACAAGCGAAAGCACAGCCGCCCTGG GCTGCCTGGTGAAGGACTACTTTCCCGAGCCCGTGACCGTG AGCTGGAATAGCGGAGCCCTCACCTCCGGAGTCCACACATT TCCCGCCGTCCTGCAGAGCAGCGGCCTGTACTCCCTGAGCT CCGTGGTGACCGTGCCTTCCTCCAGCCTGGGCACCAAGACC TACACCTGCAACGTGGACCACAAGCCTAGCAATACCAAGGT GGACAAGAGGGTGGAATCCAAGTACGGCCCCCCTTGCCCTC CTTGTCCTGCCCCCGAATTTCTGGGCGGCCCTTCCGTGTTCC TGTTCCCTCCCAAGCCCAAGGATACCCTGATGATCAGCAGG ACCCCTGAGGTGACCTGTGTGGTGGTGGACGTGAGCCAGGA GGACCCCGAGGTGCAGTTCAACTGGTACGTGGATGGCGTGG AAGTGCACAATGCCAAGACAAAGCCCAGGGAGGAGCAGTT CAATAGCACCTACAGGGTGGTCAGCGTGCTCACAGTGCTGC ACCAGGACTGGCTGAACGGAAAGGAGTACAAGTGCAAAGT GTCCAACAAGGGCCTGCCCTCCTCCATCGAAAAGACCATCT CCAAGGCCAAAGGCCAGCCCAGGGAGCCCCAAGTGTATAC CCTCCCCCCTAGCCAGGAGGAAATGACCAAAAACCAGGTCT CCCTGACCTGTCTGGTGAAGGGCTTCTATCCCAGCGACATC GCTGTGGAGTGGGAGAGCAACGGCCAACCCGAGAACAACT ATAAGACCACACCCCCGTCCTGGACTCCGATGGCTCCTTCT TCCTGTACAGCAGGCTGACCGTCGACAAGTCCAGGTGGCAG GAAGGGAAACGTGTTCTCCTGTAGCGTCATGCACGAGGCCCT GCACAACCACTATACCCAGAAGTCCCTGTCCCTGAGCCTGG GCAAGTGA |
| 43 | αFXI-18623p HC-IgG4 (S228P( (E1) | EVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSS*AST KGPSVFPLAPCSRSTSESTAALGCLVKDYFPEPVTVSWNSGALTSG VHTFPAVLQSSGLYSLSSVVTVPSSSLGTKTYTCNVDHKPSNTKVDK RVESKYGPPCPPCPAPEFLGGPSVFLFPPKPKDTLMISRTPEVTCV VVDVSQEDPEVQFNWYVDGVEVHNAKTKPREEQFNSTYRVVSVLT VLHQDWLNGKEYKCKVSNKGLPSSIEKTISKAKGQPREPQVYTLPP SQEEMTKNQVSLTCLVKGFYPSDIAVEWESNGQPENNYKTTPPVL DSDGSFFLYSRLTVDKSRWQEGNVFSCSVMHEALHNHYTQKSLSL SLGK* |
| 44 | DNA encoding αFXI-18623p HC-IgG4 (S228P( (E1) xxx = GAA or GAG (E) | xxxGTCCAGCTGCAGGAATCCGGACCCGGCCTGGTGAAGCCT AGCCAGACCCTGAGCCTGACCTGTACCGTGTCCGGCGGAAG CATCTATTCCGGCGCCTACTACTGGTCCTGGATTAGGCAGC ACCCCGGCAAGGGCCTGGAATGGATCGGCTCCATCCACTAC AGCGGCCTGACCTATTACAACCCCTCCCTGAAGTCCAGGGT GACCATCAGCGTCGACACAAGCAAGAACCAGTTCTCCCTCA AGCTGAGCAGCGTGACCGCCGCCGACACCGCCGTGTATTAT TGCGCCAGAGACGTGGACGACTCCTCCGGAGACGAGCACTA CGGCATGGACGTCTGGGGCCAGGGCACAACAGTGACAGTG AGCAGCGCCAGCACCAAAGGACCCTCCGTCTTCCCTCTGGC CCCTTGCTCCAGGAGCACAAGCGAAAGCACAGCCGCCCTGG GCTGCCTGGTGAAGGACTACTTTCCCGAGCCCGTGACCGTG AGCTGGAATAGCGGAGCCCTCACCTCCGGAGTCCACACATT TCCCGCCGTCCTGCAGAGCAGCGGCCTGTACTCCCTGAGCT CCGTGGTGACCGTGCCTTCCTCCAGCCTGGGCACCAAGACC TACACCTGCAACGTGGACCACAAGCCTAGCAATACCAAGGT GGACAAGAGGGTGGAATCCAAGTACGGCCCCCCTTGCCCTC CTTGTCCTGCCCCCGAATTTCTGGGCGGCCCTTCCGTGTTCC TGTTCCCTCCCAAGCCCAAGGATACCCTGATGATCAGCAGG ACCCCTGAGGTGACCTGTGTGGTGGTGGACGTGAGCCAGGA GGACCCCGAGGTGCAGTTCAACTGGTACGTGGATGGCGTGG AAGTGCACAATGCCAAGACAAAGCCCAGGGAGGAGCAGTT CAATAGCACCTACAGGGTGGTCAGCGTGCTCACAGTGCTGC ACCAGGACTGGCTGAACGGAAAGGAGTACAAGTGCAAAGT |

Table of Sequences

| SEQ ID NO: | Description | Sequence |
|---|---|---|
| | | GTCCAACAAGGGCCTGCCCTCCTCCATCGAAAAGACCATCT<br>CCAAGGCCAAAGGCCAGCCCAGGGAGCCCCAAGTGTATAC<br>CCTCCCCCCTAGCCAGGAGGAAATGACCAAAAACCAGGTCT<br>CCCTGACCTGTCTGGTGAAGGGCTTCTATCCCAGCGACATC<br>GCTGTGGAGTGGGAGAGCAACGGCCAACCCGAGAACAACT<br>ATAAGACCACACCCCCGTCCTGGACTCCGATGGCTCCTTCT<br>TCCTGTACAGCAGGCTGACCGTCGACAAGTCCAGGTGGCAG<br>GAAGGAAACGTGTTCTCCTGTAGCGTCATGCACGAGGCCCT<br>GCACAACCACTATACCCAGAAGTCCCTGTCCCTGAGCCTGG<br>GCAAGTGA |
| 45 | αFXI-18611p HC IgG1 (Q1) (M105) | QVQLQESGPGLVKPSETLSLTCAVSG<u>YSISSGYFWG</u>WIRQPPG<br>KGLEWIGS<u>ILHSGVTYYNPSLKSRVT</u>ISVDTSKNQFSLKLSSVT<br>AADTAVYYCARD<u>RTTVSMIEYFQH</u>WGQGTLVTVSSASTKGPS<br>*VFPLAPSSKSTSGGTAALGCLVKDYFPEPVTVSWNSGALTSGVHTF*<br>*PAVLQSSGLYSLSSVVTVPSSSLGTQTYICNVNHKPSNTKVDKKVEP*<br>*KSCDKTHTCPPCPAPELLGGPSVFLFPPKPKDTLMISRTPEVTCVV*<br>*VDVSHEDPEVKFNWYVDGVEVHNAKTKPREEQYNSTYRVVSVLTV*<br>*LHQDWLNGKEYKCKVSNKALPAPIEKTISKAKGQPREPQVYTLPPS*<br>*RDELTKNQVSLTCLVKGFYPSDIAVEWESNGQPENNYKTTPPVLDS*<br>*DGSFFLYSKLTVDKSRWQQGNVFSCSVMHEALHNHYTQKSLSLSP*<br>*GK* |
| 46 | DNA encoding αFXI-18611p HC IgG1 (Q1) (M105) xxx = CAG or CAA (Q) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCTA<br>GCACAAAAGGACCAAGCGTGTTTCCACTGGCACCTAGCAGC<br>AAATCCACCAGCGGCGGAACAGCAGCCCTCGGGTGCCTGGT<br>GAAGGATTACTTCCCTGAGCCAGTCACAGTGTCCTGGAACT<br>CCGGAGCCCTGACATCCGGCGTGCACACCTTCCCCGCTGTG<br>CTGCAATCCAGCGGACTGTATAGCCTCAGCTCCGTCGTGAC<br>AGTCCCTTCCAGCAGCCTGGGCACACAGACTTACATTTGCA<br>ACGTGAACCACAAACCTTCCAACACTAAGGTGGACAAAAA<br>GGTGGAACCCAAATCCTGTGATAAGACCCATACATGCCCAC<br>CTTGTCCCGCTCCTGAGCTGCTGGGGGGACCTTCCGTCTTTC<br>TGTTTCCTCCAAAACCAAAAGACACACTCATGATCAGCCGG<br>ACCCCCGAAGTCACCTGTGTGGTGGTGGACGTCAGCCACGA<br>AGATCCAGAGGTCAAGTTCAATTGGTACGTGGATGGAGTGG<br>AAGTCCACAACGCAAAAACCAAACCTAGAGAAGAACAGTA<br>CAATAGCACATACAGGGTGGTGTCCGTCCTGACAGTGCTCC<br>ACCAGGACTGGCTCAATGGCAAAGAGTATAAGTGCAAGGT<br>GAGCAACAAGGCCCTGCCTGCACCAATTGAGAAAACAATTA<br>GCAAGGCAAAGGGGCAGCCACGGGAACCCCAGGTGTATAC<br>CCTGCCCCCAAGCCGGGATGAACTGACCAAAAACCAGGTCA<br>GCCTGACATGCCTGGTGAAAGGGTTTTACCCAAGCGATATT<br>GCCGTCGAGTGGGAGAGCAACGGACAGCCAGAAAACAATT<br>ACAAAACCACCCCACCTGTGCTGGACTCCGATGGGAGCTTT<br>TTCCTGTACAGCAAGCTCACAGTGGACAAGTCCAGATGGCA<br>ACAGGGCAACGTGTTTTCCTGCTCCGTGATGCACGAGGCCC<br>TCCACAACCACTATACACAAAAGTCCCTCTCCCTCAGCCCA<br>GGAAAGTGA |
| 47 | αFXI-18611p HC IgG1 (E1) (M105) | EVQLQESGPGLVKPSETLSLTCAVSG<u>YSISSGYFWG</u>WIRQPPG<br>KGLEWIGS<u>ILHSGVTYYNPSLKSRVT</u>ISVDTSKNQFSLKLSSVT<br>AADTAVYYCARD<u>RTTVSMIEYFQH</u>WGQGTLVTVSSASTKGPS<br>*VFPLAPSSKSTSGGTAALGCLVKDYFPEPVTVSWNSGALTSGVHTF*<br>*PAVLQSSGLYSLSSVVTVPSSSLGTQTYICNVNHKPSNTKVDKKVEP*<br>*KSCDKTHTCPPCPAPELLGGPSVFLFPPKPKDTLMISRTPEVTCVV*<br>*VDVSHEDPEVKFNWYVDGVEVHNAKTKPREEQYNSTYRVVSVLTV*<br>*LHQDWLNGKEYKCKVSNKALPAPIEKTISKAKGQPREPQVYTLPPS*<br>*RDELTKNQVSLTCLVKGFYPSDIAVEWESNGQPENNYKTTPPVLDS*<br>*DGSFFLYSKLTVDKSRWQQGNVFSCSVMHEALHNHYTQKSLSLSP*<br>*GK* |

| SEQ ID NO: | Description | Sequence |
|---|---|---|
| 48 | DNA encoding αFXI-18611p HC IgG1 (Q1) (M105) xxx = GAA or GAG (E) | xxxGTCCAGCTGCAGGAGAGCGGCCCTGGCCTGGTGAAGCCT AGCGAGACACTGTCCCTGACCTGCGCCGTGAGCGGCTACAG CATCTCCAGCGGCTATTTCTGGGGATGGATCAGACAGCCCC CTGGCAAGGGCCTGGAATGGATCGGTTCTATCCTGCACTCC GGCGTGACATACTATAACCCTAGCCTGAAGAGCAGGGTGAC CATCTCCGTGGATACCAGCAAGAATCAGTTCAGCCTGAAGC TCAGCAGCGTGACCGCCGCCGATACCGCTGTGTACTACTGC GCCAGAGACAGGACCACCGTCTCCATGATCGAGTACTTCCA GCACTGGGGCCAAGGCACCCTGGTCACCGTGTCCTCCGCTA GCACAAAAGGACCAAGCGTGTTTCCACTGGCACCTAGCAGC AAATCCACCAGCGGCGGAACAGCAGCCCTCGGGTGCCTGGT GAAGGATTACTTCCCTGAGCCAGTCACAGTGTCCTGGAACT CCGGAGCCCTGACATCCGGCGTGCACACCTTCCCCGCTGTG CTGCAATCCAGCGGACTGTATAGCCTCAGCTCCGTCGTGAC AGTCCCTTCCAGCAGCCTGGGCACACAGACTTACATTTGCA ACGTGAACCACAAACCTTCCAACACTAAGGTGGACAAAAA GGTGGAACCCAAATCCTGTGATAAGACCCATACATGCCCAC CTTGTCCCGCTCCTGAGCTGCTGGGGGGACCTTCCGTCTTTC TGTTTCCTCCAAAACCAAAAGACACACTCATGATCAGCCGG ACCCCCGAAGTCACCTGTGTGGTGGTGGACGTCAGCCACGA AGATCCAGAGGTCAAGTTCAATTGGTACGTGGATGGAGTGG AAGTCCACAACGCAAAAACCAAACCTAGAGAAGAACAGTA CAATAGCACATACAGGGTGGTGTCCGTCCTGACAGTGCTCC ACCAGGACTGGCTCAATGGCAAAGAGTATAAGTGCAAGGT GAGCAACAAGGCCCTGCCTGCACCAATTGAGAAAACAATTA GCAAGGCAAAGGGGCAGCCACGGGAACCCCAGGTGTATAC CCTGCCCCCAAGCCGGGATGAACTGACCAAAAACCAGGTCA GCCTGACATGCCTGGTGAAAGGGTTTTACCCAAGCGATATT GCCGTCGAGTGGGAGAGCAACGGACAGCCAGAAAACAATT ACAAAACCACCCCACCTGTGCTGGACTCCGATGGGAGCTTT TTCCTGTACAGCAAGCTCACAGTGGACAAGTCCAGATGGCA ACAGGGCAACGTGTTTTCCTGCTCCGTGATGCACGAGGCCC TCCACAACCACTATACACAAAAGTCCCTCTCCCTCAGCCCA GGAAAGTGA |
| 49 | αFXI-18611 HC IgG1 (Q1) (L105) | QVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSSASTKGPSV FPLAPSSKSTSGGTAALGCLVKDYFPEPVTVSWNSGALTSGVHTFP AVLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQVSLTCLVKGFYPSDIAVEWESNGQPENNYKTTPPVLDS DGSFFLYSKLTVDKSRWQQGNVFSCSVMHEALHNHYTQKSLSLSP GK |
| 50 | DNA encoding αFXI-18611 HC IgG1 (Q1) (L105) xxx = CAG or CAA (Q) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCT AGCACAAAAGGACCAAGCGTGTTTCCACTGGCACCTAGCAG CAAATCCACCAGCGGCGGAACAGCAGCCCTCGGGTGCCTGG TGAAGGATTACTTCCCTGAGCCAGTCACAGTGTCCTGGAAC TCCGGAGCCCTGACATCCGGCGTGCACACCTTCCCCGCTGT GCTGCAATCCAGCGGACTGTATAGCCTCAGCTCCGTCGTGA CAGTCCCTTCCAGCAGCCTGGGCACACAGACTTACATTTGC AACGTGAACCACAAACCTTCCAACACTAAGGTGGACAAAA AGGTGGAACCCAAATCCTGTGATAAGACCCATACATGCCCA CCTTGTCCCGCTCCTGAGCTGCTGGGGGGACCTTCCGTCTTT CTGTTTCCTCCAAAACCAAAAGACACACTCATGATCAGCCG GACCCCCGAAGTCACCTGTGTGGTGGTGGACGTCAGCCACG AAGATCCAGAGGTCAAGTTCAATTGGTACGTGGATGGAGTG GAAGTCCACAACGCAAAAACCAAACCTAGAGAAGAACAGT ACAATAGCACATACAGGGTGGTGTCCGTCCTGACAGTGCTC CACCAGGACTGGCTCAATGGCAAAGAGTATAAGTGCAAGG TGAGCAACAAGGCCCTGCCTGCACCAATTGAGAAAACAATT AGCAAGGCAAAGGGGCAGCCACGGGAACCCCAGGTGTATA |

-continued

Table of Sequences

| SEQ ID NO: | Description | Sequence |
|---|---|---|
| | | CCCTGCCCCCAAGCCGGGATGAACTGACCAAAAACCAGGTC AGCCTGACATGCCTGGTGAAAGGGTTTTACCCAAGCGATAT TGCCGTCGAGTGGGAGAGCAACGGACAGCCAGAAAACAAT TACAAAACCACCCCACCTGTGCTGGACTCCGATGGGAGCTT TTTCCTGTACAGCAAGCTCACAGTGGACAAGTCCAGATGGC AACAGGGCAACGTGTTTTCCTGCTCCGTGATGCACGAGGCC CTCCACAACCACTATACACAAAAGTCCCTCTCCCTCAGCCC AGGAAAGTGA |
| 51 | αFXI-18611 HC IgG1 (E1)(L105) | EVQLQESGPGLVKPSETLSLTCAVSG<u>YSISSGYFWG</u>WIRQPPG KGLEWIGS<u>ILHSGVTYYNPSLKS</u>RVTISVDTSKNQFSLKLSSVT AADTAVYYCARD<u>RTTVSLIEYFQ</u>HWGQGTLVTVSS*ASTKGPSV FPLAPSSKSTSGGTAALGCLVKDYFPEPVTVSWNSGALTSGVHTFP AVLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQVSLTCLVKGFYPSDIAVEWESNGQPENNYKTTPPVLDS DGSFFLYSKLTVDKSRWQQGNVFSCSVMHEALHNHYTQKSLSLSP GK* |
| 52 | DNA encoding αFXI-18611 HC IgG1 (E1)(L105) xxx = GAA or GAG (E) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCT AGCACAAAAGGACCAAGCGTGTTTCCACTGGCACCTAGCAG CAAATCCACCAGCGGCGGAACAGCAGCCCTCGGGTGCCTGG TGAAGGATTACTTCCCTGAGCCAGTCACAGTGTCCTGGAAC TCCGGAGCCCTGACATCCGGCGTGCACACCTTCCCCGCTGT GCTGCAATCCAGCGGACTGTATAGCCTCAGCTCCGTCGTGA CAGTCCCTTCCAGCAGCCTGGGCACACAGACTTACATTTGC AACGTGAACCACAAACCTTCCAACACTAAGGTGGACAAAA AGGTGGAACCCAAATCCTGTGATAAGACCCATACATGCCCA CCTTGTCCCGCTCCTGAGCTGCTGGGGGGACCTTCCGTCTTT CTGTTTCCTCCAAAACCAAAAGACACACTCATGATCAGCCG GACCCCCGAAGTCACCTGTGTGGTGGTGGACGTCAGCCACG AAGATCCAGAGGTCAAGTTCAATTGGTACGTGGATGGAGTG GAAGTCCACAACGCAAAAACCAAACCTAGAGAAGAACAGT ACAATAGCACATACAGGGTGGTGTCCGTCCTGACAGTGCTC CACCAGGACTGGCTCAATGGCAAAGAGTATAAGTGCAAGG TGAGCAACAAGGCCCTGCCTGCACCAATTGAGAAAACAATT AGCAAGGCAAAGGGGCAGCCACGGGAACCCCAGGTGTATA CCCTGCCCCCAAGCCGGGATGAACTGACCAAAAACCAGGTC AGCCTGACATGCCTGGTGAAAGGGTTTTACCCAAGCGATAT TGCCGTCGAGTGGGAGAGCAACGGACAGCCAGAAAACAAT TACAAAACCACCCCACCTGTGCTGGACTCCGATGGGAGCTT TTTCCTGTACAGCAAGCTCACAGTGGACAAGTCCAGATGGC AACAGGGCAACGTGTTTTCCTGCTCCGTGATGCACGAGGCC CTCCACAACCACTATACACAAAAGTCCCTCTCCCTCAGCCC AGGAAAGTGA |
| 53 | αFXI-18623p HC IgG1 (1Q) | QVQLQESGPGLVKPSQTLSLTCTVSGG<u>SIYSGAYYWS</u>WIRQHP GKGLEWIGS<u>IHYSGLTYYNPSLKS</u>RVTISVDTSKNQFSLKLSSV TAADTAVYYCARD<u>VDDSSGDEHYGMD</u>VWGQGTTVTVSS*AST KGPSVFPLAPSSKSTSGGTAALGCLVKDYFPEPVTVSWNSGALTSG VHTFPAVLQSSGLYSLSSVVTVPSSSLGTQTYICNVNHKPSNTKVDK KVEPKSCDKTHTCPPCPAPELLGGPSVFLFPPKPKDTLMISRTPEV TCVVVDVSHEDPEVKFNWYVDGVEVHNAKTKPREEQYNSTYRVVS VLTVLHQDWLNGKEYKCKVSNKALPAPIEKTISKAKGQPREPQVY TLPPSRDELTKNQVSLTCLVKGFYPSDIAVEWESNGQPENNYKTTP PVLDSDGSFFLYSKLTVDKSRWQQGNVFSCSVMHEALHNHYTQKS LSLSPGK* |

| SEQ ID NO: | Description | Sequence |
|---|---|---|
| 54 | DNA encoding αFXI-18623p HC IgG1 (1Q) xxx = CAG or CAA (Q) | xxxGTCCAGCTGCAGGAATCCGGACCCGGCCTGGTGAAGCCT<br>AGCCAGACCCTGAGCCTGACCTGTACCGTGTCCGGCGGAAG<br>CATCTATTCCGGCGCCTACTACTGGTCCTGGATTAGGCAGC<br>ACCCCGGCAAGGGCCTGGAATGGATCGGCTCCATCCACTAC<br>AGCGGCCTGACCTATTACAACCCCTCCCTGAAGTCCAGGGT<br>GACCATCAGCGTCGACACAAGCAAGAACCAGTTCTCCCTCA<br>AGCTGAGCAGCGTGACCGCCGCCGACACCGCCGTGTATTAT<br>TGCGCCAGAGACGTGGACGACTCCTCCGGAGACGAGCACTA<br>CGGCATGGACGTCTGGGGCCAGGGCACAACAGTGACAGTG<br>AGCAGCGCTAGCACAAAAGGACCAAGCGTGTTTCCACTGGC<br>ACCTAGCAGCAAATCCACCAGCGGCGGAACAGCAGCCCTC<br>GGGTGCCTGGTGAAGGATTACTTCCCTGAGCCAGTCACAGT<br>GTCCTGGAACTCCGGAGCCCTGACATCCGGCGTGCACACCT<br>TCCCCGCTGTGCTGCAATCCAGCGGACTGTATAGCCTCAGC<br>TCCGTCGTGACAGTCCCTTCCAGCAGCCTGGGCACACAGAC<br>TTACATTTGCAACGTGAACCACAAACCTTCCAACACTAAGG<br>TGGACAAAAAGGTGGAACCCAAATCCTGTGATAAGACCCAT<br>ACATGCCCACCTTGTCCCGCTCCTGAGCTGCTGGGGGGACC<br>TTCCGTCTTTCTGTTTCCTCCAAAACCAAAAGACACACTCAT<br>GATCAGCCGGACCCCCGAAGTCACCTGTGTGGTGGTGGACG<br>TCAGCCACGAAGATCCAGAGGTCAAGTTCAATTGGTACGTG<br>GATGGAGTGGAAGTCCACAACGCAAAAACCAAACCTAGAG<br>AAGAACAGTACAATAGCACATACAGGGTGGTGTCCGTCCTG<br>ACAGTGCTCCACCAGGACTGGCTCAATGGCAAAGAGTATAA<br>GTGCAAGGTGAGCAACAAGGCCCTGCCTGCACCAATTGAGA<br>AAACAATTAGCAAGGCAAAGGGGCAGCCACGGGAACCCCA<br>GGTGTATACCCTGCCCCCAAGCCGGGATGAACTGACCAAAA<br>ACCAGGTCAGCCTGACATGCCTGGTGAAAGGGTTTTACCCA<br>AGCGATATTGCCGTCGAGTGGGAGAGCAACGGACAGCCAG<br>AAAACAATTACAAAACCACCCCACCTGTGCTGGACTCCGAT<br>GGGAGCTTTTTCCTGTACAGCAAGCTCACAGTGGACAAGTC<br>CAGATGGCAACAGGGCAACGTGTTTTCCTGCTCCGTGATGC<br>ACGAGGCCCTCCACAACCACTATACACAAAAGTCCCTCTCC<br>CTCAGCCCAGGAAAGTGA |
| 55 | αFXI-18623p HC IgG1 (1E) | EVQLQESGPGLVKPSQTLSLTCTVSGGS<u>IYSGAYYWS</u>WIRQHP<br>GKGLEWIGS<u>IHYSGLTYYNPSLKS</u>RV<u>TIS</u>VDTSKN<u>QF</u>SLKLSSV<br>TAADTAVYY<u>CARDVDDSSGDEHYGMD</u>VWGQGTTVTVSS*AST*<br>*KGPSVFPLAPSSKSTSGGTAALGCLVKDYFPEPVTVSWNSGALTSG*<br>*VHTFPAVLQSSGLYSLSSVVTVPSSSLGTQTYICNVNHKPSNTKVDK*<br>*KVEPKSCDKTHTCPPCPAPELLGGPSVFLFPPKPKDTLMISRTPEV*<br>*TCVVVDVSHEDPEVKFNWYVDGVEVHNAKTKPREEQYNSTYRVVS*<br>*VLTVLHQDWLNGKEYKCKVSNKALPAPIEKTISKAKGQPREPQVY*<br>*TLPPSRDELTKNQVSLTCLVKGFYPSDIAVEWESNGQPENNYKTTP*<br>*PVLDSDGSFFLYSKLTVDKSRWQQGNVFSCSVMHEALHNHYTQKS*<br>*LSLSPGK* |
| 56 | DNA encoding αFXI-18623p HC IgG1 (1E) xxx = GAA or GAG (E) | xxxGTCCAGCTGCAGGAATCCGGACCCGGCCTGGTGAAGCCT<br>AGCCAGACCCTGAGCCTGACCTGTACCGTGTCCGGCGGAAG<br>CATCTATTCCGGCGCCTACTACTGGTCCTGGATTAGGCAGC<br>ACCCCGGCAAGGGCCTGGAATGGATCGGCTCCATCCACTAC<br>AGCGGCCTGACCTATTACAACCCCTCCCTGAAGTCCAGGGT<br>GACCATCAGCGTCGACACAAGCAAGAACCAGTTCTCCCTCA<br>AGCTGAGCAGCGTGACCGCCGCCGACACCGCCGTGTATTAT<br>TGCGCCAGAGACGTGGACGACTCCTCCGGAGACGAGCACTA<br>CGGCATGGACGTCTGGGGCCAGGGCACAACAGTGACAGTG<br>AGCAGCGCTAGCACAAAAGGACCAAGCGTGTTTCCACTGGC<br>ACCTAGCAGCAAATCCACCAGCGGCGGAACAGCAGCCCTC<br>GGGTGCCTGGTGAAGGATTACTTCCCTGAGCCAGTCACAGT<br>GTCCTGGAACTCCGGAGCCCTGACATCCGGCGTGCACACCT<br>TCCCCGCTGTGCTGCAATCCAGCGGACTGTATAGCCTCAGC<br>TCCGTCGTGACAGTCCCTTCCAGCAGCCTGGGCACACAGAC<br>TTACATTTGCAACGTGAACCACAAACCTTCCAACACTAAGG<br>TGGACAAAAAGGTGGAACCCAAATCCTGTGATAAGACCCAT<br>ACATGCCCACCTTGTCCCGCTCCTGAGCTGCTGGGGGGACC<br>TTCCGTCTTTCTGTTTCCTCCAAAACCAAAAGACACACTCAT<br>GATCAGCCGGACCCCCGAAGTCACCTGTGTGGTGGTGGACG<br>TCAGCCACGAAGATCCAGAGGTCAAGTTCAATTGGTACGTG<br>GATGGAGTGGAAGTCCACAACGCAAAAACCAAACCTAGAG<br>AAGAACAGTACAATAGCACATACAGGGTGGTGTCCGTCCTG<br>ACAGTGCTCCACCAGGACTGGCTCAATGGCAAAGAGTATAA<br>GTGCAAGGTGAGCAACAAGGCCCTGCCTGCACCAATTGAGA<br>AAACAATTAGCAAGGCAAAGGGGCAGCCACGGGAACCCCA |

| Table of Sequences | | |
|---|---|---|
| SEQ ID NO: | Description | Sequence |
| | | GGTGTATACCCTGCCCCCAAGCCGGGATGAACTGACCAAAA<br>ACCAGGTCAGCCTGACATGCCTGGTGAAAGGGTTTTACCCA<br>AGCGATATTGCCGTCGAGTGGGAGAGCAACGGACAGCCAG<br>AAAACAATTACAAAACCACCCCACCTGTGCTGGACTCCGAT<br>GGGAGCTTTTTCCTGTACAGCAAGCTCACAGTGGACAAGTC<br>CAGATGGCAACAGGGCAACGTGTTTTCCTGCTCCGTGATGC<br>ACGAGGCCCTCCACAACCACTATACACAAAAGTCCCTCTCC<br>CTCAGCCCAGGAAAGTGA |
| 57 | αFXI-18611p IgG4 HC (S228P) (Q1) (M105) (C-terminal K-less) | QVQLQESGPGLVKPSETLSLTCAVSG<u>YSISSGYFWG</u>WIRQPPG<br>KGLEWIGS<u>ILHSGVTYYNPSLKS</u>RVT<u>I</u>SVDTSKN<u>Q</u>FSLKLSSVT<br>AADTAVYY<u>CARDRTTVSMIEYFQH</u>WGQGTLVTVSS*ASTKGPS<br>VFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVES<br>KYGPPCPPCPAPEFLGGPSVFLFPPKPKDTLMISRTPEVTCVVVDV<br>SQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEE<br>MTKNQVSLTCLVKGFYPSDIAVEWESNGQPENNYKTTPPVLDSDG<br>SFFLYSRLTVDKSRWQEGNVFSCSVMHEALHNHYTQKSLSLSLG* |
| 58 | DNA encoding αFXI-18611p IgG4 HC (S228P)(Q1) (M105); xxx = CAG or CAA (Q) (C-terminal K-less) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCCT<br>CCACCAAGGGCCCTAGCGTGTTTCCTCTGGCCCCCTGCTCCA<br>GATCCACAAGCGAGAGCACCGCTGCCCTGGGCTGTCTGGTC<br>AAGGACTACTTCCCCGAGCCCGTGACAGTGTCCTGGAACAG<br>CGGCGCCCTGACAAGCGGCGTCCATACATTCCCCGCCGTGC<br>TGCAGTCCAGCGGACTGTATAGCCTGAGCTCCGTGGTGACC<br>GTGCCTTCCAGCAGCCTGGGAACCAAGACATATACCTGCAA<br>CGTGGACCATAAGCCCAGCAACACAAAAGTCGACAAGAGG<br>GTGGAGAGCAAGTACGGACCCCCTTGTCCCCCTTGTCCTGC<br>TCCCGAGTTCCTCGGCGGACCTAGCGTGTTCCTGTTTCCTCC<br>CAAGCCCAAGGATACCCTGATGATCAGCAGGACCCCTGAGG<br>TCACCTGCGTGGTGGTCGACGTGTCCCAGGAGGACCCTGAG<br>GTCCAGTTTAACTGGTACGTGGACGGAGTGGAGGTGCACAA<br>CGCCAAGACCAAGCCCAGAGAGGAGCAGTTCAATTCCACCT<br>ACAGGGTGGTGAGCGTCCTGACCGTGCTGCACCAGGACTGG<br>CTGAATGGAAAGGAGTACAAATGCAAGGTCTCCAACAAGG<br>GCCTCCCTAGCAGCATCGAGAAGACCATCTCCAAGGCCAAG<br>GGCCAGCCTAGGGAGCCCCAGGTGTACACCCTGCCTCCTAG<br>CCAGGAGGAAATGACCAAGAACCAGGTGTCCCTGACATGC<br>CTGGTGAAGGGCTTCTATCCTAGCGACATCGCCGTGGAGTG<br>GGAGAGCAATGGCCAGCCCGAGAATAACTACAAGACCACC<br>CCCCCTGTGCTCGATAGCGACGGCAGCTTCTTTCTGTACAGC<br>AGGCTGACCGTGGACAAGAGCAGGTGGCAAGAGGGCAACG<br>TGTTTAGCTGCTCCGTCATGCACGAGGCCCTGCATAACCACT<br>ACACCCAAAAATCCCTGTCCCTGTCCCTGGGC |
| 59 | αFXI-18611p IgG4 HC (S228P) (E1) (M105) (C-terminal K-less) | EVQLQESGPGLVKPSETLSLTCAVSG<u>YSISSGYFWG</u>WIRQPPG<br>KGLEWIGS<u>ILHSGVTYYNPSLKS</u>RVT<u>I</u>SVDTSKN<u>Q</u>FSLKLSSVT<br>AADTAVYY<u>CARDRTTVSMIEYFQH</u>WGQGTLVTVSS*ASTKGPS<br>VFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVES<br>KYGPPCPPCPAPEFLGGPSVFLFPPKPKDTLMISRTPEVTCVVVDV<br>SQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEE<br>MTKNQVSLTCLVKGFYPSDIAVEWESNGQPENNYKTTPPVLDSDG<br>SFFLYSRLTVDKSRWQEGNVFSCSVMHEALHNHYTQKSLSLSLG* |
| 60 | DNA encoding αFXI-18611p IgG4 HC S228P; (E1)(M105) xxx = GAA or GAG (E) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCCT |

| SEQ ID NO: | Description | Sequence |
|---|---|---|
|  | (C-terminal K-less) | CCACCAAGGGCCCTAGCGTGTTTCCTCTGGCCCCCTGCTCCA GATCCACAAGCGAGAGCACCGCTGCCCTGGGCTGTCTGGTC AAGGACTACTTCCCCGAGCCCGTGACAGTGTCCTGGAACAG CGGCGCCCTGACAAGCGGCGTCCATACATTCCCCGCCGTGC TGCAGTCCAGCGGACTGTATAGCCTGAGCTCCGTGGTGACC GTGCCTTCCAGCAGCCTGGGAACCAAGACATATACCTGCAA CGTGGACCATAAGCCCAGCAACACAAAAGTCGACAAGAGG GTGGAGAGCAAGTACGGACCCCCTTGTCCCCCTTGTCCTGC TCCCGAGTTCCTCGGCGGACCTAGCGTGTTCCTGTTTCCTCC CAAGCCCAAGGATACCCTGATGATCAGCAGGACCCCTGAGG TCACCTGCGTGGTGGTCGACGTGTCCCAGGAGGACCCTGAG GTCCAGTTTAACTGGTACGTGGACGGAGTGGAGGTGCACAA CGCCAAGACCAAGCCCAGAGAGGAGCAGTTCAATTCCACCT ACAGGGTGGTGAGCGTCCTGACCGTGCTGCACCAGGACTGG CTGAATGGAAAGGAGTACAAATGCAAGGTCTCCAACAAGG GCCTCCCTAGCAGCATCGAGAAGACCATCTCCAAGGCCAAG GGCCAGCCTAGGGAGCCCCAGGTGTACACCCTGCCTCCTAG CCAGGAGGAAATGACCAAGAACCAGGTGTCCCTGACATGC CTGGTGAAGGGCTTCTATCCTAGCGACATCGCCGTGGAGTG GGAGAGCAATGGCCAGCCCGAGAATAACTACAAGACCACC CCCCCTGTGCTCGATAGCGACGGCAGCTTCTTTCTGTACAGC AGGCTGACCGTGGACAAGAGCAGGTGGCAAGAGGGCAACG TGTTTAGCTGCTCCGTCATGCACGAGGCCCTGCATAACCACT ACACCCAAAAATCCCTGTCCCTGTCCCTGGGC |
| 61 | αFXI-18611 IgG4 HC S228P)(Q1) (L105) (C-terminal K-less) | QVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSSASTKGPSV FPLAPCSRSTSESTAALGCLVKDYFPEPVTVSWNSGALTSGVHTFP AVLQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDG SFFLYSRLTVDKSRWQEGNVFSCSVMHEALHNHYTQKSLSLSLG |
| 62 | DNA encoding αFXI-18611 IgG4 HC S228P); (Q1) (L105) xxx = CAG or CAA (Q) (C-terminal K-less) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCC AGCACCAAGGGCCCTTCCGTCTTCCCTCTGGCCCCCTTGCAGC AGAAGCACCTCCGAGTCCACAGCCGCCCTGGGATGCCTCGT GAAGGATTACTTCCCCGAGCCCGTCACAGTCCTGGAACT CCGGCGCTCTGACCAGCGGAGTGCACACCTTCCCCGCCGTG CTGCAAAGCAGCGGCCTGTACAGCCTGTCCAGCGTGGTCAC CGTGCCTTCCTCCAGCCTGGGCACCAAGACCTACACATGCA ACGTGGACCACAAGCCTTCCAACACCAAGGTGGACAAGAG AGTGGAAAGCAAGTACGGCCCCCCTGCCCCCCTTGTCCTG CCCCCGAGTTTCTGGGAGGACCCTCCGTGTTCCTCTTTCCTC CCAAGCCTAAGGACACCCTGATGATCTCCAGGACCCCCGAA GTGACCTGCGTGGTCGTGGACGTGTCCCAGGAGGACCCTGA GGTGCAGTTTAACTGGTACGTGGACGGCGTGGAGGTGCACA ACGCCAAGACCAAGCCCAGGGAGGAGCAGTTCAATAGCAC CTACAGGGTGGTGTCCGTGCTGACCGTGCTGCACCAGGACT GGCTGAACGGCAAAGAGTACAAGTGCAAAGTCAGCAACAA GGGCCTGCCCCTCCTCCATCGAGAAGACCATTAGCAAGGCCA AGGGCCAGCCTAGGGAGCCTCAGGTGTACACCCTGCCCCCC AGCCAGGAGGAGATGACCAAGAACCAGGTGTCCCTGACCT GCCTGGTCAAGGGATTTTACCCCAGCGACATCGCTGTGGAA TGGGAGAGCAATGGCCAGCCCGAGAACAACTACAAGACCA CCCCTCCCGTGCTCGATTCCGACGGCAGCTTTTTCCTGTACA GCAGGCTGACCGTGGATAAGAGCAGGTGGCAGGAAGGCAA CGTGTTCTCCTGTTCCGTGATGCATGAGGCCCTGCACAACCA CTACACACAGAAGAGCCTGTCCCTGTCCCTGGGC |

Table of Sequences

| SEQ ID NO: | Description | Sequence |
|---|---|---|
| 63 | αFXI-18611 IgG4 HC (S228P) (E1) (L105) (C-terminal K-less) | EVQLQESGPGLVKPSETLSLTCAVSGYSISSGYFWGWIRQPPG KGLEWIGSILHSGVTYYNPSLKSRVTISVDTSKNQFSLKLSSVT AADTAVYYCARDRTTVSLIEYFQHWGQGTLVTVSSASTKGPSV FPLAPCSRSTSESTAALGCLVKDYFPEPVTVSWNSGALTSGVHTFP AVLQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDG SFFLYSRLTVDKSRWQEGNVFSCSVMHEALHNHYTQKSLSLSLG |
| 64 | DNA encoding αFXI-18611 IgG4 HC (S228P) (Q1) (L105) xxx = GAA or GAG (E) (C-terminal K-less) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCC AGCACCAAGGGCCCTTCCGTCTTCCCTCTGGCCCCTTGCAGC AGAAGCACCTCCGAGTCCACAGCCGCCCTGGGATGCCTCGT GAAGGATTACTTCCCCGAGCCCGTCACAGTCTCCTGGAACT CCGGCGCTCTGACCAGCGGAGTGCACACCTTCCCCGCCGTG CTGCAAAGCAGCGGCCTGTACAGCCTGTCCAGCGTGGTCAC CGTGCCTTCCTCCAGCCTGGGCACCAAGACCTACACATGCA ACGTGGACCACAAGCCTTCCAACACCAAGGTGGACAAGAG AGTGGAAAGCAAGTACGGCCCCCCCTGCCCCCCTTGTCCTG CCCCCGAGTTTCTGGGAGGACCCTCCGTGTTCCTCTTTCCTC CCAAGCCTAAGGACACCCTGATGATCTCCAGGACCCCCGAA GTGACCTGCGTGGTCGTGGACGTGTCCCAGGAGGACCCTGA GGTGCAGTTTAACTGGTACGTGGACGGCGTGGAGGTGCACA ACGCCAAGACCAAGCCCAGGGAGGAGCAGTTCAATAGCAC CTACAGGGTGGTGTCCGTGCTGACCGTGCTGCACCAGGACT GGCTGAACGGCAAAGAGTACAAGTGCAAAGTCAGCAACAA GGGCCTGCCCTCCTCCATCGAGAAGACCATTAGCAAGGCCA AGGGCCAGCCTAGGGAGCCTCAGGTGTACACCCTGCCCCCC AGCCAGGAGGAGATGACCAAGAACCAGGTGTCCCTGACCT GCCTGGTCAAGGGATTTTACCCCAGCGACATCGCTGTGGAA TGGGAGAGCAATGGCCAGCCCGAGAACAACTACAAGACCA CCCCCTCCCGTGCTCGATTCCGACGGCAGCTTTTTCCTGTACA GCAGGCTGACCGTGGATAAGAGCAGGTGGCAGGAAGGCAA CGTGTTCTCCTGTTCCGTGATGCATGAGGCCCTGCACAACCA CTACACACAGAAGAGCCTGTCCCTGTCCCTGGGC |
| 65 | αFXI-18623p HC-IgG4 (S228P(Q1) (C-terminal K-less) | QVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSSAST KGPSVFPLAPCSRSTSESTAALGCLVKDYFPEPVTVSWNSGALTSG VHTFPAVLQSSGLYSLSSVVTVPSSSLGTKTYTCNVDHKPSNTKVDK RVESKYGPPCPPCPAPEFLGGPSVFLEPPKPKDTLMISRTPEVTCV VVDVSQEDPEVQFNWYVDGVEVHNAKTKPREEQFNSTYRVVSVLT VLHQDWLNGKEYKCKVSNKGLPSSIEKTISKAKGQPREPQVYTLPP SQEEMTKNQVSLTCLVKGFYPSDIAVEWESNGQPENNYKTTPPVL DSDGSFFLYSRLTVDKSRWQEGNVFSCSVMHEALHNHYTQKSLSL SLG |
| 66 | DNA encoding αFXI-18623p HC-IgG4 (S228P(Q1) xxx = CAG or CAA (Q) (C-terminal K-less) | xxxGTCCAGCTGCAGGAATCCGGACCCGGCCTGGTGAAGCCT AGCCAGACCCTGAGCCTGACCTGTACCGTGTCCGGCGGAAG CATCTATTCCGGCGCCTACTACTGGTCCTGGATTAGGCAGC ACCCCGGCAAGGGCCTGGAATGGATCGGCTCCATCCACTAC AGCGGCCTGACCTATTACAACCCCTCCCTGAAGTCCAGGGT GACCATCAGCGTCGACACAAGCAAGAACCAGTTCTCCCTCA AGCTGAGCAGCGTGACCGCCGCCGACACCGCCGTGTATTAT TGCGCCAGAGACGTGGACGACTCCTCCGGAGACGAGCACTA CGGCATGGACGTCTGGGGCCAGGGCACAACAGTGACAGTG AGCAGCGCCAGCACCAAAGGACCCTCCGTCTTCCCTCTGGC CCCTTGCTCCAGGAGCACAAGCGAAAGCACAGCCGCCCTGG GCTGCCTGGTGAAGGACTACTTTCCCGAGCCCGTGACCGTG AGCTGGAATAGCGGAGCCCTCACCTCCGGAGTCCACACATT TCCCGCCGTCCTGCAGAGCAGCGGCCTGTACTCCCTGAGCT CCGTGGTGACCGTGCCTTCCTCCAGCCTGGGCACCAAGACC TACACCTGCAACGTGGACCACAAGCCTAGCAATACCAAGGT |

Table of Sequences

| SEQ ID NO: | Description | Sequence |
|---|---|---|
| | | GGACAAGAGGGTGGAATCCAAGTACGGCCCCCCTTGCCCTC<br>CTTGTCCTGCCCCCGAATTTCTGGGCGGCCCTTCCGTGTTCC<br>TGTTCCCTCCCAAGCCCAAGGATACCCTGATGATCAGCAGG<br>ACCCCTGAGGTGACCTGTGTGGTGGTGGACGTGAGCCAGGA<br>GGACCCCGAGGTGCAGTTCAACTGGTACGTGGATGGCGTGG<br>AAGTGCACAATGCCAAGACAAAGCCCAGGGAGGAGCAGTT<br>CAATAGCACCTACAGGGTGGTCAGCGTGCTCACAGTGCTGC<br>ACCAGGACTGGCTGAACGGAAAGGAGTACAAGTGCAAAGT<br>GTCCAACAAGGGCCTGCCCTCCTCCATCGAAAAGACCATCT<br>CCAAGGCCAAAGGCCAGCCCAGGGAGCCCCAAGTGTATAC<br>CCTCCCCCCTAGCCAGGAGGAAATGACCAAAAACCAGGTCT<br>CCCTGACCTGTCTGGTGAAGGGCTTCTATCCCAGCGACATC<br>GCTGTGGAGTGGGAGAGCAACGGCCAACCCGAGAACAACT<br>ATAAGACCACACCCCCGTCCTGGACTCCGATGGCCTTCT<br>TCCTGTACAGCAGGCTGACCGTCGACAAGTCCAGGTGGCAG<br>GAAGGAAACGTGTTCTCCTGTAGCGTCATGCACGAGGCCCT<br>GCACAACCACTATACCCAGAAGTCCCTGTCCCTGAGCCTGG<br>GC |
| 67 | αFXI-18623p HC-IgG4 (S228P (E1) (C-terminal K-less) | EVQLQESGPGLVKPSQTLSLTCTVSGGSIYSGAYYWSWIRQHP<br>GKGLEWIGSIHYSGLTYYNPSLKSRVTISVDTSKNQFSLKLSSV<br>TAADTAVYYCARDVDDSSGDEHYGMDVWGQGTTVTVSS*AST*<br>*KGPSVFPLAPCSRSTSESTAALGCLVKDYFPEPVTVSWNSGALTSG*<br>*VHTFPAVLQSSGLYSLSSVVTVPSSSLGTKTYTCNVDHKPSNTKVDK*<br>*RVESKYGPPCPPCPAPEFLGGPSVFLFPPKPKDTLMISRTPEVTCV*<br>*VVDVSQEDPEVQFNWYVDGVEVHNAKTKPREEQFNSTYRVVSVLT*<br>*VLHQDWLNGKEYKCKVSNKGLPSSIEKTISKAKGQPREPQVYTLPP*<br>*SQEEMTKNQVSLTCLVKGFYPSDIAVEWESNGQPENNYKTTPPVL*<br>*DSDGSFFLYSRLTVDKSRWQEGNVFSCSVMHEALHNHYTQKSLSL*<br>*SLG* |
| 68 | DNA encoding αFXI-18623p HC-IgG4 (S228P (E1) xxx = GAA or GAG (E) (C-terminal K-less) | xxxGTCCAGCTGCAGGAATCCGGACCCGGCCTGGTGAAGCCT<br>AGCCAGACCCTGAGCCTGACCTGTACCGTGTCCGGCGGAAG<br>CATCTATTCCGGCGCCTACTACTGGTCCTGGATTAGGCAGC<br>ACCCCGGCAAGGGCCTGGAATGGATCGGCTCCATCCACTAC<br>AGCGGCCTGACCTATTACAACCCCTCCCTGAAGTCCAGGGT<br>GACCATCAGCGTCGACACAAGCAAGAACCAGTTCTCCCTCA<br>AGCTGAGCAGCGTGACCGCCGCCGACACCGCCGTGTATTAT<br>TGCGCCAGAGACGTGGACGACTCCTCCGGAGACGAGCACTA<br>CGGCATGGACGTCTGGGGCCAGGGCACAACAGTGACAGTG<br>AGCAGCGCCAGCACCAAAGGACCCTCCGTCTTCCCTCTGGC<br>CCCTTGCTCCAGGAGCACAAGCGAAAGCACAGCCGCCCTGG<br>GCTGCCTGGTGAAGGACTACTTTCCCGAGCCCGTGACCGTG<br>AGCTGGAATAGCGGAGCCCTCACCTCCGGAGTCCACACATT<br>TCCCGCCGTCCTGCAGAGCAGCGGCCTGTACTCCCTGAGCT<br>CCGTGGTGACCGTGCCTTCCTCCAGCCTGGGCACCAAGACC<br>TACACCTGCAACGTGACCACAAGCCTAGCAATACCAAGGT<br>GGACAAGAGGGTGGAATCCAAGTACGGCCCCCCTTGCCCTC<br>CTTGTCCTGCCCCCGAATTTCTGGGCGGCCCTTCCGTGTTCC<br>TGTTCCCTCCCAAGCCCAAGGATACCCTGATGATCAGCAGG<br>ACCCCTGAGGTGACCTGTGTGGTGGTGGACGTGAGCCAGGA<br>GGACCCCGAGGTGCAGTTCAACTGGTACGTGGATGGCGTGG<br>AAGTGCACAATGCCAAGACAAAGCCCAGGGAGGAGCAGTT<br>CAATAGCACCTACAGGGTGGTCAGCGTGCTCACAGTGCTGC<br>ACCAGGACTGGCTGAACGGAAAGGAGTACAAGTGCAAAGT<br>GTCCAACAAGGGCCTGCCCTCCTCCATCGAAAAGACCATCT<br>CCAAGGCCAAAGGCCAGCCCAGGGAGCCCCAAGTGTATAC<br>CCTCCCCCCTAGCCAGGAGGAAATGACCAAAAACCAGGTCT<br>CCCTGACCTGTCTGGTGAAGGGCTTCTATCCCAGCGACATC<br>GCTGTGGAGTGGGAGAGCAACGGCCAACCCGAGAACAACT<br>ATAAGACCACACCCCCGTCCTGGACTCCGATGGCCTTCT<br>TCCTGTACAGCAGGCTGACCGTCGACAAGTCCAGGTGGCAG<br>GAAGGAAACGTGTTCTCCTGTAGCGTCATGCACGAGGCCCT<br>GCACAACCACTATACCCAGAAGTCCCTGTCCCTGAGCCTGG<br>GC |
| 69 | αFXI-18611p HC IgG1 (Q1) (M105) (C-terminal K-less) | QVQLQESGPGLVKPSETLSLTCAVSG<u>YSISSGYFWG</u>WIRQPPG<br>KGLEWIGS<u>ILHSGVTYYNPSLKSRV</u>TISVDTSKNQFSLKLSSVT<br>AADTAVY<u>YCARDRTTVSMIEYFQ</u>HWGQGTLVTVSS*A*STKGPS<br>*VFPLAPSSKSTSGGTAALGCLVKDYFPEPVTVSWNSGALTSGVHTF*<br>*PAVLQSSGLYSLSSVVTVPSSSLGTQTYICNVNHKPSNTKVDKKVEP*<br>*KSCDKTHTCPPCPAPELLGGPSVFLFPPKPKDTLMISRTPEVTCVV*<br>*VDVSHEDPEVKFNWYVDGVEVHNAKTKPREEQYNSTYRVVSVLTV*<br>*LHQDWLNGKEYKCKVSNKALPAPIEKTISKAKGQPREPQVYTLPPS* |

| SEQ ID NO: | Description | Sequence |
|---|---|---|
| | | RDELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>G |
| 70 | DNA encoding αFXI-18611p HC IgG1 (Q1) (M105)<br>xxx = CAG or CAA (Q)<br>(C-terminal K-less) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCTA<br>GCACAAAAGGACCAAGCGTGTTTCCACTGGCACCTAGCAGC<br>AAATCCACCAGCGGCGGAACAGCAGCCCTCGGGTGCCTGGT<br>GAAGGATTACTTCCCTGAGCCAGTCACAGTGTCCTGGAACT<br>CCGGAGCCCTGACATCCGGCGTGCACACCTTCCCCGCTGTG<br>CTGCAATCCAGCGGACTGTATAGCCTCAGCTCCGTCGTGAC<br>AGTCCCTTCCAGCAGCCTGGGCACACAGACTTACATTTGCA<br>ACGTGAACCACAAACCTTCCAACACTAAGGTGGACAAAAA<br>GGTGGAACCCAAATCCTGTGATAAGACCCATACATGCCCAC<br>CTTGTCCCGCTCCTGAGCTGCTGGGGGGACCTTCCGTCTTTC<br>TGTTTCCTCCAAAACCAAAAGACACACTCATGATCAGCCGG<br>ACCCCCGAAGTCACCTGTGTGGTGGTGGACGTCAGCCACGA<br>AGATCCAGAGGTCAAGTTCAATTGGTACGTGGATGGAGTGG<br>AAGTCCACAACGCAAAAACCAAACCTAGAGAAGAACAGTA<br>CAATAGCACATACAGGGTGGTGTCCGTCCTGACAGTGCTCC<br>ACCAGGACTGGCTCAATGGCAAAGAGTATAAGTGCAAGGT<br>GAGCAACAAGGCCCTGCCTGCACCAATTGAGAAAACAATTA<br>GCAAGGCAAAGGGGCAGCCACGGGAACCCCAGGTGTATAC<br>CCTGCCCCCAAGCCGGGATGAACTGACCAAAAACCAGGTCA<br>GCCTGACATGCCTGGTGAAAGGGTTTTACCCAAGCGATATT<br>GCCGTCGAGTGGGAGAGCAACGGACAGCCAGAAAACAATT<br>ACAAAACCACCCCACCTGTGCTGGACTCCGATGGGAGCTTT<br>TTCCTGTACAGCAAGCTCACAGTGGACAAGTCCAGATGGCA<br>ACAGGGCAACGTGTTTTCCTGCTCCGTGATGCACGAGGCCC<br>TCCACAACCACTATACACAAAAGTCCCTCTCCCTCAGCCCA<br>GGA |
| 71 | αFXI-18611p HC IgG1 (E1) (M105) (C-terminal K-less) | EVQLQESGPGLVKPSETLSLTCAVSGYSISSGYFWGWIRQPPG<br>KGLEWIGSILHSGVTYYNPSLKSRVTISVDTSKNQFSLKLSSVT<br>AADTAVYYCARDRTTVSMIEYFQHWGQGTLVTVSSASTKGPS<br>VFPLAPSSKSTSGGTAALGCLVKDYFPEPVTVSWNSGALTSGVHTF<br>PAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVLTV<br>LHQDWLNGKEYKCKVSNKALPAPIEKTISKAKGQPREPQVYTLPPS<br>RDELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>G |
| 72 | DNA encoding αFXI-18611p HC IgG1 (Q1) (M105)<br>xxx = GAA or GAG (E)<br>(C-terminal K-less) | xxxGTCCAGCTGCAGGAGAGCGGCCCTGGCCTGGTGAAGCCT<br>AGCGAGACACTGTCCCTGACCTGCGCCGTGAGCGGCTACAG<br>CATCTCCAGCGGCTATTTCTGGGGATGGATCAGACAGCCCC<br>CTGGCAAGGGCCTGGAATGGATCGGTTCTATCCTGCACTCC<br>GGCGTGACATACTATAACCCTAGCCTGAAGAGCAGGGTGAC<br>CATCTCCGTGGATACCAGCAAGAATCAGTTCAGCCTGAAGC<br>TCAGCAGCGTGACCGCCGCCGATACCGCTGTGTACTACTGC<br>GCCAGAGACAGGACCACCGTCTCCATGATCGAGTACTTCCA<br>GCACTGGGGCCAAGGCACCCTGGTCACCGTGTCCTCCGCTA<br>GCACAAAAGGACCAAGCGTGTTTCCACTGGCACCTAGCAGC<br>AAATCCACCAGCGGCGGAACAGCAGCCCTCGGGTGCCTGGT<br>GAAGGATTACTTCCCTGAGCCAGTCACAGTGTCCTGGAACT<br>CCGGAGCCCTGACATCCGGCGTGCACACCTTCCCCGCTGTG<br>CTGCAATCCAGCGGACTGTATAGCCTCAGCTCCGTCGTGAC<br>AGTCCCTTCCAGCAGCCTGGGCACACAGACTTACATTTGCA<br>ACGTGAACCACAAACCTTCCAACACTAAGGTGGACAAAAA<br>GGTGGAACCCAAATCCTGTGATAAGACCCATACATGCCCAC<br>CTTGTCCCGCTCCTGAGCTGCTGGGGGGACCTTCCGTCTTTC<br>TGTTTCCTCCAAAACCAAAAGACACACTCATGATCAGCCGG<br>ACCCCCGAAGTCACCTGTGTGGTGGTGGACGTCAGCCACGA<br>AGATCCAGAGGTCAAGTTCAATTGGTACGTGGATGGAGTGG<br>AAGTCCACAACGCAAAAACCAAACCTAGAGAAGAACAGTA<br>CAATAGCACATACAGGGTGGTGTCCGTCCTGACAGTGCTCC |

| SEQ ID NO: | Description | Sequence |
|---|---|---|
| | | ACCAGGACTGGCTCAATGGCAAAGAGTATAAGTGCAAGGT GAGCAACAAGGCCCTGCCTGCACCAATTGAGAAAACAATTA GCAAGGCAAAGGGGCAGCCACGGGAACCCCAGGTGTATAC CCTGCCCCCAAGCCGGGATGAACTGACCAAAAACCAGGTCA GCCTGACATGCCTGGTGAAAGGGTTTTACCCAAGCGATATT GCCGTCGAGTGGGAGAGCAACGGACAGCCAGAAAACAATT ACAAAACCACCCCACCTGTGCTGGACTCCGATGGGAGCTTT TTCCTGTACAGCAAGCTCACAGTGGACAAGTCCAGATGGCA ACAGGGCAACGTGTTTTCCTGCTCCGTGATGCACGAGGCCC TCCACAACCACTATACACAAAAGTCCCTCTCCCTCAGCCCA GGA |
| 73 | αFXI-18611 HC IgG1 (Q1)(L105) (C-terminal K-less) | QVQLQESGPGLVKPSETLSLTCAVSG<u>YSISSGYFWG</u>WIRQPPG KGLEWIGSILHSGVTYYNPSLKSRVTISVDTSKNQFSLKLSSVT AADTAVYYCARDRTTVSLIEYFQHWGQGTLVTVSS*ASTKGPSV FPLAPSSKSTSGGTAALGCLVKDYFPEPVTVSWNSGALTSGVHTFP AVLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQVSLTCLVKGFYPSDIAVEWESNGQPENNYKTTPPVLDS DGSFFLYSKLTVDKSRWQQGNVFSCSVMHEALHNHYTQKSLSLSP G* |
| 74 | DNA encoding αFXI-18611 HC IgG1 (Q1)(L105) xxx = CAG or CAA (Q) (C-terminal K-less) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCT AGCACAAAAGGACCAAGCGTGTTTCCACTGGCACCTAGCAG CAAATCCACCAGCGGCGGAACAGCAGCCCTCGGGTGCCTGG TGAAGGATTACTTCCCTGAGCCAGTCACAGTGTCCTGGAAC TCCGGAGCCCTGACATCCGGCGTGCACACCTTCCCCGCTGT GCTGCAATCCAGCGGACTGTATAGCCTCAGCTCCGTCGTGA CAGTCCCTTCCAGCAGCCTGGGCACACAGACTTACATTTGC AACGTGAACCACAAACCTTCCAACACTAAGGTGGACAAAA AGGTGGAACCCAAATCCTGTGATAAGACCCATACATGCCCA CCTTGTCCCGCTCCTGAGCTGCTGGGGGGACCTTCCGTCTTT CTGTTTCCTCCAAAACCAAAAGACACACTCATGATCAGCCG GACCCCCGAAGTCACCTGTGTGGTGGTGGACGTCAGCCACG AAGATCCAGAGGTCAAGTTCAATTGGTACGTGGATGGAGTG GAAGTCCACAACGCAAAAACCAAACCTAGAGAAGAACAGT ACAATAGCACATACAGGGTGGTGTCCGTCCTGACAGTGCTC CACCAGGACTGGCTCAATGGCAAAGAGTATAAGTGCAAGG TGAGCAACAAGGCCCTGCCTGCACCAATTGAGAAAACAATT AGCAAGGCAAAGGGGCAGCCACGGGAACCCCAGGTGTATA CCCTGCCCCCAAGCCGGGATGAACTGACCAAAAACCAGGTC AGCCTGACATGCCTGGTGAAAGGGTTTTACCCAAGCGATAT TGCCGTCGAGTGGGAGAGCAACGGACAGCCAGAAAACAAT TACAAAACCACCCCACCTGTGCTGGACTCCGATGGGAGCTT TTTCCTGTACAGCAAGCTCACAGTGGACAAGTCCAGATGGC AACAGGGCAACGTGTTTTCCTGCTCCGTGATGCACGAGGCC CTCCACAACCACTATACACAAAAGTCCCTCTCCCTCAGCCC AGGA |
| 75 | αFXI-18611 HC IgG1 (E1)(L105) (C-terminal K-less) | EVQLQESGPGLVKPSETLSLTCAVSG<u>YSISSGYFWG</u>WIRQPPG KGLEWIGSILHSGVTYYNPSLKSRVTISVDTSKNQFSLKLSSVT AADTAVYYCARDRTTVSLIEYFQHWGQGTLVTVSS*ASTKGPSV FPLAPSSKSTSGGTAALGCLVKDYFPEPVTVSWNSGALTSGVHTFP AVLQSSGLYSLSSVVTVPSSSLGTQTYICNVNHKPSNTKVDKKVEPK SCDKTHTCPPCPAPELLGGPSVFLFPPKPKDTLMISRTPEVTCVVV DVSHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQVSLTCLVKGFYPSDIAVEWESNGQPENNYKTTPPVLDS DGSFFLYSKLTVDKSRWQQGNVFSCSVMHEALHNHYTQKSLSLSP G* |

| SEQ ID NO: | Description | Sequence |
|---|---|---|
| 76 | DNA encoding αFXI-18611 HC IgG1 (E1)(L105) xxx = GAA or GAG (E) (C-terminal K-less) | xxxGTCCAGCTGCAGGAGAGCGGCCCTGGACTCGTGAAGCC CTCCGAAACCCTGAGCCTCACATGCGCCGTCTCCGGATACA GCATCAGCAGCGGATACTTCTGGGGCTGGATCAGACAGCCC CCCGGCAAAGGCCTGGAGTGGATCGGTTCTATTCTCCACAG CGGCGTGACATACTACAACCCCTCCCTGAAGAGCAGGGTGA CCATCAGCGTGGACACCTCCAAGAACCAGTTTTCCCTCAAG CTGAGCAGCGTGACCGCCGCTGACACAGCCGTGTATTACTG CGCCAGGGACAGGACCACCGTGTCCCTGATTGAGTACTTCC AGCATTGGGGCCAGGGCACACTGGTGACCGTCAGCAGCGCT AGCACAAAAGGACCAAGCGTGTTTCCACTGGCACCTAGCAG CAAATCCACCAGCGGCGGAACAGCAGCCCTCGGGTGCCTGG TGAAGGATTACTTCCCTGAGCCAGTCACAGTGTCCTGGAAC TCCGGAGCCCTGACATCCGGCGTGCACACCTTCCCCGCTGT GCTGCAATCCAGCGGACTGTATAGCCTCAGCTCCGTCGTGA CAGTCCCTTCCAGCAGCCTGGGCACACAGACTTACATTTGC AACGTGAACCACAAACCTTCCAACACTAAGGTGGACAAAA AGGTGGAACCCAAATCCTGTGATAAGACCCATACATGCCCA CCTTGTCCCGCTCCTGAGCTGCTGGGGGGACCTTCCGTCTTT CTGTTTCCTCCAAAACCAAAAGACACACTCATGATCAGCCG GACCCCCGAAGTCACCTGTGTGGTGGTGGACGTCAGCCACG AAGATCCAGAGGTCAAGTTCAATTGGTACGTGGATGGAGTG GAAGTCCACAACGCAAAAACCAAACCTAGAGAAGAACAGT ACAATAGCACATACAGGGTGGTGTCCGTCCTGACAGTGCTC CACCAGGACTGGCTCAATGGCAAAGAGTATAAGTGCAAGG TGAGCAACAAGGCCCTGCCTGCACCAATTGAGAAAACAATT AGCAAGGCAAAGGGGCAGCCACGGGAACCCCAGGTGTATA CCCTGCCCCCAAGCCGGGATGAACTGACCAAAAACCAGGTC AGCCTGACATGCCTGGTGAAAGGGTTTTACCCAAGCGATAT TGCCGTCGAGTGGGAGAGCAACGGACAGCCAGAAAACAAT TACAAAACCACCCCACCTGTGCTGGACTCCGATGGGAGCTT TTTCCTGTACAGCAAGCTCACAGTGGACAAGTCCAGATGGC AACAGGGCAACGTGTTTTCCTGCTCCGTGATGCACGAGGCC CTCCACAACCACTATACACAAAAGTCCCTCTCCCTCAGCCC AGGA |
| 77 | αFXI-18623p HC IgG1 (1Q) (C-terminal K-less) | QVQLQESGPGLVKPSQTLSLTCTVSGGSIYSGAYYWSWIRQHP GKGLEWIGSIHYSGLTYYNPSLKSRVTISVDTSKNQFSLKLSSV TAADTAVYYCARDVDDSSGDEHYGMDVWGQGTTVTVSSAST KGPSVFPLAPSSKSTSGGTAALGCLVKDYFPEPVTVSWNSGALTSG VHTFPAVLQSSGLYSLSSVVTVPSSSLGTQTYICNVNHKPSNTKVDK KVEPKSCDKTHTCPPCPAPELLGGPSVFLFPPKPKDTLMISRTPEV TCVVVDVSHEDPEVKFNWYVDGVEVHNAKTKPREEQYNSTYRVVS VLTVLHQDWLNGKEYKCKVSNKALPAPIEKTISKAKGQPREPQVY TLPPSRDELTKNQVSLTCLVKGFYPSDIAVEWESNGQPENNYKTTP PVLDSDGSFFLYSKLTVDKSRWQQGNVFSCSVMHEALHNHYTQKS LSLSPG |
| 78 | DNA encoding αFXI-18623p HC IgG1 (1Q) xxx = CAG or CAA (Q) (C-terminal K-less) | xxxGTCCAGCTGCAGGAATCCGGACCCGGCCTGGTGAAGCCT AGCCAGACCCTGAGCCTGACCTGTACCGTGTCCGGCGGAAG CATCTATTCCGGCGCCTACTACTGGTCCTGGATTAGGCAGC ACCCCGGCAAGGGCCTGGAATGGATCGGTCCATCCACTAC AGCGGCCTGACCTATTACAACCCCTCCCTGAAGTCCAGGGT GACCATCAGCGTGGACACAAGCAAGAACCAGTTCTCCCTCA AGCTGAGCAGCGTGACCGCCGCCGACACCGCCGTGTATTAT TGCGCCAGAGACGTGGACGACTCCTCCGGAGACGAGCACTA CGGCATGGACGTCTGGGGCCAGGGCACAACAGTGACAGTG AGCAGCGCTAGCACAAAAGGACCAAGCGTGTTTCCACTGGC ACCTAGCAGCAAATCCACCAGCGGCGGAACAGCAGCCCTC GGGTGCCTGGTGAAGGATTACTTCCCTGAGCCAGTCACAGT GTCCTGGAACTCCGGAGCCCTGACATCCGGCGTGCACACCT TCCCCGCTGTGCTGCAATCCAGCGGACTGTATAGCCTCAGC TCCGTCGTGACAGTCCCTTCCAGCAGCCTGGGCACACAGAC TTACATTTGCAACGTGAACCACAAACCTTCCAACACTAAGG TGGACAAAAAGGTGGAACCCAAATCCTGTGATAAGACCCAT ACATGCCCACCTTGTCCCGCTCCTGAGCTGCTGGGGGGACC TTCCGTCTTTCTGTTTCCTCCAAAACCAAAAGACACACTCAT GATCAGCCGGACCCCCGAAGTCACCTGTGTGGTGGTGGACG TCAGCCACGAAGATCCAGAGGTCAAGTTCAATTGGTACGTG GATGGAGTGGAAGTCCACAACGCAAAAACCAAACCTAGAG AAGAACAGTACAATAGCACATACAGGGTGGTGTCCGTCCTG ACAGTGCTCCACCAGGACTGGCTCAATGGCAAAGAGTATAA GTGCAAGGTGAGCAACAAGGCCCTGCCTGCACCAATTGAGA AAACAATTAGCAAGGCAAAGGGGCAGCCACGGGAACCCCA |

| SEQ ID NO: | Description | Sequence |
|---|---|---|
| | | GGTGTATACCCTGCCCCCAAGCCGGGATGAACTGACCAAAA<br>ACCAGGTCAGCCTGACATGCCTGGTGAAAGGGTTTTACCCA<br>AGCGATATTGCCGTCGAGTGGGAGAGCAACGGACAGCCAG<br>AAAACAATTACAAAACCACCCCACCTGTGCTGGACTCCGAT<br>GGGAGCTTTTTCCTGTACAGCAAGCTCACAGTGGACAAGTC<br>CAGATGGCAACAGGGCAACGTGTTTTCCTGCTCCGTGATGC<br>ACGAGGCCCTCCACAACCACTATACACAAAAGTCCCTCTCC<br>CTCAGCCCAGGA |
| 79 | αFXI-18623p HC IgG1 (1E) (C-terminal K-less) | EVQLQESGPGLVKPSQTLSLTCTVSGGS<u>IYSGAYYWS</u>WIRQHP<br>GKGLEWIGS<u>IHYSGLTYYNPSLKS</u>RVTISVDTSKNQFSLKLSSV<br>TAADTAVYYC<u>ARDVDDSSGDEHYGMD</u>VWGQGTTVTVSS*AST<br>KGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEV<br>TCVVVDVSHEDPEVKFNWYVDGVEVHNAKTKPREEQYNSTYRVVS<br>VLTVLHQDWLNGKEYKCKVSNKALPAPIEKTISKAKGQPREPQVY<br>TLPPSRDELTKNQVSLTCLVKGFYPSDIAVEWESNGQPENNYKTTP<br>PVLDSDGSFFLYSKLTVDKSRWQQGNVFSCSVMHEALHNHYTQKS<br>LSLSPG* |
| 80 | DNA encoding αFXI-18623p HC IgG1 (1E) xxx = GAA or GAG (E) (C-terminal K-less) | xxxGTCCAGCTGCAGGAATCCGGACCCGGCCTGGTGAAGCCT<br>AGCCAGACCCTGAGCCTGACCTGTACCGTGTCCGGCGGAAG<br>CATCTATTCCGGCGCCTACTACTGGTCCTGGATTAGGCAGC<br>ACCCCGGCAAGGGCCTGGAATGGATCGGCTCCATCCACTAC<br>AGCGGCCTGACCTATTACAACCCCTCCCTGAAGTCCAGGGT<br>GACCATCAGCGTCGACACAAGCAAGAACCAGTTCTCCCTCA<br>AGCTGAGCAGCGTGACCGCCGCCGACACCGCCGTGTATTAT<br>TGCGCCAGAGACGTGGACGACTCCTCCGGAGACGAGCACTA<br>CGGCATGGACGTCTGGGGCCAGGGCACAACAGTGACAGTG<br>AGCAGCGCTAGCACAAAAGGACCAAGCGTGTTTCCACTGGC<br>ACCTAGCAGCAAATCCACCAGCGGCGGAACAGCAGCCCTC<br>GGGTGCCTGGTGAAGGATTACTTCCCTGAGCCAGTCACAGT<br>GTCCTGGAACTCCGGAGCCCTGACATCCGGCGTGCACACCT<br>TCCCCGCTGTGCTGCAATCCAGCGGACTGTATAGCCTCAGC<br>TCCGTCGTGACAGTCCCTTCCAGCAGCCTGGGCACACAGAC<br>TTACATTTGCAACGTGAACCACAAACCTTCCAACACTAAGG<br>TGGACAAAAAGGTGGAACCCAAATCCTGTGATAAGACCCAT<br>ACATGCCCACCTTGTCCCGCTCCTGAGCTGCTGGGGGGACC<br>TTCCGTCTTTCTGTTTCCTCCAAAACCAAAAGACACACTCAT<br>GATCAGCCGGACCCCCGAAGTCACCTGTGTGGTGGTGGACG<br>TCAGCCACGAAGATCCAGAGGTCAAGTTCAATTGGTACGTG<br>GATGGAGTGGAAGTCCACAACGCAAAAACCAAACCTAGAG<br>AAGAACAGTACAATAGCACATACAGGGTGGTGTCCGTCCTG<br>ACAGTGCTCCACCAGGACTGGCTCAATGGCAAAGAGTATAA<br>GTGCAAGGTGAGCAACAAGGCCCTGCCTGCACCAATTGAGA<br>AAACAATTAGCAAGGCAAAGGGGCAGCCACGGGAACCCCA<br>GGTGTATACCCTGCCCCCAAGCCGGGATGAACTGACCAAAA<br>ACCAGGTCAGCCTGACATGCCTGGTGAAAGGGTTTTACCCA<br>AGCGATATTGCCGTCGAGTGGGAGAGCAACGGACAGCCAG<br>AAAACAATTACAAAACCACCCCACCTGTGCTGGACTCCGAT<br>GGGAGCTTTTTCCTGTACAGCAAGCTCACAGTGGACAAGTC<br>CAGATGGCAACAGGGCAACGTGTTTTCCTGCTCCGTGATGC<br>ACGAGGCCCTCCACAACCACTATACACAAAAGTCCCTCTCC<br>CTCAGCCCAGGA |
| 81 | Human FXI | ECVTQLLKDTCFEGGDITTVFTPSAKYCQVVCTYHPRCLLFTFT<br>AESPSEDPTRWFTCVLKDSVTETLPRVNRTAAISGYSFKQCSH<br>QISACNKDIYVDLDMKGINYNSSVAKSAQECQERCTDDVHCH<br>FFFTYATRQFPSLEHRNICLLKHTQTGTPTRITKLDKVVSGFSLK<br>SCALSNLACIRDIFPNTVFADSNIDSVMAPDAFVCGRICTHHPG<br>CLFFTFFSQEWPKESQRNLCLLKTSESGLPSTRIKKSKALSGFSL<br>QSCRHSIPVFCHSSFYHDTDFLGEELDIVAAKSHEACQKLCTNA<br>VRCQFFTYTPAQASCNEGKGKCYLKLSSNGSPTKILHGRGGIS<br>GYTLRLCKMDNECTTKIKPRIVGGTASVRGEWPWQVTLHTTS<br>PTQRHLCGGSIIGNQWILTAAHCFYGVESPKILRVYSGILNQSEI<br>KEDTSFFGVQEIIIHDQYKMAESGYDIALLKLETTVNYTDSQRP<br>ICLPSKGDRNVIYTDCWVTGWGYRKLRDKIQNTLQKAKIPLVT<br>NEECQKRYRGHKITHKMICAGYREGGKDACKGDSGGPLSCKH<br>NEVWHLVGITSWGEGCAQRERPGVYTNVVEYVDWILEKTQA<br>V |
| 82 | Epitope A | DIFPNTVF |

Table of Sequences

| SEQ ID NO: | Description | Sequence |
|---|---|---|
| 83 | Epitope B | PSTRIKKSKALSG |
| 84 | anti-RSV Kappa Light Chain | MAPVQLLGLLVLFLPAMRCDIQMTQSPSTLSASVGDRVTITCKCQLS VGYMHWYQQKPGKAPKLLIYDTSKLASGVPSRFSGSGSGTEFTLTIS SLQPDDFATYYCFQGSGYPFTFGGGTKLEIK*RTVAAPSVHFPPSDEQL KSGTASVVCLLNNEYPREAKVQWKVDNALQSGNSQESVTEQDSKDSTYSL SSTLTLSKADYEKHKVYACEVTHQGLSSPVTKSFNRGEC* |
| 85 | anti-RSV IgG4 HC S228P | MAVVQLLGLLVLFLPAMRCQVTLRESGPALVKPTQTLTLTCTFSGFS LSTSGMSVGWIRQPPGKALEWLADIWWDDKKDYNPSLKSRLTISKD TSKNQVVLKVTNMDPADTATYYCARSMITNWYFDVWGAGTTVTV *SSASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVES KYGPPCPPCPAPEFLGGPSVFLEPPKPKDTLMISRTPEVTCVVVDVSQED PEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQE GNVFSCSVMHEALHNHYTQKSLSLSLGK* |

Constant regions are shown in italics.
Amino acid sequences underlined are CDRs.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for therapeutic or prophylactic treatment of a thromboembolic disorder or disease in a subject comprising:
   administering to the subject an effective amount of an antibody or antigen binding fragment comprising:
   (i) six complimentary determining regions (CDRs) of an anti-FXI antibody of the αFXI-18611 family, wherein the six CDRs comprise
   (a) CDR1, CDR2, and CDR3 of the heavy chain (HC) having the amino acid sequence shown in SEQ ID NO: 37 or 39; and
   (b) CDR1, CDR2, and CDR3 of the light chain (LC) having the amino acid sequence shown in SEQ ID NO: 26.

2. The method of claim 1, wherein the antibody or antigen binding fragment comprises (a) a heavy chain complementarity determining region (HC-CDR) 1 having the amino acid sequence shown in SEQ ID NO: 1, an HC-CDR 2 having the amino acid sequence shown in SEQ ID NO: 2, and an HC-CDR 3 having the amino acid sequence shown in SEQ ID NO: 4 and (b) a light chain complementarity determining region (LC-CDR) 1 having the amino acid sequence shown in SEQ ID NO: 5, an LC-CDR 2 having the amino acid sequence shown in SEQ ID NO: 6, and an LC-CDR 3 comprises having the amino acid sequence shown in SEQ ID NO: 7.

3. The method of claim 2, wherein the antibody or antigen binding fragment comprises an HC variable domain having the amino acid sequence shown in SEQ ID NO: 23 or 24 and an LC variable domain having the amino acid sequence shown in SEQ ID NO: 25.

4. The method of claim 1, wherein the antibody comprises a HC constant domain comprising the amino acid sequence shown in SEQ ID NO:16, 17, 18, or 19.

5. The method of claim 1, wherein the antibody comprises a LC constant domain comprising the amino acid sequence shown in SEQ ID NO:20.

6. The method of claim 1, wherein the antibody or antigen binding fragment binds the apple 3 domain of coagulation factor XI (FXI) and inhibits activation of FXI and/or Factor XIa-mediated activation of Factor IX.

7. The method of claim 1, wherein the antibody comprises:
   (a) an HC having a constant domain and a variable domain wherein the variable domain comprises a heavy chain-complementary determining region (HC-CDR) 1 having the amino acid sequence shown in SEQ ID NO: 1, a HC-CDR 2 having the amino acid sequence shown in SEQ ID NO: 2, and a HC-CDR 3 having the amino acid sequence shown in SEQ ID NO: 4; and
   (b) an LC having a constant domain and a variable domain wherein the variable domain comprises a light chain-complementary determining region (LC-CDR) 1 having the amino acid sequence shown in SEQ ID NO: 5, a LC-CDR 2 having the amino acid sequence shown in SEQ ID NO: 6, and a LC-CDR 3 having the amino acid sequence shown in SEQ ID NO: 7.

8. The method of claim 7, wherein the antibody comprises an HC constant domain comprising the amino acid sequence shown in SEQ ID NO: 16, 17, 18, or 19.

9. The method of claim 7, wherein the antibody comprises an LC constant domain comprising the amino acid sequence shown in SEQ ID NO: 20.

10. The method of claim 1, wherein the antibody comprises a heavy chain having the amino acid sequence shown in SEQ ID NO: 37 and a light chain having the amino acid sequence shown in SEQ ID NO: 26.

11. The method of claim 1, wherein the antibody comprises a heavy chain having the amino acid sequence shown in SEQ ID NO: 39 and a light chain having the amino acid sequence shown in SEQ ID NO: 26.

12. The method of claim 1, wherein the antibody comprises a heavy chain having the amino acid sequence shown in SEQ ID NO: 61 and a light chain having the amino acid sequence shown in SEQ ID NO: 26.

13. The method of claim 1, wherein the antibody comprises a heavy chain having the amino acid sequence shown in SEQ ID NO: 63 and a light chain having the amino acid sequence shown in SEQ ID NO: 26.

14. The method of claim 1, wherein the subject has end-stage renal disease (ESRD).

15. The method of claim 1, wherein the thromboembolic disorder or disease is venous thromboembolism (VTE).

16. The method of claim 1, wherein the therapeutic or prophylactic treatment of a thromboembolic disorder or disease in a subject is for Stroke Prevention in Atrial Fibrillation (SPAF).

17. The method of claim 1, wherein the thromboembolic disorder or disease is medical device-related.

18. The method of claim 17, wherein the medical device is a stent, endovascular stent graft, cardiac or venous catheter, continuous flow ventricular assist device (CF-LVAD), hemodialysis device, cardiopulmonary bypass device, Extracorporeal Membrane Oxygenation (ECMO) device, or ventricular assist device (VAD).

* * * * *